(12) United States Patent
Ali et al.

(10) Patent No.: US 7,910,592 B2
(45) Date of Patent: Mar. 22, 2011

(54) CETP INHIBITORS

(75) Inventors: Amjad Ali, Freehold, NJ (US); Zhijian Lu, Clinton, NJ (US); Peter J. Sinclair, Scotch Plains, NJ (US); Yi-Heng Chen, Whippany, NJ (US); Cameron J. Smith, Lawrenceville, NJ (US); Hong Li, Edison, NJ (US); Christopher F. Thompson, Clark, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/087,185

(22) PCT Filed: Dec. 29, 2006

(86) PCT No.: PCT/US2006/049503
§ 371 (c)(1),
(2), (4) Date: Jun. 26, 2008

(87) PCT Pub. No.: WO2007/081569
PCT Pub. Date: Jul. 19, 2007

(65) Prior Publication Data
US 2009/0042892 A1    Feb. 12, 2009

Related U.S. Application Data

(60) Provisional application No. 60/755,541, filed on Dec. 30, 2005.

(51) Int. Cl.
| A61K 31/497 | (2006.01) |
| A61K 31/427 | (2006.01) |
| A61K 31/422 | (2006.01) |
| A61K 31/506 | (2006.01) |
| C07D 239/02 | (2006.01) |
| C07D 241/02 | (2006.01) |
| C07D 401/02 | (2006.01) |
| C07D 277/02 | (2006.01) |
| C07D 263/02 | (2006.01) |

(52) U.S. Cl. ............ 514/255.05; 514/256; 514/365; 514/376; 544/242; 544/336; 546/271.4; 548/202; 548/230

(58) Field of Classification Search ........... 514/255.05, 514/256, 365, 376; 544/242, 336; 546/271.4; 548/202, 230
See application file for complete search history.

(56) References Cited

U.S. PATENT DOCUMENTS

| 4,797,130 | A |   | 1/1989  | Clausen et al. |
| 5,378,724 | A | * | 1/1995  | Uhr et al. ............ 514/424 |
| 6,395,732 | B1 |  | 5/2002  | Zimmermann et al. |
| 6,451,830 | B1 |  | 9/2002  | Sikorski et al. |
| 6,653,476 | B2 |  | 11/2003 | Yasuma et al. |
| 2006/0040999 | A1 | | 2/2006  | Ali et al. |

FOREIGN PATENT DOCUMENTS

| EP | 0 605 729     |   | 7/1994 |
| EP | 1 188 747 A1  |   | 3/2002 |
| WO | WO 03/031435  | * | 4/2003 |
| WO | WO 2005/085241| * | 9/2005 |

OTHER PUBLICATIONS

McKay et al.: "Cyclizations of B-Chloroethyl Substituted Ammonocarbonic Acids", Journal of Organic Chemistry, vol. 16, No. 11, 1951, pp. 1829-1834.
Cutugno et al.: "The Reaction of beta-Amino Alcohols with 1,1-Carbonyldiimidazole-Influence of the Nitrogen Substituent on the Reaction Course", European Journal of Organic Chemistry, vol. 3, 2001, pp. 517-522.
Supplementary European Search Report for EP 06 84 9230; Performed in Munich; Completed Jul. 30, 2010.

* cited by examiner

*Primary Examiner* — Rebecca L Anderson
*Assistant Examiner* — Samantha L Shterengarts
(74) *Attorney, Agent, or Firm* — Mark R. Daniel; James L. McGinnis

(57) ABSTRACT

Compounds having the structure of Formula (I), including pharmaceutically acceptable salts of the compounds, are CETP inhibitors and are useful for raising HDL-cholesterol, reducing LDL-cholesterol, and for treating or preventing atherosclerosis. In the compounds of Formula (I), B is a cyclic group other than phenyl, and B has a cyclic substituent at a position that is ortho to the position at which B is connected to the remainder of the structure of Formula (I). The 5-membered ring of Formula (I) has a second cyclic substituent in addition to B.

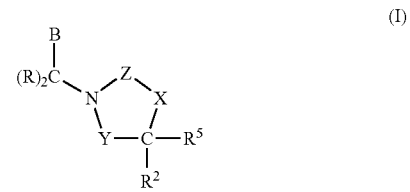

15 Claims, No Drawings

CETP INHIBITORS

CROSS REFERENCE TO RELATED APPLICATIONS

This application is a U.S. National Phase application under 35 U.S.C. §371 of PCT Application No. PCT/US2006/049503, filed Dec. 29, 2006, which claims priority under 35 U.S.C. §119(e) from U.S. Application No. 60/755,541, filed Dec. 30, 2005.

FIELD OF THE INVENTION

This invention relates to a class of chemical compounds that inhibit cholesterol ester transfer protein (CETP) and therefore have utility in raising HDL-C, lowering LDL-C, and in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoBliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S., and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. Clinical trials of the CETP inhibitor torcetrapib were terminated due to increased mortality in outcomes studies. New compounds are needed so that one or more pharmaceutical compounds can be found that are safe and effective. The novel compounds described herein are very potent CETP inhibitors.

SUMMARY OF THE INVENTION

Compounds having Formula I, including pharmaceutically acceptable salts of the compounds, are CETP inhibitors, having the utilities described below:

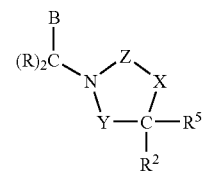

In the compound of formula I, Y is selected from the group consisting of —C(=O)— and —(CRR$^1$)—;

X is selected from the group consisting of —O—, —NH—, —N(C$_1$-C$_5$alkyl)-, and —(CRR$^6$)—;

Z is selected from the group consisting of —C(=O)—, —S(O)$_2$—, and —C(—N—R$^9$)—, wherein R$^9$ is selected from the group consisting of H, —CN, and C$_1$-C$_5$alkyl optionally substituted with 1-1 halogens;

Each R is independently selected from the group consisting of H, —C$_1$-C$_5$ alkyl, and halogen, wherein —C$_1$-C$_5$ alkyl is optionally substituted with 1-11 halogens;

B is selected from the group consisting of A$^1$ and A$^2$, wherein A$^1$ has the structure:

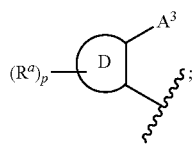

$R^1$ and $R^6$ are each selected from the group consisting of H, —$C_1$-$C_5$ alkyl, halogen, and —$(C(R)_2)_nA^2$, wherein —$C_1$-$C_5$ alkyl is optionally substituted with 1-11 halogens;

$R^2$ is selected from the group consisting of H, —$C_1$-$C_5$ alkyl, halogen, $A^1$, and —$(C(R)_2)_nA^2$, wherein —$C_1$-$C_5$ alkyl is optionally substituted with 1-11 halogens;

Wherein one of B and $R^2$ is $A^1$; and one of B, $R^1$, $R^2$, and $R^6$ is $A^2$ or —$(C(R)_2)_nA^2$; so that the compound of Formula I comprises one group $A^1$ and one group $A^2$;

D is selected from the group consisting of:
(a) naphthyl;
(b) a phenyl ring fused to a 5-7 membered non-aromatic cycloalkyl ring, which optionally comprises 1-2 double bonds;
(c) a 5-6-membered heterocyclic ring having 14 heteroatoms independently selected from N, S, O, and —N(O)—, and optionally also comprising 1-3 double bonds and a carbonyl group; and
(d) an 8-11-membered bicyclic heteroaromatic ring system comprising 2 fused rings and 1-5 heteroatoms independently selected from N, —S(O)$_x$—, O, and —N(O)—, wherein the ring system optionally comprises 1-5 double bonds, so that each ring is independently saturated, partly unsaturated, or aromatic;

wherein $A^1$ comprises an $A^3$ group which is attached to a carbon atom of ring D, and ring D is connected to the remainder of the structure of Formula I through a carbon atom in the ring that is adjacent to the carbon atom to which the $A^3$ group is attached;

$A^3$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 14 heteroatoms independently selected from N, S, O, and —N(O)—, and optionally also comprising 1-3 double bonds and a carbonyl group; and
(d) an 8-11-membered bicyclic heteroaromatic ring system comprising 2 fused rings and 1-5 heteroatoms independently selected from N, —S(O)$_x$—, O, and —N(O)—, wherein the ring system optionally comprises 1-5 double bonds, so that each ring is independently saturated, partly unsaturated, or aromatic;

wherein the point of attachment of $A^3$ to the ring D to which $A^3$ is attached is a carbon atom of ring $A^3$;

wherein $A^3$ is optionally substituted with 1-5 substituent groups independently selected from $R^b$;

$A^2$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 14 heteroatoms independently selected from N, S, O, and —N(O)—, and optionally also comprising 1-3 double bonds and a carbonyl group;
(d) an 8-11-membered bicyclic heteroaromatic ring system comprising 2 fused rings and 1-5 heteroatoms independently selected from N, —S(O)$_x$—, O, and —N(O)—, wherein the ring system optionally comprises 1-5 double bonds, so that each ring is independently saturated, partly unsaturated, or aromatic; and
(e) a —$C_3$-$C_8$ cycloalkyl ring optionally having 1-3 double bonds;

wherein $A^2$ is optionally substituted with 1-5 substituent groups independently selected from $R^a$;

wherein the point of attachment of $A^2$ to the structure of formula I to which $A^2$ is attached is a carbon atom of ring $A^2$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)$SC_1$-$C_6$alkyl, —OH, —$NR^3R^4$, —C(=O)$NR^3R^4$, —$NR^3$C(=O)$OC_1$-$C_6$alkyl, —$NR^3$C(=O)$NR^3R^4$, —S(O)$_xC_1$-$C_6$ alkyl, —S(O)$_yNR^3R^4$, —$NR^3$S(O)$_yNR^3R^4$, halogen, —CN, —$NO_2$, phenyl, naphthyl, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom;

wherein for compounds in which $R^a$ is a cyclic group selected from phenyl, naphthyl, —$C_3$-$C_8$ cycloalkyl optionally having 1-3 double bonds, and a heterocyclic ring, $R^a$ is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —$CO_2C_1$-$C_6$alkyl, —C(=O)$SC_1$-$C_6$alkyl, —$NR^3$C(=O)$OC_1$-$C_6$alkyl, and —S(O)$_xC_1$-$C_6$ alkyl, $R^a$ is optionally substituted with 1-15 halogens and is optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$C_1$-$C_2$ alkyl and phenyl, (f) —$OC_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

Each $R^b$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)$SC_1$-$C_6$alkyl, —$NR^3R^4$, —C(=O)$NR^3R^4$, —$NR^3$C(=O)$OC_1$-$C_6$alkyl, —$NR^3$C(=O)$NR^3R^4$, —S(O)$_xC_1$-$C_6$ alkyl, S(O)$_yNR^3R^4$, —$NR^3$S(O)$_yNR^3R^4$, halogen, —CN, —$NO_2$, phenyl, naphthyl, and a 5-6-membered heterocyclic ring having 1-4 heteroatoms independently selected from N, S, and O, said heterocyclic ring optionally also comprising a carbonyl group and optionally also comprising 1-3 double bonds, wherein when $R^b$ is selected from the group consisting of a heterocyclic ring, —$C_3$-$C_8$ cycloalkyl, naphthyl, —$OC_3$-$C_8$ cycloalkyl, and —C(═O)$C_3$-$C_8$ cycloalkyl, then the heterocyclic ring, naphthyl, and —$C_3$-$C_8$ cycloalkyl groups of $R^b$ are optionally substituted with 1-5 substituent groups independently selected from halogen, —$C_1$-$C_3$ alkyl, —$C_2$-$C_3$ alkenyl, —$NR^3R^4$, —$OC_1$-$C_3$ alkyl, —$CO_2H$, —CN, and —$CO_2C_1$-$C_3$alkyl, wherein —$C_1$-$C_3$ alkyl and —$C_2$-$C_3$ alkenyl in all uses are optionally substituted with 1-7 halogens and optionally one group —OH, wherein when $R^b$ is selected from the group consisting of —$C_1$-$C_6$ alkyl, —$C_2$-$C_6$ alkenyl, —$C_2$-$C_6$ alkynyl, —$OC_1$-$C_6$alkyl, —$OC_2$-$C_6$ alkenyl, —$OC_2$-$C_6$ alkynyl, —C(═O)$C_1$-$C_6$alkyl, —$CO_2C_1$-$C_6$alkyl, —C(═O)S$C_1$-$C_6$alkyl, —$NR^3$C(═O)O$C_1$-$C_6$alkyl, and —S(O)$_x$$C_1$-$C_6$ alkyl, then the alkyl, alkenyl, and alkynyl groups of $R^b$ are optionally substituted with 1-13 halogens and are optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl, (f) —$OC_3$-$C_8$ cycloalkyl optionally having 1-3 double bonds and optionally substituted with 1-15 halogens, (g) —$CO_2H$, (h) —C(═O)$CH_3$, (i) —$CO_2C_1$-$C_4$alkyl which is optionally substituted with 1-9 halogens, and (l) phenyl which is optionally substituted with 1-3 groups independently selected from halogen, —$CH_3$, —$CF_3$, —$OCH_3$, and —$OCF_3$;

and when $R^b$ is phenyl, said phenyl is optionally substituted with 1-5 halogens and is also optionally substituted with 1-3 substituents independently selected from —$C_1$-$C_4$ alkyl, —$C_2$-$C_4$ alkenyl, —$C_2$-$C_4$ alkynyl, —$C_3$-$C_6$ cycloalkyl, —$OC_1$-$C_4$alkyl, —$OC_2$-$C_4$ alkenyl, —$OC_2$-$C_4$ alkynyl, —$OC_3$-$C_6$ cycloalkyl, —C(═O)$C_1$-$C_4$alkyl, —C(═O)H, —$CO_2H$, —$CO_2C_1$-$C_4$alkyl, —$NR^3R^4$, —C(═O)$NR^3R^4$, —$NR^3$C(═O)O$C_1$-$C_4$ alkyl, —$NR^3$C(═O)$NR^3R^4$, —S(O)$_x$$C_1$-$C_4$ alkyl, —S(O)$_y$$NR^3R^4$, —$NR^3$S(O)$_y$$NR^3R^4$, —CN, —$NO_2$, and a 5-6-membered heterocyclic ring having 14 heteroatoms independently selected from N, S, and O, said heterocyclic ring optionally also comprising a carbonyl group and optionally also comprising 1-3 double bonds and optionally comprising 1-3 substituents independently selected from halogen, —$CH_3$, —$OCH_3$, —$CF_3$, and —$OCF_3$; wherein when the substituents on phenyl when $R^b$ is phenyl are selected from —$C_1$-$C_4$alkyl, —$C_2$-$C_4$ alkenyl, —$C_2$-$C_4$ alkynyl, —$C_3$-$C_6$ cycloalkyl, —$OC_1$-$C_4$alkyl, —$OC_2$-$C_4$ alkenyl, —$OC_2$-$C_4$ alkynyl, —$OC_3$-$C_6$ cycloalkyl, —C(═O)$C_1$-$C_4$alkyl, —$CO_2C_1$-$C_4$alkyl, —$NR^3$C(═O)O$C_1$-$C_4$alkyl, and —S(O)$_x$$C_1$-$C_4$ alkyl, then the alkyl, alkenyl, alkynyl, and cycloalkyl groups of said substituent groups optionally comprise 1-5 halogen substituents and also optionally comprise one substituent selected from —OH, —$NR^3R^4$, —$OCH_3$ optionally substituted with 1-3 F, and phenyl which is optionally substituted with 1-3 substituents independently selected from halogen, —$CH_3$, —$OCH_3$, —$CF_3$, and —$OCF_3$;

n is 0 or 1;
p is an integer from 0-4;
x is 0, 1, or 2;
y is 1 or 2;
$R^3$ and $R^4$ are each independently selected from H, —$C_1$-$C_5$ alkyl, —C(═O)$C_1$-$C_5$ alkyl and —S(O)$_y$$C_1$-$C_5$ alkyl, wherein —$C_1$-$C_5$ alkyl in all instances is optionally substituted with 1-11 halogens; and $R^5$ is selected from the group consisting of H, —OH, —$C_1$-$C_5$ alkyl, and halogen, wherein —$C_1$-$C_5$ alkyl is optionally substituted with 1-11 halogens.

In the compounds of Formula I and in compounds described below, alkyl, alkenyl, and alkynyl groups can be either linear or branched, unless otherwise stated.

DETAILED DESCRIPTION OF THE INVENTION

In embodiments of the invention, the compound of Formula I has the structures shown below as Formula Ia, Ib, and Id, including pharmaceutically acceptable salts thereof:

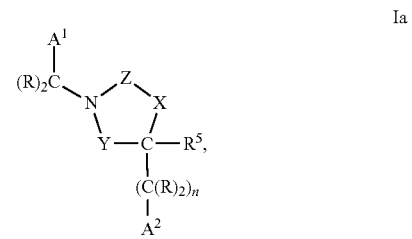

Ia

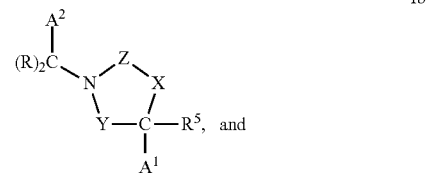

Ib

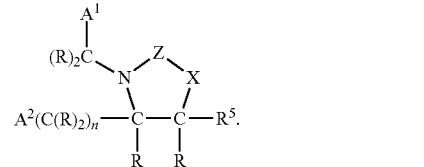

Id

Embodiments of the compounds having formula I, Ia, Ib, and Ib, including pharmaceutically acceptable salts thereof, may have one or more of the following definitions:
Y is —(CH$R^1$)—.
X is —O—.
Z is —C(═O)—.
R is H.
n is 0.
p is an integer from 0-2.
$R^1$ and $R^5$ are each independently selected from the group consisting of H and —$C_1$-$C_3$ alkyl.

In further embodiments, including pharmaceutically acceptable salts thereof, D is selected from the group consisting of naphthyl, pyridyl, quinolyl, indanyl, benzothienyl, tetrahydronaphthyl, isoxazolyl, thienyl, imidazolyl, pyrrolyl, pyrazolyl, pyridyl, N-oxido-pyridyl, 1,3-thiazolyl, 1,3-oxazolyl, pyridazinyl, pyrimidinyl, pyrazinyl, pyridazinyl, benzofuranyl, dihydrobenzofuranyl, benzothienyl-5-oxide, benzothienyl-5-dioxide, dihydroindolyl; dihydroisoindolyl, dihydroisobenzofuranyl, and benzodioxolanyl. In further embodiments, including pharmaceutically acceptable salts thereof, D is selected from the group consisting of naphthyl, pyridyl, quinolyl, indanyl, benzothienyl, tetrahydronaphthyl, isoxazolyl, 1,3-thiazolyl, pyrimidinyl, pyrazinyl, dihydroisoindolyl, dihydroisobenzofuranyl, and benzodioxolanyl.

In further embodiments, including pharmaceutically acceptable salts thereof, $A^3$ is selected from the group consisting of phenyl, naphthyl, tetrahydronaphthyl, pyridyl, thienyl, imidazolyl, pyrrolyl, pyrazolyl, N-oxido-pyridyl, 1,3-thiazolyl, 1,3-oxazolyl, pyridazinyl, pyrimidinyl, pyrazinyl, indanyl, benzothienyl, benzothienyl-5-oxide, benzothienyl-5-dioxide, dihydroindolyl; dihydroisoindolyl, dihydroisobenzofuranyl, and benzodioxolanyl. In further embodiments, including pharmaceutically acceptable salts thereof, $A^3$ is selected from the group consisting of phenyl, naphthyl, indanyl, and tetrahydronaphthyl.

In further embodiments, including pharmaceutically acceptable salts thereof, $A^2$ is selected from the group consisting of phenyl, thienyl, imidazolyl, thiazolyl, pyrrolyl, pyrazolyl, 1,2,4-triazolyl, tetrazolyl, benzodioxolyl, pyridyl, N-oxido-pyridyl, pyridazinyl, pyrimidinyl, pyrazinyl, cyclopentyl, cyclohexyl, and tetrahydropyranyl. In further embodiments, including pharmaceutically acceptable salts thereof, $A^2$ is phenyl.

In further embodiments, including pharmaceutically acceptable salts thereof, $R^a$ and $R^b$ are each independently selected from the group consisting of —$C_1$-$C_5$ alkyl, —$C_2$-$C_5$ alkenyl, —$C_3$-$C_6$ cycloalkyl optionally having 1-2 double bonds, —$OC_1$-$C_3$alkyl, —C(=O)H, —$CO_2$H, —$CO_2C_1$-$C_4$alkyl, —OH, —$NR^3R^4$, halogen, —CN, —$NO_2$, phenyl, and a 5-6-membered heterocyclic ring having 14 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-3 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ and $R^b$ are selected from the group consisting of —$C_1$-$C_5$ alkyl, —$C_2$-$C_5$ alkenyl, —$OC_1$-$C_3$alkyl, and —$CO_2C_1$-$C_4$alkyl, $R^a$ is optionally substituted with 1-7 halogens and is optionally substituted with one substituent group —H;

and for compounds in which $R^a$ and $R^b$ are selected from the group consisting of phenyl and —$C_3$-$C_6$ cycloalkyl optionally having 1-2 double bonds, $R^a$ is optionally substituted with 1-5 halogens and is optionally substituted with 1-3 groups independently selected from —$C_1$-$C_5$ alkyl, —$C_2$-$C_5$ alkenyl, —$C_3$-$C_6$ cycloalkyl optionally having 1-2 double bonds, —$OC_1$-$C_3$alkyl, —C(=O)H, —$CO_2$H, —$CO_2C_1$-$C_4$alkyl, —OH, —$NR^3R^4$, halogen, —CN, and —$NO_2$, wherein —$C_1$-$C_5$ alkyl, —$C_2$-$C_5$ alkenyl, —$C_3$-$C_6$ cycloalkyl optionally having 1-2 double bonds, —$OC_1$-$C_3$alkyl, and —$CO_2C_1$-$C_4$alkyl are optionally substituted with 1-5 halogens, and —$C_1$-$C_5$ alkyl also is optionally substituted with one —OH; and $R^3$ and $R^4$ are each independently selected from H and $C_1$-$C_3$alkyl.

In further embodiments, including pharmaceutically acceptable salts thereof, Y is —(CHR$^1$)—, wherein R$^1$ is selected from H and $C_1$-$C_2$ alkyl.

In further embodiments, including pharmaceutically acceptable salts thereof, $R^2$ is $A^2$, where $A^2$ is phenyl which is optionally substituted with 1-3 substituents independently selected from halogen, —$C_1$-$C_3$ alkyl which is optionally substituted with 1-3 halogens, and —$OC_1$-$C_3$alkyl which is optionally substituted with 1-3 halogens.

In further embodiments, including pharmaceutically acceptable salts thereof, B is $A^1$ where $A^1$ has the structure:

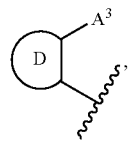

wherein D is selected from the group consisting of naphthyl, pyridyl, quinolyl, indanyl, benzothienyl, tetrahydronaphthyl, isoxazolyl, 1,3-thiazolyl, pyrimidinyl, pyrazinyl, dihydroisoindolyl, dihydroisobenzofuranyl, and benzodioxolanyl, wherein D is optionally substituted with 1 substituent group selected from (a) halogen, (b) —$C_1$-$C_5$ alkyl which is optionally substituted with 1-3 halogens, (c) —$C_2$-$C_3$ alkenyl, (d) —$C_3$-$C_6$ cycloalkyl, (e) —$C_5$-$C_6$ cycloalkenyl, (t) —$OC_1$-$C_3$alkyl optionally substituted with 1-3 halogens; (g) —$SC_1$-$C_3$alkyl, (h) —$SO_2C_1$-$C_3$alkyl, (i) —C(=O)OCH$_2$Phenyl, (j) Phenyl optionally substituted with 1-3 substituents independently selected from halogen, CH$_3$, CF$_3$, —OCH$_3$, and —OCF$_3$, (k) —NR$^3$R$^4$, where R$^3$ and R$^4$ are each independently selected from H and CH$_3$, (l) —CN, and (m) —NO$_2$.

In further embodiments, including pharmaceutically acceptable salts thereof, $A^3$ is selected from the group consisting of phenyl, naphthyl, indanyl, and tetrahydronaphthyl, wherein $A^3$ is substituted with 1-3 substituents independently selected from (a) halogen, (b) —$C_1$-$C_5$ alkyl which is optionally substituted with 1-3 halogens and optionally 1 group selected from —OH, —$CO_2$H, and —$CO_2C_1$-$C_3$ alkyl, (c) —$C_2$-$C_3$ alkenyl, (d) —$C_3$-$C_6$ cycloalkyl which is optionally substituted with one group selected from [i] —$CO_2$H, [ii] —OH, and [iii] —$C_1$-$C_5$ alkyl which is optionally substituted with 1-3 halogens and optionally with 1 group selected from —OH, —$CO_2$H, and —$CO_2$CH$_3$, (e) —$C_5$-$C_6$ cycloalkenyl, (f) phenyl which is optionally substituted with 1-2 substituent groups independently selected from halogen, CH$_3$, CF$_3$, —OCH$_3$, —OCF$_3$, and optionally one group —$CO_2$H or —$CO_2C_1$-$C_3$ alkyl, and (g) —$OC_1$-$C_3$alkyl optionally substituted with 1-3 halogens.

Definitions

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—CH$_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated (e.g., cycloalkyl may be defined as having one or more double bonds). The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"EDC" is 1-ethyl-3-(3-dimethylaminopropyl)carbodiimide.

"Heterocyclyl," "heterocycle," and "heterocyclic" means a fully or partially saturated or aromatic 5-6 membered ring containing 14 heteroatoms independently selected from N, S and O, unless otherwise stated.

"Benzoheterocycle" represents a phenyl ring fused to a 5-6-membered heterocyclic ring having 1-2 heteroatoms, each of which is O, N, or S, where the heterocyclic ring may be saturated or unsaturated. Examples include indole, benzofuran, 2,3-dihydrobenzofuran and quinoline.

"DIPEA" is diisopropylethylamine.

"Halogen" includes fluorine, chlorine, bromine and iodine.

"HOBT" is 1-Hydroxybenzotriazole.

"IPAC" is isopropyl acetate.

"Me" represents methyl.

"Weinreb amine" is N,O-dimethylhydroxylamine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

Compounds of Formula I may contain one or more asymmetric centers and can thus occur as racemates, racemic mixtures, single enantiomers, diastereomeric mixtures and individual diastereomers. The present invention is meant to include all such isomeric forms of the compounds of Formula I and all mixtures of the compounds. When structures are shown with a stereochemical representation, other stereochemical structures are also included individually and collectively, such as enantiomers, diastereoisomers (where diastereomers are possible), and mixtures of the enantiomers and/or diastereomers, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein are observed as mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts-Metabolites—Prodrugs Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are particularly effective in raising HDL-C and/or increasing the ratio of HDL-C to LDL-C. They are also effective in lowering LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other thereapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a crosslinked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD-4522.

Finally compounds of this invention can be used with compounds that are useful for treating other diseases, such as diabetes, hypertension and obesity, as well as other anti-atherosclerostic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

These other active ingredients that may be used in combination with the current invention also include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and $\beta_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2) angiotensin converting enzyme inhibitors (ACE inhibitors), such as enalapril and captopril; (3) calcium channel blockers such as nifedipine and diltiazam; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, aminone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nornifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6, beta-Ala11, Phe13, Nle14]Bn(6-14) and [D-Phe6, Phe13]Bn(6-13)propylamide; (32) CNTF (Ciliary neurotrophic factors), such as GI-181771 (Glaxo-Smith-Kline), SR146131 (Sanofi Synthelabo), butabindide, PD170, 292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) a minorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP Assay

An in vitro continuous assay for determining $IC_{50}$'s to identify compounds that are CETP inhibitors was performed based on a modification of the method described by Epps et al. employing BODIPY®-CE as the cholesteryl ester lipid donor. See Epps et al. (1995) *Method for measuring the* activities of cholesteryl ester transfer protein (lipid transfer protein), *Chem. Phys. Lipids.* 77, 51-63.

Particles used in the assay were created from the following sources: Synthetic donor HDL particles containing DOPC (Dioleoyl Phosphatidyl Choline), BODIPY®-CE (Molecular Probes C-3927), triolein (a triglyceride), and apoHDL were essentially created by probe sonication as described by Epps et al, but with the addition of a non-diffusable quencher molecule, dabcyl dicetylamide, in order to reduce background fluorescence. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), and half the final concentration of acceptor particles was prepared, and 100 μL of the assay cocktail was added to each well of the plate. Test compounds in DMSO were added in a volume of 3 μL. The plate was mixed on a plate shaker and then incubated at 25° C. for 1 hour. A second assay cocktail containing donor particles, the remaining acceptor particles and 1×CETP buffer was prepared. 47 μL of the second assay cocktail was added to the reaction wells to start the assay. Assays were performed at 25° C. in a final volume of 150 μL. Final concentrations of materials were: 5 ng/μL donor particles, 30 ng/μL acceptor particles (each expressed by protein content), 1×CETP buffer, 0.8 nM recombinant human CETP (expressed in CHO cells and partially purified), and up to 2% DMSO when testing compounds. The assay was followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well.

Data was evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate $IC_{50}$.

EXAMPLES

The following schemes and examples are provided so that the invention will be more fully appreciated and understood. Starting materials are made using known procedures or as shown below.

The examples should not be construed as limiting the invention in any way. The scope of the invention is defined by the appended claims. Compounds of this invention have an $IC_{50}$ value as measured using the assay described above of less than or equal to 50 μM. The compounds in general have $IC_{50}$ values in the range of 5 nM to 20 μM, preferably in the range of 5 nM to 5 μM, more preferably in the range of 5 nM to 200 nM, and even more preferably in the range of 5 nM to 100 nM.

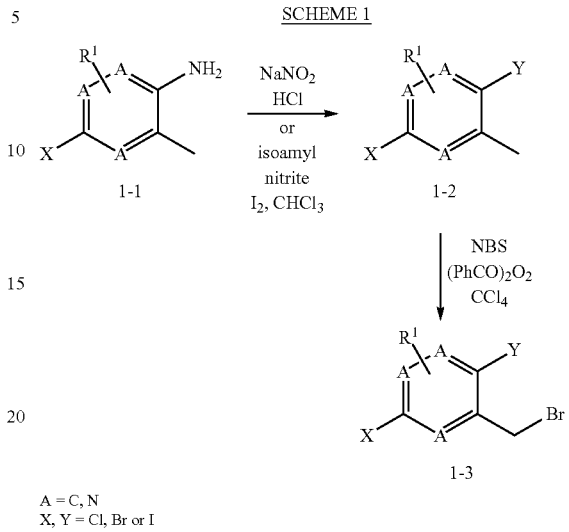

A = C, N
X, Y = Cl, Br or I

Intermediates of the present invention wherein $R^1$ is described in the claims can be prepared as shown in Scheme 1. The aryl halide 1-2 can be obtained by treatment of an appropriately substituted pyridyl amine 1-1 which can be purchased or prepared by known methods with reagents such as isoamylnitrite, n-pentylnitrite, t-butyl nitrite or the like in the presence of diiodomethane (see for example: Smith et al., *J. Org. Chem.* 55, 2543, (1990) and references cited therein) either neat or in a solvent such as THF or acetonitrile. Alternatively, the pyridyl halide can be prepared first by diazonium formation using isoamyl nitrite, n-pentyl nitrite, t-butyl nitrite, sodium nitrite in hydrochloric acid, nitrous acid or the like followed by the addition of bromine iodine or an halo salt such as copper chloride, copper bromide, copper iodide, sodium iodide, potassium iodide, tetrabutylammonium iodide or the like. Heating pyridyl methyl derivative 1-2 with brominating agents such as N-bromosuccinimide or the like and a radical initiator such as benzoyl bromide, AIBN or the like in carbon tetrachloride affords the corresponding bromomethylpyridines 1-3.

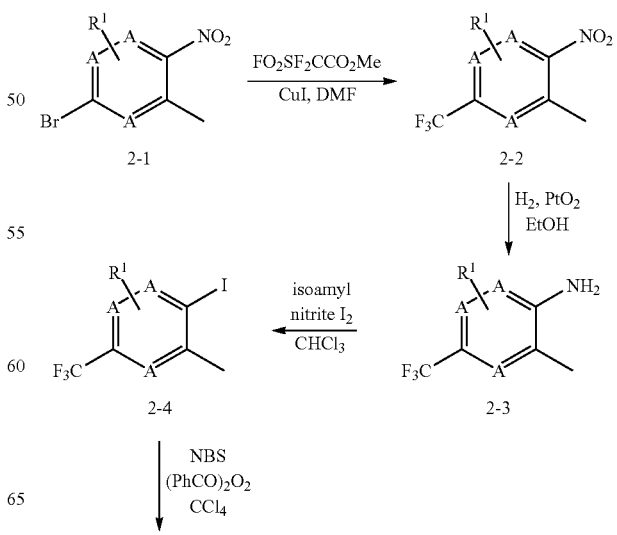

-continued

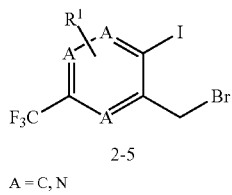

2-5

A = C, N

Intermediates of the present invention wherein $R^1$ is described in the claims can be prepared as shown in Scheme 2. The trifluoromethylpyridine 2-2 can be obtained by heating of an appropriately substituted nitropyridine 2-1, which can be purchased or prepared by known methods and the halogen is preferably iodo or bromo, with reagents such as methyl 2,2-difluoro-2-(fluorosulfonyl)acetate and copper iodide or 2-chloro-2,2-difluoroacetate, potassium fluoride and copper iodide in solvents such as DMF or the like. Reduction of the nitropyridine by catalytic hydrogenation with catalysts such as platinum oxide, Raney nickel and palladium on carbon or the like in solvents such as MeOH, EtOH, THF or the like or with other reducing agents such as tin(II) chloride in the presence of hydrochloric acid in solvents such as MeOH or the like, affords the corresponding pyridyl amine 2-3. These intermediates can be transformed into intermediates 2-5 via 24 using procedures such as those described in Scheme 1 for the transformation of intermediates 1-1 to 1-3 via 1-2.

SCHEME 3

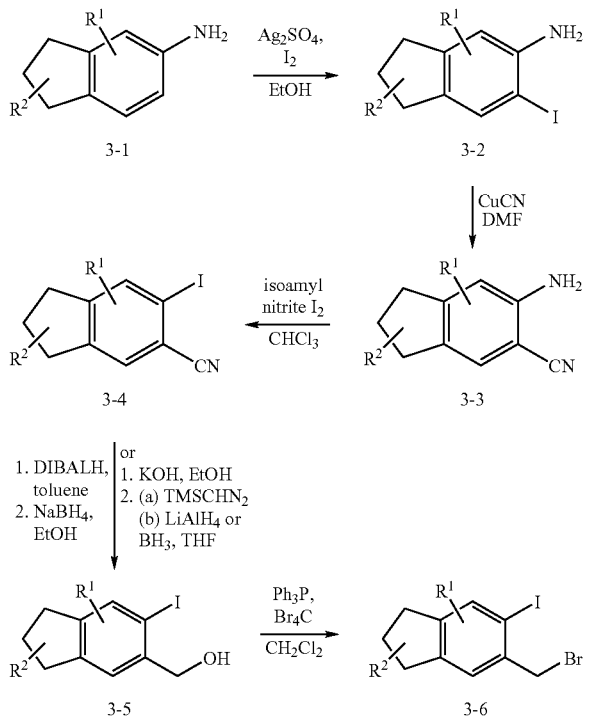

Intermediates of the present invention wherein $R^1$ and $R^2$ are described in the claims can be prepared as shown in Scheme 3. Treatment of an appropriately substituted aryl amine 3-1, which can be purchased or prepared by known methods, with reagents such as iodine in the presence of silver sulfate or the like in solvents such as MeOH, EtOH or the like or bromine in solvents such as $CH_2Cl_2$ or $CHCl_3$ or the like affords the corresponding 2-haloaryl amine 3-2. This intermediate 3-2 where the halogen is preferably iodo or bromo is treated with CuCN in DMF at elevated temperature to afford the corresponding 2-cyanoaniline 3-3. Alternatively, the nitrile 3-3 can be prepared by treatment of 3-2 with KCN and CuI in the presence of a palladium (II) salt or in the presence of certain copper or nickel complexes (See: Smith, M. B. and March, J. "March's Advanced Organic Chemistry", $5^{th}$ Ed., John Wiley and Sons, New York, pp. 867 (2001) and references therein). Treatment of arylamine 3-3 with reagents, such as those described in Scheme 1 for the transformation of intermediate 1-1 into 1-2, gives the corresponding aryl halide 3-4. Reduction of aryl nitrile 34 with reagents such as diisobutyl aluminum hydride or the like in solvents such as toluene or $CH_2Cl_2$ or the like followed by sodium borohydride in solvents such as MeOH, EtOH or the like affords the corresponding benzyl alcohol 3-5. Alternatively, nitrile 3-4 can be heated with a base such as sodium hydroxide or potassium hydroxide or the like in an appropriate aqueous alcohol such as EtOH, PrOH or the like to afford the corresponding carboxylic acid (See: Smith, M. B. and March, J. "March's Advanced Organic Chemistry", $5^{th}$ Ed., John Wiley and Sons, New York, pp. 1179-1180 (2001) and references therein). This can be reduced to alcohol 3-5 with reducing agents such as borane in solvents such as THF or the like (See: Smith, M. B. and March, J. "March's Advanced Organic Chemistry", $5^{th}$ Ed., John Wiley and Sons, New York, pp. 1549 (2001) and references therein). Alternatively, the carboxylic acid can be esterified by known methods including treatment with trimethylsilyldiazomethane and the resulting ester reduced to alcohol 3-5 with lithium aluminum hydride or the like. Treatment of 3-5 with carbon tetrabromide and triphenylphosphine in solvents such as dichloromethane, dichloroethane or the like gives the corresponding aryl methyl bromide 3-6 (See: Smith, M. B. and March, J. "March's Advanced Organic Chemistry", 5th Ed., John Wiley and Sons, New York, pp. 518-519 (2001) and references therein).

SCHEME 4

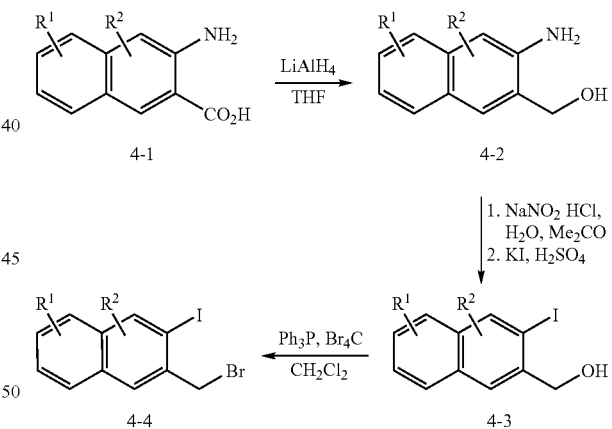

Intermediates of the present invention wherein $R^1$ and $R^2$ are described in the claims can be prepared as shown in Scheme 4. Treatment of an appropriately substituted carboxylic acid 4-1, which can be purchased or prepared by known methods, with reagents such as lithium aluminum hydride or the like in solvents such as THF, $Et_2O$ or the like affords the corresponding alcohol 4-2. Treatment of arylamine 4-2 with reagents such as sodium nitrite and hydrochloric acid in aqueous acetone followed by potassium iodide and sulfuric acid or those described in Scheme 1 for the transformation of intermediate 1-1 into 1-2, gives the corresponding aryl halide 4-3. Treatment of alcohol 4-3 with reagents, such as those described in Scheme 3 for the transformation of intermediate 3-5 into 3-6, gives the corresponding aryl methyl bromide 4-4.

SCHEME 5

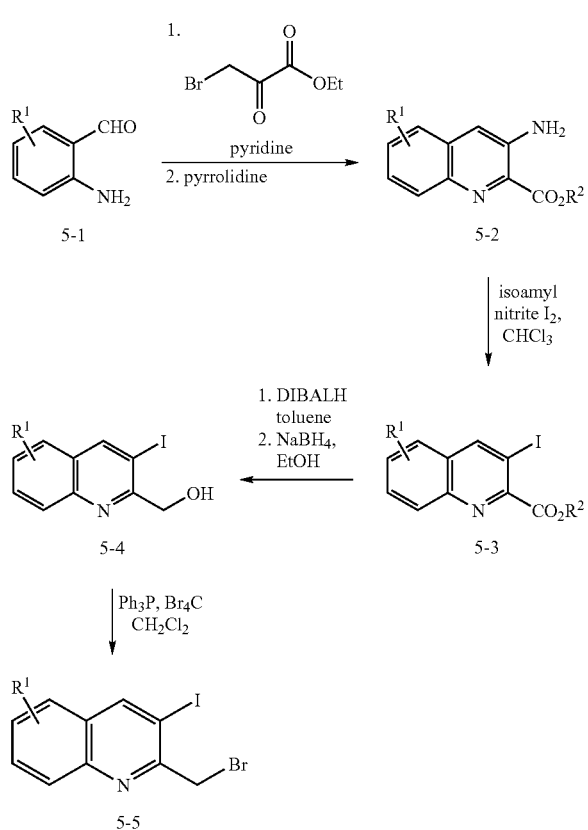

Intermediates of the present invention wherein $R^A$ is described in the claims can be prepared as shown in Scheme 5. Heating an appropriately substituted 2-aminobenzaldehyde 5-1, which can be purchased or prepared by known methods, with reagents such as ethyl bromopyruvate and pyridine in solvents such as EtOH followed by heating with pyrrolidine affords the corresponding 2-amino-3-carboxyquinoline 5-2. Treatment of arylamine 5-2 with reagents, such as those described in Scheme 1 for the transformation of intermediate 1-1 into 1-2, gives the corresponding aryl halide 5-3. Reduction of aryl ester 5-3 with reagents such as diisobutyl aluminum hydride or the like in solvents such as toluene or $CH_2Cl_2$ or the like followed by sodium borohydride in solvents such as MeOH, EtOH or the like affords the corresponding benzyl alcohol 5-4. Treatment of alcohol 5-4 with reagents, such as those described in Scheme 3 for the transformation of intermediate 3-5 into 3-6, gives the corresponding aryl methyl bromide 5-5.

SCHEME 6

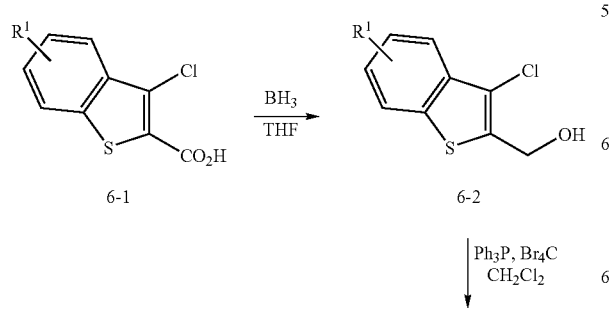

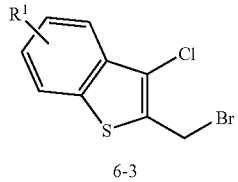

Intermediates of the present invention wherein $R^1$ is described in the claims can be prepared as shown in Scheme 6. Treatment of an appropriately substituted carboxylic acid 6-1, which can be purchased or prepared by known methods, with reagents such as borane in solvents such as THF, or the like affords the corresponding alcohol 6-2. Treatment of alcohol 6-2 with reagents, such as those described in Scheme 3 for the transformation of intermediate 3-5 into 3-6, gives the corresponding aryl methyl bromide 6-3.

SCHEME 7

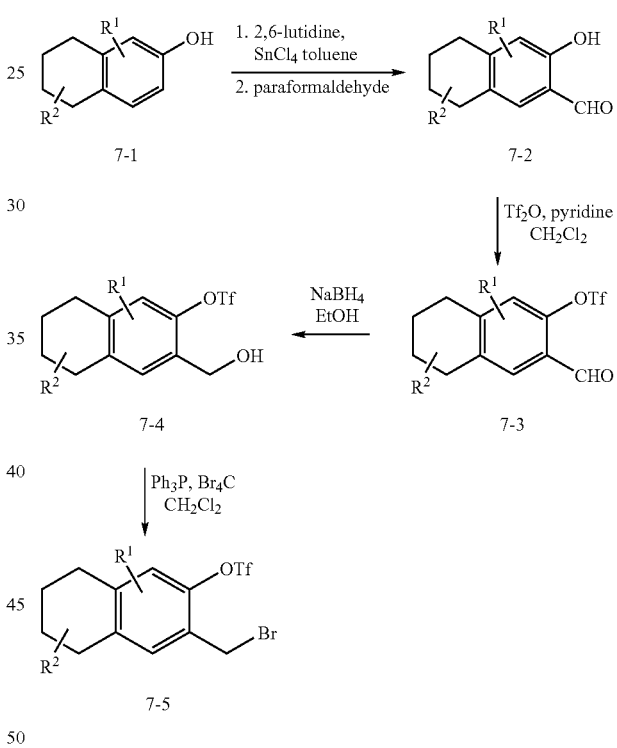

Intermediates of the present invention wherein $R^1$ and $R^2$ are described in the claims can be prepared as shown in Scheme 7. Treatment of an appropriately substituted phenol 7-1, which can be purchased or prepared by known methods, with reagents such as 2,6-lutidine and tin (IV) chloride in solvents such as toluene or the like followed by heating with paraformaldehyde affords the corresponding 2-hydroxybenzaldehyde 7-2. Treatment of phenol 7-2 with trifluoroacetic anhydride and bases such as pyridine or the like in solvents such as $CH_2Cl_2$ or the like affords the corresponding aryl triflate 7-3. Reduction of aldehyde 7-3 with reagents such as sodium borohydride in solvents such as MeOH, EtOH or the like affords the corresponding alcohol 7-4. Treatment of alcohol 7-4 with reagents, such as those described in Scheme 3 for the transformation of intermediate 3-5 into 3-6, gives the corresponding aryl methyl bromide 7-5.

SCHEME 8

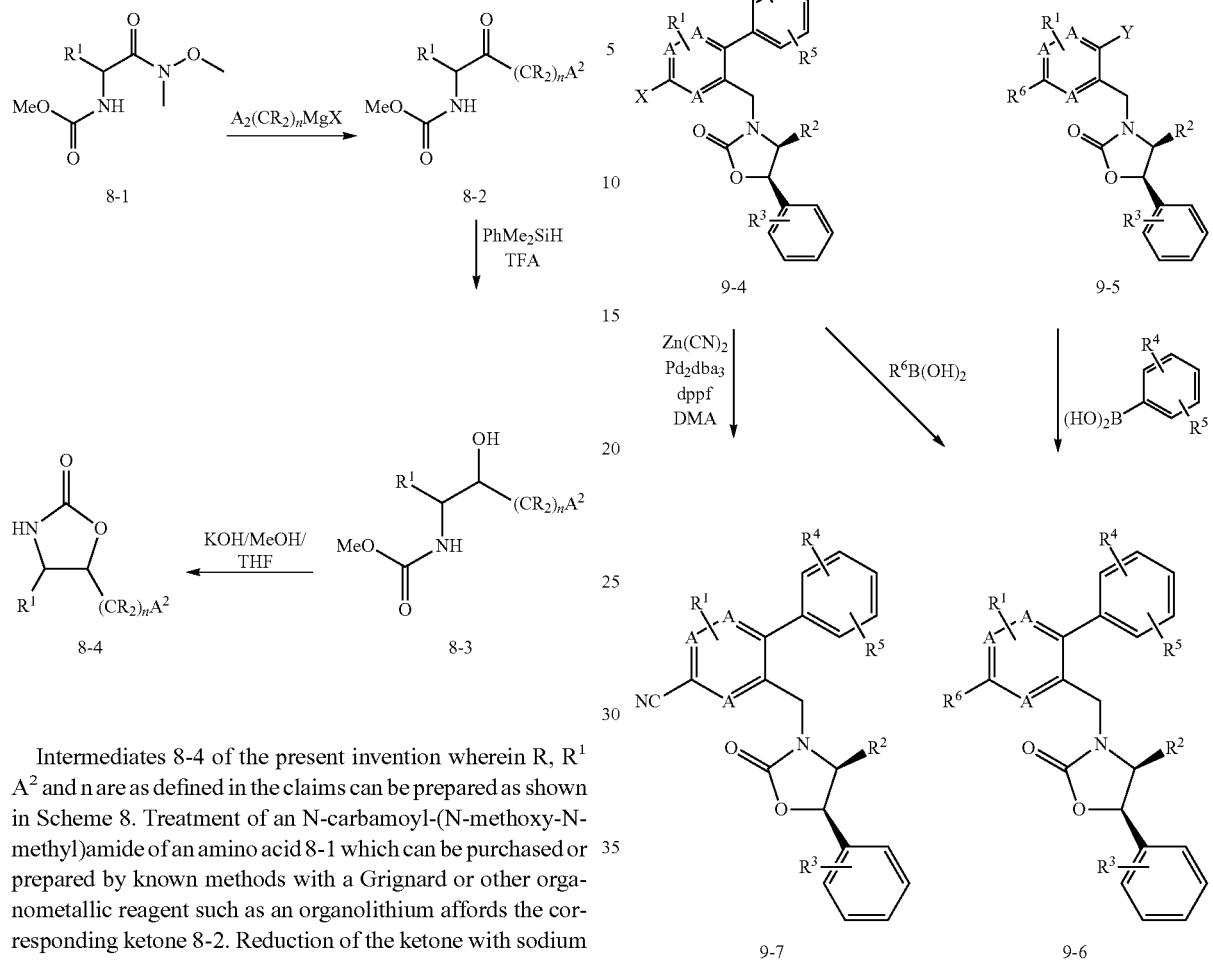

Intermediates 8-4 of the present invention wherein R, $R^1$ $A^2$ and n are as defined in the claims can be prepared as shown in Scheme 8. Treatment of an N-carbamoyl-(N-methoxy-N-methyl)amide of an amino acid 8-1 which can be purchased or prepared by known methods with a Grignard or other organometallic reagent such as an organolithium affords the corresponding ketone 8-2. Reduction of the ketone with sodium borohydride or zinc borohydride in alcoholic solvents or THF or the like or with other reducing agents such as phenyldimethyl silane in trifluoroacetic acid affords alcohol 8-3 which can be cyclized to oxazolidinone 8-4 upon treatment with base such as KOH in solvents such as MeOH, EtOH or the like and THF, dioxane, dimethoxyethane or the like.

SCHEME 9

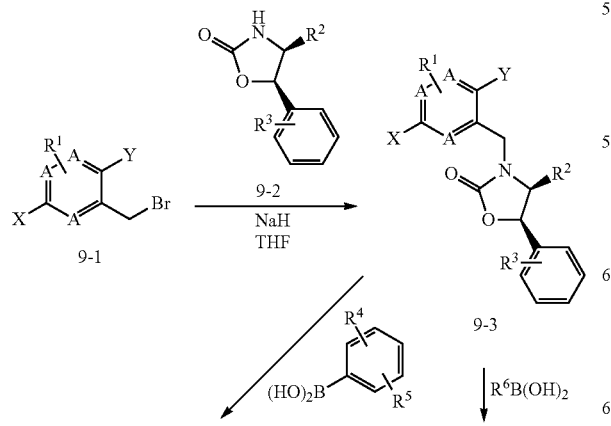

X, Y = Cl, Br, I, OTf
A = C, N

Compounds of the present invention 9-4, 9-6, and 9-7 wherein $R^1$, $R^2$, $R^3$, $R^4$, $R^5$ and $R^6$ are as defined in the claims can be prepared as shown in Scheme 9. Oxazolidinones 9-2, prepared as shown in Scheme 8 can be alkylated with aryl methyl bromides 9-1 which are prepared as shown in Schemes 1 to 7 inclusive using bases such as sodium hexamethyldisilazide or sodium hydride in solvents like tetrahydrofuran, dimethoxyethane, diethyl ether or the like to afford products 9-3. Compounds 9-6 are then prepared via 9-4 or 9-5 by two sequential Suzuki or Stille reactions or variation thereof employing palladium catalyzed cross coupling of aryl halide or aryl triflate 9-3 with an appropriately substituted alkyl-, aryl- or heteroaryl-boronic acid, -boronate ester or -trialkyl tin as described in Miyaua et al., Chem. Rev. 95, 2457 (1995) and references cited within and as described in Smith, M. B. and March, J. "March's Advanced Organic Chemistry", 5th Ed., John Wiley and Sons, New York, pp. 868-869 (2001) and references cited therein. Aryl nitrile 9-7 can be prepared from the corresponding aryl halide 9-4 by a palladium catalyzed cross coupling of zinc cyanide in solvents such as dimethylacetamide or the like or by heating with copper cyanide in solvents such as DMF, dimethylacetamide or the like.

SCHEME 10

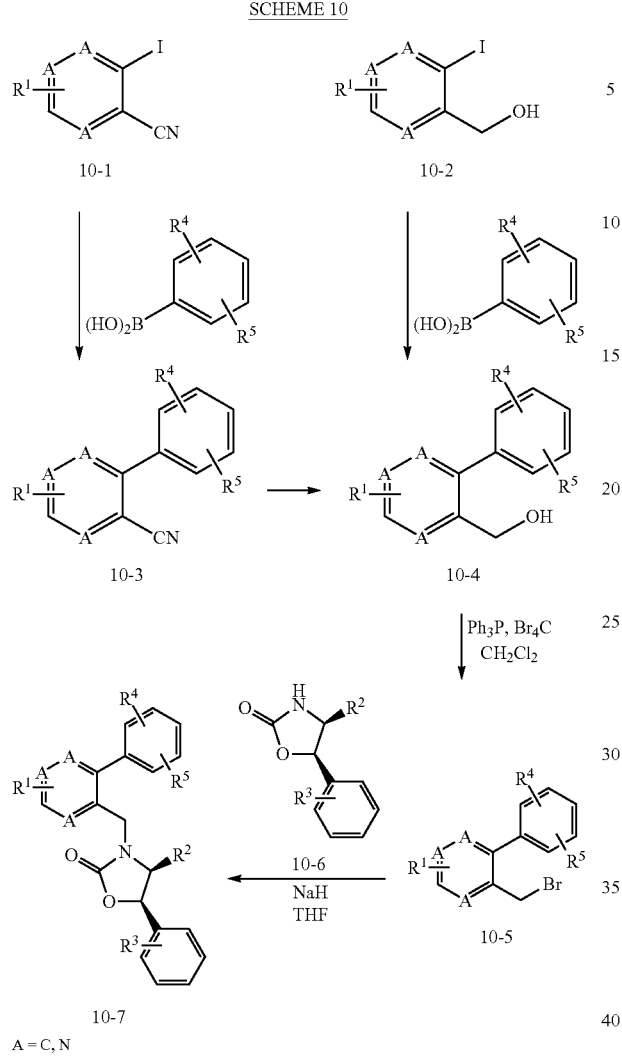

A = C, N

SCHEME 11

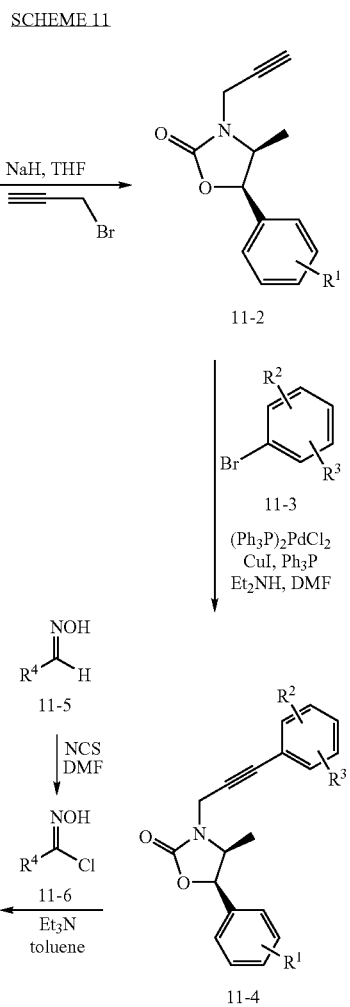

sodium hexamethyldisiliazide or sodium hydride in solvents like tetrahydrofuran, dimethoxyethane, diethyl ether, dimethylformamide, dimethylacetamide, or the like to afford products 10-7.

Alternatively, compounds of the present invention 10-7 wherein $R^1$, $R^2$, $R^3$, $R^4$ and $R^5$ are as defined in the claims can be prepared as shown in Scheme 10. Haloaryl nitriles 10-1 can be purchased or prepared according to the procedures outlined in Scheme 3. Aryl methyl alcohols 10-2 can be purchased or prepared according to the procedures outlined in Scheme 4 to 7 inclusive. Compounds 10-3 and 10-4 are prepared via a Suzuki or Stille reaction or variation thereof employing palladium catalyzed cross coupling of aryl halide 10-1 and 10-2 respectively with an appropriately substituted alkyl-, aryl- or heteroaryl-boronic acid, -boronate ester or -trialkyl tin as described in Miyaua et al., *Chem. Rev.* 95, 2457 (1995) and references cited within and as described in Smith, M. B. and March, J. "March's Advanced Organic Chemistry", $5^{th}$ Ed., John Wiley and Sons, New York, pp. 868-869 (2001) and references cited therein. Treatment of aryl nitrile 10-3 with reagents such as those described in Scheme 3 for the transformation of intermediate 3-4 into 3-5, gives the corresponding aryl methyl alcohol 10-4. Treatment of alcohol 10-4 with reagents such as those described in Scheme 3 for the transformation of intermediate 3-5 into 3-6, gives the corresponding aryl methyl bromide 10-5. Oxazolidinones 10-6, prepared as shown in Scheme 8 can be alkylated with aryl methyl bromides 10-5 using bases such as Compounds of the present invention 11-6 wherein $R^1$, $R^2$, $R^3$ and $R^4$ are as defined in the claims can be prepared as shown in Scheme 11. Oxazolidinones 11-1, prepared as shown in Scheme 8 can be alkylated with propargyl bromide using bases such as sodium hexamethyldisiliazide or sodium hydride in solvents such as tetrahydrofuran, dimethoxyethane, diethyl ether, dimethylformamide, dimethylacetamide, or the like to afford products 11-2. Compound 11-4 is prepared via a Sonogashira reaction or variation thereof employing palladium catalyzed cross coupling of acetylene 11-2 with an appropriately substituted aryl- or heteroaryl-halides 11-3 in the presence of copper iodide and bases such as diethylamine or the like in solvents such as DMF or the like. Compound 11-7 is prepared by cycloaddition to acetylene 11-4 of the corresponding isonitrile generated from alkyl- or arylhydroximidoyl chloride 11-6 in situ by heating with a base such as triethylamine or the like in solvents such as toluene or the like. Alkyl- or arylhydroximidoyl chloride 11-6 can be prepared by treatment with the corresponding hydroxy imine 11-5, which can be purchased or prepared by known methods, with reagents such as N-chlorosuccinimide or the like in solvents such as DMF or the like.

INTERMEDIATE 1

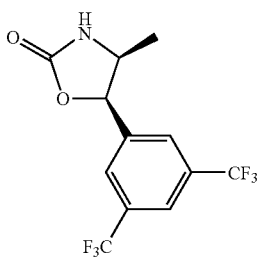

(4S,5R)-5-[3,5-Bis(trifluoromethyl)phenyl]-4-methyl-1,3-oxazolidin-2-one

This intermediate can be made directly from the chiral starting material CBZ-L-alanine by the 3-step route shown below. The compound (4R,5S)-5-[3,5-bis(trifluoromethyl)phenyl]-4-methyl-1,3-oxazolidin-2-one can be made by an analogous route starting from CBZ-D-alanine.

Step A: benzyl {(1S)-2-[methoxy(methyl)amino]-1-methyl-2-oxoethyl}carbamate

CBZ-L-Alanine (6.5 kg, 28.5 mol), HOBT-hydrate (4.8 kg, 34.8 mol), N,O-dimethylhydroxylamine hydrochloride (3.4 kg, 36.2 mol) and THF (32 L) are charged to a clean flask under nitrogen. The mixture is cooled to 0-10° C. and then DIPEA (12.4 L) is slowly added at a temperature less than 20° C. EDC-HCl (7 Kg, 36.2 mol) is then added slowly with slight cooling at 15-25° C. The slurry is aged overnight at 20-25° C. The mixture is then cooled to 0-10° C. and 3 N HCl (13 L) is added slowly. Then IPAC (45.5 L) is added and the layers are separated. The organic layer is washed once with HCl (13 L) and twice with 8% NaHCO$_3$ (13 L). The organic layer is then concentrated under vacuum to <20 L at 50° C. The clear solution is cooled slowly to room temperature, allowing the product to crystallize. Heptane (~70 L) is then added slowly. The slurry is filtered, washed with heptane (18 L), and dried at room temperature on the filter pot. Product is obtained with >99.9% ee measured by chiral HPLC.

Step B: benzyl {(1S)-2-[3,5-bis(trifluoromethyl)phenyl]-1-methyl-2-oxoethyl}carbamate Benzyl {(1S)-2-[methoxy(methyl)amino]-1-methyl-2-oxoethyl}carbamate (6 kg, 22.5 mol) and 3,5-bis(trifluoromethyl)bromobenzene (4.85 L, 28.1 mol) are dissolved in anhydrous THF (24 L). The solution is purged with nitrogen to remove distilled oxygen. The solution is cooled to −10° C. and i-PrMgCl in THF (56.4 mol) is slowly added (2 h) to the reaction via addition funnel, maintaining a reaction temperature ≦−5° C. The solution is allowed to warm to 20° C. and aged overnight at 20° C. The reaction is then cooled to −10° C. under nitrogen and is quenched slowly over 2 h into 5N HCl (14 L) that is maintained at 0-5° C. MTBE (60 L) is added and the biphasic mixture is agitated for 5 min. After warming to 20-25° C., it is allowed to settle for 30 min, and then the layers are separated. The organic layer is washed with water twice (12 L).

The organic layer is vacuum transferred through a 1-micron in-line PTFE filter into a distillation flask and is then concentrated to ~12 L under vacuum (internal temperature<40° C.). Heptane is added and the distillation is continued under vacuum at 40-55° C. until the final volume is 40 L. The solution is cooled to 35-37° C., seeded (~0.5%, 30 g) and then aged for 30 min to allow for a full seed bed to grow. The slurry is cooled to 10° C. over 2-3 h. The slurry is then filtered, washed with 5° C. heptane (18 L), and allowed to dry fully on the filter pot using a vacuum/nitrogen sweep overnight. The dried solid is obtained with >99.9% ee. The amide can be recrystallized from straight heptane if the optical purity is not sufficient.

Step C: (4S,5R)-5-[3,5-bis(trifluoromethyl)phenyl]-4-methyl-1,3-oxazolidin-2-one TFA (9 L) is added to a 100 L Buchi reactor under an inert atmosphere and is cooled to −5° C. Benzyl {(1S)-2-[3,5-bis(trifluoromethyl)phenyl]-1-methyl-2-oxoethyl}carbamate (5.50 kg, 13.1 mol) is added as a solid followed by a TFA rinse (2 L). The solution is cooled to −5° C. and is stirred until all the solid dissolves. Phenyldimethylsilane (2.18 kg, 15.7 mol) is added slowly over ~1 h (in two portions) while keeping the temperature at <0° C. The reaction is aged at −2 to −6° C. for 15-20 h, at which time LC reveals<2% of the ketone remains. A 50 w/w % KOH solution is prepared by adding 13.6 kg of KOH pellets (87 w %) slowly to 10 L water while keeping the highly exothermic dissolution at <30° C. The solution is stored in a refrigerator. The reaction is quenched with ~2 L of the 50 w/w % KOH solution with vigorous stirring and cooling, keeping temp at ~20° C. Cold THF (16.5 L, previously stored in freezer) is added, followed by slow addition of the remainder of the KOH solution (~13.7 L), followed by a 2 L water rinse while keeping temp<20° C. After complete addition of KOH, the reaction is aged at room temperature. The reaction is quenched after 3 h with 27.5 L IPAC and 20 L 20% w/v aq NaCl. The aqueous and organic layers are separated. The organic layer is washed with 26 L of 20% w/v aq NaCl, then with 36 L water, then with 31 L 0.5N HCl, and finally with 32 L of water. The organic layer is concentrated to ~10 L. Heptane (20 L) is added, yielding crystals. The organic layer is concentrated to ~10 L. Heptane (20 L) is added again, and the organic layer is concentrated to ~10 L. Heptane (22 L) is added and the slurry is aged at r.t. The solid is filtered and washed with 24 L heptane. A solid product is obtained (98.8% purity, >99.95% ee, by LC). The solid is then re-dissolved in 12.5 L CH$_3$OH (endothermic). At r.t., 3 L water is added, and the mixture is aged to initiate crystallization. Water (9.5 L) is added over ~60 min at r.t. After aging for 60 min, the slurry is filtered and the solid is washed with 5 L CH$_3$OH/water (1/1.5), 5 L CH$_3$OH/water (1/4) and then 4 L water. The solid product is dried at 50° C. under vacuum (99.9% pure by LC, >99.95% ee). R$_f$=0.38 (50% EtOAc/hexanes). LCMS calc.=314.06; found=314.1 (M+1)$^+$. $^1$H NMR (CDCl$_3$, 600 MHz) δ 7.90 (br s, 1H), 7.79 (br s, 2H), 5.83 (d, J=8.0 Hz, 1H), 5.34 (br s, 1H), 4.31 (br pentet, J=7.0 Hz, 1H), 0.84 (d, J=6.6 Hz, 1H).

HPLC Method for Assays Used in Step C:
Ace-C8 column 250×4.6 mm A: MeCN; B: 0.1% H$_3$PO$_4$ in H$_2$O;
Gradient: 5A:95B at 0 min to 95A:5B at 9 min; hold 95A:5B until 13 min; return to 5A:95B 13-15 min.
Conditions: 35° C., 1.5 mL/min, 210 nm

INTERMEDIATE 2

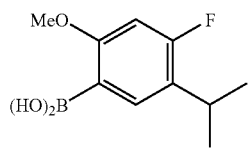

(4-Fluoro-5-isopropyl-2-methoxyphenyl)boronic acid

Step A: 2-(2-fluoro-4-methoxyphenyl)propan-2-ol

To a solution of 2'-fluoro-4'-methoxyacetophenone (4.45 g, 26.5 mmol) in dry THF (50 mL) at 0° C., a solution of 2.4 M methyl magnesium bromide (11.6 mL, 27.8 mmol) was added. The mixture was stirred at 0° C. and then room temperature for 4 h. The reaction was quenched with saturated NH$_4$Cl solution. The organic was extracted with EtOAc (3×50 mL). The combined EtOAc layers were washed with brine and dried over Na$_2$SO$_4$. The resulting alcohol was obtained as an oil after flash chromatography using EtOAc: hexane=2:8 as the eluant.

Step B: 2-fluoro-1-isopropenyl-4-methoxybenzene

To a solution of 2-(2-fluoro-4-methoxyphenyl)propan-2-ol (3.89 g, 21.14 mmol) in CH$_2$Cl$_2$ (50 mL) at 0° C., methylsulfonyl chloride (1.95 mL, 25.4 mmol) and triethylamine (6.52 mL, 46.5 mmol) were added. The solution was stirred at 0° C. and then room temperature for 2 h. The solution was diluted with CH$_2$Cl$_2$ (100 mL), washed with water, and dried over Na$_2$SO$_4$. The title compound was obtained as an oil after flash chromatography using EtOAc:hexane=1:9 as the eluant. $^1$H NMR (CDCl$_3$, 500 MHz) δ 7.25 (t, J=9.0 Hz, 1H), 6.68 (dd, J=8.5, 2.5 Hz, 1H), 6.63 (dd, J=13, 2.5 Hz, 1H), 5.20 (d, J=17.0 Hz, 2H), 3.82 (s, 3H), 2.18 (s, 3H).

Alternate Route to
2-fluoro-1-isopropenyl-4-methoxybenzene

A solution of sodium bis(trimethylsilyl)-amide, 11.0M in tetrahydrofuran (714 mL, 0.714 mol) was added to a suspension of methyltriphenylphosphonum bromide (255 g, 0.714 mol) in THF (2.50 L) cooled with an ice bath. The resultant yellow colored suspension was stirred for 30 min at ice bath temperature and then cooled to −78° C. A solution of 2-fluoro-4-methoxyacetophenone (100 g, 0.595 mol) in THF (200 mL) was added dropwise and stirred at −78° C. for 1.5 h. The reaction mixture was allowed to warm to room temperature for one hour, quenched with acetic acid (~80 mL) where color change was observed from yellow to off white and stirred for 30 min (pH ~7)(slight exotherm noted). The mixture was concentrated to a slush, diluted with 7:2 hexane: EtOAc, and was allowed to sit overnight. Solids were removed by filtration and the filtrate was concentrated to yellow oil. The title compound was obtained after flash chromatography using 9:1 hexane:EtOAc as the eluant.

Step C:
1-fluoro-4-iodo-2-isopropyl-5-methoxybenzene

A solution of 2-fluoro-1-isopropenyl-4-methoxybenzene (1.96 g, 11.81 mmol) in CH$_3$OH (30 mL) was charged with hydrogen at 1 atm with catalytic amount of palladium on carbon. The mixture was stirred at room temperature for 1 h. The mixture was filtered through Celite. The filtrate was then added to a mixture of silver sulfate (3.68 g, 11.81 mmol) and iodine (3.00 g, 11.81 mmol) in CH$_3$OH (10 mL). The mixture was stirred at room temperature for 3 h until the color of solution became light yellow. The mixture was filtered and the filtrate was concentrated. The title compound was obtained after flash chromatography using EtOAc:hexane 5:95 as the eluant. $^1$H NMR (CDCl$_3$, 500 MHz) δ 7.61 (d, J=8.0 Hz, 1H), 6.56 (d, J=12.5 Hz, 1H), 3.90 (s, 3H), 3.18 (m, 1H), 1.28 (m, 6H).

Step D:
(4-fluoro-5-isopropyl-2-methoxyphenyl)boronic acid

To a solution of 1-fluoro-4-iodo-2-isopropyl-5-methoxybenzene (2.61 g, 8.88 mmol) in THF at −78° C., n-butyl lithium (2.5 M, 4.26 mL, 10.65 mmol) was added dropwise. The solution was stirred at −78° C. for 30 min. Trimethyl borate (2.98 mL, 26.6 mmol) was added. The solution was then stirred at −78° C. for 3 h. The reaction was quenched at −78° C. with saturated NH$_4$Cl and the mixture was warmed to room temperature. The organic was extracted with EtOAc (3×50 mL). The combined EtOAc layers were washed with brine and dried over Na$_2$SO$_4$. The title compound was obtained as a solid pure enough for next step. Further purification with silica gel caused decomposition of product. $^1$H NMR (CDCl$_3$, 500 MHz) δ 7.74 (d, J=10.0 Hz, 1H), 6.62 (d, J=12.5 Hz, 1H), 5.65 (br s, 2H), 3.92 (s, 3H), 3.20 (m, 1H), 1.22 (m, 6H).

INTERMEDIATE 3

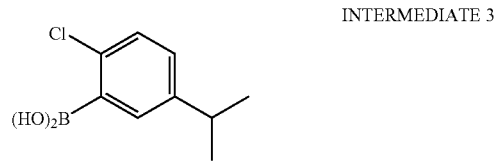

(2-Chloro-5-isopropylphenyl)boronic acid

Step A: 2-bromo-1-chloro-4-isopropylbenzene

To a mixture of copper (II) chloride (0.37 g, 2.8 mmol), isoamyl nitrite (0.41 g, 3.5 mmol) in dry CH$_3$CN (5 ml) at 65° C., a solution of 2-bromo-4-isopropylaniline (0.50 g, 2.33 mmol) in dry CH$_3$CN (2 ml) was added. The mixture was stirred at 65° C. for 1 h. The solvent was removed and the title compound was obtained after flash chromatography using hexane as the eluant. $^1$H NMR (CDCl$_3$, 500 MHz): δ 7.49 (d, J=2.5 Hz, 1H), 7.37 (d, J=8 Hz, 1H), 7.15 (dd, J=8.5, 2.5 Hz, 1H), 2.93 (m, 1H), 1.25 (m, 3H).

Step B: (2-chloro-5-isopropylphenyl)boronic acid

To a solution of 2-bromo-1-chloro-4-isopropylbenzene (0.37 g, 1-59 mmol) in dry THF (5 mL) at −78° C., n-butyl lithium (0.76 mL, 1.90 mmol, 2.5 M) was added. The solution was stirred at −78° C. for 30 min. Trimethyl borate (0.53 mL, 4.76 mmol) was added. The solution was stirred at −78° C. for 2.5 h. The reaction was quenched with saturated aqueous NH$_4$Cl. The aqueous layer was extracted with EtOAc (3×15 mL). The combined EtOAc layers were dried over Na$_2$SO$_4$. The residue was used without further purification after evaporation of the solvent.

INTERMEDIATE 4

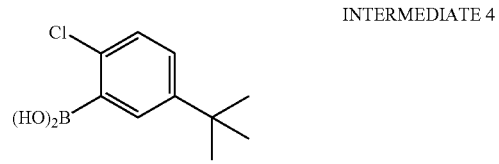

(5-tert-Butyl-2-chlorophenyl)boronic acid

Step A: 4-tert-butyl-2-iodoaniline

A solution of commercially available 4-tert-butylaniline (2.00 g, 13.4 mmol) in MeOH (10 mL) was added to a mixture of silver sulfate (4.17 g, 13.4 mmol) and iodine (3.39 g, 13.4 mmol) in MeOH (30 mL). The mixture was stirred at room temperature for 4 h. The mixture was filtered. The filtrate was concentrated. The title compound was obtained after flash chromatography using EtOAc:hexane/2:8 as the eluant. $^1$H NMR (CDCl$_3$, 500 MHz): B7.65 (d, J=2. Hz, 1H), 7.20 (dd, J=8.5, 2.5 Hz, 1H), 6.75 (d, J=8.5 Hz, 1H), 1.30 (s, 9H).

Step B: 4-tert-butyl-1-chloro-2-iodobenzene

To a mixture of copper (11) chloride (0.34 g, 2.53 mmol), isoamyl nitrite (0.37 g, 3.16 mmol) in dry CH$_3$CN (5 mL) at 65° C., a solution of 4-tert-butyl-2-iodoaniline (0.58 g, 2.10 mmol) in CH$_3$CN (2 mL) was added. The mixture was stirred at 65° C. for 2 h. The solvent was removed and the title compound was obtained after flash chromatography using hexane as the eluant. $^1$H NMR (CDCl$_3$, 500 MHz): δ 7.85 (d, J=2 Hz, 1H), 7.37 (d, J=8.5 Hz, 1H), 7.31 (dd, J=8, 2 Hz, 1H), 1.30 (m, 9H).

Step C: (5-tert-butyl-2-chlorophenyl)boronic acid

To a solution of 4-tert-butyl-1-chloro-2-iodobenzene (0.47 g, 1.60 mmol) in dry THF (5 mL) at −78° C., n-butyl lithium (0.76 mL, 1.92 mmol, 2.5 M) was added. The solution was stirred at −78° C. for 30 min. Trimethyl borate (0.53 mL, 4.79 mmol) was added. The solution was stirred at −78° C. for 3 h. The reaction was quenched with saturated aqueous NH$_4$Cl. The aqueous layer was extracted with EtOAc (3×15 mL). The combined EtOAc layers were dried over Na$_2$SO$_4$. The residue was used without further purification after evaporation of the solvent.

INTERMEDIATE 5

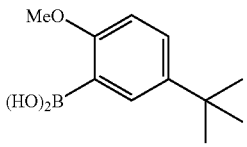

(5-tert-Butyl-2-methoxyphenyl)boronic acid

Step A: 4-tert-butyl-2-iodo-1-methoxybenzene

A solution of 1-tert-butyl-4-methoxybenzene (0.10 g, 0.61 mmol) in MeOH (2 mL) was added to a mixture of silver sulfate (0.19 g, 0.61 mmol) and iodine (0.154 g, 0.61 mmol) in MeOH (1 mL). The mixture was stirred at room temperature for 1 h. The mixture was filtered. The filtrate was concentrated. The title compound was obtained. $^1$H NMR (CDCl$_3$, 500 MHz): δ 7.82 (d, J=2.5 Hz, 1H), 7.36 (dd, J=8.5, 2.5 Hz, 1H), 6.80 (d, J=8.5 Hz, 1H), 1.35 (s, 9H).

Step B: (5-tert-butyl-2-methoxyphenyl)boronic acid

To a solution of 4-tert-butyl-2-iodo-1-methoxybenzene (0.164 g, 0.56 mmol) in dry THF (5 mL) at −78° C., n-butyl lithium (0.27 mL, 0.68 mmol, 2.5 M) was added. The solution was stirred at −78° C. for 30 min. Trimethyl borate (0.19 mL, 1.70 mmol) was added. The solution was stirred at −78° C. for 3 h. The reaction was quenched with saturated aqueous NH$_4$Cl. The aqueous layer was extracted with EtOAc (3×15 mL). The combined EtOAc layers were dried over Na$_2$SO$_4$. The residue was used without further purification after evaporation of the solvent.

INTERMEDIATE 6

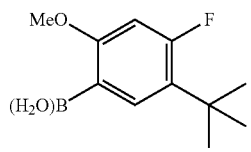

(5-tert-Butyl-4-fluoro-2-methoxyphenyl)boronic acid

Step A: 1-tert-butyl-2-fluoro-4-methoxybenzene 2-chloro-2-methylpropane 1.00 g, 1.18 mL, 10.8 mmol) was added to a stirred mixture of iron (III) chloride (2.63 g, 16.2 mmol) and 3-fluoroanisole (5.45 g, 4.94 mL, 43.2 mmol) at room temperature. The mixture was heated to 90° C. for 5 h. The mixture was partitioned between 1N HCl (100 mL) and Et$_2$O (75 mL). The organic layer was separated and the aqueous layer was extracted with Et$_2$O (75 mL) and CH$_2$Cl$_2$ (2×75 mL). The combined extracts were dried (MgSO$_4$) and concentrated in vacuo to give the crude product. This was purified by flash chromatography (Si, 40×160 mm, 0-20% EtOAc in hexanes gradient) to afford an inseparable mixture of 3-fluoroanisole, 1-tert-butyl-2-fluoro-4-methoxybenzene and some minor diastereoisomers.

Step B: 1-tert-butyl-2-fluoro-5-iodo-4-methoxybenzene

Iodine (1.24 g, 4.90 mmol) and silver sulfate (1.53 g, 4.90 mmol) were added successively to a stirred solution of 1-tert-butyl-2-fluoro-4-methoxybenzene and 3-fluoroanisole (0.755 g, 4.90 mmol) in EtOH (38.3 mL) at room temperature under N$_2$. The mixture was stirred at room temperature for 4 h, then filtered through a plug of Celite. The mixture was partitioned between 50% saturated Na$_2$SO$_3$ and Et$_2$O. The aqueous layer was separated and extracted with Et$_2$O (×2). The combined organic extracts were washed with brine, dried (MgSO$_4$) and concentrated in vacuo to remove volatile byproducts and afford 1-tert-butyl-2-fluoro-5-iodo-4-methoxybenzene. R$_f$=0.34 (100% hexanes). $^1$H NMR (600 MHz, CDCl$_3$): δ 7.63 (d, J=9.0 Hz, 1H); 6.53 (d, J=13.8 Hz, 1H); 3.84 (s, 3H); 1.33 (s, 9H).

Step C: (5-tert-butyl-4-fluoro-2-methoxyphenyl)boronic acid n-Butyl lithium (1.6 M in hexanes, 406 µL, 0.649 mmol) was added to a stirred solution of 1-tert-butyl-2-fluoro-5-iodo-4-methoxybenzene (200 mg, 0.649 mmol) in dry THF (2 mL) at −78° C. under N$_2$. The reaction was stirred at −78° C. for 1 h then triisopropyl borate (214 mg, 262 µL, 1.14 mmol) was added dropwise. The reaction was stirred at −78° C. for 1 h and 0° C. for 1 h. 1N HCl was added and the reaction was extracted with EtOAc (3×). The combined extracts were dried (Na$_2$SO$_4$) and concentrated in vacuo to afford (5-tert-butyl-4-fluoro-2-methoxyphenyl)boronic acid. $^1$H NMR (600 MHz, CDCl$_3$): δ 6.86 (d, J=8.0 Hz, 1H); 6.57 (d, J=13.0 Hz, 1H); 3·85 (s, 3H); 1.33 (s, 9H).

INTERMEDIATE 7

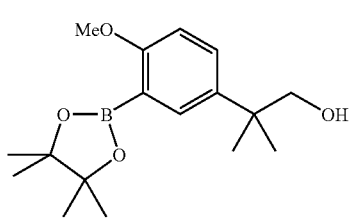

2-[4-Methoxy-3-(4,45,54-tetramethyl-1,3,2-dioxaborolan-2-yl)phenyl]-2-methylpropan-1-ol Step A:
2-(3-iodo-4-methoxyphenyl)-2-methylpropan-1-ol To a solution of 2-(4-methoxyphenyl)-2-methylpropan-1-ol (661.7 mg, 3.68 mmol) (2-(4-methoxyphenyl)-2-methylpropan-1-ol has been described in the literature. See *Helv. Chim. Acta.* 1971, 54, p. 868-897.) in EtOH (40 mL) was added silver sulfate (1.15 g, 3.68 mmol) followed by I2 (934 mg, 3.68 mmol). The reaction was stirred at room temperature for 2 b, and then the solids were filtered off through a pad of Celite. The filtrate was concentrated to 10 mL and then diluted with EtOAc (50 mL). The organic solution was washed with water, aq. NaHSO3, and brine (15 mL each). The organic layer was then diluted with 50 mL of hexanes and filtered through a short plug of silica gel with (50/50 EtOAc/hexanes). The filtrate was concentrated to afford 2-(3-iodo-4-methoxyphenyl)-2-methylpropan-1-ol. $^1$H NMR (CDCl$_3$, 500 MHz) δ 7.76 (d, J=2.3 Hz, 1H), 7.32 (dd, J=8.7, 2.3 Hz, 1H), 6.79 (d, J=8.7 Hz, 1H), 3.87 (s, 3H), 3.57 (s, 2H), 1.30 (s, 6H).

Step B: 2-[4-methoxy-3-(4,4,5,5-tetramethyl-1,3,2-dioxaborolan-2-yl)phenyl]-2-methylpropan-1-ol In a dry flask were placed 2-(3-iodo-4-methoxyphenyl)-2-methylpropan-1-ol (180.0 mg, 0.584 mmol), [1,1'-bis(diphenylphosphino)-ferrocene]dichloropalladium(II).CH$_2$Cl$_2$ (47.7 mg, 0.0584 mmol), KOAc (115 mg, 1.17 mmol), and DMSO (8 mL). Bis(pinacolato)diboron (185.6 mg, 0.73 mmol) was dissolved in THF (340 μL) and added to the reaction. The reaction was degassed with N$_2$ and heated to 40° C. for 1 hour, then 60° C. for 1 h, then at 80° C. for 12 h. The reaction was then cooled to room temperature, diluted with EtOAc (75 mL), and washed with water (3×25 mL) and brine (25 mL). The organic layer was dried over Na$_2$SO$_4$, filtered, and concentrated. Purification of the residue by flash chromatography on silica gel (5 to 100% EtOAc/hexanes) afforded 2-[4-methoxy-3-(4,4,5,5-tetramethyl-1,3,2-dioxaborolan-2-yl)phenyl]-2-methylpropan-1-ol. R$_f$=0.25 (40% EtOAc/hexanes). $^1$H NMR (CDCl$_3$, 600 MHz) δ 7.64 (d, J=2.6 Hz, 1H), 7.40 (dd, J=8.6, 2.7 Hz, 1H), 6.83 (d, J=8.7 Hz, 1H), 3.82 (s, 3H), 3.59 (d, J=6.6 Hz, 2H), 1.35 (s, 12H), 1.32 (s, 6H).

INTERMEDIATE 8

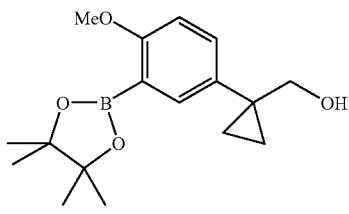

{1-[4-methoxy-3-(4,4,5,5-tetramethyl-1,3,2-dioxaborolan-2-yl)phenyl]cyclopropyl}methanol To a solution of 1-(4-methoxyphenyl)cyclopropanecarboxylic acid (1.0 g, 5.20 mmol) in THF (50 mL) was added borane (7.8 mL of a 1M solution in THF, 7.8 mmol). The reaction was stirred at room temperature for 15 h, and then quenched carefully by dropwise addition of water (10 mL). The solution volume was reduced to ~20 mL and then the mixture was extracted with EtOAc (75 mL). The organic layer was washed with water and brine (25 mL each), dried over Na$_2$SO$_4$, filtered, and concentrated, to afford [1-(3-iodo-4-methoxyphenyl)cyclopropyl]methanol. $^1$H NMR (CDCl$_3$, 500 MHz) δ 7.26-7.31 (m, 2H), 6.84-6.88 (m, 2H), 3.79 (s, 3H), 3.62 (s, 2H), 0.79-0.85 (m, 4H). This material was processed as described in the example above to afford {1-[4-methoxy-3-(4,4,5,5-tetramethyl-1,3,2-dioxaborolan-2-yl)phenyl]cyclopropyl}methanol in two steps.

INTERMEDIATE 9

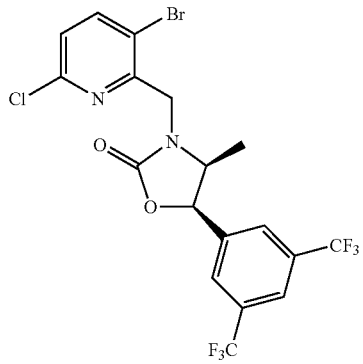

(4S,5R)-5-[3,5-bis(trifluoromethyl)phenyl]-3-[(3-bromo-6-chloropyridin-2-yl)methyl]-4-methyl-1,3-oxazolidin-2-one Step A: 3-bromo-6-chloro-2-methylpyridine Sodium nitrite (4.5 g, 66 mmol) was added slowly to a solution of 6-amino-3-bromo-2-methylpyridine (3.07 g, 16.4 mmol) in concentrated HCl (40 mL) at −20° C. After 1 h, the reaction was allowed to warm to room temperature and stirred overnight. The reaction was carefully neutralized with ice-cold 5N NaOH until pH=11. The aqueous layer was extracted with Et$_2$O (3×75 mL). The combined organic layers were washed with brine (1×75 mL), dried (Na$_2$SO$_4$) and concentrated in vacuo to afford 3-bromo-6-chloro-2-methylpyridine, as a white solid, which was used in the next step without further purification. LCMS calc.=205.9; found=206.0

(M+1)⁺. ¹H NMR (500 MHz, CDCl₃) δ 7.76 (d, J=8.2 Hz, 1H); 7.07 (d, J=8.1 Hz, 1H); 2.66 (s, 3H).

Step B: 3-bromo-2-(bromomethyl)-6-chloropyridine

A solution of 3-bromo-6-chloro-2-methylpyridine (2.0 g, 9.7 mmol), N-bromosuccinimide (1.9 g, 10.6 mmol) and benzoyl peroxide (235 mg, 0.97 mmol) in dry CCl₄ (60 mL) was heated at reflux overnight. The succinimide formed was removed by filtration. The filtrate was washed successively with water (1×40 mL) and brine (1×40 mL), dried (Na₂SO₄) and concentrated in vacuo. The residue was purified by flash chromatography (Si, 1% EtOAc in hexanes) to afford 3-bromo-2-(bromomethyl)-6-chloropyridine containing about 30% starting material (3-bromo-6-chloro-2-methylpyridine). The mixture was carried forward to the next step. LCMS calc.=283.9; found=283.9 (M+1)⁺. ¹H NMR (500 MHz, CDCl₃) δ 7.83 (d, J=8.4 Hz, 1H); 7.18 (d, J=8.3 Hz, 1H); 4.65 (s, 2H).

Step C: (4S,5R)-5-[3,5-bis(trifluoromethyl)phenyl]-3-[(3-bromo-6-chloropyridin-2-yl)methyl]-4-methyl-1,3-oxazolidin-2-one To a solution of (4S,5R)-5-[3,5-bis(trifluoromethyl)phenyl]-4-methyl-1,3-oxazolidin-2-one (4.55 g, 14.5 mmol) in THF (165 mL) was added sodium hydride (60% dispersion in mineral oil) (968 mg, 24.2 mmol) as a powder. The mixture was stirred at room temperature for 20 min. A solution of 3-bromo-2-(bromomethyl)-6-chloropyridine (2.5 g) in THF (30 mL) was added. The resulting mixture was stirred overnight at room temperature. The reaction was quenched with saturated NH₄Cl and extracted with EtOAc (3×). The combined organic layers were washed with brine (1×), dried (Na₂SO₄) and concentrated in vacuo. The residue was purified by flash chromatography (Si, hexanes/EtOAc) to recover the unreacted 3-bromo-6-chloro-2-methylpyridine and to afford the title compound (4S,5R)-5-[3,5-bis(trifluoromethyl)phenyl]-3-[(3-bromo-6-chloropyridin-2-yl)methyl]-4-methyl-1,3-oxazolidin-2-one. LCMS calc.=517.0; found=517.0 (M+1)⁺. ¹H NMR (500 MHz, CDCl₃) δ 7.92 (s, 1H); 7.84 (d, J=8.2 Hz, 1H); 7.83 (s, 2H); 7.21 (d, J=8.2 Hz, 1H); 5.89 (d, J=8.3 Hz, 1H); 5.04 (d, J=17.2 Hz, 1H); 4.47-4.41 (m, 1H); 4.35 (d, J=17.2 Hz, 1H); 0.83 (d, J=6.6 Hz, 3H).

INTERMEDIATE 10

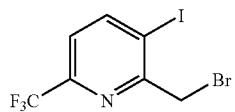

2-(Bromomethyl)-3-iodo-6-(trifluoromethyl)pyridine

Step A: 3-iodo-2-methyl-6-(trifluoromethyl)pyridine

A mixture of 3-amino-2-methyl-6-(trifluoromethyl)pyridine (500 mg, 2.84 mmol), isoamyl nitrite 760 µL, 5.68 mmol) and iodide. (793 mg, 3.12 mmol) in dry CHCl₃ (10 mL) was stirred at room temperature for 0.5 h. The mixture was heated at 80° C. under N₂ for 4 h. The reaction mixture was quenched with saturated Na₂S₂O₃ then partitioned between CH₂Cl₂ and water. The organic layer was dried (Na₂SO₄) and concentrated in vacuo. The residue was purified by flash chromatography (Si, 1% EtOAc in hexanes) to afford 3-iodo-2-methyl-6-(trifluoromethyl)pyridine. LCMS calc.=288.0; found=288.0 (M+1)⁺. ¹H NMR (500 MHz, CDCl₃) δ 8.25 (d, J=8.0 Hz, 1H); 7.22 (d, J=8.1 Hz, 1H); 2.83 (s, 3H).

Step B: 2-(bromomethyl)-3-iodo-6-(trifluoromethyl)pyridine

Following the procedure described for INTERMEDIATE 9, Step B, 2-(bromomethyl)-3-iodo-6-(trifluoromethyl)pyridine was synthesized.

INTERMEDIATE 11

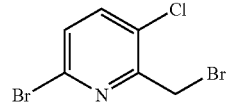

6-Bromo-2-(bromomethyl)-3-chloropyridine

Step A: 6-bromo-3-chloro-2-methylpyridine

Isoamyl nitrite (215 µL, 1.61 mmol) was added to a mixture of copper(II) chloride (173 mg, 1.28 mmol) in dry CH₃CN (3 mL) at room temperature under N₂. A solution of 5-amino-2-bromo-6-picoline (200 mg, 1.07 mmol) in dry CH₃CN (2.4 mL) was added via cannula. The resulting mixture was heated at 65° C. under N₂ for 4 h. The reaction mixture was diluted with EtOAc and washed with water. The aqueous layer was extracted with EtOAc (1×). The combined organic extracts were dried (Na₂SO₄) and concentrated in vacuo. The residue was purified by flash chromatography (Si, 1% of EtOAc in hexanes) to afford 6-bromo-3-chloro-2-methylpyridine. LCMS calc.=206.0; found=206.0 (M+1)⁺. ¹H NMR (500 MHz, CDCl₃) δ 7.48 (d, J=8.2 Hz, 1H); 7.29 (d, J=8.2 Hz, 1H); 2.62 (s, 3H).

Step B: 6-bromo-2-(bromomethyl)-3-chloropyridine

Following the procedure described for INTERMEDIATE 9, Step B, 6-bromo-2-(bromomethyl)-3-chloropyridine was prepared.

INTERMEDIATE 12

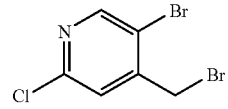

5-Bromo-4-(bromomethyl)-2-chloropyridine

Following the procedure described for INTERMEDIATE 9, Step B, 5-bromo-4-(bromomethyl)-2-chloropyridine was synthesized from 5-bromo-2-chloro-4-picoline.

INTERMEDIATE 13

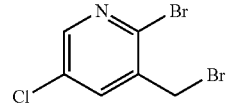

2-Bromo-3-(bromomethyl)-5-chloropyridine

Following the procedure described for INTERMEDIATE 9, Step B, 2-bromo-3-(bromomethyl)-5-chloropyridine was synthesized from 2-bromo-5-chloro-3-picoline.

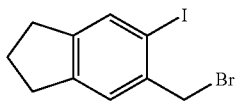

INTERMEDIATE 14

5-(Bromomethyl)-6-iodoindane

Step A: 6-iodoindan-5-amine

A mixture of 5-aminoindan (423 mg, 3.17 mmol), silver sulfate (990 mg, 3.17 mmol) and iodide (805 mg, 3.17 mmol) in $CH_3OH$ (20 mL) was stirred at room temperature overnight. The mixture was filtered and the solid was washed with a small amount of $CH_3OH$. The filtrate was quenched with saturated $Na_2S_2O_3$ and then diluted with water. The aqueous layer was extracted with EtOAc (3×). The combined organic layers were washed with brine (1×), dried ($Na_2SO_4$) and concentrated in vacuo. Flash chromatography (Si, hexanes/EtOAc) of the residue afforded 6-iodoindan-5-amine. LCMS calc.=260.0; found=260.0 (M+1)$^+$. $^1$H NMR (500 MHz, $CDCl_3$) δ 7.51 (s, 1H), 6.69 (s, 1H), 3.97 (br, s, 2H), 3.02-2.90 (m, 1H), 2.81 (d, J=7.1 Hz, 3H), 2.12-2.02 (m, 2H).

Step B: 6-aminoindane-5-carbonitrile

To a solution of 6-iodoindan-5-amine (135 mg, 0.52 mmol) in DMF (2 mL), was added copper (I) cyanide (93 mg, 1.04 mmol). The mixture was heated at 160° C. for 1.5 h. The reaction mixture was poured into 10% $NH_4OH$. An equal amount of $CH_2Cl_2$ was added and resulting mixture was filtered. The filtrate was partitioned between two layers. The aqueous layer was extracted with $CH_2Cl_2$ (1×). The combined organic layers were concentrated in vacuo. The residue was dissolved in $Et_2O$. The $Et_2O$ layer was washed with aqueous $Na_2S_2O_3$, dried ($Na_2SO_4$) and concentrated in vacuo. The residue was purified by flash chromatography (Si, hexanes/EtOAc) yielding 6-aminoindane-5-carbonitrile. LCMS calc.=159.1; found=159.1 (M+1)$^+$. $^1$H NMR (500 MHz, $CDCl_3$) δ 7.22 (s, 1H), 6.64 (s, 1H), 4.25 (br, s, 2H), 2.85 (t, J=7.4 Hz, 2H), 2.80 (t, J=7.4 Hz, 2H), 2.09-2.03 (m, 2H).

Step C: 6-iodoindane-5-carbonitrile

A mixture of 6-aminoindane-5-carbonitrile (48.5 mg, 0.307 mmol), isoamyl nitrite (82 μL, 0.614 mmol) and iodide (85.7 mg, 0.338 mmol) in dry $CHCl_3$ (2 mL) was stirred at room temperature for 0.5 h. The mixture was then heated at 80° C. under $N_2$ for 2 h. The reaction mixture was quenched with saturated $Na_2S_2O_3$ and partitioned between $CH_2Cl_2$ and water. The organic layer was dried ($Na_2SO_4$) and concentrated in vacuo. The residue was purified by flash chromatography (Si, 1% EtOAc in hexanes) to afford 6-iodoindane-5-carbonitrile. LCMS calc.=270.0; found=270.0 (M+1)$^+$. $^1$H NMR (500 MHz, $CDCl_3$) δ 7.78 (s, 1H), 7.48 (s, 1H), 2.96 (t, J=7.5 Hz, 2H), 2.92 (t, J=7.5 Hz, 2H), 2.16-2.10 (m, 2H).

Step D: 6-iodoindane-5-carbaldehyde

To a solution of 6-iodoindane-5-carbonitrile (36.5 mg, 0.136 mmol) in $CH_2Cl_2$ (1.0 mL) under $N_2$ at −78° C. was added a solution of 1N diisobutyl aluminum hydride in toluene (272 μL, 0.272 mmol) dropwise. The reaction was stirred at −78° C. for 15 min. Keeping the temperature at −78° C., another two portions of diisobutyl aluminum hydride (100 μL each) were added until the starting material disappeared by TLC. The reaction mixture was poured into 2N HCl (45 mL) and diluted with $Et_2O$. The mixture was stirred for 0.5 h. The $Et_2O$ layer was separated. The aqueous layer was extracted with $Et_2O$ (2×). The organic extracts were combined, dried ($Na_2SO_4$) and concentrated in vacuo. The residue was purified by flash chromatography (Si, hexanes/EtOAc) to afford 6-iodoindane-5-carbaldehyde. $^1$H NMR (500 MHz, $CDCl_3$) δ 10.08 (s, 1H), 7.83 (s, 1H), 7.79 (s, 1H), 2.98 (t, J=7.5 Hz, 2H), 2.94 (t, J=7.5 Hz, 2H,), 2.19-2.13 (m, 2H).

Step E: (6-iodo-2,3-dihydro-1H-inden-5-yl)methanol

To a solution of 6-iodoindane-5-carbaldehyde (35.5 mg, 0.131 mmol) in anhydrous EtOH (3 mL) under $N_2$ at 0° C., was added sodium borohydride (20 mg, 0.522 mmol) as a powder. The mixture was warmed to room temperature and stirred for 0.5 h. The mixture was quenched with water. The aqueous layer was extracted with EtOAc (3×). The combined organic extracts were dried ($Na_2SO_4$) and concentrated in vacuo. The residue was purified by flash chromatography (Si, hexanes/EtOAc) to afford (6-iodo-2,3-dihydro-1H-inden-5-yl)methanol. $^1$H NMR (500 MHz, $CDCl_3$) δ 7.70 (s, 1H), 7.33 (s, 1H), 4.68 (d, J=6.3 Hz, 2H), 2.92-2.88 (m, 4H), 2.12-2.06 (m, 2H), 1.96 (t, J=6.4 Hz, 1H).

Step F: 5-(bromomethyl)-6-iodoindane

To a solution of (6-iodo-2,3-dihydro-1H-inden-5-yl)methanol (36 mg, 0.131 mmol) and carbon tetrabromide (52 mg, 0.158 mmol) in $CH_2Cl_2$ (1 mL) at 0° C. under $N_2$, was added triphenylphosphine (41 mg, 0.158 mmol). The resulting solution was allowed to warm to room temperature and was stirred for 4 h. Another portion of carbon tetrabromide (52 mg, 0.158 mmol) and triphenylphosphine (41 mg, 0.158 mmol) was added to the mixture at 0° C. The reaction mixture was stirred at room temperature overnight. The reaction mixture was concentrated in vacuo. The residue was purified by flash chromatography (Si, 1% EtOAc in hexanes) to afford 5-(bromomethyl)-6-iodoindane. $^1$H NMR (500 MHz, $CDCl_3$) δ 7.72 (s, 1H), 7.36 (s, 1H), 4.62 (s, 2H), 2.89 (m, 4H), 2.11-2.07 (m, 2H).

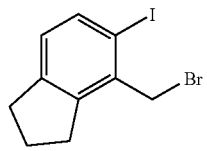

INTERMEDIATE 15

4-(Bromomethyl)-5-iodoindane

Step A: 2-Hydroxyimino-N-indan-5-yl-acetamide

To a solution of chloral hydrate (8.34 g, 50.4 mmol) and anhydrous $Na_2SO_4$ (43 g, 303 mmol) in water (135 mL) was added a mixture of hydroxylamine sulfate (38.4 g, 234 mmol), 5-aminoindan (6 g, 45 mmol), concentrated HCl (4.71 mL) in water (45 mL). The mixture was heated at 45° C. for 1 h and at 75° C. for 2 h. The reaction mixture was cooled to room temperature. The solid formed was filtered and washed with water. The solid was dried under vacuo to afford 2-hydroxyimino-N-indan-5-yl-acetamide. $^1$H NMR (500 MHz, DMSO-$d_6$) δ 12.08 (s, 1H); 10.01 (s, 1H); 7.62 (s, 1H);

7.57 (s, 1H); 7.36 (d, J=8.1 Hz, 1H); 7.14 (d, J=8.1 Hz, 1H); 2.83-2.77 (m, 4H); 2.00-1.96 (m, 2H).

Step B: 1,5,6,7-tetrahydrocyclopenta[f]indole-2,3-dione

2-Hydroxyimino-N-indan-5-yl-acetamide (8.98 g, 44.0 mmol) was added in small portions at 65° C. to concentrated sulfuric acid (42 mL) and the mixture was heated at 80° C. for 15 min. The mixture was cooled to room temperature and poured into ice water (380 mL). The resulting mixture was extracted with EtOAc (3×). The combined organic layers were washed with brine, dried (Na$_2$SO$_4$) and concentrated in vacuo to provide 1,5,6,7-tetrahydrocyclopenta[U]indole-2,3-dione as a red solid which contained about 12% of 1,5,6,7-tetrahydrocyclopenta[e]indole-2,3-dione as a by-product. LCMS calc.=188.1; found=188.2 (M+1)$^+$. $^1$H NMR (500 MHz, DMSO-d$_6$): δ 10.87 (s, 1H); 7.31 (s, 1H); 6.76 (s, 1H); 2.86 (t, J=7.5 Hz, 2H); 2.77 (t, J=7.4 Hz, 2H); 2.02-1.96 (m, 2H).

Step C: methyl 6-aminoindane-5-carboxylate

30% Aqueous hydrogen peroxide solution (5.4 mL) was added to a solution of a mixture of 1,5,6,7-tetrahydrocyclopenta[f]indole-2,3-dione and 1,5,6,7-tetrahydrocyclopenta[e]indole-2,3-dione (3.9 g, 20.8 mmol) in 2 N sodium hydroxide (41 mL) over a period of 5 min. The mixture was then stirred at room temperature for 3 h. 1N HCl was added to adjust the pH to 5. The resulting mixture was extracted with EtOAc (3×). The combined organic layers were washed with brine, dried (Na$_2$SO$_4$) and concentrated in vacuo to afford 6-aminoindane-5-carboxylic acid. The solid was dissolved in EtOAc (4 mL) and ethanol (4 mL). To the solution above was added (trimethylsily)diazomethane (2 M in hexane) (18 mL, 36 mmol) at room temperature and The mixture was stirred for 16 h. The solvent was removed in vacuo. Flash chromatography of the residue (Si, hexanes/EtOAc) afforded methyl 6-aminoindane-5-carboxylate which contained about 10% methyl 5-aminoindane-4-carboxylate. LCMS calc.=192.1; found=192.2 (M+1)$^+$. $^1$H NMR (500 MHz, CDCl$_3$) δ 7.71 (s, 1H); 6.60 (s, 1H); 3.87 (s, 3H); 2.85-2.79 (m, 4H); 2.08-2.02 (m, 2H).

Step D: methyl 6-[(isopropoxycarbonyl)amino]indane-5-carboxylate and methyl 5-[(isooropoxycarbonyl)amino]indane-4-carboxylate To a solution of a mixture of methyl 6-aminoindane-5-carboxylate and methyl 5-aminoindane-4-carboxylate (760 mg, 3.98 mmol), and pyridine (805 uL, 9.95 mmol) in CH$_2$Cl$_2$ (8 mL) at 0° C. under N$_2$ was added isopropyl chloroformate (1 M in toluene) (3.98 mL, 3.98 mmol). The resulting mixture was stirred at room temperature for 16 h. 1M HCl was added to the reaction mixture and the organic layer was separated. The aqueous layer was extracted with CH$_2$Cl$_2$ (2×). The combined organic layers were dried (Na$_2$SO$_4$) and concentrated in vacuo. The residue was purified by flash chromatography (Si, hexanes/EtOAc) to afford methyl 6-[(isopropoxycarbonyl)amino]indane-5-carboxylate. LCMS calc.=300.1; found=299.9 (M+Na)$^+$. $^1$H NMR (500 MHz, CDCl$_3$) δ 10.43 (s, 1H); 8.34 (s, 1H); 7.86 (s, 1H); 5.06-5.00 (m, 1H); 3.92 (s, 3H); 2.96 (t, J=7.5 Hz, 2H); 2.88 (t, J=7.4 Hz, 2H); 2.13-2.07 (m, 2H); 1.33 (d, J=6.2 Hz, 6H). Methyl 5-[(isopoxycarbonyl)amino]indane-4-carboxylate was isolated as a by-product. LCMS calc.=300.1; found=299.9 (M+Na)$^+$. $^1$H NMR (500 MHz, CDCl$_3$) a 10.07 (s, 1H); 8.21 (d, J=8.4 Hz, 1H); 7.36 (d, J=8.4 Hz, 1H); 5.06-5.00 (m, 1H); 3.93 (s, 3H); 3.19 (t, J=7.5 Hz, 2H); 2.89 (t, J=7.5 Hz, 2H); 2.08-2.02 (m, 2H); 1.32 (d, J=6.2 Hz, 6H).

Step E: Methyl 5-aminoindane-4-carboxylate

Aluminium trichloride (146 mg, 1.09 mmol) was added to dry toluene (2 mL) at 0° C. Methyl 5-[(isopropoxycarbonyl)amino]indane-4-carboxylate (76 mg, 0.274 mmol) was added portionwise as a powder to the mixture above. The thick suspension was stirred at room temperature for 15 min and heated at 80° C. for 6 h. The mixture was poured into ice water and extracted with EtOAc (3×). The combined organic layers were dried (Na$_2$SO$_4$) and concentrated in vacuo to afford methyl 5-aminoindane-4-carboxylate. LCMS calc.=192.1; found=192.2 (M+1)$^+$. $^1$H NMR (500 MHz, CDCl$_3$) δ 7.14 (d, J=8.1 Hz, 1H); 6.55 (d, J=8.1 Hz, 1H); 3.88 (s, 3H); 3.17 (t, J=7.5 Hz, 2H); 2.82 (t, J=7.5 Hz, 2H); 2.05-1.98 (m, 2H).

Starting from methyl 5-aminoindane-4-carboxylate, the title compound 4-(bromomethyl)-5-iodoindane was prepared according to the procedure described in step C, D and F for INTERMEDIATE 14.

INTERMEDIATE 16

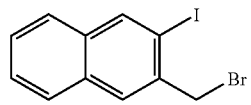

2-(Bromomethyl)-3-iodonaphthalene

Step A: (3-amino-2-naphthyl)methanol

A solution of 3-amino-2-naphthoic acid (85%, 1.17 g, 5.34 mmol) in dry THF (20 mL) was added dropwise over 30 min to a stirred solution of lithium aluminum hydride (95%, 0.53 g, 13.4 mmol) in dry THF (20 mL) at 0° C. under N$_2$. The mixture was stirred at room temperature overnight. Water (20 mL) was added and the mixture was adjusted to basic pH with 1N NaOH (20 mL). The mixture was filtered and extracted with Et$_2$O (4×100 mL). The combined extracts were dried (MgSO$_4$) and concentrated in vacuo to afford (3-amino-2-naphthyl)methanol. LCMS calc.=174.1; found=174.2 (M+1)$^+$. $^1$H NMR (500 MHz, CD$_3$OD): δ 7.66 (d, J=8.0 Hz, 1H); 7.61 (s, 1H); 7.55 (d, J=8.2 Hz, 1H); 7.30-7.27 (m, 1H); 7.18-7.14 (m, 1H); 7.08 (s, 1H); 4.74 (s, 2H).

Step B: (3-iodo-2-naphthyl)methanol

A solution of (3-amino-2-naphthyl)methanol (500 mg, 2.89 mmol) in water (3 mL), acetone (3 mL) and concentrated HCl (1.6 mL) was cooled to 0° C. and a solution of sodium nitrite (219 mg, 3.18 mmol) in water (0.7 mL) was added. The reaction was stirred for 2 h at 0° C. and a solution of potassium iodide (719 mg, 4.33 mmol) and concentrated H$_2$SO$_4$ (0.16 mL) in water (1.2 mL) was added. The reaction mixture was heated at 60° C. for 2-3 h. The reaction mixture was cooled to room temperature and 50% saturated Na$_2$SO$_3$ (30 mL) was added. The mixture was extracted with CH$_2$Cl$_2$ (3×20 mL) and the combined extracts were washed with brine (20 mL), dried (Na$_2$SO$_4$) and concentrated in vacuo to give the crude product. This was purified by flash chromatography (Si, 25×160 mm, 0-40% EtOAc in hexanes gradient) to afford (3-iodo-2-naphthyl)methanol. R$_f$=0.47 (20% EtOAc/hexanes). $^1$H NMR (600 MHz, CD$_3$OD): δ 8.35 (s, 1H); 7.91 (s, 1H); 7.81 (d, J=8.0 Hz, 1H); 7.71 (d, J=8.0 Hz, 1H); 7.47-7.42 (m, 2H); 4.69 (s, 2H).

Step C: 2-(bromomethyl)-3-iodonaphthalene

A solution of triphenylphosphine (469 mg, 1.79 mmol) in dry CH$_2$Cl$_2$ (2 mL) was added dropwise to a stirred solution of carbon tetrabromide (592 mg, 1.79 mmol) and (3-iodo-2-naphthyl)methanol (423 mg, 1.49 mmol) in dry CH$_2$Cl$_2$ (11 mL) at room temperature under N$_2$. The reaction was stirred for 4 h at room temperature and was concentrated in vacuo to give the crude product. This was purified by flash chromatography (Si, 25×160 mm, 0-50% EtOAc in hexanes gradient) to afford 2-(bromomethyl)-3-iodonaphthalene, as a colorless solid. R$_f$=0.84 (20% EtOAc/hexanes). $^1$H NMR (600 MHz, CDCl$_3$): δ 8.39 (s, 1H); 7.94 (s, 1H); 7.78-7.76 (m, 1H); 7.71-7.69 (m, 1H); 7.52-7.48 (m, 2H); 4.76 (s, 2H).

INTERMEDIATE 17

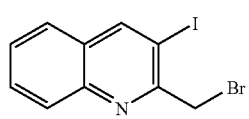

2-(Bromomethyl)-3-iodoquinoline

Step A: ethyl 3-aminoquinoline-2-carboxylate

A solution of ethyl bromopyruvate (1.69 g, 1.09 mL, 8.68 mmol) in dry EtOH (16 mL) was added dropwise over 20 min to a stirred solution of pyridine (684 mg, 699 µL, 8.68 mmol) in dry EtOH (24 mL). The resulting solution was heated at 60-70° C. for 1 h and cooled to room temperature. 2-Aminobenzaldehyde (1.00 g, 8.26 mmol) and pyridine (1.6 mL) were added and the resulting yellow solution was heated at reflux for 4½ h. Pyrrolidine (1.40 g, 1.64 mL, 19.7 mmol) was added and the resulting mixture was heated at reflux for 3 h and concentrated in vacuo to give the crude product. This was purified by flash chromatography (Si, 65×160 mm, 0-40% EtOAc in hexanes gradient) to afford ethyl 3-aminoquinoline-2-carboxylate, as a yellow solid. R$_f$=0.31 (20% EtOAc/hexanes). LCMS calc.=217.1; found=217.1 (M+1). $^1$H NMR (500 MHz, CDCl$_3$): δ 8.04-8.02 (m, 1H); 7.53-7.51 (m, 1H); 7.44-7.38 (m, 2H); 7.32 (s, 1H); 4.53 (q, J=7.1 Hz, 2H); 1.48 (t, J=7.1 Hz, 3H).

Step B: ethyl 3-iodoquinoline-2-carboxylate

Isoamyl nitrite (542 mg, 618 mL, 4.62 mmol) was added to a stirred solution of iodine (646 mg, 2.54 mmol) and ethyl 3-aminoquinoline-2-carboxylate (500 mg, 2.31 mmol) in dry CHCl$_3$ (10 mL) at room temperature under N$_2$. The mixture was heated at reflux overnight. The reaction was cooled to room temperature and quenched with saturated Na$_2$SO$_3$ (15 mL) and water (5 mL). The organic layer was separated and the aqueous layer was extracted with CH$_2$C$_2$ (2×20 mL). The combined organic layers were dried (Na$_2$SO$_4$) and concentrated in vacuo to give the crude product. This was purified by flash chromatography (Si, 25×160 mm, 0-20% EtOAc in hexanes gradient) to afford a 3:1 inseparable mixture of ethyl 3-iodoquinoline-2-carboxylate and 3-methylbutyl 3-iodoquinoline-2-carboxylate. Ethyl ester: LCMS calc.=217.1; found=327.7 (M+1)$^+$. $^1$H NMR (500 MHz, CDCl$_3$): δ 8.66 (s, 1H); 8.07 (d, J=8.5 Hz, 1H); 7.74-7.70 (m, 1H); 7.66 (d, J=7.6 Hz, 1H); 7.59-7.51 (m, 1H); 4.52 (q, J=7.2 Hz, 2H); 1.45 (t, J=7.2 Hz, 3H).

Step C: (3-iodoquinolin-2-yl)methanol

A solution of diisobutyl aluminum hydride in toluene (1M, 652 µL, 0.652 mmol) was added to a stirred solution of a 3:1 mixture of ethyl 3-iodoquinoline-2-carboxylate and 3-methylbutyl 3-iodoquinoline-2-carboxylate (100 mg, 0.297 mmol) in dry THF (3 mL) at 0° C. under N$_2$. The reaction was stirred for 4 h at 0° C. The reaction was quenched with saturated NH$_4$Cl (5 mL) and water (5 mL) and extracted with EtOAc (3×20 mL). The combined extracts were dried (Na$_2$SO$_4$) and concentrated in vacuo to give the crude product. Sodium borohydride was added to a stirred solution of the crude product in EtOH (3 mL) and the reaction was stirred at room temperature for 20 min. The reaction was diluted with water (10 mL) and extracted with EtOAc (3×20 mL). The combined extracts were washed with brine, dried (Na$_2$SO$_4$) and concentrated in vacuo to give the crude product. This was purified by flash chromatography (Si, 12×160 mm, 0-50% EtOAc in hexanes gradient) to afford (3-iodoquinolin-2-yl)methanol, as a colorless solid. R$_f$=0.88 (50% EtOAc/hexanes). LCMS calc.=286.0; found=286.0 (M+1)$^+$. $^1$H NMR (500 MHz, CDCl$_3$): δ 8.56 (s, 1H); 8.03 (d, J=8.4 Hz, 1H); 7.74-7.71 (m, 1H); 7.70 (d, J=8.1 Hz, 1H); 7.54 (t, J=7.1 Hz, 1H); 4.90 (br s, 1H); 4.78 (s, 2H).

Step D: 2-(bromomethyl)-3-iodoquinoline

Triphenylphosphine (31.1 mg, 0.119 mmol) was added to a stirred solution of (3-iodoquinolin-2-yl)methanol (28.2 mg, 0.0989 mmol) and carbon tetrabromide (39.4 mg, 0.119 mmol) in dry CH$_2$Cl$_2$ (1 mL) at 0° C. under N$_2$. The reaction was allowed to warm to room temperature overnight. The reaction was diluted with water (5 mL) and saturated NaHCO$_3$ (5 mL) and the mixture was extracted with CH$_2$Cl$_2$ (3×20 mL). The combined extracts were dried and concentrated in vacuo to give the crude product. This was purified by flash chromatography (Si, 12×160 mm, 0-20% EtOAc in hexanes gradient) to afford a 1:1 inseparable mixture of 2-(bromomethyl)-3-iodoquinoline and 3-iodo-2-methylquinoline. Desired product: R$_f$=0.77 (20% EtOAc/hexanes). LCMS calc.=349.6; found=349.9 (M+1)$^+$. $^1$H NMR (500 MHz, CDCl$_3$): δ 8.59 (s, 1H); 8.01 (d, J=8.5 Hz, 1H); 7.72-7.68 (m, 1H); 7.65 (d, J=7.8 Hz, 1H); 7.54-7.50 (m, 1H); 4.88 (s, 2H).

INTERMEDIATE 18

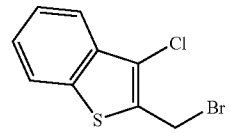

2-(Bromomethyl)-3-chloro-1-benzothiophene

Step A: (3-chloro-1-benzothien-2-yl)methanol

Borane (1M in THF, 6.11 mL, 6.11 mmol) was added to a stirred suspension of 3-chloro-1-benzothiophene-2-carboxylic acid (1.00 g, 4.70 mmol) in dry THF (2 mL) at 0° C. under N$_2$. The reaction was allowed to warm to room temperature and was heated at reflux for 1½ h. The reaction was quenched with water (5 mL) and saturated K₂CO₃ (10 mL), then extracted with EtOAc (3×30 mL). The combined extracts were dried (MgSO₄) and concentrated in vacuo to afford (3-chloro-1-benzothien-2-yl)methanol. ¹H NMR (500 MHz, CDCl₃): δ 7.79-7.77 (m, 2H); 7.45-7.42 (m, 1H); 7.39-7.36 (m, 1H); 4.96 (s, 2H); 2.48 (s, 1H).

Step B: 2-(bromomethyl)-3-chloro-1-benzothiophene

A solution of triphenylphosphine (1.74 g, 6.62 mmol) in dry CH₂Cl₂ (6 mL) was added dropwise to a stirred solution of carbon tetrabromide (2.20 g, 6.62 mmol) and (3-chloro-1-benzothien-2-yl)methanol (0.94 g, 4.73 mmol) in dry CH₂Cl₂ (35 mL) at 0° C. under N₂. The reaction was allowed to warm to room temperature and was stirred for 4 h then concentrated in vacuo to give the crude product. This was purified by flash chromatography (Si, 40×160 nm, 0-25% EtOAc in hexanes gradient) to afford 2-(bromomethyl)-3-chloro-1-benzothiophene. R_f=0.93 (20% EtOAc/hexanes). ¹H NMR (600 MHz, CDCl₃): δ 7.81 (dd, J=1.3, 7-1 Hz, 1H); 7.78 (dd, J=1.2, 7.2 Hz, 1H); 7.47-7.41 (m, 2H); 4.81 (s, 2H).

INTERMEDIATE 19

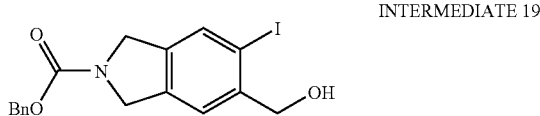

Benzyl 5-(hydroxymethyl)-6-iodo-1,3-dihydro-2H-isoindole-2-carboxylate

Step A: 5-Nitroisoindoline

To a stirred solution of isoindoline (2 g, 16.8 mmol) at 0° C., was added slowly concentrated H₂SO₄ (10 mL). Then a mixture of 70% HNO₃ (2.1 mL, 33.6 mmol) and concentrated H₂SO₄ (2 mL) was added. After addition the mixture was stirred at 0° C. for 30 min. The reaction mixture was poured into ice water. The mixture was carefully neutralized with 50% aq. NaOH to pH 10 and extracted with EtOAc (3×). The combined organic layers were washed with brine, dried (Na₂SO₄), filtered and concentrated in vacuo to afford 5-nitroisoindoline as a brown solid. LCMS calc.=165.1; found=164.9 (M+H)⁺. ¹H NMR (500 MHz, CDCl₃): δ 8.11 (d, J=8.0 Hz, 2H); 7.39 (d, J=7.8 Hz, 1H); 4.33 (s, 4H); 2.31 (br s, 1H).

Step B: Benzyl 5-nitro-1,3-dihydro-2H-isoindole-2-carboxylate

To a solution of 5-nitroisoindoline (1.16 g, 7.79 mmol) in CH₂Cl₂ (100 mL), was added diisopropylethylamine (2.7 mL, 15.6 mmol) followed by benzylchloroformate (1.2 mL, 8.56 mmol). The mixture was stirred at room temperature under N₂ for 1 h. The reaction mixture was diluted with CH₂Cl₂ and washed with 1N HCl. The organic layer was dried (Na₂SO₄), filtered and the solvent was evaporated in vacuo. The residue was purified by flash chromatography on silica gel to provide benzyl 5-nitro-1,3-dihydro-2H-isoindole-2-carboxylate. LCMS calc.=321.1; found=320.8 (M+Na)⁺. ¹H NMR (500 MHz, CDCl₃): δ 8.22-8.14 (m, 2H); 7.49-7.37 (m, 6H); 5.27 (s, 2H); 4.89 (s, 2H); 4.87 (s, 2H).

Step C: Benzyl 5-amino-1,3-dihydro-2H-isoindole-2-carboxylate

To a solution of benzyl 5-nitro-1,3-dihydro-2H-isoindole-2-carboxylate (1.34 g, 4.49 mmol) in DMF (30 mL) was added SnCl₂.2H₂O (5.1 g, 22.5 mmol) as a powder. The mixture was stirred overnight. The reaction mixture was adjusted to basic pH with sat. aq. NaHCO₃. The white precipitate formed was extracted with EtOAc (3×150 mL). The combined organic layers were washed with brine, dried (Na₂SO₄), filtered and concentrated in vacuo. The residue was purified by flash chromatography on silica gel to provide benzyl 5-amino-1,3-dihydro-2H-isoindole-2-carboxylate. LCMS calc.=269.1; found=268.9 (M+H)⁺. ¹H NMR (500 MHz, CDCl₃): δ 7.46-7.34 (m, 5H); 7.12-6.93 (2 d, J=8.1, 1H); 6.66-6.53 (m, 2H); 5.25 (s, 2H); 4.69 (t, J=9.8 Hz, 4H); 3.71 (br s, 2H).

Step D: Benzyl 5-amino-6-iodo-1,3-dihydro-2H-isoindole-2-carboxylate

To a solution of benzyl 5-amino-1,3-dihydro-2H-isoindole-2-carboxylate (560 mg, 2.09 mmol) in a mixture of CH₂Cl₂ (10 mL) and MeOH (2.5 mL), was added NaHCO₃ (263 mg, 3.13 mmol) followed by 1M ICl in CH₂Cl₂ (2.1 mL, 2.1 mmol). The mixture was stirred for 30 min and then quenched with sat. aq. NaHSO₃. The resulting mixture was extracted with EtOAc (3×). The combined organic layers were washed with brine, dried (Na₂SO₄), filtered and concentrated in vacuo. The residue was purified by flash chromatography on silica gel to provide benzyl 5-amino-6-iodo-1,3-dihydro-2H-isoindole-2-carboxylate. LCMS calc.=395.0; found=394.7 (M+H)⁺. ¹H NMR (500 MHz, CDCl₃): δ 7.58-7.51 (2 s, 1H); 7.45-7.35 (m, 5H); 6.70-6.64 (2 s, 1H); 5.24 (s, 2H); 4.67 (s, 2H); 4.65 (s, 2H); 4.15 (br, s, 2H).

Step E: 2-Benzyl 5-methyl 6-amino-1,3-dihydro-2H-isoindole-2,5-dicarboxylate

Palladium(II) acetate (46.1 mg, 0.0685 mmol), DPPF (38 mg, 0.0685 mmol), K₂CO₃ (284 mg, 2.06 mmol) and Et₃N (95 uL, 0.685 mmol) were added to a solution of benzyl 5-amino-6-iodo-1,3-dihydro-2H-isoindole-2-carboxylate (270 mg, 0.685 mmol) in MeCN (5 mL) and MeOH (2.5 mL). The reaction mixture was purged with N₂, the flask was capped and a CO balloon was attached to it. After bubbling CO gas into the solution through a needle attached to the balloon for 5 min, the mixture was heated under a CO balloon at 70° C. for 4 h. The mixture was diluted with EtOAc (50 mL), filtered through Celite, then washed with water (3×10 mL), brine (1×), dried (Na₂SO₄), filtered and the solvent was evaporated in vacuo. The residue was purified by flash chromatography on silica gel to provide 2-benzyl 5-methyl 6-amino-1,3-dihydro-2H-isoindole-2,5-dicarboxylate LCMS calc.=327.1; found=326.8 (M+H)⁺. ¹H NMR (500 MHz, CDCl₃): δ 7.80-7.75 (2 s, 1H); 7.45-7.35 (m, 5H); 6.61-6.55 (2 s, 1H); 5.79 (br s, 2H); 5.25 (s, 2H); 4.68 (t, J=13.5 Hz, 4H); 3.91-3.90 (2 s, 3H).

Step F: 2-Benzyl 5-methyl 6-iodo-1,3-dihydro-2H-isoindole-2,5-dicarboxylate

To a solution of 2-benzyl 5-methyl 6-amino-1,3-dihydro-2H-isoindole-2,5-dicarboxylate (149 mg, 0.456 mmol) in CHCl₃ (5 mL) was added t-butyl nitrite (108 uL, 0.912 mmol). The mixture was stirred for 20 min. I₂ (34.7 mg, 1.37 mmol) was added and the resulting mixture was stirred at room temperature for 15 min. The mixture was then heated at 80° C. overnight. The reaction was quenched with sat. aq. NaHSO₃ and extracted with CH₂Cl₂ (3×). The combined organic layers were washed with brine, dried (Na₂SO₄), filtered and concentrated in vacuo. The residue was purified by flash chromatography on silica gel to provide 2-benzyl 5-methyl 6-iodo-1,3-dihydro-2H-isoindole-2,5-dicarboxylate. LCMS calc.=438.0; found=437.8 (M+H)+. $^1$H NMR (500 MHz, CDCl$_3$): δ 7.94-7.88 (2 s, 1H); 7.77-7.71 (2 s, 1H); 7.44-7.32 (m, 5H); 5.25 (s, 2-H); 4.76 (t, J=11.6 Hz, 4H); 3.98-3.94 (2 s, 3H).

Step G: Benzyl 5-(hydroxymethyl)-6-iodo-1,3-dihydro-2H-isoindole-2-carboxylate

To a solution of 2-benzyl 5-methyl 6-iodo-1,3-dihydro-2H-isoindole-2,5-dicarboxylate (104 mg, 0.238 mmol) in THF (5 mL) at −78° C. under N$_2$, was added dropwise 1N Super Hydride in THF (476 uL, 0.476 mmol). The mixture was stirred at −78° C. for 2 h. The reaction mixture was quenched with 1N HCl. The aqueous layer was extracted with EtOAc (3×). The combined organic layers were washed with brine, dried (Na$_2$SO$_4$), filtered and concentrated in vacuo. The residue was purified by flash chromatography on silica gel to provide benzyl 5-(hydroxymethyl)-6-iodo-1,3-dihydro-2H-isoindole-2-carboxylate. LCMS calc.=432.0; found=431.9 (M+Na)+. $^1$H NMR (500 MHz, CDCl$_3$): δ 7.76-7.70 (2 s, 1H); 7.45-7.35 (m, 6H); 5.24 (s, 2H); 4.76-4.67 (m, 4H); 2.18 (br s, 1H).

INTERMEDIATE 20, 21

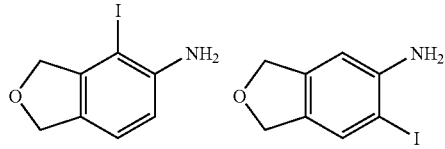

4-Iodo-1,3-dihydro-2-benzofuran-5-amine and 6-iodo-1,3-dihydro-2-benzofuran-5-amine Starting from 1,3-dihydro-2-benzofuran-5-amine, the procedure described in step D for INTERMEDIATE 19 was followed to afford 2 regio-isomers 4-iodo-1,3-dihydro-2-benzofuran-5-amine LCMS calc.=262.0; found=261.8 (M+H)+ and 6-iodo-1,3-dihydro-2-benzofuran-5-amine LCMS calc.=262.0; found=261.8 (M+H)+.

INTERMEDIATE 22

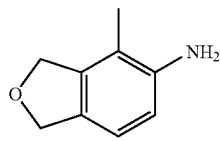

4-Methyl-1,3-dihydro-2-benzofuran-5-amine

To a solution of 4-iodo-1,3-dihydro-2-benzofuran-5-amine (563 g, 2.16 mmol) in 1,4-dioxane (15 mL) under N$_2$ was added CsF (1.15 g, 7.56 mmol), MeB(OH)$_2$ (387 g, 6.47 mmol) and PdCl$_2$(DPPF) (176 mg, 0.216 mmol). The mixture was heated at 80° C. for 4 h. The mixture was cooled to room temperature and then diluted with EtOAc (40 mL) and water (40 mL). The mixture was filtered through Celite. The organic layer was separated and the aqueous layer was extracted with EtOAc (2×15 mL). The combined organic layers were washed with brine, dried (Na$_2$SO$_4$), filtered and concentrated in vacuo. The residue was purified by flash chromatography on silica gel to afford 4-methyl-1,3-dihydro-2-benzofuran-5-amine. LCMS calc.=150.1; found=149.9 (M+H)+. $^1$H NMR (500 MHz, CDCl$_3$): δ 6.92 (d, J=7.8 Hz, 1H); 6.66 (d, J=7.9 Hz, 1H); 5.11 (s, 4H); 3.63 (br s, 2H); 2.08 (s, 3H)

INTERMEDIATE 23

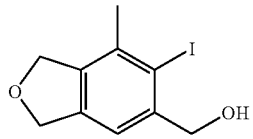

(6-Iodo-7-methyl-1,3-dihydro-2-benzofuran-5-yl)methanol

Starting from 4-methyl-1,3-dihydro-2-benzofuran-5-amine, the procedures described in step D, E and F for INTERMEDIATE 19 and the procedure described in step C for INTERMEDIATE 17 were followed to give (6-iodo-7-methyl-1,3-dihydro-2-benzofuran-5-yl)methanol. LCMS calc.=313.0; found=312.6 (M+Na)+.

INTERMEDIATE 24

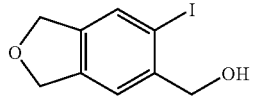

(6-Iodo-1,3-dihydro-2-benzofuran-5-yl)methanol

Starting from 6-iodo-1,3-dihydro-2-benzofuran-5-amine (INTERMEDIATE 21), the procedures described in step E and F for INTERMEDIATE 19 and the procedure described in step C for INTERMEDIATE 17 were followed to afford methyl (6-iodo-1,3-dihydro-2-benzofuran-5-yl)methanol. LCMS calc.=277.0; found=276.8 (M+H)+.

INTERMEDIATE 25

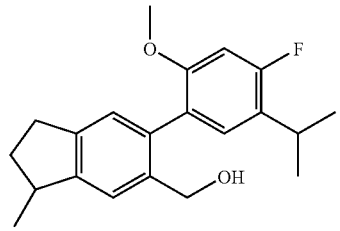

[6-(4-Fluoro-5-isopropyl-2-methoxyphenyl)-3-methyl-2,3-dihydro-1H-inden-5-yl]methanol Step A: Methyl 6-[(isopropoxycarbonyl)amino]-3-oxoindane-5-carboxylate Methyl 6-[(isopropoxycarbonyl)amino]indane-5-carboxylate (730 mg, 2.63 mmol) obtained following the procedure described in step A to D for INTERMEDIATE 15 was dissolved in AcOH (20 mL). A mixture of CrO$_3$ (659 mg, 6.59 mmol) in AcOH (2.5 mL) and water (1.1 mL) was added dropwise to the solution above. The reaction was stirred at room temperature overnight. The reaction mixture pH was carefully adjusted to pH 9 using 2N NaOH. The mixture was extracted with EtOAc (3×). The combined organic layers were washed with brine, dried (Na$_2$SO$_4$), filtered and concentrated in vacuo to give methyl 6-[(isopropoxycarbonyl)amino]-3-oxoindane-5-carboxylate. LCMS calc.=292.1;

found=291.9 (M+H)⁺. ¹H NMR (500 MHz, CDCl₃): δ 10.80 (s, 1H); 8.62 (s, 1H); 8.49 (s, 1H); 5.08-5.04 (m, 1H); 3.96 (s, 3H); 3.18 (t, J=6.1 Hz, 2H); 2.73 (t, J=6.1 Hz, 2H); 1.35 (d, J=6.2 Hz, 6H).

Step B: Methyl 6-amino-3-oxoindane-5-carboxylate

The procedure described in step E for INTERMEDIATE 15 was followed to give methyl 6-amino-3-oxoindane-5-carboxylate from methyl 6-[(isopropoxycarbonyl)amino]-3-oxoindane-5-carboxylate. LCMS calc.=206.1; found=206.1 (M+H)⁺.

Step C: Methyl 6-iodo-3-oxoindane-5-carboxylate

The procedure described in step F for INTERMEDIATE 19 was followed to give methyl 6-iodo-3-oxoindane-5-carboxylate from methyl 6-amino-3-oxoindane-5-carboxylate. LCMS calc.=317.0; found=316.8 (M+H)⁺.

Step D: Methyl 6-(4-fluoro-5-isopropyl-2-methoxyphenyl)-3-oxoindane-5-carboxylate The procedure described in step F for EXAMPLE 1 was followed to give methyl 6-(4-fluoro-5-isopropyl-2-methoxyphenyl)-3-oxoindane-5-carboxylate from methyl 6-iodo-3-oxoindane-5-carboxylate and (4-fluoro-5-isopropyl-2-methoxyphenyl)boronic acid. LCMS calc.=357.1; found=356.9 (N+H)⁺.

Step E: Methyl 6-(4-fluoro-5-isopropyl-2-methoxyphenyl)-3 hydroxy-3-methylindane-5-carboxylate To a solution of methyl 6-(4-fluoro-5-isopropyl-2-methoxyphenyl)-3-oxoindane-5-carboxylate (45.9 mg, 0.129 mmol) in heptane (1 mL) and THF (1 mL) at −20° C. under N₂, was added dropwise 3N MeMgCl in THF (86 uL, 0.258 mmol). The reaction mixture was stirred at −20° C. for 2 h. The mixture was quenched with sat. aq. NH₄Cl and extracted with EtOAc (3×). The combined organic layers were washed with brine, dried (Na₂SO₄) and concentrated in vacuo. The residue was purified by flash chromatography on silica gel to give methyl 6-(4-fluoro-5-isopropyl-2-methoxyphenyl)-3-hydroxy-3-methylindane-5-carboxylate. LCMS calc.=395.2; found=394.9 (M+Na)⁺. ¹H NMR (500 MHz, CDCl₃): δ 7.89 (s, 1H); 7.20 (s, 1H); 7.09 (d, J=8.6 Hz, 1H); 6.62 (d, J=12.1 Hz, 1H); 3.72 (s, 3H); 3.70 (s, 3H); 3.28-3.20 (m, 1H); 3.15-3.09 (m, 1H); 2.96-2.90 (m, 1H); 2.36-2.24 (m, 2H); 1.91 (br s, 1H); 1.66 (s, 3H); 1.30 (d, J=6.9 Hz, 6H).

Step F: Methyl 6-(4-fluoro-5-isopropyl-2-methoxyphenyl)-3-methyl-1H-indene-5-carboxylate To a solution of methyl 6-(4-fluoro-5-isopropyl-2-methoxyphenyl)-3-hydroxy-3-methylindane-5-carboxylate (22.6 mg, 0.061 mmol) in toluene (1 mL) at room temperature was added TsOH (5.8 mg, 0.030 mmol). The reaction mixture was heated at 80° C. for 1.5 h. The reaction mixture was diluted with EtOAc. The organic layer was washed consecutively with sat. aq. NaHCO₃ (1×) and brine (1×), dried (Na₂SO₄), filtered and concentrated in vacuo to give methyl 6-(4-fluoro-5-isopropyl-2-methoxyphenyl)-3-methyl-1H-indene-5-carboxylate. LCMS calc.=377.2; found=376.9 (M+Na)⁺. ¹H NMR (500 MHz, CDCl₃): δ 7.85 (s, 1H); 7.41 (s, 1H); 7.14 (d, J=8.7 Hz, 1H); 6.63 (d, J=12.1 Hz, 1H); 6.30 (t, J=1.5 Hz, 1H); 3.72 (s, 3H); 3.72 (s, 3H); 3.42 (d, J=1.5 Hz, 2H); 3.29-3.21 (m, 1H); 2.25 (s, 3H); 1.31 (d, J=6.9 Hz, 6H).

Step G: Methyl 6-(4-fluoro-5-isopropyl-2-methoxyphenyl)-3-methylindane-5-carboxylate To a solution of methyl 6-(4-fluoro-5-isopropyl-2-methoxyphenyl)-3-methyl-1H-indene-5-carboxylate (21.5 mg, 0.061 mmol) in EtOH (2 mL), was added a catalytic amount of 10% Pd/C. The flask was stirred at room temperature under H₂ overnight. The mixture was filtered through Celite. The solvent was evaporated in vacuo to give methyl 6-(4-fluoro-5-isopropyl-2-methoxyphenyl)-3-methylindane-5-carboxylate. LCMS calc.=379.2; found=378.9 (M+Na)⁺. ¹H NMR (500 MHz, CDCl₃): δ 7.72 (s, 1H); 7.18 (s, 1H); 7.11 (d, J=8.6 Hz, 1H); 6.62 (d, J=12.0 Hz, 1H); 3.73 (s, 3H); 3.69 (s, 3H); 3.29-3.23 (m, 2H); 3.02-2.90 (m, 2H); 2.45-2.34 (m, 1H); 1.73-1.66 (m, 1H); 1.38 (d, J=6.2 Hz, 3H); 1.30 (d, J=6.6 Hz, 6H).

Step H: [6-(4-Fluoro-5-isopropyl-2-methoxyphenyl)-3-methyl-2,3-dihydro-1H-inden-5-yl]methanol The procedure described in step C for INTERMEDIATE 17 was followed to give [6-(4-fluoro-5-isopropyl-2-methoxyphenyl)-3-methyl-2,3-dihydro-1H-inden-5-yl]methanol from methyl 6-(4-fluoro-5-isopropyl-2-methoxyphenyl)-3-methylindane-5-carboxylate. LCMS calc.=351.2; found=350.9 (M+Na)⁺.

INTERMEDIATE 26

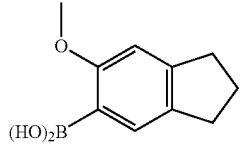

(6-Methoxy-2,3-dihydro-2,3-dihydro-1H-inden-5-yl)boronic acid

Step A: 5-Iodo-6-methoxyindane

A mixture of silver sulfate (2.10 g; 6.75 mmol) and iodine (1.71 g; 6.75 mmol) in methanol (20 mL) was treated dropwise over 10 min with a solution of 5-methoxyindane (1 g; 6.75 mmol) in methanol (5 mL). The resultant suspension was stirred at room temperature for 3 h. The reaction was filtered and concentrated in vacuo, slurried with EtOAc (20 mL), and filtered again. The filtrate was concentrated and the residue was purified by flash silica gel chromatography (0-15% EtOAc/hexanes gradient) to afford 5-iodo-6-methoxyindane as a white solid. ¹H NMR (500 MHz, CDCl₃): δ 7.63 (s, 1H), 6.78 (s, 1H), 3.87 (s, 3H), 2.91-2.85 (m, 4H), 2.15-2.06 (m, 2H).

Step B: (6-Methoxy-2,3-dihydro-2,3-dihydro-1H-inden-5-yl)boronic acid

A solution of 5-iodo-6-methoxyindane (1.0 g; 3.62 mmol) in THF (8 mL) was cooled to −78° C. and treated in a dropwise manner with n-BuLi (1.6 M in hexanes; 2.24 mL; 3.58 mmol). The resultant mixture was stirred at −78° C. for 1 h and tri-isopropyl borate (1.47 mL; 6.40 mmol) was added. The reaction was allowed to warm slowly to 0° C. and stirred for an additional 30 min. The reaction was quenched by the addition of 1N HCl (10 mL) and the layers were separated. The aqueous layer was extracted with EtOAc (3×50 mL) and the combined organic extracts were washed with brine (100 mL) The solution was dried (MgSO₄), concentrated and the crude product was purified by silica gel chromatography eluting with hexanes and ethyl acetate, 4:1 to afford (6-methoxy-2,3-dihydro-2,3-dihydro-1H-inden-5-yl)boronic acid
¹H NMR (500 MHz, CDCl₃): δ 7.68 (s, 1H), 6.82 (s, 1H), 6.03 (br s, 2H), 3.89 (s, 3H), 2.94 (t, J=7.4 Hz, 2H), 2.88 (t, J=7.4 Hz, 2H), 2.14-2.06 (m, 2H).

The intermediates in Table 1 were prepared by methods analogous to those described for INTERMEDIATE 26.

TABLE 1

| Intermediate | Structure | LCMS (M + Na)+ |
|---|---|---|
| 27 | (HO)₂B-naphthyl-OMe | 203.2 |
| 28 | (HO)₂B-5,6,7,8-tetrahydronaphthyl-OMe | 229.1 |
| 29 | (HO)₂B-5,6,7,8-tetrahydronaphthyl-OMe (isomer) | 229.1 |

Example 1

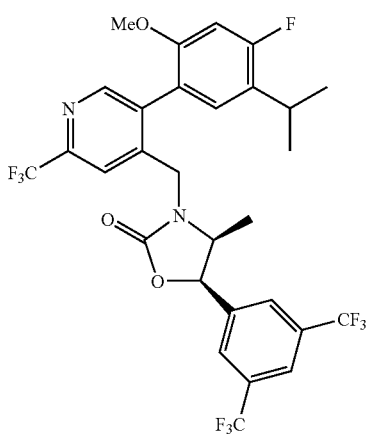

(4S,5R)-5-[3,5-Bis(trifluoromethyl)phenyl]-3-{[5-(4-fluoro-5-isopropyl-2-methoxyphenyl)-2-(trifluoromethyl)pyridin-4-yl]methyl}-4-methyl-1,3-oxazolidin-2-one Step A: 4-methyl-5-nitro-2-(trifluoromethyl)pyridine A mixture of 2-bromo-5-nitro-4-pyridine (100 mg, 0.461 mmol), copper (I) iodide (73.1 mg, 0.384 mmol) and methyl 2,2-difluoro-2-(fluorosulfonyl)acetate (177 mg, 117 μL, 0.922 mmol) in dry DMF (1 mL) was heated under N₂ at 120° C. overnight. The reaction mixture was cooled to room temperature and diluted with saturated NH₄Cl (3.6 mL) and NH₄OH (0.4 mL). The mixture was stirred until homogenous (a little water was added). The mixture was extracted with EtOAc (3×20 mL). The combined extracts were washed with brine (10 mL), dried (Na₂SO₄) and concentrated in vacuo to give the crude product. This was purified by flash chromatography (Si, 12×160 mm, 0-20% EtOAc in hexanes gradient) to afford 4-methyl-5-nitro-2-(trifluoromethyl)pyridine. LCMS calc.=207.1; found=207.1 (M+1)⁺. ¹H NMR (500 MHz, CDCl₃): δ 9.17 (s, 1H); 7.70 (s, 1H); 2.72 (s, 3H).

Step B: 4-methyl-6-(trifluoromethyl)pyridin-3-amine

A suspension of platinum oxide (36.9 mg) in a solution of 4-methyl-5-nitro-2-(trifluoromethyl)pyridine (369.4 mg, 0.162 mmol) in EtOH (12.7 mL) was stirred under a balloon of H₂ for 5½ h. The reaction mixture was filtered through a plug of Celite and the filtrate was concentrated in vacuo to afford 4-methyl-6-(trifluoromethyl)pyridin-3-amine. LCMS calc.=177.1; found=177.1 (M+1)⁺. ¹H NMR (600 MHz, CDCl₃): δ 8.04 (s, 1H); 7.27 (s, 1H); 4.28 (s, 2H); 2.15 (s, 3H).

Step C: 5-iodo-4-methyl-2-(trifluoromethyl)pyridine

Isoamyl nitrite (96%, 59 μL, 49.9 mg, 0.426 mmol) was added to a solution of 4-methyl-6-(trifluoromethyl)pyridin-3-amine (50.0 mg, 0.284 mmol) and iodine (79.2 mg, 0.312 mmol) in CHCl₃ (1 mL) at room temperature under N₂. The solution was stirred for 5 min then heated at reflux for 2 h. The reaction mixture was diluted with CHCl₃, washed with saturated Na₂SO₃, dried (MgSO₄) and concentrated in vacuo to give the crude product. This was purified by flash chromatography (Si, 12×160 mm, 1-5% EtOAc in hexanes gradient) to afford 5-iodo-4-methyl-2-(trifluoromethyl)pyridine. $R_f$=0.77 (10% EtOAc/hexanes). LCMS calc.=288.0; found=288.0 (M+1)⁺. ¹H NMR (600 MHz, CDCl₃): δ 8.96 (s, 1H); 7.54 (s, 1H); 2.50 (s, 3H).

Step D: 4-(bromomethyl)-5-iodo-2-(trifluoromethyl)pyridine

A mixture of 5-iodo-4-methyl-2-(trifluoromethyl)pyridine (39.1 mg, 0.136 mmol), N-bromosuccinimide (29.1 mg, 0.163 mmol), and benzoyl peroxide (3.3 mg, 0.0136 mmol) in CCl₄ (1 mL) was heated at reflux under N₂ overnight. Water was added and the mixture was extracted with CH₂Cl₂ (3×20 mL). The combined extracts were dried (MgSO₄) and concentrated in vacuo to give the crude product. This was purified by flash chromatography (Si, 12×160 mm, 1-5% EtOAc in hexanes gradient) to afford 4-(bromomethyl)-5-iodo-2-(trifluoromethyl)pyridine. $R_f$=0.41 (10% EtOAc/hexanes). ¹H NMR (600 MHz, CDCl₃): δ 9.03 (s, 1H); 7.76 (s, 1H); 4.51 (s, 3H).

Step E: (4S,5R)-5-[3,5-bis(trifluoromethyl)phenyl]-3-{[5-iodo-2-(trifluoromethyl))pyridin-4-yl]methyl}-4-methyl-1,3-oxazolidin-2-one Sodium hydride (8.2 mg, 60% dispersion in mineral oil, 0.205 mmol) was added to a solution of (4S,5R)-5-[3,5-bis(trifluoromethyl)phenyl]-4-methyl-1,3-oxazolidin-2-one (42.8 mg, 0.137 mmol) in dry THF (1 mL) at room temperature under N₂. After stirring for 15 min at room temperature a solution of 4-(bromomethyl)-5-iodo-2-(trifluoromethyl)pyridine (25.0 mg, 0.0683 mmol) in dry THF (2 mL) was added via cannula. The reaction mixture was stirred overnight at room temperature. Saturated NH₄Cl (10 mL) was added and the mixture was extracted with EtOAc (3×20 mL). The combined extracts were dried (Na₂SO₄) and concentrated in vacuo to give the crude product. This was purified by flash chromatography (Si, 12×160 mm, 0-60% EtOAc in hexanes gradient) to afford (4S,5R)-5-[3,5-bis(trifluoromethyl)phenyl]-3-{[S-iodo-2-(trifluoromethyl)pyridin-4-yl]methyl}-4-methyl-1,3-oxazolidin-2-one, as a colorless oil. $R_f$=0.17 (20% EtOAc/hexanes). LCMS calc.=599.0; found=599.0 (M+1)⁺. ¹H NMR (500 MHz, CDCl₃): δ 9.04 (s, 1H); 7.92 (s, 1H); 7.80 (s, 2H); 7.62 (s, 1H); 5.82 (d, J=7.0 Hz, 1H); 4.79 (d, J=16.7 Hz, 1H); 4.35 (d, J=16.7 Hz, 1H); 4.18-4.12 (m, 1H); 0.82 (d, J=6.5 Hz, 3H).

Step F: (4S,5R)-5-[3,5-bis(trifluoromethyl)phenyl]-3-{[5-(4-fluoro-5-isopropyl-2-methoxyphenyl)-2-(trifluoromethyl)pyridin-4-yl]methyl}-4-methyl-1,3-oxazolidin-2-one A mixture of (4S,5R)-5-[3,5-bis(trifluoromethyl)phenyl]-3-{[5-iodo-2-(trifluoromethyl)pyridin-4-yl]methyl}-4-methyl-1,3-oxazolidin-2-one (9.7 mg, 0.0162 mmol), (4-fluoro-5-isopropyl-2-methoxyphenyl)boronic acid (5.2 mg, 0.0243 mmol), and 1,1'-bis(di-t-butylphosphinoferrocene)palladium dichloride (1.0 mg, 0.00162 mmol) in 1N aqueous potassium carbonate (0.7 mL) and THF (0.7 mL) was heated at 85° C. in a sealed tube for 2 h. The reaction mixture was cooled to room temperature and water (10 mL) was added. The mixture was extracted with EtOAc (3×20 mL) and the combined organic extracts were dried (Na$_2$SO$_4$) and concentrated in vacuo to give the crude product. This was purified by flash chromatography (Si, 12×160 mm, 0-40% EtOAc in hexanes gradient) to afford (4S,5R)-5-[3,5-bis(trifluoromethyl)phenyl]-3-{[5-(4-fluoro-5-isopropyl-2-methoxyphenyl)-2-(trifluoromethyl)pyridin-4-yl]methyl}-4-methyl-1,3-oxazolidin-2-one. R$_f$=0.40 (20% EtOAc/hexanes). LCMS calc. 639.2; found 639.2 (M+1)$^+$. $^1$H NMR (500 MHz, CDCl$_3$, 1:1 mixture of atropisomers): δ 8.55 (s, 1H); 7.87 (s, 1H); 7.74-7.68 (m, 3H); 7.02 (dd, J=4.5, 8.1 Hz, 1H); 6.72 (d, J=11.7 Hz, 1H); 5.64 (d, J=8.0 Hz, 0.5H); 5.48 (d, J=7.9 Hz, 0.5H); 4.84 (d, J=16.4 Hz, 0.5H); 4.77 (d, J=16.5 Hz, 0.5H); 4.21 (d, J=16.5 Hz, 0.5H); 3.96 (d, J=16.3 Hz, 0.5H); 3.92-3.85 (m, 0.5H); 3.8-3.73 (m, 3.5H); 3.25-3.17 (m, 1H); 1.30-1.18 (m, 6H); 0.56 (d, J=6.4 Hz, 1.5H); 0.42 (d, J=6.5 Hz, 1.5H).

The compounds in Table 2 were synthesized by methods analogous to those described in EXAMPLE 1, Steps E and F, from phenyl oxazolidinones, aryl methyl halides and boronic acids whose syntheses are described above.

TABLE 2

| Example | R | LCMS (M + 1)+ |
|---|---|---|
| 2 | MeO, F, isopropyl-naphthyl | 620.4 |
| 3 | MeO, t-butyl-phenyl-naphthyl | 616.0 |
| 4 | MeO, C(CH$_3$)$_2$OH-phenyl-naphthyl | 631.9 |
| 5 | MeO, cyclopropyl-CH$_2$OH-phenyl-naphthyl | 629.9 |
| 6 | MeO, F, t-butyl-phenyl-naphthyl | 633.9 |
| 7 | MeO, F, isopropyl-phenyl-quinolinyl | 621.0 |
| 8 | MeO, t-butyl-phenyl-quinolinyl | 617.0 |

TABLE 2-continued

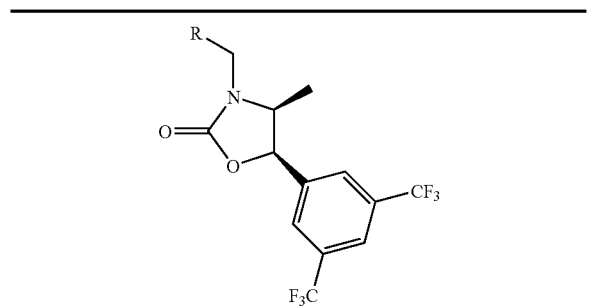

| Example | R | LCMS (M + 1)+ |
|---|---|---|
| 9 | 2,3-dihydro-1H-indene with MeO, F, iPr aryl substituent | 610.3 |
| 10 | 2,3-dihydro-1H-indene with MeO, tBu aryl substituent | 606.2 |
| 11 | 2,3-dihydro-1H-indene with MeO, F, tBu aryl substituent | 623.9 |
| 12 | 2,3-dihydro-1H-indene with Cl, tBu aryl substituent | 610.2 |
| 13 | 2,3-dihydro-1H-indene with MeO, C(CH3)2OH aryl substituent | 622.2 |
| 14 | 2,3-dihydro-1H-indene with MeO, cyclopropyl-CH2OH aryl substituent | 620.5 |

TABLE 2-continued

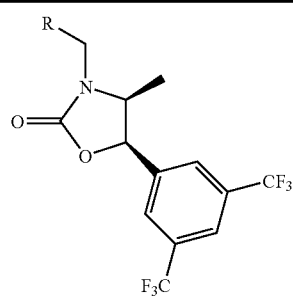

| Example | R | LCMS (M + 1)+ |
|---|---|---|
| 15 | dihydroindene with MeO, F, iPr aryl substituent | 610.2 |
| 16 | benzothiophene with MeO, F, iPr aryl substituent | 625.8 |
| 17 | benzothiophene with MeO, F, tBu aryl substituent | 639.8 |
| 18 | 6-chloropyridine with MeO, F, iPr aryl substituent | 605.2 |
| 19 | 6-trifluoromethylpyridine with MeO, F, iPr aryl substituent | 639.2 |
| 20 | 6-chloropyridine with MeO, F, iPr aryl substituent | 605.1 |

TABLE 2-continued

| Example | R | LCMS (M + 1)+ |
|---|---|---|
| 21 | (MeO, F, N, Cl, isopropyl-substituted pyridine-phenyl group) | 605.2 |
| 22 | (MeO, N, Cl, t-butyl-substituted pyridine-phenyl group) | 601.3 |
| 23 | (Cl, N, Cl, t-butyl-substituted pyridine-phenyl group) | 605.3 |
| 24 | (Cl, N, Cl, isopropyl-substituted pyridine-phenyl group) | 591.2 |

Example 26

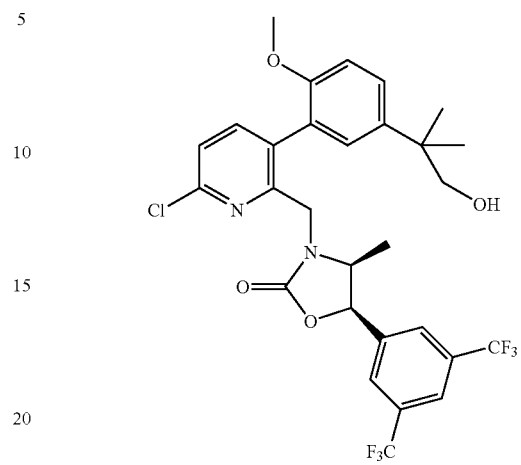

(4S,5R)-5-[3,5-bis(trifluoromethyl)phenyl]-3-({6-chloro-3-[5-(2-hydroxy-1,1-dimethylethyl)-2-methoxyphenyl]pyridin-2-yl}methyl)-4-methyl-1,3-oxazolidin-2-one To a solution of (4S,5R)-5-[3,5-bis(trifluoromethyl)phenyl]-3-[(3-bromo-6-chloropyridin-2-yl)methyl]-4-methyl-1,3-oxazolidin-2-one (INTERMEDIATE 9) (107.0 mg, 0.207 mmol) and 2-[4-methoxy-3-(4,4,5,5-tetramethyl-1,3,2-dioxaborolan-2-yl)phenyl]-2-methylpropan-1-ol (64 mg, 0.207 mmol) in THF (2.3 mL) was added aqueous potassium carbonate (1.6 mL of a 1M solution, 1.6 mmol). The mixture was degassed with nitrogen. While stirring the reaction vigorously at room temperature, 1,1-bis(di-t-butylphosphino)ferrocene palladium chloride (6.7 mg, 0.01 mmol) was added. The reaction was stirred vigorously at room temperature for 15 min, and then diluted with EtOAc (50 mL). The organics were washed with water and brine (15 mL each). The organic layer was dried over $Na_2SO_4$, filtered, and concentrated. Purification of the residue by flash chromatography on silica gel (5 to 50% EtOAc/hexanes) afforded impure product, which was repurified with 1:1:1 $CH_2Cl_2$:hexanes:$Et_2O$ on silica gel to afford (4S,5R)-5-[3,5-bis(trifluoromethyl)phenyl]-3-({6-chloro-3-[5-(2-hydroxy-1,1-dimethylethyl)-2-methoxyphenyl]pyridin-2-yl}methyl)-4-methyl-1,3-oxazolidin-2-one. $R_f$=0.29 (40% EtOAc/hexanes). LCMS=616.9 (M+1)+. $^1$H NMR (CDCl$_3$, 500 MHz, rotamers present) δ 6.94-7.85 (m, 8H), 5.40-5.55 (m, 1H), 4.81-5.08 (m, 1H), 3.54-4.36 (m, 7H), 1.95-2.59 (m, 1H), 1.30-1.34 (m, 6H), 0.62-0.74 (m, 3H).

In a similar manner, the following compound was prepared:

| Compound | Molecular structure | LCMS (M + 1)+ |
|---|---|---|
| 27 | 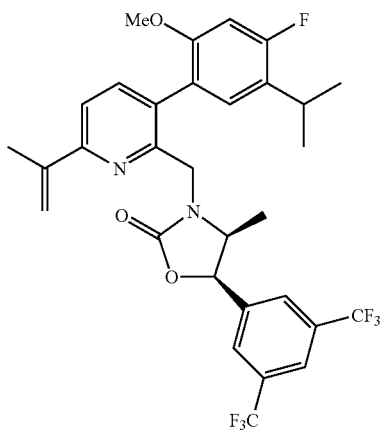 | 614.9 |

Example 28

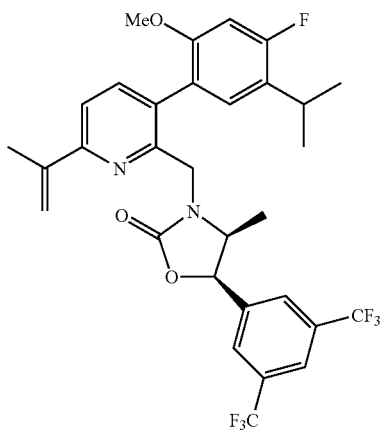

(4S,5R)-5-[3,5-bis(trifluoromethyl)phenyl]-3-{[3-(4-fluoro-5-isopropyl-2-methoxyphenyl)-6-isopropenylpyridin-2-yl]methyl}-4-methyl-1,3-oxazolidin-2-one A mixture of (4S,5R)-5-[3,5-bis(trifluoromethyl)phenyl]-3-{[6-chloro-3-(4-fluoro-5-isopropyl-2-methoxyphenyl)pyridin-2-yl]methyl}-4-methyl-1,3-oxazolidin-2-one (EXAMPLE 18) (43 mg, 0.071 mmol) and isopropenyl boronic acid (Molander, G. A.; et. al. *J. Am. Chem. Soc.* 2003, 125, 11148-11149) (122 mg, 1.42 mmol) in THF (3 mL) and 1N aqueous potassium carbonate (3 mL). 1,1-Bis(di-t-Bu-phosphino)ferrocene palladium dichloride (4.6 mg, 0.0071 mmol) was heated at 80° C. for 4 h in a sealed tube. The mixture was cooled to room temperature and filtered through Celite. The filtrate was diluted with water and extracted with EtOAc (3×). The combined organic extracts were washed with brine (1×), dried (Na$_2$SO$_4$) and concentrated in vacuo. The residue was purified by flash chromatography (Si, hexanes/EtOAc) to afford (4S,5R)-5-[3,5-bis(trifluoromethyl)phenyl]-3-{[3-(4-fluoro-5-isopropyl-2-methoxyphenyl)-6-isopropenylpyridin-2-yl]methyl}-4-methyl-1,3-oxazolidin-2-one. LCMS calc.=611.2; found=611.2 (M+1)+. $^1$H NMR (500 MHz, CDCl$_3$, 1:1 mixture of atropisomers) δ 7.88 (s, 1H); 7.75 (s, 2H); 7.51 (s, 2H); 7.04 (br, s, 0.5H); 6.99 (br, s, 0.5H); 6.71 (s, 0.5H); 6.69 (s, 0.5H); 5.98 (s, 1H); 5.68 (br, s, 0.5H); 5.66 (br, s, 0.5H); 5.37 (m, 1H); 5.00-4.74 (m, 1H); 4.56-4.20 (m, 1H); 4.20-3.90 (m, 1H); 3.77 (s, 3H); 3.25-3.18 (m, 1H); 2.28 (s, 3H); 1.32-1.22 (m, 6H); 0.74 (br, s, 1.5H); 0.64 (br, s, 1.5H).

Example 29

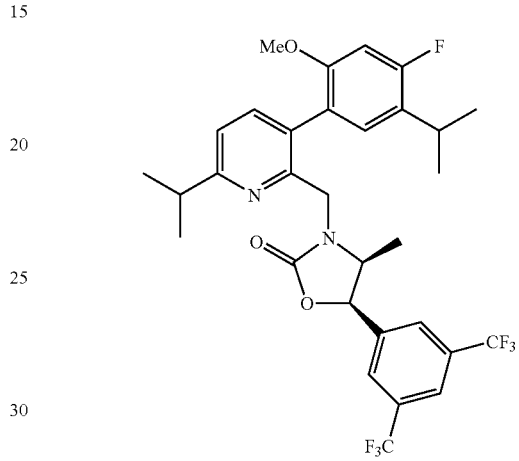

(4S,5R)-5-[3,5-bis(trifluoromethyl)phenyl]-3-{[3-(4-fluoro-5-isopropyl-2-methoxyphenyl)-6-isopropylpyridin-2-yl]methyl}-4-methyl-1,3-oxazolidin-2-one To a solution of (4S,5R)-5-[3,5-bis(trifluoromethyl)phenyl]-3-{[3-(4-fluoro-5-isopropyl-2-methoxyphenyl)-6-isopropenylpyridin-2-yl]methyl}-4-methyl-1,3-oxazolidin-2-one (20 mg, 0.033 mmol) in anhydrous EtOH (3 mL), was added a catalytic amount of 10% of palladium on carbon. The mixture was stirred under 1 atm of hydrogen for 2 h. The reaction mixture was filtered through Celite. The solvent was concentrated in vacuo. Flash chromatography of the residue (Si, hexanes/EtOAc) afforded (4S,5R)-5-[3,5-bis(trifluoromethyl)phenyl]-3-{[3-(4-fluoro-5-isopropyl-2-methoxyphenyl)-6-isopropylpyridin-2-yl]methyl}-4-methyl-1,3-oxazolidin-2-one. LCMS calc.=613.2; found=613.3 (M+1)+. $^1$H NMR (500 MHz, CDCl$_3$, 1:1 mixture of atropisomers): δ 7.88 (s, 1H); 7.75 (s, 2H); 7.45 (d, J=7.8 Hz, 1H); 7.17 (d, J=7.8 Hz, 1H); 7.04 (br, s, 0.5H); 6.98 (br, s, 0.5H); 6.70 (s, 0.5H); 6.68 (s, 0.5H); 5.72-5.56 (br, m, 1H); 4.95-4.76 (br, m, 1H); 4.41 (br, m, 0.5H); 4.23 (br, m, 0.5H); 4.18-3.89 (br, m, 1H); 3.77 (s, 3H); 3.25-3.19 (m, 1H); 3.16-3.08 (m, 1H); 1.37 (m, 6H); 1.28 (d, J=6.9 Hz, 6H); 0.73 (br, s, 1.5H); 0.62 (br, s, 1.5H).

Following procedures analogous to those described in EXAMPLE 28 and EXAMPLE 29, the compounds listed in Table 3 were prepared from the corresponding aryl halide and alkyl or alkenyl boronic acid following by catalytic hydrogenation where required:

TABLE 3

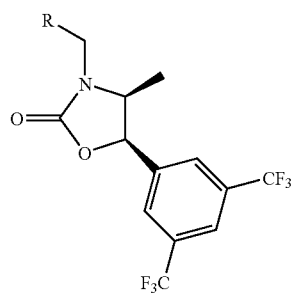

| Example | R | LCMS (M + 1)+ |
|---|---|---|
| 30 | (MeO, F, isopropyl phenyl-pyridine with 6-methyl) | 585.2 |
| 31 | (MeO, F, isopropyl phenyl-pyridine with 6-cyclopropyl) | 611.2 |
| 32 | (MeO, F, isopropyl phenyl-pyridine with 6-cyclopentenyl) | 637.0 |
| 33 | (MeO, F, isopropyl phenyl-pyridine with 6-cyclopentyl) | 639.0 |
| 34 | (MeO, F, isopropyl phenyl-pyridine with 2-methyl, different substitution) | 585.2 |

TABLE 3-continued

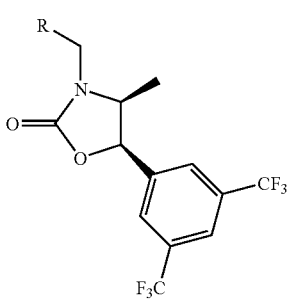

| Example | R | LCMS (M + 1)+ |
|---|---|---|
| 35 | (MeO, F, isopropyl phenyl-pyridine with 6-cyclopropyl) | 611.2 |
| 36 | (MeO, F, isopropyl phenyl-pyridine with methyl) | 585.2 |
| 37 | (MeO, F, isopropyl phenyl-pyridine with 5-cyclopropyl) | 611.2 |
| 38 | (MeO, t-Bu phenyl-pyridine with isopropyl) | 609.5 |
| 39 | (MeO, t-Bu phenyl-pyridine with cyclopropyl) | 607.2 |

TABLE 3-continued
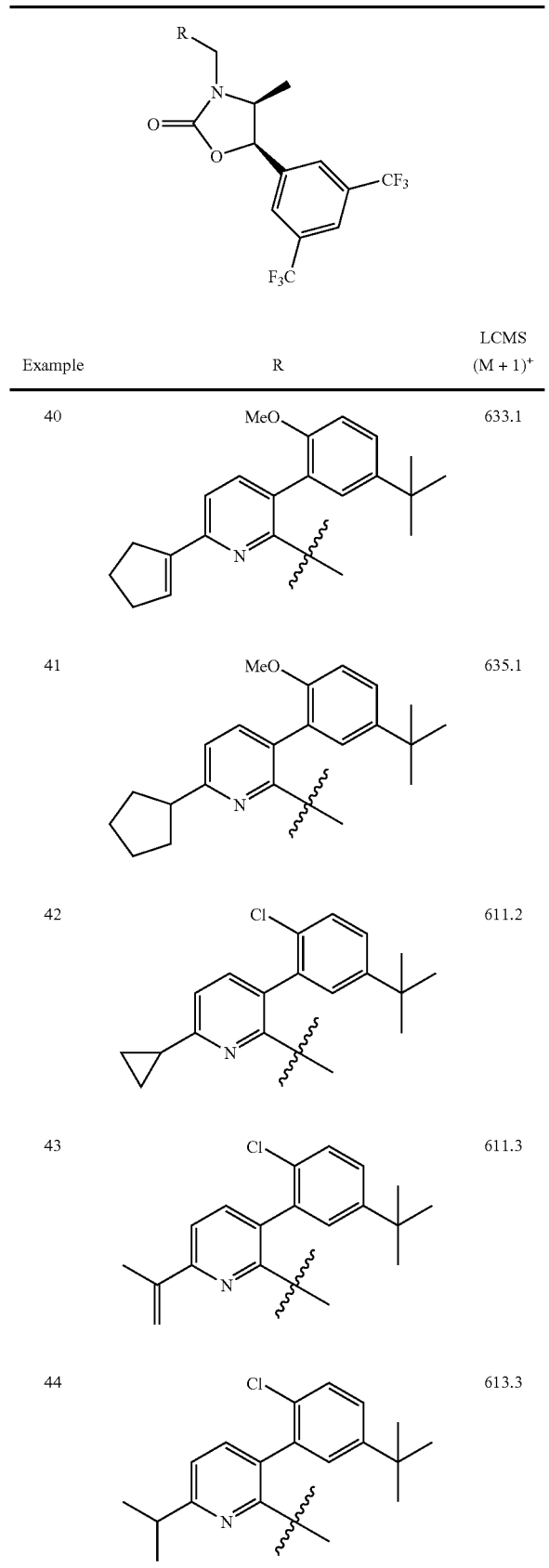
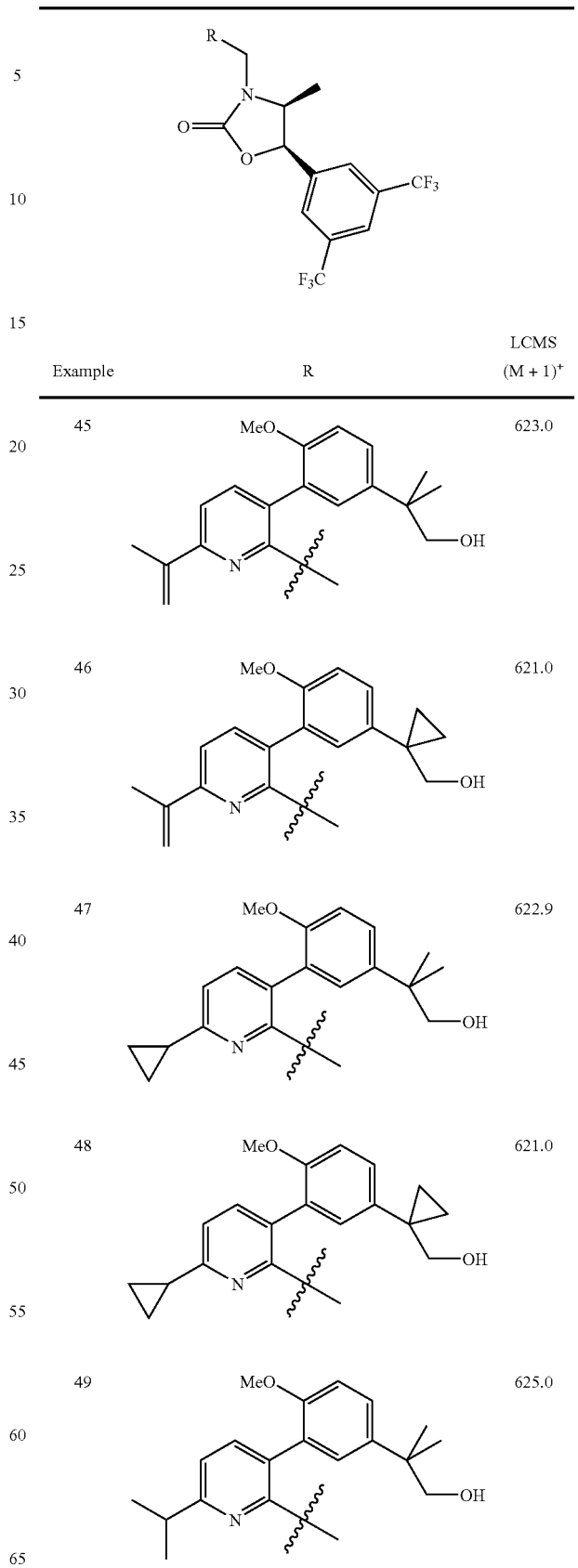

TABLE 3-continued

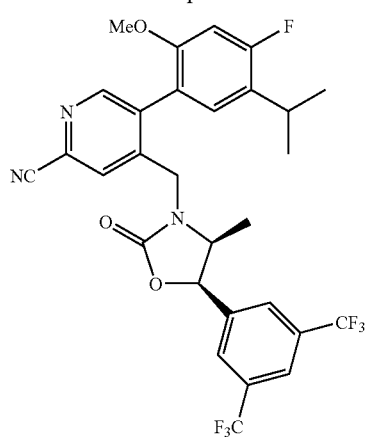

| Example | R | LCMS (M + 1)+ |
|---|---|---|
| 50 | (MeO, isopropyl pyridine, cyclopropyl-CH2OH structure) | 623.0 |

Example 51

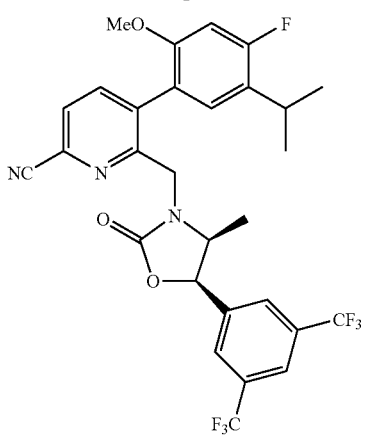

4-({(4S,5R)-5-[3,5-bis(trifluoromethyl)phenyl]-4-methyl-2-oxo-1,3-oxazolidin-3-yl}methyl)-5-(4-fluoro-5-isopropyl-2-methoxyphenyl)pyridine-2-carbonitrile A mixture of (4S,5R)-5-[3,5-bis(trifluoromethyl)phenyl]-3-{[6-chloro-3-(4-fluoro-5-isopropyl-2-methoxyphenyl)pyridin-2-yl]methyl})-4-methyl-1,3-oxazolidin-2-one (30 mg, 0.05 mmol), zinc cyanide (11.6 mg, 0.10 mmol), tris(dibenzylideneacetonedipalladium (0) (1.8 mg, 0.002 mmol) and 1,1'-bis(diphenylphosphino)ferrocene (2.2 mg, 0.004 mmol) in dimethylacetamide (400 uL) was added to a microwave tube (0.5-2 mL). The resulting mixture was subjected to microwave irradiation at 150° C. for 60 min. The reaction mixture was diluted with EtOAc and washed successively with NH4OH (2N) and brine. The organic layer was dried with Na2SO4 and concentrated in vacuo. The residue was purified by preparative TLC (Si, hexanes/EtOAc 8:2) to afford 4-({(4S,5R)-5-[3,5-bis(trifluoromethyl)phenyl]-4-methyl-2-oxo-1,3-oxazolidin-3-yl}methyl)-5-(4-fluoro-5-isopropyl-2-methoxyphenyl)pyridine-2-carbonitrile. LCMS calc.=596.2; found=596.2 (M+1)+. 1H NMR (500 MHz, CDCl3, 1:1 mixture of atropisomers): δ 8.56 (s, 1H); 7.90 (s, 1H); 7.79 (s, 0.5H); 7.75 (s, 0.5H); 7.73 (s, 2H); 7.03 (s, 0.5H); 7.02 (s, 0.5H); 6.75 (s, 0.5H); 6.73 (s, 0.5H); 5.70 (d, J=8.1 Hz, 0.5H); 5.57 (d, J=7.9 Hz, 0.5H); 4.86 (d, J=16.7 Hz, 0.5H); 4.76 (d, J=16.4 Hz, 0.5H); 4.17 (d, J=16.4 Hz, 0.5H); 3.91 (d, J=16.5 Hz, 0.5H); 3.98-3.80 (m, 1H); 3.80 (s, 1.5H); 3.78 (s, 1.5H); 3.23 (m, 1H); 1.32-1.18 (m, 6H); 0.59 (d, J=6.2 Hz, 1.5H); 0.46 (d, J=6.4 Hz, 1.5H).

Example 52

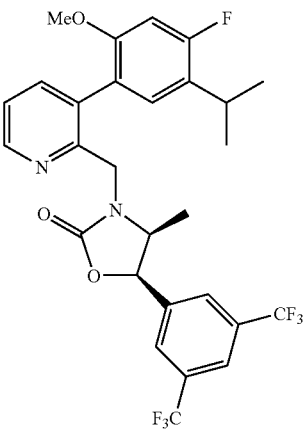

6-({(4S,5R)-5-[3,5-bis(trifluoromethyl)phenyl]-4-methyl-2-oxo-1,3-oxazolidin-3-yl}methyl)-5-(4-fluoro-5-isopropyl-2-methoxyphenyl)pyridine-2-carbonitrile Following the same procedure described as in EXAMPLE 51, the title compound was synthesized. LCMS calc. 596.2; found=596.2 (M+1).

Example 53

(4S,5R)-5-[3,5-bis(trifluoromethyl)phenyl]-3-{[3-(4-fluoro-5-isopropyl-2-methoxyphenyl)pyridin-2-yl]methyl}-4-methyl-1,3-oxazolidin-2-one To a solution of (4S,5R)-5-[3,5-bis(trifluoromethyl)phenyl]-3-{[6-chloro-3-(4-fluoro-5-isopropyl-2-methoxyphenyl)pyridin-2-yl]methyl}-4-methyl-1,3-oxazolidin-2-one (13.1 mg, 0.022 mmol) and NaOAc.3H2O (4.43 mg, 0.0325 mmol) in CH3OH (3 mL), was added a catalytic amount of 10% palladium on carbon. The mixture was stirred at room temperature under 1 atm of hydrogen overnight. The mixture was filtered through Celite. The solvent was concentrated in vacuo. The residue was redissolved in water and basified with 5N NaOH. The aqueous layer was extracted with CH2C2 (2×).

The combined organic extracts were washed with brine (1×), dried (Na₂SO₄) and concentrated in vacuo. Flash chromatography of the residue afforded (4S,5R)-5-[3,5-bis(trifluoromethyl)phenyl]-3-{[3-(4-fluoro-5-isopropyl-2-methoxyphenyl)pyridin-2-yl]methyl}-A-methyl-1,3-oxazolidin-2-one. LCMS calc.=571.2; found=571.2 (M+1)⁺. ¹H NMR (500 MHz, CDCl₃, 1:1 mixture of atropisomers): δ 8.64 (br, s, 0.5H); 8.61 (br, s, 0.5H); 7.87 (s, 1H); 7.76 (s, 2H); 7.55 (d, J=1.6 Hz, 0.5H); 7.53 (d, J=1.6 Hz, 0.5H); 7.33-7.29 (m, 1H); 7.03 (br, s, 0.5H); 6.99 (br, s, 0.5H); 6.71 (s, 0.5H); 6.69 (s, 0.5H); 5.67 (d, J=7.7 Hz, 0.5H); 5.59 (d, J=7.7 Hz, 0.5H); 4.91 (d, J=17.5 Hz, 0.5H); 4.86 (d, J=17.5 Hz, 0.5H); 4.32 (m, 0.5H); 4.18 (d, J=16.8 Hz, 0.5H); 4.16 (m, 0.5H); 4.03 (d, J=15.8 Hz, 0.5H); 3.79 (s, 1.5H); 3.77 (s, 1.5H); 3.22 (m, 1H); 1.39-1.16 (m, 6H); 0.68 (d, J=7.4 Hz, 1.5H); 0.57 (d, J=7.3 Hz, 1.5H).

Example 54

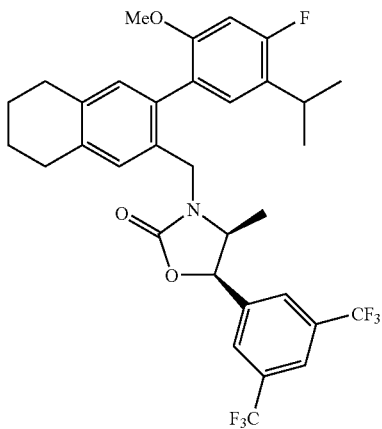

(4S,5R)-5-[3,5-Bis(trifluoromethyl)phenyl]-3-{[3-(4-fluoro-5-isopropyl-2-methoxyphenyl)-5,6,7,8-tetrahydronaphthalen-2-yl]methyl}-4-methyl-1,3-oxazolidin-2-one Step A: 3-hydroxy-5,6,7,8-tetrahydronaphthalene-2-carbaldehyde and 2-hydroxy-5,6,7,8-tetrahydronaphthalene-1-carbaldehyde 2,6-lutidine (579 mg, 629 μL, 5.40 mmol) was added to a stirred solution of 5,6,7,8-tetrahydro-2-naphthol (500 mg, 3.37 mmol) in dry toluene (6.7 mL) at room temperature under N₂. A solution of tin (IV) chloride (352 mg, 156 μL, 1.35 mmol) in dry toluene (6.7 mL) was added dropwise via cannula and the reaction was stirred for 1 h. A brown/fawn precipitate formed. Solid paraformaldehyde (405 mg, 13.5 mmol) was added and the reaction was heated at reflux overnight. The reaction was cooled and quenched with 3N HCl (15 ml) to pH 2. The mixture was filtered through a plug of Celite and washed through with CH₂Cl₂ (100-150 mL). The aqueous phase was separated and extracted with CH₂Cl₂ (3×40 mL). The combined organic extracts were washed with saturated NH₄Cl (25 mL), brine (25 mL), dried (Na₂SO₄) and concentrated in vacuo to give the crude product. This was purified by flash chromatography (Si, 40×160 mm, 0-40% EtOAc in hexanes gradient) to afford a 5.5:1 inseparable mixture of 3-hydroxy-5,6,7,8-tetrahydronaphthalene-2-carbaldehyde and 2-hydroxy-5,6,7,8-tetrahydronaphthalene-1-carbaldehyde. Major diastereoisomer: R_f=0.61 (10% EtOAc/hexanes). LCMS calc.=177.2; found=177.1 (N+1)⁺. ¹H NMR (500 MHz, CDCl₃): δ 10.70 (s, 1H); 9.76-9.75 (m, 1H); 7.19 (s, 1H); 6.66 (s, 1H); 2.79-2.75 (m, 2H); 2.74-2.70 (m, 2H); 1.80-1.76 (m, 4H).

Step B: 3-formyl-5,6,7,8-tetrahydronaphthalen-2-yl trifluoromethanesulfonate and 1-formyl-5,6,7,8-tetrahydronaphthalen-2-yl trifluoromethanesulfonate Trifluoroacetic anhydride (366 mg, 218 mL, 1.30 mmol) was added dropwise to a stirred solution of a 5.5:1 mixture of 3-hydroxy-5,6,7,8-tetrahydronaphthalene-2-carbaldehyde and 2-hydroxy-5,6,7,8-tetrahydronaphthalene-1-carbaldehyde (152.3 mg, 0.864 mmol) and pyridine (137 mg, 140 μL, 1.73 mmol) in dry CH₂Cl₂ (5 mL) at 0° C. under N₂. The reaction was allowed to warm to room temperature overnight. The reaction was then quenched with water (20 mL) and extracted with CH₂Cl₂ (3×20 mL). The combined extracts were washed with brine, dried (MgSO₄) and concentrated in vacuo to give the crude product. This was purified by flash chromatography (Si, 25×160 mm, 0-40% EtOAc in hexanes gradient) to afford 3-formyl-5,6,7,8-tetrahydronaphthalen-2-yl trifluoromethanesulfonate and 1-formyl-5,6,7,8-tetrahydronaphthalen-2-yl trifluoromethanesulfonate. Major diastereoisomer: R_f=0.42 (10% EtOAc/hexanes). ¹H NMR (600 MHz, CDCl₃): δ 10.16 (s, 1H); 7.66 (s, 1H); 7.07 (s, 1H); 2.87-2.81 (m, 4H); 1.84-1.82 (m, 4H).

Step C: 3-(hydroxymethyl)-5,6,7,8-tetrahydronaphthalen-2-yl trifluoromethanesulfonate Sodium borohydride (36.3 mg, 0.959 mmol) was added to a stirred solution of 3-formyl-5,6,7,8-tetrahydronaphthalen-2-yl trifluoromethanesulfonate (98.5 mg, 0.320 mmol) in EtOH (5 mL) at room temperature. The reaction was stirred for 112 h at room temperature. The reaction mixture was diluted with water (20 mL) washed with brine and dried (Na₂SO₄) then concentrated in vacuo to afford the crude product. This was purified by flash chromatography (Si, 25×160 mm, 0-30% EtOAc in hexanes gradient) to afford 3-(hydroxymethyl)-5,6,7,8-tetrahydronaphthalen-2-yl trifluoromethanesulfonate. R_f=0.49 (20% EtOAc/hexanes). ¹H NMR (500 MHz, CDCl₃): δ 7.25 (s, 1H); 6.95 (s, 1H); 4.69 (d, J=4.9 Hz, 2H); 2.76 (br s, 4H); 2.25 (t, J=5.4 Hz, 1H); 1.80-1.77 (m, 4H).

Step D: 3-(bromomethyl)-5,6,7,8-tetrahydronaphthalen-2-yl trifluoromethanesulfonate Triphenylphosphine (46.8 mg, 0.178 mmol) was added to a stirred solution of 3-(hydroxymethyl)-5,6,7,8-tetrahydronaphthalen-2-yl trifluoromethanesulfonate (46.1 mg, 0.149 mmol) and carbon tetrabromide (59.2 mg, 0.178 mmol) in dry CH₂Cl₂ (1 mL) at 0° C. under N₂. The reaction mixture was loaded directly onto a column and purified by flash chromatography (Si, 12×160 mm, 0-20% EtOAc in hexanes gradient) to afford 3-(bromomethyl)-5,6,7,8-tetrahydronaphthalen-2-yl trifluoromethanesulfonate, as a colorless solid. R_f=0.95 (20% EtOAc/hexanes). ¹H NMR (600 MHz, CDCl₃): δ 7.21 (s, 1H); 7.01 (s, 1H); 4.48 (s, 2H); 2.81-2.74 (m, 4H); 1.83-1.78 (m, 4H).

Step E: 3-({(4S,5R)-5-[3,5-bis(trifluoromethyl)phenyl]-4-methyl-2-oxo-1,3-oxazolidin-3-yl}methyl)-5,6,7,8-tetrahydronaphthalen-2-yl trifluoromethanesulfonate Sodium hydride (6-8 mg, 60% dispersion in mineral oil, 0.205 mmol) was added to a solution of (4S,5R)-5-[3,5-bis(trifluoromethyl)phenyl]-4-methyl-1,3-oxazolidin-2-one (49.0 mg, 0.156 mmol) in dry THF (2 mL) at room temperature under N₂. After stirring for 15 min at room temperature a solution of 3-(bromomethyl)-5,6,7,8-tetrahydronaphthalen-2-yl trifluoromethanesulfonate (48.6 mg, 0.130 mmol) in dry THF (3 mL) was added via cannula. The reaction mixture was stirred for 4 h at room temperature. Saturated NH₄Cl (10 mL) was added and the mixture was extracted with EtOAc (3×20 mL). The combined extracts were dried (Na₂SO₄) and concentrated in vacuo to give the crude product. This was purified by flash chromatography (Si, 12×160 mm, 0-20% EtOAc in hexanes gradient) to afford 3-({(4S,5R)-5-[3,5-bis(trifluoromethyl)phenyl]-4-methyl-2-oxo-1,3-oxazolidin-3-yl}methyl)-5,6,7,8-tetrahydronaphthalen-2-yl trifluoromethanesulfonate, as a colorless oil. R$_f$=0.51 (20% EtOAc/hexanes). LCMS calc.=606.1; found 606.2 (M+1)⁺. ¹H NMR (500 MHz, CDCl₃): δ 7.88 (s, 1H); 7.76 (s, 2H); 7.20 (s, 1H); 6.99 (s, 1H); 5.69 (d, J=7.9 Hz, 1H); 4.80 (d, J=15.6 Hz, 1H); 4.25 (d, J=15.6 Hz, 1H); 4.08-4.02 (m, 1H); 2.81-2.74 (m, 4H); 1.82-1.80 (m, 4H); 0.77 (d, J=6.5 Hz, 3H).

Step F: (4S,5R)-5-[3,5-bis(trifluoromethyl)phenyl]-3-{[3-(4-fluoro-5-isopropyl-2-methoxyphenyl)-5,6,7,8-tetrahydronaphthalen-2-yl]methyl}-4-methyl-1,3-oxazolidin-2-one A mixture of 3-({(4S,5R)-5-[3,5-bis(trifluoromethyl)phenyl]-4-methyl-2-oxo-1,3-oxazolidin-3-yl}methyl)-5,6,7,8-tetrahydronaphthalen-2-yl trifluoromethanesulfonate (12.4 mg, 0.0204 mmol), (4-fluoro-5-isopropyl-2-methoxyphenyl) boronic acid (13.0 mg, 0.0614 mmol), and tetrakis(triphenylphosphine)palladium (0) (2.8 mg, 0.00246 mmol), sodium carbonate (18.2 mg, 0.172 mmol) in benzene (1.4 mL), EtOH (0.2 mL) and water (0.6 mL) was heated at 95° C. in a sealed tube overnight. The reaction mixture was cooled to room temperature and water (10 mL) was added. The mixture was extracted with EtOAc (3×20 mL) and the combined organic extracts were dried (Na₂SO₄) and concentrated in vacuo to give the crude product. This was purified by flash chromatography (Si, 12×160 mm, 0-20% EtOAc in hexanes gradient) and chiral HPLC (IA column, 20×250 mm, 3% i-PrOH in heptane) to afford (4S,5R)-5-[3,5-bis(trifluoromethyl)phenyl]-3-{[3-(4-fluoro-5-isopropyl-2-methoxyphenyl)-5,6,7,8-tetrahydronaphthalen-2-yl]methyl}-4-methyl-1,3-oxazolidin-2-one. R$_f$=0.49 (20% EtOAc/hexanes). LCMS calc.=624.2; found=624.2 (M+1)⁺. ¹H NMR (600 MHz, CDCl₃, 1:1 mixture of atropisomers): δ 7.83 (s, 1H); 7.67 (s, 1H); 7.65 (s, 1H); 7.17 (s, 0.5H); 7.06 (s, 0.5H); 7.01 (d, J=8.6 Hz, 0.5H); 6.98 (d, J=8.6 Hz, 0.5H); 6.94 (s, 0.5H); 6.91 (s, 0.5H); 6.65 (d, J=9.6 Hz, 0.5H); 6.63 (d, J=9.5 Hz, 0.5H); 5.52 (d, J=8.2 Hz, 0.5H); 5.23 (d, J=8.0 Hz, 0.5H); 4.85 (d, J=15.2 Hz, 0.5H); 4.79 (d, J=15.3 Hz, 0.5H); 3.95 (d, J=15.3 Hz, 0.5H); 3.77-3.71 (m, 4.5H); 3.22-3.14 (m, 1H); 2.84-2.77 (m, 4H); 1.86-1.80 (m, 4H); 1.27-1.21 (m, 4.5H); 1.15 (d, J=7.0 Hz, 1.5H); 0.50 (d, J=6.5 Hz, 1.5H); 0.28 (d, J=6.5 Hz, 1.5H).

Example 55

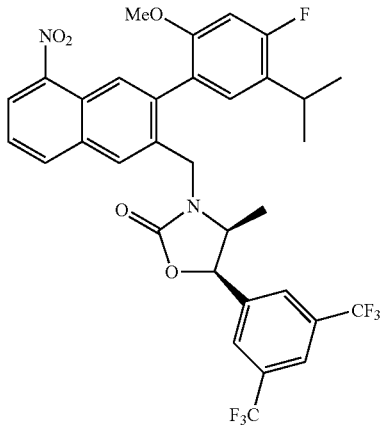

(4S,5R)-5-[3,5-Bis(trifluoromethyl)phenyl]-3-{[3-(4-fluoro-5-isopropyl-2-methoxyphenyl)-5-nitro-2-naphthyl]methyl}-4-methyl-1,3-oxazolidin-2-one Step A: (4S,5R)-5-[3,5-bis(trifluoromethyl)phenyl]-3-[(3-iodo-5-nitro-2-naphthyl)methyl]-4-methyl-1,3-oxazolidin-2-one Fuming nitric acid was added dropwise to a stirred solution of (4S,5R)-5-[3,5-bis(trifluoromethyl)phenyl]-3-[(3-iodo-2-naphthyl)methyl]-4-methyl-1,3-oxazolidin-2-one (synthesized from INTERMEDIATE 16 using a method analogous to that described in EXAMPLE 1, Step E) in acetic acid at room temperature. The reaction was stirred at room temperature for 3 h. The reaction was diluted with saturated NaHCO₃ (10 mL) and extracted with EtOAc (3×20 mL). The combined extracts were dried (Na₂SO₄) and concentrated in vacuo to give the crude product as a mixture of product isomers. The main isomer was purified by flash chromatography (Si, 12×160 mm, 0-20% EtOAc in hexanes gradient) to afford (4S,5R)-5-[3,5-bis(trifluoromethyl)phenyl]-3-[(3-iodo-5-nitro-2-naphthyl)methyl]-4-methyl-1,3-oxazolidin-2-one. R$_f$=0.11 (20% EtOAc/hexanes). LCMS calc.=625.0; found=624.6 (M+1)⁺. ¹H NMR (600 MHz, CDCl₃): δ 9.20 (s, 1H); 8.28 (dd, J=1.0, 7.7 Hz, 1H); 8.10 (d, J=8.2 Hz, 1H); 7.93 (s, 1H); 7.89 (s, 1H); 7.81 (s, 2H); 7.61 (t, J=7.9 Hz, 1H); 5.82 (d, J=7.9 Hz, 1H); 4.98 (d, J=15.9 Hz, 1H); 4.48 (d, J=15.9 Hz, 1H); 4.21-4.15 (m, 1H); 0.84 (d, J=6.5 Hz, 3H).

Step B: (4S,5R)-5-[3,5-bis(trifluoromethyl)phenyl]-3-{[3-(4-fluoro-5-isopropyl-2-methoxyphenyl)-5-nitro-2-naphthyl]methyl}-4-methyl-1,3-oxazolidin-2-one A mixture of (4S,5R)-5-[3,5-bis(trifluoromethyl)phenyl]-3-[(3-iodo-5-nitro-2-naphthyl)methyl]-4-methyl-1,3-oxazolidin-2-one (34.0 mg, 0.0545 mmol), (4-fluoro-5-isopropyl-2-methoxyphenyl)boronic acid (23.1 mg, 0.0109 mmol), and 1,1'-bis(di-t-butylphosphinoferrocene)palladium dichloride (3.5 mg, 0.00545 mmol) in 1N aqueous potassium carbonate (2 mL) and THF (2 mL) was heated at 85° C. in a sealed tube for 2 h. The reaction mixture was cooled to room temperature and water (10 mL) was added. The mixture was extracted with EtOAc (3×20 mL) and the combined organic extracts were dried (Na₂SO₄) and concentrated in vacuo to give the crude product. This was purified by flash chromatography (Si, 12×160 mm, 0-30% EtOAc in hexanes gradient) to afford (4S,5R)-5-[3,5-bis(trifluoromethyl)phenyl]-3-{[3-(4-fluoro-5-isopropyl-2-methoxyphenyl)-5-nitro-2-naphthyl]methyl}-4-methyl-1,3-oxazolidin-2-one. R$_f$=0.23 (20% EtOAc/hexanes). LCMS calc.=665.2; found=664.9 (M+1)⁺. ¹H NMR (500 MHz, CDCl₃, 1:1 mixture of atropisomers): δ 8.46 (s, 1H); 8.26 (d, J=7.5 Hz, 1H); 8.17 (t, J=9.0 Hz, 1H); 8.07 (s, 0.5H); 7.95 (s, 0.5H); 7.85 (s, 1H); 7.69 (s, 2H); 7.58 (t, J=7.9 Hz, 1H); 7.14 (d, J=8.4 Hz, 0.5H); 7.10 (d, J=8.4 Hz, 0.5H); 6.72 (d, J=12.0 Hz, 0.5H); 6.71 (d, J=12.0 Hz, 0.5H); 5.57 (d, J=8.1 Hz, 0.5H); 5.44 (d, J=8.0 Hz, 0.5H); 4.97 (d, J=15.9 Hz, 0.5H); 4.93 (d, J=15.9 Hz, 0.5H); 4.29 (d, J=15.9 Hz, 0.5H); 4.03 (d, J=15.8 Hz, 0.5H); 3.91-3.83 (m, 0.5H); 3.77 (m, 3.5H); 3.26-3.18 (m, 1H); 1.28-1.24 (m, 4.5H); 1.20 (d, J=6.9 Hz, 1.5H); 0.58 (d, J=6.5 Hz, 1.5H); 0.40 (d, J=6.6 Hz, 1.5H).

Example 56

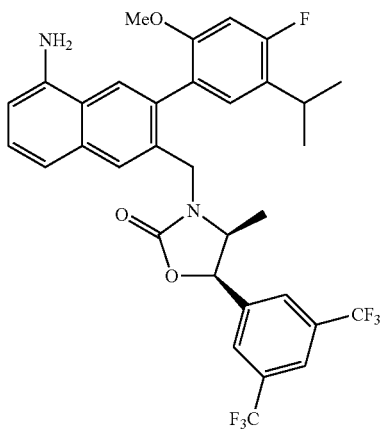

(4S,5R)-3-{[5-Amino-3-(4-fluoro-5-isopropyl-2-methoxyphenyl)-2-naphthyl]methyl}-5-[3,5-bis(trifluoromethyl)phenyl]-4-methyl-1,3-oxazolidin-2-one A suspension of 10% palladium on carbon (4.0 mg) in a solution of (4S,5R)-5-[3,5-bis(trifluoromethyl)phenyl]-3-{[3-(4-fluoro-5-isopropyl-2-methoxyphenyl)-5-nitro-2-naphthyl]methyl}-4-methyl-1,3-oxazolidin-2-one (21.3 mg, 0.0321 mmol) in EtOAc (2.5 mL) was stirred under $H_2$ (double balloon pressure) overnight. The reaction mixture was filtered through a plug of Celite and the filtrate was concentrated in vacuo to afford (4S,5R)-3-{[5-amino-3-(4-fluoro-5-isopropyl-2-methoxyphenyl)-2-naphthyl]methyl}-5-[3,5-bis(trifluoromethyl)phenyl]-4-methyl-1,3-oxazolidin-2-one. LCMS calc.=635.2; found=634.8 $(M+1)^+$.

Example 57

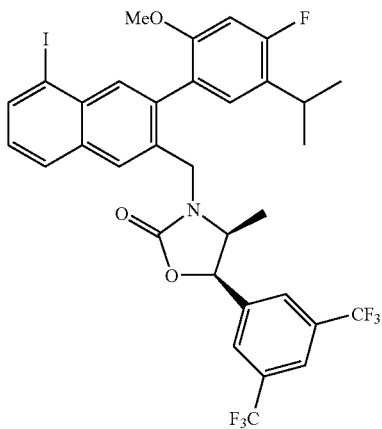

(4S,5R)-5-[3,5-Bis(trifluoromethyl)phenyl]-3-{[3-(4-fluoro-5-isopropyl-2-methoxyphenyl)-5-iodo-2-naphthyl]methyl}-4-methyl-1,3-oxazolidin-2-one t-Butyl nitrite (90%, 6.5 mg, 8.3 µL, 0.0627 mmol) was added to a suspension of (4S,5R)-3-{[5-amino-3-(4-fluoro-5-isopropyl-2-methoxyphenyl)-2-naphthyl]methyl}-5-[3,5-bis(trifluoromethyl)phenyl]-4-methyl-1,3-oxazolidin-2-one (19.9 mg, 0.0314 mmol) in $CH_2I_2$ (1 mL). Dry $CHCl_3$ (0.5 mL) was added to dissolve the precipitate formed. The solution was heated at 80° C. for 5 h. The reaction mixture was concentrated in vacuo and the resulting slurry was purified by flash chromatography (Si, 12×160 mm, 0-20% EtOAc in hexanes gradient) to afford (4S,5R)-5-[3,5-bis(trifluoromethyl)phenyl]-3-{[3-(4-fluoro-5-isopropyl-2-methoxyphenyl)-5-iodo-2-naphthyl]methyl}-4-methyl-1,3-oxazolidin-2-one. $R_f$=0.47 (20% EtOAc/hexanes). LCMS calc.=746.1; found 745.8 $(M+1)^+$. $^1$H NMR (500 MHz, $CDCl_3$, 1:1 mixture of atropisomers): δ 8.11 (d, J=7.2 Hz, 1H); 7.92 (d, J=4.7 Hz, 1H); 7.88-7.85 (m, 1.5H); 7.84 (s, 1H); 7.75 (s, 0.5H); 7.67 (s, 2H); 7.22 (t, J=7.7 Hz, 1H); 7.16 (d, J=8.5 Hz, 0.5H); 7.12 (d, J=8.5 Hz, 0.5H); 6.76-6.70 (m, 1H); 5.54 (d, J=8.1 Hz, 0.5H); 5.34 (d, J=8.0 Hz, 0.5H); 5.01 (d, J=15.7 Hz, 0.5H); 5.00 (d, J=15.7 Hz, 0.5H); 4.22 (d, J=15.7 Hz, 0.5H); 3.98 (d, J=15.7 Hz, 0.5H); 3.81-3.72 (m, 4H); 3.28-3.20 (m, 1H); 1.32-1.24 (m, 4.5H); 1.21 (d, J=6.9 Hz, 1.5H); 0.57 (d, J=6.5 Hz, 1.5H); 0.37 (d, J=6.5 Hz, 1.5H).

Example 58

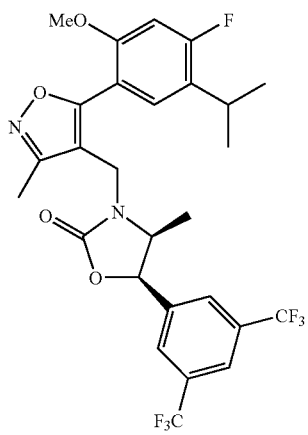

(4S,5R)-5-[3,5-Bis(trifluoromethyl)phenyl]-3-{[5-(4-fluoro-5-isopropyl-2-methoxyphenyl)-3-methylisoxazol-4-yl]methyl}-4-methyl-1,3-oxazolidin-2-one Step A: (4S,5R)-5-[3,5-bis(trifluoromethyl)phenyl]-4-methyl-3-prop-2-yn-1-yl-1,3-oxazolidin-2-one Sodium hydride (192 mg, 60% dispersion in mineral oil, 4.79 mmol) was added to a solution of (4S,5R)-5-[3,5-bis(trifluoromethyl)phenyl]-4-methyl-1,3-oxazolidin-2-one (1.00 g, 3.19 mmol) in dry THF (30 mL) at room temperature under $N_2$. After stirring for 30 min at room temperature, propargyl bromide (80 wt % solution in toluene, 712 µL, 570 mg, 4.17 mmol) was added. The reaction mixture was stirred overnight at room temperature. Saturated $NH_4Cl$ (20 mL) was added and the mixture was extracted with EtOAc (3×20 mL). The combined extracts were dried ($MgSO_4$) and concentrated in vacuo to give the crude product. This was purified by flash chromatography (Si, 40×160 mm, 0-40% EtOAc in hexanes gradient) to afford (4S,5R)-5-[3,5-bis(trifluoromethyl)phenyl]-4-methyl-3-prop-2-yn-1-yl-1,3-oxazolidin-2-one. $R_f$=0.31 (20% EtOAc/hexanes). LCMS calc.=352.1; found=352.1 $(M+1)^+$. $^1$H NMR (600 MHz, $CDCl_3$): δ 7.88 (s, 1H); 7.76 (s, 2H); 5-74 (d, J=8.2 Hz, 1H); 4.454-39 (m, 2H); 3.81 (dd, J=2.5, 17.8 Hz, 1H); 2.33 (t, J=2.5 Hz, 1H); 0.84 (d, J=6.6 Hz, 4H).

Step B: (4S,5R)-5-[3,5-bis(trifluoromethyl)phenyl]-3-[3-(4-fluoro-5-isopropyl-2-methoxyphenyl)prop-2-yn-1-yl]-4-methyl-1,3-oxazolidin-2-one A mixture of (4S,5R)-5-[3,5-bis(trifluoromethyl)phenyl]-4-methyl-3-prop-2-yn-1-yl-1,3-oxazolidin-2-one (100 mg, 0.285 mmol), 1-bromo-4-fluoro-5-isopropyl-2-methoxybenzene (27.4 wt % in toluene, 233 mg, 0.259 mmol), bis(triphenylphosphine)palladium dichloride (18.2 mg, 0.0259 mmol), copper (I) iodide (4.9 mg, 0.0259 mmol), triphenylphosphine (13.6 mg, 0.0518 mmol), and diethylamine (283 mg, 406 μL, 3.88 mmol) in dry DMF (0.5 mL) was degassed and subjected to microwave irradiation (120° C., 60 min). The reaction mixture was diluted with 0.1N HCl (10 mL) and extracted with EtOAc (3×20 mL). The combined extracts were dried (Na$_2$SO$_4$) and concentrated in vacuo to give the crude product. This was purified by flash chromatography (Si, 12×160 mm, 0-30% EtOAc in hexanes gradient) to afford (4S,5R)-5-[3,5-bis(trifluoromethyl)phenyl]-3-[3-(4-fluoro-5-isopropyl-2-methoxyphenyl)prop-2-yn-1-yl]-4-methyl-1,3-oxazolidin-2-one. R$_f$=0.38 (20% EtOAc/hexanes). LCMS calc.=518.2; found=518.2 (M+1)$^+$. $^1$H NMR (500 MHz, CDCl$_3$): δ 7.89 (s, 1H); 7.78 (s, 2H); 7.26 (d, J=8.4 Hz, 1H); 6.56 (d, J=12.0 Hz, 1H); 5.76 (d, J=8.3 Hz, 1H); 4.70 (d, J=17.8 Hz, 1H); 4.53-4.47 (m, 1H); 4.08 (d, J=17.8 Hz, 1H); 3.82 (s, 3H); 3.17-3.09 (m, 1H); 1.22 (d, J=6.9 Hz, 6H); 0.90 (d, J=6.5 Hz, 3H).

Step C: (4S,5R)-5-[3,5-bis(trifluoromethyl)phenyl]-3-{[5-(4-fluoro-5-isopropyl-2-methoxyphenyl)-3-methylisoxazol-4-yl]methyl}-4-methyl-1,3-oxazolidin-2-one N-Chlorosuccinimide (10.4 g, 78.1 mmol) was added to a stirred solution of acetaldoxime (3.55 g, 60.1 mmol) in dry DMF at 0° C. under N$_2$. The reaction was allowed to warm to room temperature and was stirred for 3 h. Water (100 mL) was added and the mixture was extracted with Et$_2$O (4×80 mL). The combined extracts were washed with water (50 mL) and brine (50 mL), dried (Na$_2$SO$_4$) and concentrated in vacuo to afford N-hydroxyethanimidoyl chloride, as a colorless oil. $^1$H NMR (500 MHz, CDCl$_3$): δ 8.96 (br s, 1H), 2.26 (s, 3H).

Triethylamine (123.4 mg, 170 μL, 1.21 mmol) was added to a stirred solution of (4S,5R)-5-[3,5-bis(trifluoromethyl)phenyl]-3-[3-(4-fluoro-5-isopropyl-2-methoxyphenyl)prop-2-yn-1-yl]-4-methyl-1,3-oxazolidin-2-one (21.9 mg, 0.0423 mmol) and N-hydroxyethanimidoyl chloride (124.4 mg, 1.33 mmol) in dry toluene (2 mL) at room temperature under N$_2$. The reaction was heated at reflux for 2 days. The reaction mixture was cooled to room temperature, diluted with 1N HCl and extracted with EtOAc (3×20 mL). The combined extracts were dried (Na$_2$SO$_4$) and concentrated in vacuo to give the crude product. This was purified by flash chromatography (Si, 12×160 mm, 0-30% EtOAc in hexanes gradient) to afford (4S,5R)-5-[3,5-bis(trifluoromethyl)phenyl]-3-{[5-(4-fluoro-5-isopropyl-2-methoxyphenyl)-3-methylisoxazol-4-yl]methyl}-4-methyl-1,3-oxazolidin-2-one. R$_f$=0.38 (20% EtOAc/hexanes). LCMS calc.=575.2; found=575.3 (M+1)$^+$. $^1$H NMR (600 MHz, CDCl$_3$): δ 7.84 (s, 1H); 7.64 (s, 2H); 7.31 (d, J=8.3 Hz, 1H); 6.68 (d, J=11.8 Hz, 1H); 5.27 (d, J=8.0 Hz, 1H); 4.78 (d, J=15.6 Hz, 1H); 4.00 (d, J=15.6 Hz, 1H); 3.82 (s, 3H); 3.72-3.68 (m, 1H); 3.22-3.16 (m, 1H); 2.38 (s, 3H); 1.24 (d, J=7.0 Hz, 3H); 1.22 (d, J=7.0 Hz, 3H); 0.42 (d, J=6.6 Hz, 3H).

Example 59

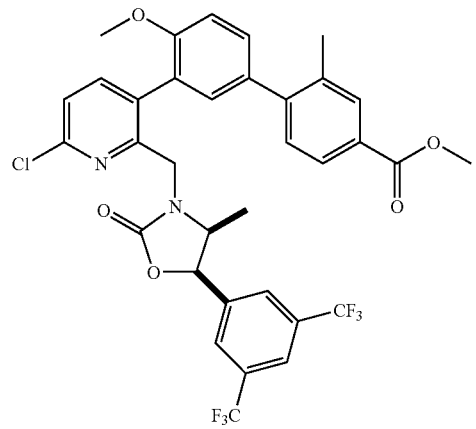

Methyl 3'-[2-({(4S,5R)-5-[3,5-bis(trifluoromethyl)phenyl]-4-methyl-2-oxo-1,3-oxazolidin-3-yl}methyl)-6-chloropyridin-3-yl]-4'-methoxy-2-methylbiphenyl-4-carboxylate Step A: methyl 4'-methoxy-2-methyl-3'-(4,4,5,5-tetramethyl-1,3,2-dioxaborolan-2-yl)biphenyl-4-carboxylate Methyl 3'-iodo-4'-methoxy-2-methylbiphenyl-4-carboxylate (500 mg, 1.31 mmol), bis(pinacolato)diboron (353 mg, 1.57 mmol), 1,1'-bis(diphenylphosphino)ferrocene-palladium dichloride dichloromethane adduct (214 mg, 0.262 mmol), potassium acetate (257 mg, 2.616 mmol) and 1,4-dioxane (2.5 mL) were sealed in a microwave vessel. The reaction mixture was subjected to microwave irradiation at 140° C. for 20 min then at 130° C. for additional 30 min. The crude reaction was treated with brine followed by EtOAc extraction. The combined extracts were dried over Na$_2$SO$_4$, filtered and concentrated in vacuo to afford crude methyl 4'-methoxy-2-methyl-3'-(4,4,5,5-tetramethyl-1,3,2-dioxaborolan-2-yl)biphenyl-4-carboxylate, as a dark oil. This was used as is in the next reaction. LCMS calc.=382.20; found=383.41 (M+1)$^+$.

Step B: methyl 3'-[2-({(4S,5R)-5-[3,5-bis(trifluoromethyl)phenyl]-4-methyl-2-oxo-1,3-oxazolidin-3-yl}methyl)-6-chloropyridin-3-yl]-4'-methoxy-2-methylbiphenyl-4-carboxylate (4S,5R)-5-[3,5-bis(3-trifluoromethyl)phenyl]-3-[(3-bromo-6-chloropyridin-2-yl)methyl]-4-methyl-1,3-oxazolidin-2-one (INTERMEDIATE 9) (500 mg, 0.966 mmol), methyl 4'-methoxy-2-methyl-3-(4,4,5,5-tetramethyl-1,3,2-dioxaborolan-2-yl)biphenyl-4-carboxylate (554 mg, 1.45 mmol), 1,1'-bis(diphenylphosphino)ferrocene-palladium dichloride dichloromethane adduct (158 mg, 20%), aqueous potassium carbonate (966 μL, 2M, 1.93 mmol) and ethanol (5 mL) were heated in an 80° C. oil bath for 1 h. Volatiles were then removed from the crude mixture under reduced pressure.

The pot residue was treated with water followed by EtOAc extraction. The combined extracts were dried over Na₂SO₄ followed by filtration and concentration to afford a dark oil. The resulting oil was purified by flash chromatography (SiO₂, Biotage 40+M cartridge, 0-40% EtOAc in hexanes) to afford methyl 3'-[2-({(4S,5R)-5-[3,5-bis(trifluoromethyl)phenyl]-4-methyl-2-oxo-1,3-oxazolidin-3-yl}methyl)-6-chloropyridin-3-yl]-4'-methoxy-2-methylbiphenyl-4-carboxylate (152 mg), as a yellow glass. LCMS calc.=692.15; found=693.19 (M+1).

Example 60

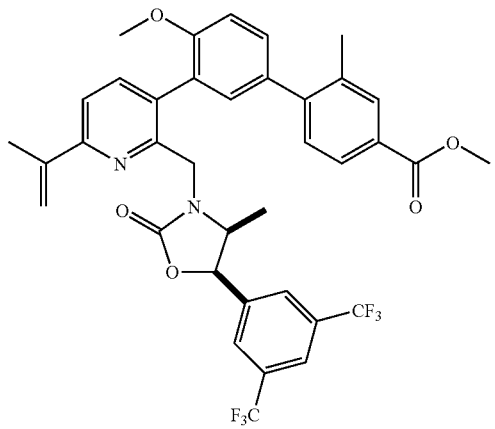

Methyl 3'-[2-({(4S,5R)-5-[3,5-bis(trifluoromethyl) phenyl]-4-methyl-2-oxo-1,3-oxazolidin-3-yl}methyl)-6-isopropenylpyridin-3-yl]-4'-methoxy-2-methylbiphenyl-4-carboxylate Methyl 3'-[2-({(4S,5R)-5-[3,5-bis(trifluoromethyl)phenyl]-4-methyl-2-oxo-1,3-oxazolidin-3-yl}methyl)-6-chloropyridin-3-yl]-4'-methoxy-2-methylbiphenyl-4-carboxylate (120 mg, 0.966 mmol), isopropenylboronic acid (74.4 mg, 0.865 mmol), 1,1'-bis(di-tert-butylphosphino) ferrocene palladium dichloride (23.5 mg, 20%), aqueous potassium carbonate (1.21 mL, 1M, 1.21 mmol) and THF (1.2 mL) were heated in an 80° C. oil bath for 1 h and 25 min. Volatiles were then removed from the crude mixture under reduced pressure. The pot residue was treated with water followed by EtOAc extraction. The combined extracts were dried over Na₂SO₄ followed by filtration and concentration to afford a dark colored oil. The resulting oil was purified by a reversed-phase prep-HPLC (Kromasil 100-5C18, 100×21.1 mm) eluting with a MeCN (0.1% TPA, v/v)/H₂O (0.1% TFA, v/v) gradient mixture. Related fractions were pooled and evaporated in vacuo to afford a light yellow oil. The oil was dissolved with CH₂Cl₂ and then washed with NaHCO₃ (sat. aq.). The organic layer was separated and back washed with water, separated and dried over Na₂SO₄, filtered and concentrated in vacuo to afford methyl 3'-[2-({(4S,5R)-5-[3,5-bis(trifluoromethyl)phenyl]-4-methyl-2-oxo-1,3-oxazolidin-3-yl}methyl)-6-isopropenylpyridin-3-yl]-4'-methoxy-2-methylbiphenyl-4-carboxylate, as a light yellow glass. LCMS calc.=698.22; found 699.23 (M+1).

Example 61

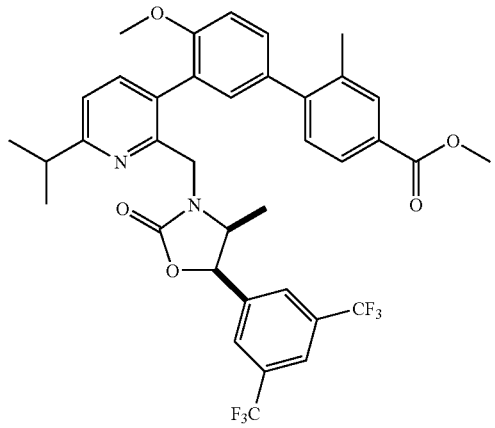

Methyl 3'-[2-({(4S,5R)-5-[3,5-bis(trifluoromethyl) phenyl]-4-methyl-2-oxo-1,3-oxazolidin-3-yl}methyl)-6-isopropylpyridin-3-yl]-4'-methoxy-2-methylbiphenyl-4-carboxylate Methyl 3'-[2-({(4S,5R)-5-[3,5-bis(trifluoromethyl)phenyl]-4-methyl-2-oxo-1,3-oxazolidin-3-yl}methyl)-6-isopropenylpyridin-3-yl]-4'-methoxy-2-methylbiphenyl-4-carboxylate (131 mg, 0.189 mmol) and a catalytic amount of palladium on carbon and CH₃OH (5 mL) were stirred vigorously under a balloon atmosphere of hydrogen for 1 h and 20 min at 20° C. The reaction mixture was filtered then the filtrate was concentrated in vacuo to afford methyl 3'-[2-({(4S,5R)-5-[3,5-bis(trifluoromethyl)phenyl]-4-methyl-2-oxo-1,3-oxazolidin-3-yl}methyl)-6-isopropylpyridin-3-yl]-4'-methoxy-2-methylbiphenyl-4-carboxylate, as a light yellow glass. LCMS calc.=700.24; found=701.29 (M+1).

Example 62

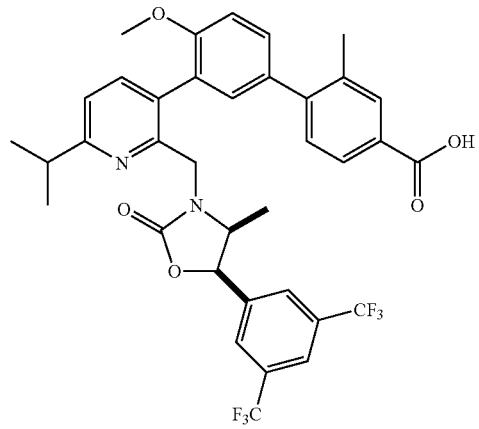

3'-[2-({(4S,5R)-5-[3,5-bis(trifluoromethyl)phenyl]-4-methyl-2-oxo-1,3-oxazolidin-3-yl}methyl)-6-isopropylpyridin-3-yl]-4'-methoxy-2-methylbiphenyl-carboxylic acid To a solution of methyl 3'-[2-({(4S,5R)-5-[3,5-bis(trifluoromethyl)phenyl]-4-methyl-2-oxo-1,3-oxazolidin-3-yl}- methyl)-6-isopropylpyridin-3-yl]-4'-methoxy-2-methylbiphenyl-4-carboxylate (102 mg, 0.146 mmol) in 1,4-dioxane (3 mL) was added a solution of lithium hydroxide monohydrate (27 mg, 0.643 mmol) in water (1.8 mL). The reaction was stirred for 3 days. The crude mixture was acidified with HCl (aq, 1N, 1 mL). The crude product was purified by reverse-phase prep-HPLC (Kromasil 100-5C18, 100×21.1 mm) eluting with a MeCN (0.1% TFA, v/v)/H10 (0.1% TFA, v/v) gradient mixture. Two peaks were recorded in the prep-LC chromatogram representing the desired acid (60 A %, the faster eluting peak) and the starting ester. Corresponding fractions were pooled and evaporated in vacuo to aqueous mixtures. The resulting mixtures were extracted with EtOAc. The separated organic phases were back washed with water, separated, dried over $Na_2SO_4$, filtered and evaporated to afford 3'-[2-({(4S,5R)-5-[3,5-bis(trifluoromethyl)phenyl]-4-methyl-2-oxo-1,3-oxazolidin-3-yl}methyl)-6-isopropylpyridin-3-yl]-4'-methoxy-2-methylbiphenyl-4-carboxylic acid (59.27 mg) as a glass and the recovered starting ester. LCMS calc.=686.22; found=687.44 $(M+1)^+$. $^1H$ NMR signals are doubled because of atropoisomerism. $^1H$ NMR ($CDCl_3$, 500 MHz) 8.13 (d, J=8 Hz, 1H), 8.02-7.95 (m, 1H), 7.94-7.88 (m, 1H), 7.85 (s, 1H), 7.70-7.62 (m, 3H), 7.49 (d, J=8.5 Hz, 1H), 7.38 (s, 0.5H), 7.35-7.28 (m, 1H), 7.20-7.10 (m, 1.5H), 5.67 (d, J=7 Hz, 0.7H), 5.58 (d, J=8.0 Hz, 0.3H), 5.05 (d, J=16 Hz, 0.3H), 4.75 (d, J=16 Hz, 0.7H), 4.67 (d, J=16 Hz, 0.7H), 4.60 (d, J=16 Hz, 0.3H), 4.40-4.32 (m, 1H), 3.92 (s, 0.9H), 3.88 (s, 2.1H), 3.74-3.60 (m, 1H), 2.39 (s, 2.1H), 2.35 (s, 0.9H), 1.46 (s, 3H), 1.45 (s, 3H), 0.73 (d, J=6.5 Hz, 2.1H), 0.65 (d, J=5.5 Hz, 0.9H).

Example 63

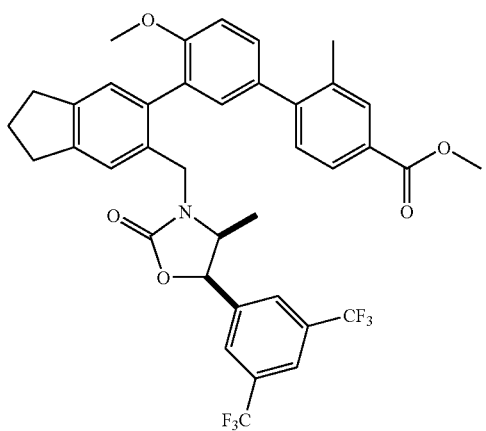

Methyl 3'-[6-({(4S,5R)-5-[3,5-bis(trifluoromethyl)phenyl]-4-methyl-2-oxo-1,3-oxazolidin-3-yl}methyl)-2,3-dihydro-1H-inden-5-yl]-4'-methoxy-2-methylbiphenyl-4-carboxylate This compound was prepared using a method analogous to that described for EXAMPLE 59, Step B. LCMS calc.=698.2; found=698.0 $(M+1)^+$.

Example 64

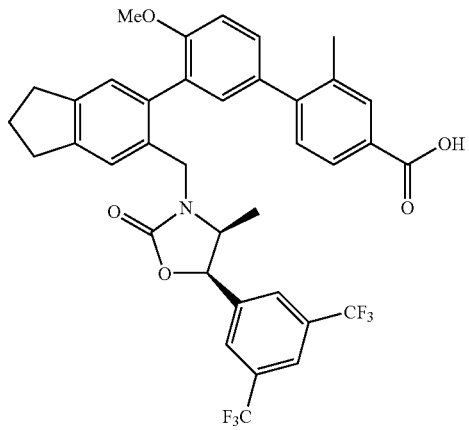

3'-[6-({(4S,5R)-5-[3,5-bis(trifluoromethyl)phenyl]-4-methyl-2-oxo-1,3-oxazolidin-3-yl}methyl)-2,3-dihydro-1H-inden-5-yl]-4'-methoxy-2-methylbiphenyl-4-carbolic acid A mixture of methyl 3'-[6-({(4S,5R)-5-[3,5-bis(trifluoromethyl)phenyl]-4-methyl-2-oxo-1,3-oxazolidin-3-yl}methyl)-2,3-dihydro-1H-inden-5-yl]-4'-methoxy-2-methylbiphenyl-4-carboxylate (23.9 mg, 0.034 mmol) in EtOH (2 mL), water (1 mL) and potassium hydroxide (3.5N, 200 μL) was stirred at room temperature for 16 h. The reaction mixture was diluted with water and adjusted to pH 5 using 1N HCl. The aqueous layer was extracted with EtOAc (3×). The combined organic layers were dried ($Na_2SO_4$) and concentrated in vacuo. The residue was purified by preparative HPLC to afford the title compound. LCMS calc.=684.2; found=684.0 $(M+1)^+$. $^1H$ NMR (500 MHz, $CDCl_3$) δ 8.03 (s, 0.5H); 8.02 (s, 0.5H); 8.00-7.93 (m, 1H); 7.88 (s, 0.5H); 7.86 (s, 0.5H); 7.71 (s, 1H); 7.63 (s, 1H); 7.41-7.26 (m, 3H); 7.20-7.20 (m, 1.5H); 7.17 (s, 0.5H); 7.09 (d, J=8.4 Hz, 0.5H); 7.07 (d, J=8.5 Hz, 0.5H); 5.58 (d, J=8.3 Hz, 0.5H); 5.25 (d, J=8.2 Hz, 0.5H); 4.97 (d, J=6.5 Hz, 0.5H); 4.94 (d, J=6.4 Hz, 0.5H); 4.09 (d, J=15.1 Hz, 0.5H); 3.91 (s, 1.5H); 3.88 (d, J=13.3 Hz, 2H); 3.84 (m, 0.5H); 3.79 (m, 0.5H); 3.03-2.98 (m, 4H); 2.74 (br, s, 1H); 2.43 (s, 1.5H); 2.37 (s, 1.5H); 2.18-2.14 (m, 2H); 0.55 (d, J=6.5 Hz, 1.5H); 0.41 (d, J=6.6 Hz, 1.5H).

From the aryl methyl alcohols described above, the corresponding aryl methyl halides were synthesized by following the procedure described in step C for INTERMEDIATE 16. The compounds in Table 4 were then synthesized by methods analogous to those described in EXAMPLE 1, steps E and/or F, from phenyl oxazolidinones, aryl methyl halides and boronic acids whose syntheses are described.

TABLE 4

| Example | R | LCMS (M+H)+ |
|---|---|---|
| 65 | 2-(benzyloxycarbonyl)-5-(4-fluoro-2-methoxy-5-isopropylphenyl)isoindolin-6-yl | 745.3 |
| 66 | 5-(4-fluoro-2-methoxy-5-isopropylphenyl)-1,3-dihydroisobenzofuran-6-yl | 611.9 |
| 67 | 6-(4-fluoro-2-methoxy-5-tert-butylphenyl)-1,3-dihydrofuro[3,4-c]pyridin-5-yl | 625.8 |
| 68 | 5-(4-fluoro-2-methoxy-5-isopropylphenyl)-4-methyl-1,3-dihydroisobenzofuran-6-yl (atropisomer 1) | 625.9 |

TABLE 4-continued

| Example | R | LCMS (M+H)+ |
|---|---|---|
| 69 | 5-(4-fluoro-2-methoxy-5-isopropylphenyl)-4-methyl-1,3-dihydroisobenzofuran-6-yl (atropisomer 2) | 625.9 |
| 70 | 5-(4-fluoro-2-methoxy-5-tert-butylphenyl)-4-methyl-1,3-dihydroisobenzofuran-6-yl (atropisomer 1) | 639.8 |
| 71 | 6-(4-fluoro-2-methoxy-5-tert-butylphenyl)-4-methyl-1,3-dihydrofuro[3,4-c]pyridin-5-yl (atropisomer 2) | 639.9 |
| 72 | 6-(4-fluoro-2-methoxy-5-isopropylphenyl)benzo[d][1,3]dioxol-5-yl | 613.8 |

TABLE 4-continued

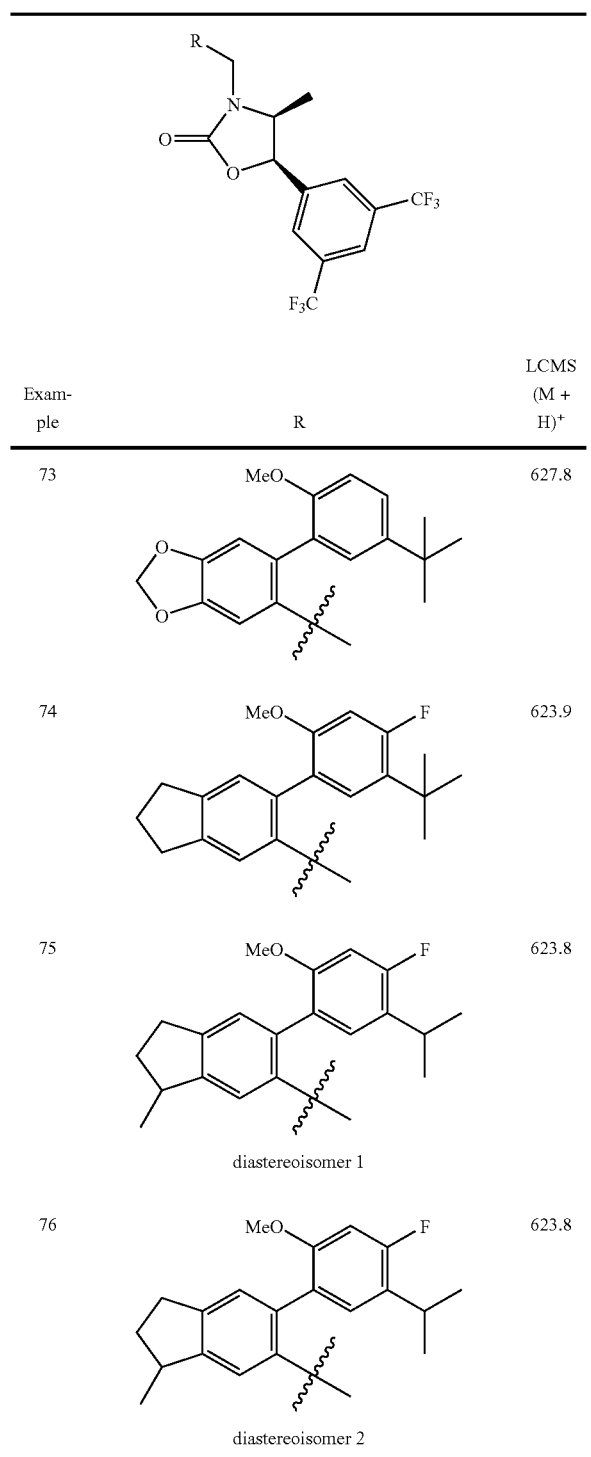

| Example | R | LCMS (M + H)+ |
|---|---|---|
| 73 | (MeO, methylenedioxy-phenyl, t-Bu substituted biaryl with indane) | 627.8 |
| 74 | (MeO, F, indanyl biaryl) | 623.9 |
| 75 | (MeO, F, iPr, methyl-indanyl biaryl) diastereoisomer 1 | 623.8 |
| 76 | (MeO, F, iPr, methyl-indanyl biaryl) diastereoisomer 2 | 623.8 |
| 77 | (MeO, bis-indanyl) | 589.9 |

TABLE 4-continued

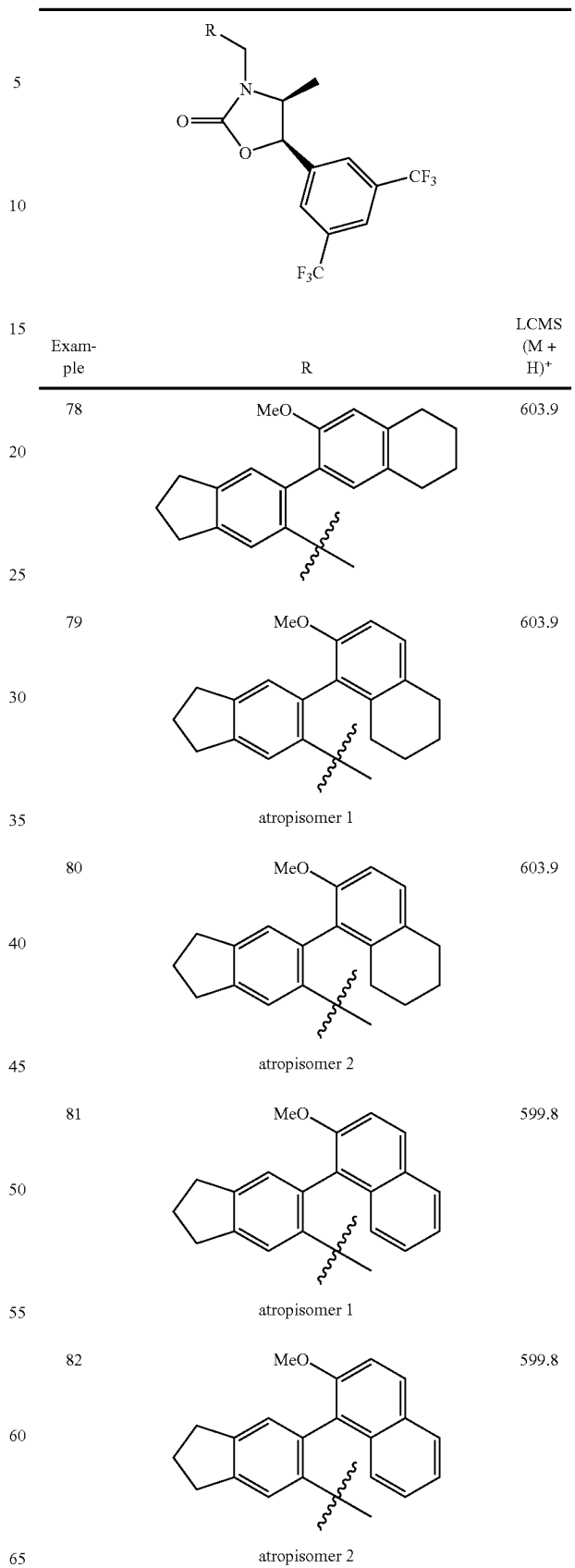

| Example | R | LCMS (M + H)+ |
|---|---|---|
| 78 | (MeO, tetrahydronaphthyl-indanyl) | 603.9 |
| 79 | (MeO, tetrahydronaphthyl-indanyl) atropisomer 1 | 603.9 |
| 80 | (MeO, tetrahydronaphthyl-indanyl) atropisomer 2 | 603.9 |
| 81 | (MeO, naphthyl-indanyl) atropisomer 1 | 599.8 |
| 82 | (MeO, naphthyl-indanyl) atropisomer 2 | 599.8 |

TABLE 4-continued

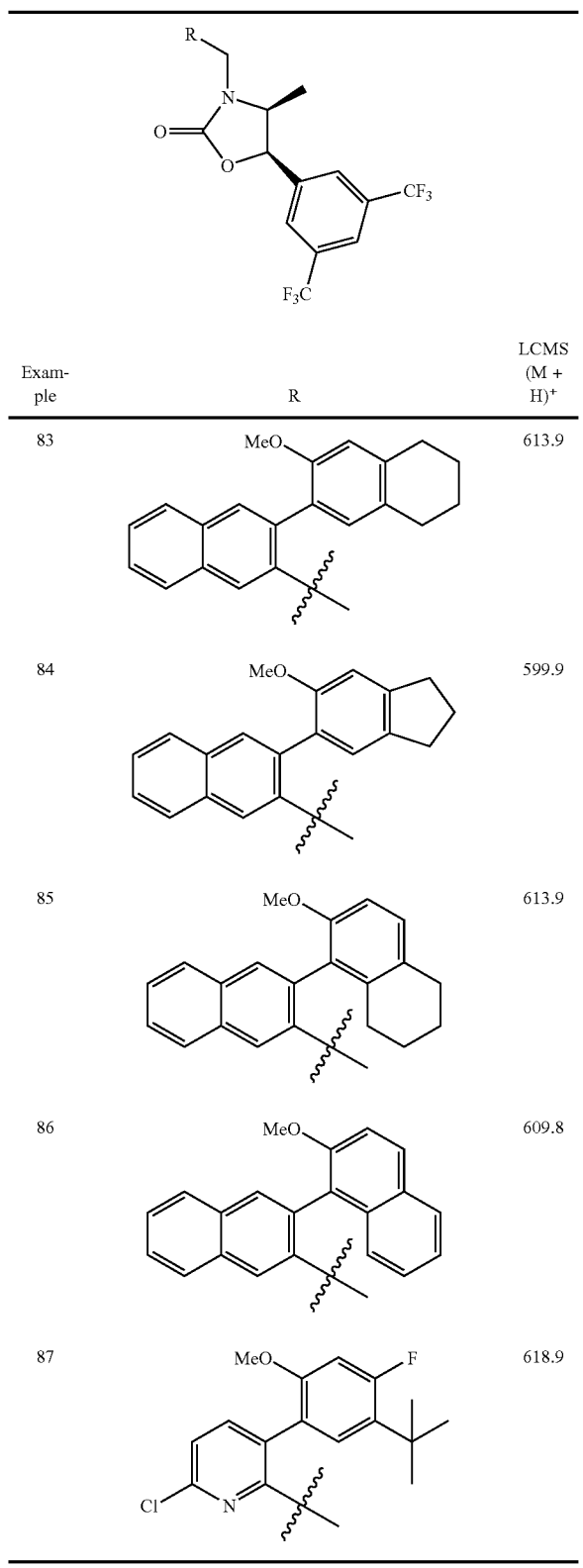

| Example | R | LCMS (M + H)+ |
|---|---|---|
| 83 | (MeO-tetrahydronaphthalene-naphthalene) | 613.9 |
| 84 | (MeO-indane-naphthalene) | 599.9 |
| 85 | (MeO-naphthalene-tetrahydronaphthalene) | 613.9 |
| 86 | (MeO-naphthalene-naphthalene) | 609.8 |
| 87 | (MeO, F, t-Bu-phenyl-chloropyridine) | 618.9 |

TABLE 5

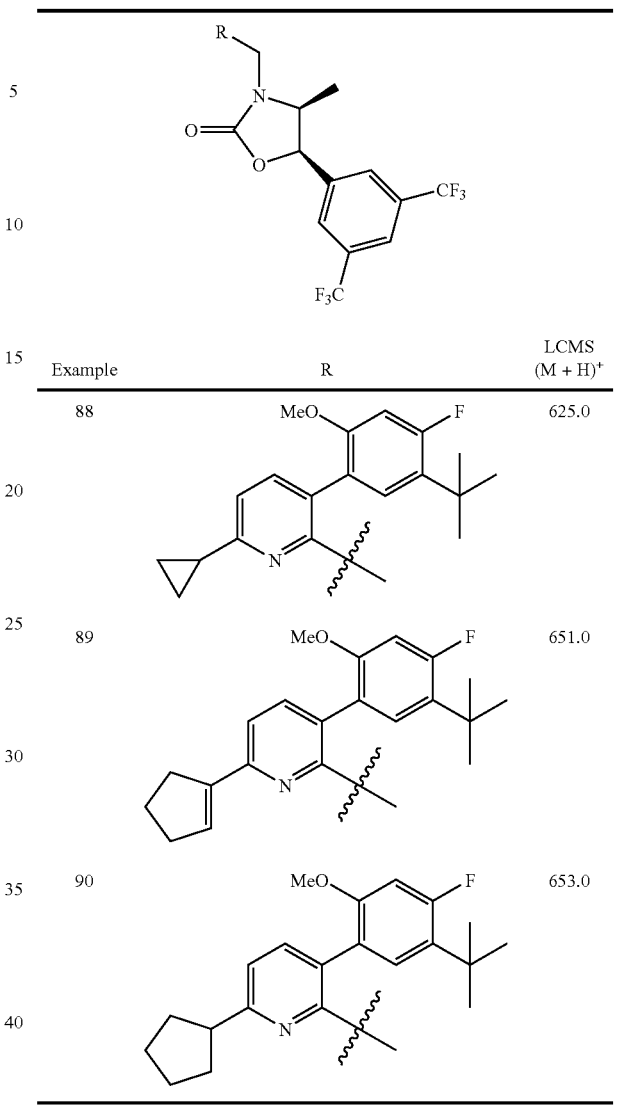

| Example | R | LCMS (M + H)+ |
|---|---|---|
| 88 | (MeO, F, t-Bu-phenyl-cyclopropylpyridine) | 625.0 |
| 89 | (MeO, F, t-Bu-phenyl-cyclopentenylpyridine) | 651.0 |
| 90 | (MeO, F, t-Bu-phenyl-cyclopentylpyridine) | 653.0 |

Following procedures analogous to those described in EXAMPLE 28 and/or EXAMPLE 29, the compounds listed in Table 5 were prepared from the corresponding aryl halide and alkyl or alkenyl boronic acid following by catalytic hydrogenation where required:

Example 91

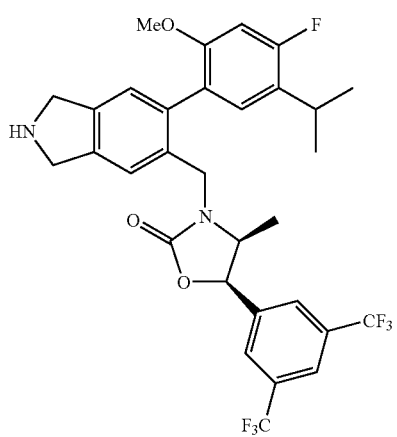

(4S,5R)-5-[3,5-Bis(trifluoromethyl)phenyl]-3-{[6-(4-fluoro-5-isopropyl-2-methoxyphenyl)-2,3-dihydro-1H-isoindol-5-yl]methyl}-4-methyl-1,3-oxazolidin-2-one To a solution of benzyl 5-({(4S,5R)-5-[3,5-bis(trifluoromethyl)phenyl]-4-methyl-2-oxo-1,3-oxazolidin-3-yl}methyl)-6-(4-fluoro-5-isopropyl-2-methoxyphenyl)-1,3-dihydro-2H-isoindole-2-carboxylate (12 mg, 0.016 mmol) in AcOH (0.5 mL) was added a catalytic amount of Pd/C (10%). The mixture was stirred at room temperature under a $H_2$ atmosphere for 2 h. The reaction mixture was filtered through Celite and the filtrate was adjusted to basic pH with sat. aq. $NaHCO_3$. The aqueous layer was extracted with EtOAc (3×). The combined organic layers were washed with brine (1×), dried ($Na_2SO_4$), filtered and concentrated in vacuo. The residue was purified by preparative reverse phase HPLC (C-18), eluting with MeCN/water. The fractions were collected and lyophilized to afford (4S,5R)-5-[3,5-bis(trifluoromethyl)phenyl]-3-{[6-(4-fluoro-5-isopropyl-2-methoxyphenyl)-2,3-dihydro-1H-isoindol-5-yl]methyl}-4-methyl-1,3-oxazolidin-2-one. LCMS calc.=611.2; found=610.8 $(M+H)^+$. $^1$H NMR (500 MHz, $CDCl_3$, 1:1 mixture of atropisomers): δ 7.87 (s, 1H); 7.70 (s, 2H); 7.42 (s, 0.5H); 7.33 (s, 0.5H); 7.14 (s, 0.5H); 7.13 (s, 0.5H); 7.04 (d, J=8.5 Hz, 0.5H); 7.00 (d, J=8.5 Hz, 0.5H); 6.70 (d, J=5.4 Hz, 0.5H); 6.67 (d, J=5.3 Hz, 0.5H); 5.57 (d, J=8.1 Hz, 0.5H); 5.39 (d, J=8.0 Hz, 0.5H); 4.85 (d, J=15.4 Hz, 0.5H); 4.81 (d, J=15.5 Hz, 0.5H); 4.33 (s, 4H); 4.08 (d, J=15.4 Hz, 0.5H); 3.83 (d, J=15.4 Hz, 0.5H); 3.78 (s, 3H); 3.86-3.75 (m, 1H); 3.26-3.18 (m, 1H); 2.61 (br s, 1H); 1.31-1.25 (m, 4H); 1.19 (d, J=6.9 Hz, 2H); 0.52 (d, J=6.5 Hz, 1.5H); 0.34 (d, J=6.5 Hz, 1.5H).

Example 92

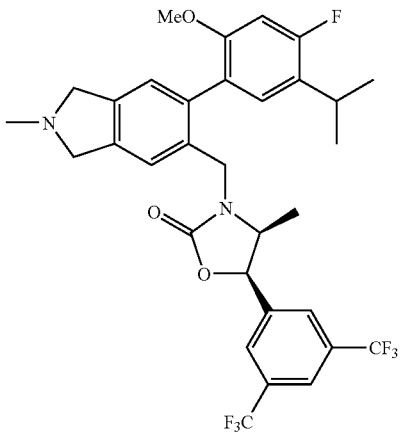

(4S,5R)-5-[3,5-Bis(trifluoromethyl)phenyl]-3-{[6-(4-fluoro-5-isopropyl-2-methoxyphenyl)-2-methyl-2,3-dihydro-1H-isoindol-5-yl]methyl}-4-methyl-1,3-oxazolidin-2-one To a solution of (4S,5R)-5-[3,5-bis(trifluoromethyl)phenyl]-3-{[6-(4-fluoro-5-isopropyl-2-methoxyphenyl)-2,3-dihydro-1H-isoindol-5-yl]methyl}-4-methyl-1,3-oxazolidin-2-one (8.3 mg, 0.0136 mmol) in MeOH (0.2 mL), was added $NaCNBH_3$ (1.0 mg, 0.0163 mmol), AcOH (3.85 uL, 0.068 mmol) and formaldehyde (38%) (1.3 uL, 0.0176 mmol). The resulting mixture was stirred at room temperature for 16 h. The reaction mixture was washed with sat. aq. $NaHCO_3$. The aqueous layer was extracted with EtOAc (2×). The combined organic layers were washed with brine (1×), dried ($Na_2SO_4$), filtered and concentrated in vacuo. The residue was purified by flash chromatography on silica gel to afford (4S,5R)-5-[3,5-bis(trifluoromethyl)phenyl]-3-{[6-(4-fluoro-5-isopropyl-2-methoxyphenyl)-2-methyl-2,3-dihydro-1H-isoindol-5-yl]methyl}-4-methyl-1,3-oxazolidin-2-one. LCMS calc. 625.2; found=624.9 $(M+H)^+$.

Example 93

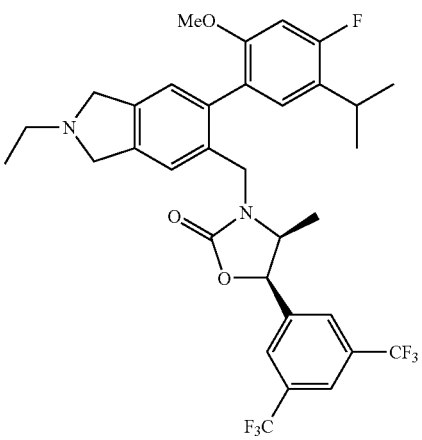

(4S,5R)-5-[3,5-Bis(trifluoromethyl)phenyl]-3-{[2-ethyl-6-(4-fluoro-5-isopropyl-2-methoxyphenyl)-2,3-dihydro-1H-isoindol-5-yl]methyl}-4-methyl-1,3-oxazolidin-2-one Following the procedure described for EXAMPLE 92, (4S,5R)-5-[3,5-bis(trifluoromethyl)phenyl]-3-{[2-ethyl-6-(4-fluoro-5-isopropyl-2-methoxyphenyl)-2,3-dihydro-1H-isoindol-5-yl]methyl}-4-methyl-1,3-oxazolidin-2-one was synthesized from (4S,5R)-5-[3,5-bis(trifluoromethyl)phenyl]-3-{[6-(4-fluoro-5-isopropyl-2-methoxyphenyl)-2,3-dihydro-1H-isoindol-5-yl]methyl}-4-methyl-1,3-oxazolidin-2-one and acetaldehyde. LCMS calc.=639.2; found 638.9 $(M+H)^+$.

INTERMEDIATE 30

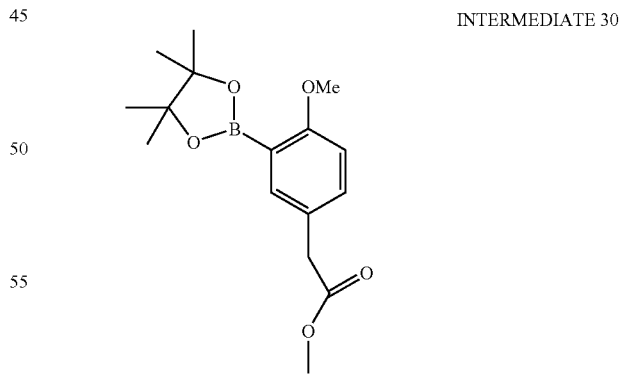

Methyl [4-methoxy-3-(4,4,5,5-tetramethyl-1,32-dioxaborolan-2-yl)phenyl]acetate

Step A: Methyl (3-iodo-4-methoxyphenyl)acetate

To a solution of methyl. (4-methoxyphenyl)acetate (1 mL, 6.3 mmol) in MeOH (40 mL) was added $Ag_2SO_4$ (1.96 g, 6.3 mmol) followed by 12 (1.6 g, 6.3 mmol). The reaction was stirred vigorously at room temperature for 1 hour and then the solids were removed by filtration. The filtrate was diluted with EtOAc (200 mL), and washed with aq. NaHSO$_3$ (2×50 mL) and brine (2×50 mL). The organic layer was dried (Na$_2$SO$_4$), filtered, and concentrated to afford methyl (3-iodo-4-methoxyphenyl)acetate. R$_f$=0.27 (15% EtOAc/hexanes). $^1$H NMR (500 MHz, CDCl$_3$): δ 7.68 (d, J=2.0 Hz, 1H), 7.21 (dd, J=8.2, 1.8 Hz, 1H), 6.76 (d, J=8.4 Hz, 1H), 3.85 (s, 3H), 3.68 (s, 3H), 3.52 (s, 2H).

Step B: Methyl [4-methoxy-3-(4,4,5,5-tetramethyl-1,3,2-dioxaborolan-2-yl)phenyl]acetate A roundbottom flask was charged with methyl (3-iodo-4-methoxyphenyl)acetate (503 mg, 1.64 mmol), bis(pinacolato)diboron (521 mg, 2.05 mmol), PdCl$_2$(dppf)CH$_2$Cl$_2$ (134 mg, 0.164 mmol), KOAc (322 mg, 3.28 mmol), and DMSO (23 mL). The reaction was degassed with N$_2$ and heated at 40° C. for 1 hour, 60° C. for 1 hour, and then 80° C. for 12 hours. The reaction was diluted with EtOAc (50 mL) and washed with water (3×25 mL) and brine (25 mL). The organic layer was dried (Na$_2$SO$_4$), filtered, and concentrated. Purification of the residue by flash chromatography on silica gel (0 to 80% EtOAc/hexanes) afforded methyl [4-methoxy-3-(4,4,5,5-tetramethyl-1,3,2-dioxaborolan-2-yl)phenyl]acetate. $^1$H NMR (500 MHz, CDCl$_3$): δ 7.55 (d, J=2.3 Hz, 1H), 7.32 (dd, J=8.5, 2.3 Hz, 1H), 6.82 (d, J=8.4 Hz, 1H), 3.82 (s, 3H), 3.67 (s, 3H), 3.56 (s, 2H), 1.35 (s, 12H).

INTERMEDIATE 31

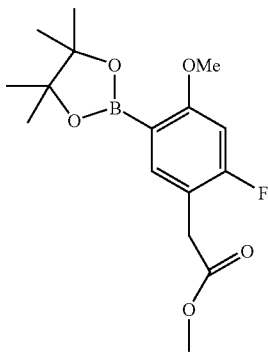

Methyl [2-fluoro-4-methoxy-5-(4,4,5,5-tetramethyl-1,3,2-dioxaborolan-2-yl)phenyl]acetate Step A: Methyl (2-fluoro-4-methoxyphenyl)acetate To a solution of (2-fluoro-4-methoxyphenyl)acetic acid (500 mg, 2.72 mmol) in toluene (20 mL) was added MeOH (3 mL) and TMS diazomethane (2.04 mL of a 2M solution in hexanes, 4.08 mmol). After 15 min, the reaction was quenched by the addition of HOAc (250 µL). The reaction was diluted with EtOAc (100 mL) and washed with saturated NaHCO$_3$ (2×25 mL) and brine (25 mL). The organic layer was dried (Na$_2$SO$_4$), filtered and concentrated. Purification of the residue by flash chromatography (0 to 25% EtOAc/hexanes) afforded methyl (2-fluoro-4-methoxyphenyl)acetate. $^1$H NMR (500 MHz, CDCl$_3$): δ 7.15 (t, J=8.6 Hz, 1H), 6.62-6.68 (m, 2H), 3.78 (s, 3H), 3.70 (s, 3H), 3.60 (s, 2H).

Methyl (2-fluoro-4-methoxyphenyl)acetate was processed as described above for INTERMEDIATE 30 to afford methyl [2-fluoro-4-methoxy-5-(4,4,5,5-tetramethyl-1,3,2-dioxaborolan-2-yl)phenyl]acetate.

INTERMEDIATE 32

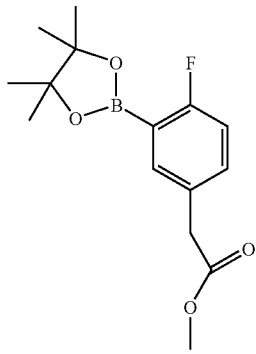

Methyl [4-fluoro-3-(4,4,5,5-tetramethyl-1,3,2-dioxaborolan-2-yl)phenyl]acetate

A roundbottom flask was charged with methyl (3-bromo-4-fluorophenyl)acetate (prepared from the corresponding acid by treatment with TMS diazomethane) (192.4 mg, 0.78 mmol), bis(pinacolato)diboron (247 mg, 0.973 mmol), bis(tricyclohexylphosphine) palladium (0) (52 mg, 0.078 mmol), KOAc (153 mg, 1.56 mmol), and dioxane (6 mL). The reaction was degassed with N$_2$ and heated at 80° C. for 2 hours. The reaction was diluted with EtOAc (50 mL) and washed with water (3×25 mL) and brine (25 mL). The organic layer was dried (Na$_2$SO$_4$), filtered, and concentrated. Purification of the reside by flash chromatography afforded methyl [4-fluoro-3-(4,4,5,5-tetramethyl-1,3,2-dioxaborolan-2-yl)phenyl]acetate. $^1$H NMR (500 MHz, CDCl$_3$): δ 7.61 (dd, J=5.7, 2.4 Hz, 1H), 7.35 (m, 1H), 6.99 (t, J=8.7 Hz, 1H), 3.69 (s, 3H), 3.60 (s, 2H), 1.36 (s, 12H).

INTERMEDIATE 33

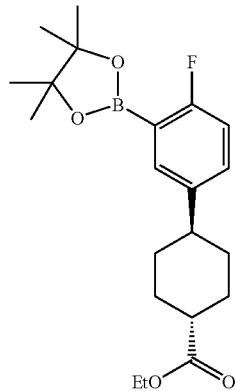

Ethyl trans-4-[4-fluoro-3-(4,4,5,5-tetramethyl-1,3,2-dioxaborolan-2-yl)phenyl]cyclohexanecarboxylate Step A: Ethyl 4-{[(trifluoromethyl)sulfonyl]oxy}cyclohex-3-ene-1-carboxylate To a −78° C. solution of ethyl 4-oxocyclohexanecarboxylate (500 µL, 3.14 mmol) in THF (17 mL) was added LiHMDS (3.93 mL of a 1M solution in THF, 3.93 mmol). After stirring for 1 hour at −78° C., 2-[N,N-bis(trifluormethyl-sulfonyl)amino]-5-chloropyridine (1.23 g, 3.14 mmol) in THF (7 mL) was added by cannula. The reaction was warmed to room temperature and stirred for 12 hours. The reaction was then poured into water (100 mL) and extracted with EtOAc/hexanes (150 mL, 2:1). The combined organics were washed with water (2×50 mL) and brine (2×50 mL), dried (Na$_2$SO$_4$), filtered, and concentrated. Purification of the residue by flash chromatography on silica gel (0 to 25% EtOAc/hexanes) afforded ethyl 4-{[(trifluoromethyl)sulfonyl]oxy}cyclohex-3-ene-1-carboxylate. $^1$H NMR (500 MHz, CDCl$_3$): δ 5.77 (m, 1H), 4.16 (q, J=7.1 Hz, 2H), 2.58 (m, 1H), 2.39-2.48 (m, 3H), 2.13 (m, 1H), 2.92 (m, 1H), 1.26 (t, J=7.1 Hz, 3H).

Step B: Ethyl 4-(3-chloro-4-fluorophenyl)cyclohex-3-ene-1-carboxylate

A flask was charged with (3-chloro-4-fluorophenyl)boronic acid (495 mg, 2.84 mmol), ethyl 4-{[(trifluoromethyl)sulfonyl]oxy}cyclohex-3-ene-1-carboxylate (686 mg, 2.27 mmol), Pd(PPh$_3$)$_4$ (262 mg, 0.227 mmol), 1M Na$_2$CO$_3$ (6.81 mL, 6.81 mmol), EtOH (2.8 mL), and DME (8.6 mL). The reaction was degassed with N$_2$, the flask was sealed, and the reaction was heated to 100° C. for 2 hours. The reaction was then cooled to room temperature and diluted with hexanes (100 mL) and EtOAc (20 mL). The mixture was washed with water (2×25 mL) and brine (2×25 mL), and the organic layer was dried (Na$_2$SO$_4$), filtered, and concentrated. Purification of the residue by flash chromatography on silica gel (0 to 10% EtOAc/hexanes) afforded ethyl 4-(3-chloro-4-fluorophenyl)cyclohex-3-ene-1-carboxylate. R$_f$=0.25 (5% EtOAc/hexanes). $^1$H NMR (500 MHz, CDCl$_3$): δ 7.37 (dd, J=7.1, 2.3 Hz, 1H), 7.20 (m, 1H), 7.05 (t, J=8.8 Hz, 1H), 6.05 (s, 1H), 4.16 (q, J=7.1 Hz, 2H), 2.36-2.62 (m, 4H), 2.17 (m, 1H), 1.84 (m, 1H), 1.27 (t, J=7.1 Hz, 3H).

Step C: Ethyl trans-4-(3-chloro-4-fluorophenyl)cyclohexanecarboxylate

To a solution of ethyl 4-(3-chloro-4-fluorophenyl)cyclohex-3-ene-1-carboxylate (270 mg, 0.955-mmoL) in EtOAc (15 mL) was added 10% Pd/C (45 mg). The reaction was put under an atmosphere of H$_2$ (balloon) and stirred vigorously at room temperature. After 30 min, the catalyst was removed by filtration, and the filtrate was concentrated to afford a mixture of cis and trans products. The desired trans isomer was separated by flash chromatography on silica gel (0 to 10% EtOAc/hexanes) to afford ethyl trans-4-(3-chloro-4-fluorophenyl)cyclohexanecarboxylate. R$_f$=0.25 (5% EtOAc/hexanes). $^1$H NMR (500 MHz, CDCl$_3$): δ 7.21 (d, J=7.3 Hz, 1H), 7.02-7.06 (m, 2H), 4-14 (q, J=7.1 Hz, 2H), 2.48 (m, 1H), 2.32 (m, 1H), 2.08-2.12 (m, 2H), 1.91-1.98 (m, 2H), 1.53-1.67 (m, 2H), 1.37-1.46 (m, 2H), 1.27 (t, J=7.1 Hz, 3H).

Ethyl trans-4-(3-chloro-4-fluorophenyl)cyclohexanecarboxylate was processed as described above for INTERMEDIATE 32 to afford ethyl trans-4-[4-fluoro-3-(4,4,5,5-tetramethyl-1,3,2-dioxaborolan-2-yl)phenyl]cyclohexanecarboxylate.

INTERMEDIATE 34

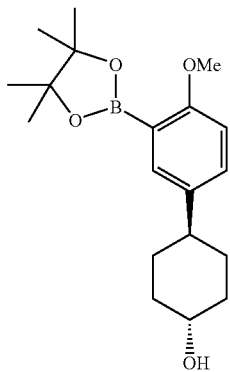

trans-4-[4-Methoxy-3-(4,4,5,5-tetramethyl-1,3,2-dioxaborolan-2-yl)phenyl]cyclohexanol Step A: 1,4-Dioxaspiro[4.5]dec-7-en-8-yl trifluoromethanesulfonate To a −78° C. solution of 1,4-dioxaspiro[4.5]decan-8-one (1.5 g, 9.6 mmol) in THF (50 mL) was added LiHMDS (11.1 mL of a 1M solution in THF, 11.1 mmol). After stirring for 1 hour at −78° C., 2-[N,N-bis(trifluormethyl-sulfonyl)amino]-5-chloropyridine (3.8 g, 9.6 mmol) in THF (20 mL) was added by cannula. The reaction was warmed to room temperature and stirred for 12 hours. The reaction was then poured into water (100 mL) and extracted with EtOAc (100 mL). The organic layer was washed with water (2×50 mL) and brine (2×50 mL), dried (Na$_2$SO$_4$), filtered, and concentrated. Purification of the residue by flash chromatography on silica gel (5 to 30% EtOAc/hexanes) afforded 1,4-dioxaspiro[4.5]dec-7-en-8-yl trifluoromethanesulfonate. $^1$H NMR (500 MHz, CDCl$_3$): δ 5.66 (m, 1H), 3.96-4.01 (m, 4H), 2.51-2.55 (m, 2H), 2.39-2.41 (m, 2H), 1.90 (t, J=6.6 Hz, 2H).

Step B:
8-(4-Methoxyphenyl)-1,4-dioxaspiro[4.5]dec-7-ene

A flask was charged with (4-methoxyphenyl)boronic acid (515 mg, 3.39 mmol), 1,4-dioxaspiro[4.5]dec-7-en-8-yl trifluoromethanesulfonate (780 mg, 2.71 mmol), 1,1'-bis(di-t-butylphosphino)ferrocene palladium dichloride (35 mg, 0.054 mmol), 1M K$_2$CO$_3$ (10 mL, 10 mmol), and THF (10 mL). The reaction was degassed with N$_2$ and heated to 50° C. for 16 hours. The reaction was cooled to room temperature and diluted with EtOAc (100 mL). The mixture was washed with water (2×25 mL) and brine (2×25 mL), and the organic layer was dried (Na$_2$SO$_4$), filtered, and concentrated. Purification of the residue by flash chromatography on silica gel (5 to 40% EtOAc/hexanes) afforded 8-(4-methoxyphenyl)-1,4-dioxaspiro[4.5]dec-7-ene. R$_f$=0.20 (25% EtOAc/hexanes). $^1$H NMR (500 MHz, CDCl$_3$): δ 7.31-7.34 (m, 2H), 6.82-6.85 (m, 2H), 5.90 (m, 1H), 4.02 (s, 4H), 3.80 (s, 3H), 2.62-2.66 (m, 2H), 2.45-2.46 (m, 2H), 1.92 (t, J=6.5 Hz, 2H).

Step C:
8-(4-Methoxyphenyl)-1,4-dioxaspiro[4.5]decane

To a solution of 8-(4-methoxyphenyl)-1,4-dioxaspiro[4.5]dec-7-ene (526.8 mg, 2.14 mmoL) in EtOH (20 mL) was added 10% Pd/C (50 mg). The reaction was put under an atmosphere of H$_2$ (balloon) and stirred vigorously at room temperature. After 1.5 hours, the catalyst was removed by filtration. The filtrate was concentrated to afford 8-(4-methoxyphenyl)-1,4-dioxaspiro[4.5]decane. $^1$H NMR (500 MHz, CDCl$_3$): δ 7.14-7.17 (m, 2H), 6.82-6.85 (m, 2H), 3.98 (s, 4H), 3.79 (s, 3H), 2.52 (m, 1H), 1.64-1.86 (m, 8H).

Step D: 4-(4-Methoxyphenyl)cyclohexanone

To a solution of 8-(4-methoxyphenyl)-1,4-dioxaspiro[4.5]decane (590 mg, 2.38 mmol) in THF (20 mL) was added 6N HCl (1.2 mL). The reaction was stirred at room temperature for 4 hours and then diluted with EtOAc (50 mL) and washed with water (2×40 mL) and saturated NaHCO$_3$/brine (2×40 mL, 1:1). The organic layer was dried (Na$_2$SO$_4$), filtered, and concentrated. Purification of the residue by flash chromatography on silica gel (0 to 25% EtOAc/hexanes) afforded 4-(4-methoxyphenyl)cyclohexanone. $^1$H NMR (600 MHz, CDCl$_3$) δ 7.15-7.18 (m, 2H), 6.85-6.88 (m, 2H), 3.80 (s, 3H), 2.99 (m, 1H), 2.46-2.54 (m, 4H), 2.17-2.22 (m, 2H), 1.87-1.95 (m, 2H).

Step E: trans-4-(4-Methoxyphenyl)cyclohexanol 4-(4-Methoxyphenyl)cyclohexanone (400 mg, 1.958 mmol) was dissolved in MeOH (20 mL) and cooled to 0° C. NaBH$_4$ (222 mg, 5.87 mmol) was added, and the reaction was stirred at 0° C. for 30 min. The reaction was then quenched with 5 mL of water, stirred for 5 min, and then diluted with EtOAc (50 mL). The organic layer was washed with water (3×50 mL) and brine (50 mL), dried (Na$_2$SO$_4$), filtered, and concentrated. The residue was purified by flash chromatography on silica gel (0 to 70% EtOAc/hexanes) to afford trans-4-(4-methoxyphenyl)cyclohexanol. $^1$H NMR (500 MHz, CDCl$_3$): δ 7.12 (d, J=8.5 Hz, 2H), 6.84 (d, J=8.7 Hz, 2H), 3.79 (s, 3H), 3.68 (m, 1H), 2.46 (m, 1H), 2.07-2.12 (m, 2H), 1.86-1.94 (m, 3H), 1.38-1.54 (m, 4H).

trans-4-(4-Methoxyphenyl)cyclohexanol was processed as described above for INTERMEDIATE 30 to afford trans-4-[4-methoxy-3-(4,4,5,5-tetramethyl-1,3,2-dioxaborolan-2-yl)phenyl]cyclohexanol.

INTERMEDIATE 35

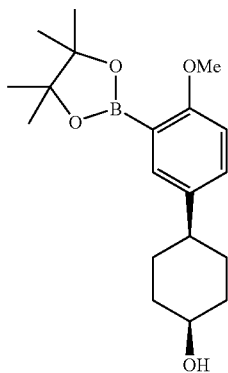

cis-4-[4-Methoxy-3-(4,4,5,5-tetramethyl-1,3,2-dioxaborolan-2-yl)phenyl]cyclohexanol

Step A: cis-4-(4-Methoxyphenyl)cyclohexanol

To a −78° C. solution of 4-(4-methoxyphenyl)cyclohexanone (456.7 mg, 2.24 mmol) (prepared as described above in INTERMEDIATE 34) in THF (22 mL) was added L-Selectride (6.71 ml of a 1M solution in THF, 6.71 mmol). The reaction was allowed to warm to 0° C. over 3 hours. The reaction was then quenched with 3 mL of acetone added dropwise and 7.5 mL of H$_2$O at 0° C. Next 3 mL of 30% H$_2$O$_2$ was added in a slow, dropwise manner. This mixture was stirred at 0° C. for 5 min and then diluted with EtOAc (50 mL). The organic layer was washed with water (2×25 mL) and brine (25 mL), dried (Na$_2$SO$_4$), filtered, and concentrated. The residue was purified by flash chromatography on silica gel (0 to 70% EtOAc/hexanes) to afford cis-4-(4-methoxyphenyl)cyclohexanol. $^1$H NMR (500 MHz, CDCl$_3$): δ 7.16 (d, J=8.7 Hz, 2H), 6.85 (d, J=8.5 Hz, 2H), 4.12 (bs, 1H), 3.79 (s, 3H), 2.50 (m, 1H), 1.62-1.90 (m, 8H).

cis-4-(4-Methoxyphenyl)cyclohexanol was processed as described above for INTERMEDIATE 30 to afford cis-4-[4-methoxy-3-(4,4,5,5-tetramethyl-1,3,2-dioxaborolan-2-yl)phenyl]cyclohexanol.

INTERMEDIATE 36

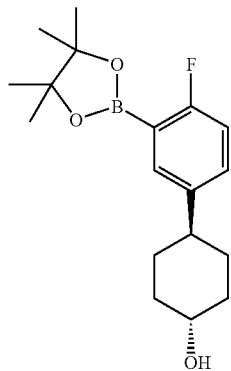

trans-4-[4-Fluoro-3-(4,4,5,5-tetramethyl-1,3,2-dioxaborolan-2-yl)phenyl]cyclohexanol

Step A: 4-(3-Chloro-4-fluorophenyl)cyclohexanone 8-(3-chloro-4-fluorophenyl)-1,4-dioxaspiro[4.5]decane was prepared using methods described above for INTERMEDIATES 33 and 34.

To a solution of 8-(3-chloro-4-fluorophenyl)-1,4-dioxaspiro[4.5]decane (401.7 mg, 1.484 mmol) in acetone (6 ml) was added 1M sulfuric acid (24 ml, 24 mmol). The reaction was stirred vigorously at room temperature for 18 hours, and then diluted with EtOAc (100 mL) and washed with water (3×50 mL), saturated NaHCO$_3$ (2×50 mL), and brine (2×50 mL). The organic layer was dried (Na$_2$SO$_4$), filtered, and concentrated to afford 4-(3-chloro-4-fluorophenyl)cyclohexanone. $^1$H NMR (500 MHz, CDCl$_3$): δ 7.06-7.28 (m, 3H), 3.00 (m, 1H), 2.49-2.52 (m, 4H), 2.19-2.23 (m, 2H), 1.85-1.93 (m, 2H).

4-(3-chloro-4-fluorophenyl)cyclohexanone was processed as described above in INTERMEDIATES 34 and 32 to afford trans-4-[4-fluoro-3-(4,4,5,5-tetramethyl-1,3,2-dioxaborolan-2-yl)phenyl]cyclohexanol.

Example 94

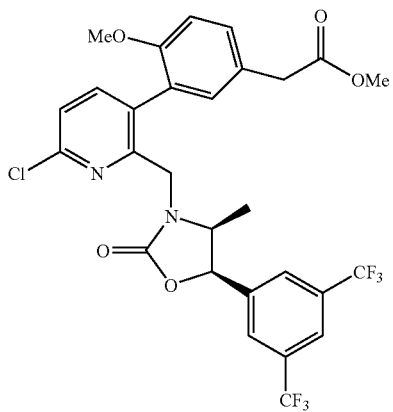

Methyl {3-[2-({(4S,5R)-5-[3,5-bis(trifluoromethyl)phenyl]-4-methyl-2-oxo-1,3-oxazolidin-3-yl}methyl)-6-chloropyridin-3-yl]-4-methoxyphenyl}acetate A flask was charged with (4S,5R)-5-[3,5-bis(trifluoromethyl)phenyl]-3-[(3-bromo-6-chloropyridin-2-yl)methyl]-4-methyl-1,3-oxazolidin-2-one (265 mg, 0.511 mmol), methyl [4-methoxy-3-(4,4,5,5-tetramethyl-1,3,2-dioxaborolan-2-yl)phenyl]acetate (156.6 mg, 0.511 mmol), 1M $K_2CO_3$ (4 mL, 4 mmol), and THF (4 mL). The reaction was degassed with $N_2$ and then 1,1'-bis(di-t-butylphosphino)ferrocene palladium dichloride (16.7 mg, 0.026 mmol) was added while the reaction was stirred vigorously. Vigorous stirring was continued for 15 min at room temperature, and then the reaction was diluted with EtOAc (40 mL) and washed with water and brine (20 mL each). The organic layer was dried ($Na_2SO_4$), filtered, and concentrated. The residue was purified by flash chromatography on silica gel (0 to 70% EtOAc/hexanes) to afford methyl {3-[2-({(4S,5R)-5-[3,5-bis(trifluoromethyl)phenyl]-4-methyl-2-oxo-1,3-oxazolidin-3-yl}methyl)-6-chloropyridin-3-yl]-4-methoxyphenyl}acetate. $R_f$=0.21 (25% EtOAc/hexanes). LCMS=617.4 (M+H)$^+$. $^1$H NMR (500 MHz, CDCl$_3$): δ 6.92-7.83 (m, 8H), 4.88-5.68 (m, 2H), 3.58-4.19 (m, 10H), 0.63 (s, 3H).

In a similar manner, using the boronic esters described above, the following examples in Table 6 were synthesized:

TABLE 6

| Example | Structure | LCMS (M + H)$^+$ |
|---|---|---|
| 95 | | 635.4 |
| 96 | | 605.3 |
| 97 | 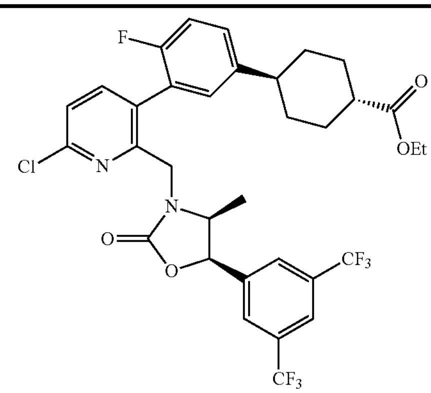 | 687.3 |
| 98 | 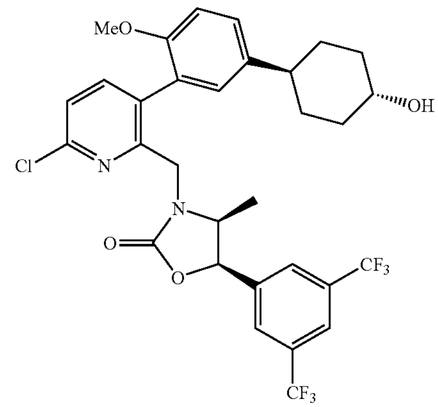 | 643.4 |
| 99 | 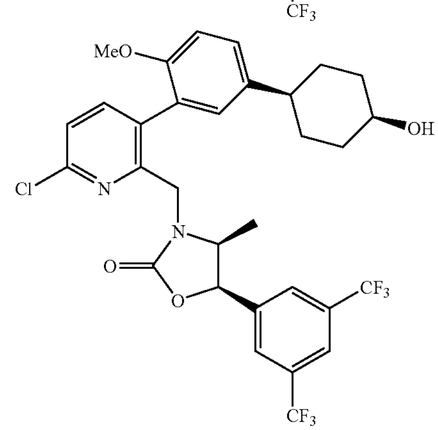 | 643.4 |
| 100 | 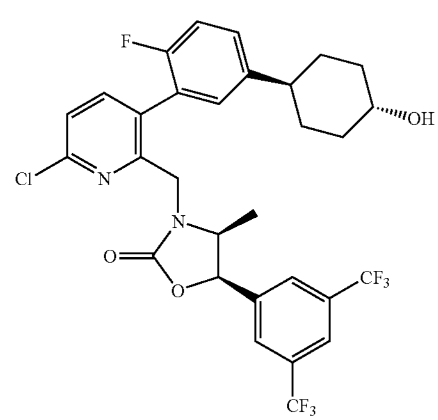 | 631.2 |

Example 101

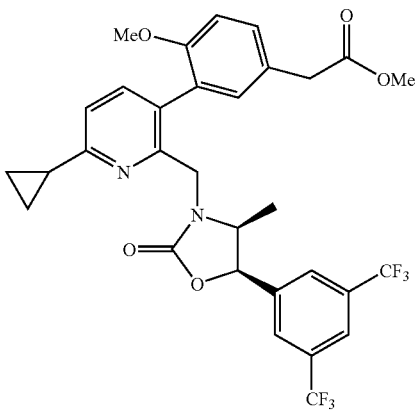

Methyl {3-[2-({(4S,5R)-5-[3,5-bis(trifluoromethyl)phenyl]-4-methyl-2-oxo-1,3-oxazolidin-3-yl}methyl)-6-cyclopropylpyridin-3-yl]-4-methoxyphenyl}acetate A flask was charged with methyl {3-[2-({(4S,5R)-5-[3,5-bis(trifluoromethyl)phenyl]-4-methyl-2-oxo-1,3-oxazolidin-3-yl}methyl)-6-chloropyridin-3-yl]-4-methoxyphenyl}acetate (42 mg, 0.0681 mmol), cyclopropyl boronic acid (58.5 mg, 0.681 mmol), 1,1'-bis(di-t-butylphosphino)ferrocene palladium dichloride (8.9 mg, 0.014 mmol), THF (1 mL), and 1M $K_2CO_3$ (1 mL, 1 mmol). The reaction was degassed with $N_2$, and heated to 60° C. for 8 hours. The reaction was then cooled to room temperature, diluted with EtOAc (35 mL) and washed with water and brine (10 mL each). The organic layer was dried ($Na_2SO_4$), filtered, and concentrated. Purification of the residue by flash chromatography (0 to 70% EtOAc/hexanes) afforded methyl {3-[2-({(4S,5R)-5-[3,5-bis(trifluoromethyl)phenyl]-4-methyl-2-oxo-1,3-oxazolidin-3-yl}methyl)-6-cyclopropylpyridin-3-yl]-4-methoxyphenyl}acetate. LCMS=623-4 (M+H)$^+$. $^1$H NMR (500 MHz, $CDCl_3$): δ 6.90-7.84 (m, 8H), 4.82-5.66 (m, 2H), 3.57-4.13 (m, 10H), 2.06 (m, 1H), 1.00-1.06 (m, 4H), 0.62 (bs, 3H).

In a similar manner the following examples in Table 7 were synthesized:

TABLE 7

| Example | Structure | LCMS (M + H)$^+$ |
|---------|-----------|------------------|
| 102 | | 641.4 |
| 103 | 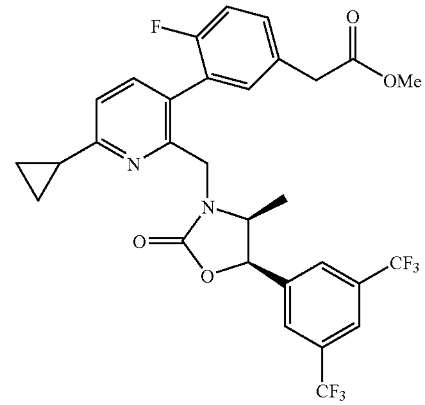 | 611.4 |
| 104 | 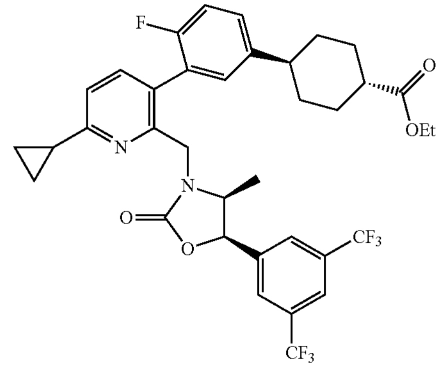 | 693.3 |
| 105 | 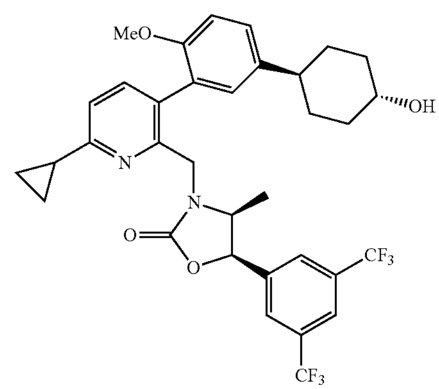 | 649.4 |
| 106 | 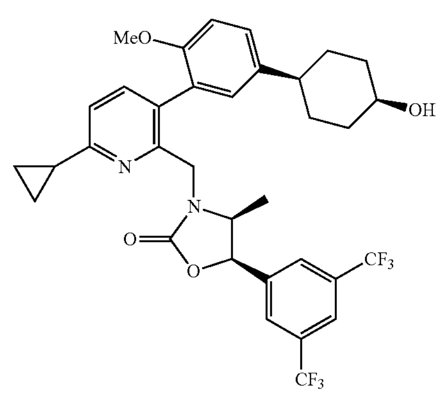 | 649.4 |

TABLE 7-continued

| Example | Structure | LCMS (M + H)+ |
|---|---|---|
| 107 | 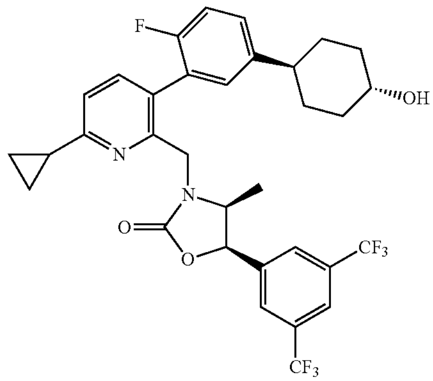 | 637.3 |

Example 108

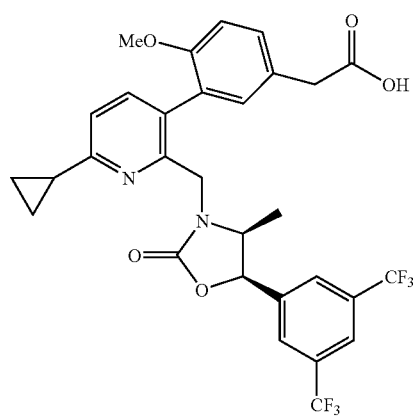

{3-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4-methoxyphenyl}acetic acid To a solution of methyl {3-[2-({(4S,5R)-5-[3,5-bis(trifluoromethyl)phenyl]-4-methyl-2-oxo-1,3-oxazolidin-3-yl}methyl)-6-cyclopropylpyridin-3-yl]-4-methoxyphenyl}acetate (43 mg, 0.069 mmol) in MeOH (4 mL) was added 4M KOH (200 µL, 0.8 mmol). The reaction was stirred at room temperature for 4 hours and then quenched with HOAc (75 µL), diluted with EtOAc (30 µL), and washed with water and brine (10 mL each). The organic layer was dried ($Na_2SO_4$), filtered, and concentrated. Purification of the residue by flash chromatography on silica gel (0 to 100% EtOAc/hexanes) afforded {3-[2-({(4S,5R)-5-[3,5-bis(trifluoromethyl)phenyl]-4-methyl-2-oxo-1,3-oxazolidin-3-yl}methyl)-6-cyclopropylpyridin-3-yl]-4-methoxyphenyl}acetic acid. LCMS=609.4 (M+H)+. $^1$H NMR (500 MHz, $CDCl_3$): δ 7.84 (s, 1H), 7.72 (s, 2H), 7.39 (d, J=7.8 Hz, 1H), 7.27 (m, 1H), 7.14 (d, J=7.8 Hz, 1H), 7.07 (bs, 1H), 6.93 (d, J=8.5 Hz, 1H), 5.53 (bs, 1H), 4.85 (d, J=16.0 Hz, 1H), 3.86-4.20 (m, 2H), 3.78 (s, 3H), 3.61 (s, 2H), 2.07 (m, 1H), 1.00-1.10 (m, 4H), 0.54-0.70 (m, 3H).

In a similar manner the following examples in Table 8 were synthesized:

TABLE 8

| Example | Structure | LCMS (M + H)+ |
|---|---|---|
| 109 | 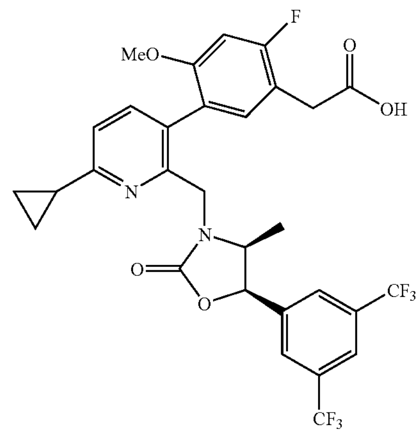 | 627.5 |
| 110 | 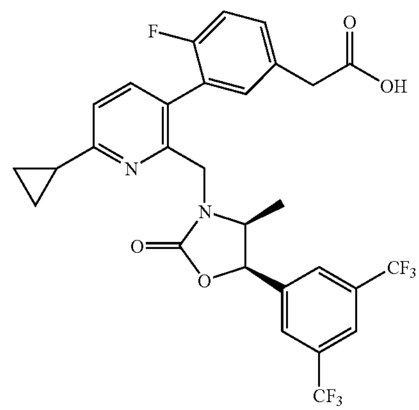 | 597.4 |
| 111 | 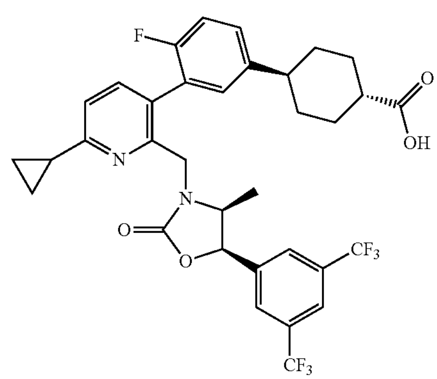 | 665.3 |

Example 112

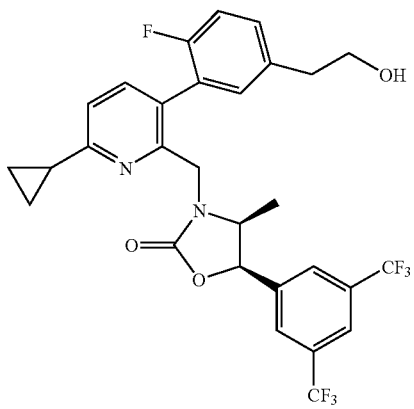

(4S,5R)-5-[3,5-Bis(trifluoromethyl)phenyl]-3-({6-cyclopropyl-3-[2-fluoro-5-(2-hydroxyethyl)phenyl]pyridin-2-yl}methyl)-4-methyl-1,3-oxazolidin-2-one To a solution of {3-[2-({(4S,5R)-5-[3,5-bis(trifluoromethyl)phenyl]-4-methyl-2-oxo-1,3-oxazolidin-3-yl}methyl)-6-cyclopropylpyridin-3-yl]-4-fluorophenyl}acetic acid (32.8 mg, 0.055 mmol) in THF (2 mL) was added BH$_3$ (0.22 mL of a 1M solution in THF, 0.22 mmol). The reaction was stirred at room temperature for 1 hour and then quenched with water (2 mL). The reaction was diluted with EtOAc (35 mL) and washed with water and brine (10 mL each). The organic layer was dried (Na$_2$SO$_4$), filtered, and concentrated. Purification of the residue by flash chromatography on silica gel (0 to 100% EtOAc/hexanes) afforded (4S,5R)-5-[3,5-bis(trifluoromethyl)phenyl]-3-({6-cyclopropyl-3-[2-fluoro-5-(2-hydroxyethyl)phenyl]pyridin-2-yl}methyl)-4-methyl-1,3-oxazolidin-2-one. $R_f$=0.44 (25% EtOAc/hexanes). LCMS=583.4 (M+H)$^+$ $^1$H NMR (500 MHz, CDCl$_3$): δ 7.85 (s, 1H), 7.69 (s, 2H), 7.48 (d, J=7.8 Hz, 1H), 7.08-7.27 (m, 4H), 5.55 (d, J=7.8 Hz, 1H), 4.93 (bs, 1H), 3.82-4.10 (m, 4H), 2.85 (t, J=5.8 Hz, 2H), 2.08 (m, 1H), 1.02-1.06 (m, 4H), 0.71 (d, J=6.7 Hz, 3H).

INTERMEDIATE 37

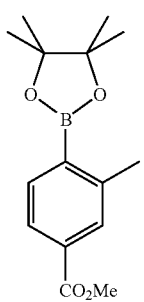

Methyl 3-methyl-4-(4,4,5,5-tetramethyl-1,3,2-dioxaborolan-2-yl)benzoate

A roundbottom flask was charged with methyl 4-bromo-3-methylbenzoate (200 mg, 0.878 mmol), bis(pinacolato)diboron (277 mg, 1.089 mmol), PdCl$_2$(dppf)CH$_2$Cl$_2$ (70 mg, 0.0873 mmol), KOAc (171 mg, 1.75 mmol), and DMSO (10 mL). The reaction was degassed with N$_2$ and heated at 40° C. for 1 h, 60° C. for 1 h, and then 80° C. for 12 h. The reaction was diluted with EtOAc (25 mL) and hexanes (75 mL) and the organics were washed with water (2×25 mL) and brine (50 mL). The organic layer was dried (Na$_2$SO$_4$), filtered, and concentrated. Purification of the residue by flash chromatography on silica gel (0 to 15% EtOAc/hexanes) afforded methyl 3-methyl-4-(4,4,5,5-tetramethyl-1,3,2-dioxaborolan-2-yl)benzoate. $^1$H NMR (500 MHz, CDCl$_3$): δ 7.82 (s, 1H), 7.80 (s, 2H), 3.91 (s, 3H), 2.57 (s, 3H), 1.35 (s, 12H).

INTERMEDIATE 38

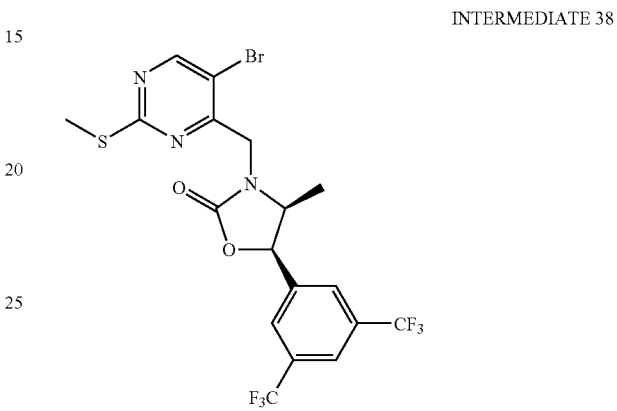

(4S,5R)-5-[3,5-Bis(trifluoromethyl)phenyl]-3-{[5-bromo-2-(methylthio)pyrimidin-4-yl]methyl}-4-methyl-1,3-oxazolidin-2-one

Step A: Methyl 5-bromo-2-(methylthio)pyrimidine-4-carboxylate 5-bromo-2-(methylthio)pyrimidine-4-carboxylic acid (2 g, 8.03 mmol) was stirred in MeOH (40 mL) at room temperature. To this stirred mixture was added (trimethylsilyl)diazomethane (12.04 mL, 2M, 24-09 mmol). LCMS of aliquot taken immediately after addition indicated there was still unreacted starting acid. Added more (trimethylsilyl)diazomethane (6 mL, 2 M, 12 mmol). LCMS indicated completion of reaction. The reaction was quenched adding about 0.5 mL of TFA into the crude mixture. Volatiles were removed under reduced pressure. The resulting crude mixture was purified by flash chromatography (SiO$_2$, Biotage 40M cartridge). The column was eluted with a EtOAc/hexanes gradient mixture (0% to 30%). Related fraction were pooled and evaporated to afford a colorless crystalline solid as the titled compound. LCMS calc.=263.94; found=264.79.

Step B: [5-Bromo-2-(methylthio)pyrimidin-4-yl]methanol

To a cold (−10° C.~0° C.) THF (19.00 mL) solution of methyl 5-bromo-2-(methylthio)pyrimidine-4-carboxylate (Step A, 1 g, 3.80 mmol) was added diisobutylaluminum hydride (1M, 9.50 mL, 9.50 mmol) while internal temperature was below 0° C. An aliquot taken immediately after addition indicated completion of reaction. The crude mixture was quenched with NH$_4$Cl (aq.). Volatiles were removed under reduced pressure. The resulting pot residue was worked up with brine, extracted with EtOAc, dried (Na$_2$SO$_4$), filtered and evaporated to afford a dark mixture. The dark residue was purified by preparative HPLC (Kromasil 100-5C18, 100× 21.1 mm) eluting with MeCN/water+0.1% TFA (10% to 80% organic in 10 min, then to 100% in 2 min). Related fractions were pooled and evaporated in vacuo to afford an aqueous mixture. The resulting mixture was extracted with EtOAc and washed with aqueous NaHCO$_3$, dried (Na$_2$SO$_4$), filtered and concentrated to afford a brown oil. After further drying under reduced pressure, this oil solidified to a crystalline solid. LCMS calc.=235.94; found=236.88.

Alternate Route to
[5-bromo-2-(methylthio)pyrimidin-4-yl]methanol

A mixture of DMF (1.554 mL, 20.07 mmol) and CH$_2$Cl$_2$ (49.9 mL) was cooled at 0° C. To this cold mixture was added oxalyl chloride (5.01 mL, 57.2 mmol). The resulting mixture was stirred cold (0° C.) for an additional 1 h. Volatiles were removed under reduced pressure to give a pale white solid, which was suspended in a mixture of THF (49.9 mL) and MeCN (49.9 mL). The resulting mixture was cooled in an ice bath. To this cold mixture was added 5-bromo-2-(methylthio) pyrimidine-4-carboxylic acid (5 g, 20.07 mmol) in portions in the course of 1 h. The resulting mixture was aged at 0° C. for additional 30 min before cooling to −78° C. NaBH$_4$ (10.04 mL, 20.07 mmol) (2M in triethylene glycol dimethyl ether) was added into this cold mixture in 40 min. The reaction mixture was stirred cold for 2 h then allowed to warm up in a MeOH/ice bath for another 1 h before quenching with HCl (1N). The reaction crude was allowed to stand overnight at ambient temp. Volatiles were removed under reduced pressure. The resulting mixture was basified by NaOH (1N, aq.). The separated aqueous layer was back extracted with EtOAc. The combined organic extracts were dried (Na$_2$SO$_4$), filtered and evaporated to afford an amber, viscous liquor. This amber gel was purified by flash chromatography (SiO$_2$, Biotage 65i cartridge). The column was eluted with a EtOAc/hexanes gradient mixture (0% to 20%). All related fractions were pooled and evaporated to give a white crystalline solid as the titled compound. LCMS calc.=235.94; found=236.88.

Step C:
5-Bromo-4-(bromomethyl)-2-(methylthio)pyrimidine

To a cold (0° C.) solution of [5-bromo-2-(methylthio)pyrimidin-4-yl]methanol (Step 13, 2.20 g, 9.34 mmol) in CH$_2$Cl$_2$ (46.7 mL) was added triphenylphosphine (3.19 g, 12.14 mmol) followed by carbon tetrabromide (4.03 g, 12.14 mmol). The resulting mixture was stirred cold for 1 h. LCMS trace of the aliquot indicated completion of reaction. Volatiles were removed under reduced pressure. Half of the crude material was purified by flash chromatography (SiO$_2$, Biotage 40M cartridge). The column was eluted with an isocratic acetone/hexanes mixture (2.5%, v/v). No purification was obtained. All fractions and reaction crude were combined and purified by preparative HPLC (Kromasil 100-5C18, 100× 21.1 mm) eluting with MeCN/water+0.1% TFA (51% to 62% organic in 10 min, hold 62% for 2 min, 20 mL/min). Related fractions were combined and evaporated under reduced pressure. The desired compound azeotroped with the water and was extracted with EtOAc, washed with brine, dried (Na$_2$SO$_4$), filtered and concentrated to afford a light brown oil as the titled compound. LCMS calc.=297.86; found=298.87.

Step D: (4S,5R)-5-[3,5-Bis(trifluoromethyl)phenyl]-3-{[5-bromo-2-(methylthio)pyrimidin-4-yl]methyl}-4-methyl-1,3-oxazolidin-2-one (4S,5R)-5-[3,5-Bis(trifluoromethyl)phenyl]-4-methyl-1,3-oxazolidin-2-one (INTERMEDIATE 1, 326 mg, 1.041 mmol) was dissolved in THF (7 mL) and cooled in an ice bath. To this solution was added NaH (27.3 mg, 1.136 mmol) all at once. The resulting bubbling/foaming mixture was stirred in an ice bath for 1 h followed by addition of 5-bromo-4-(bromomethyl)-2-(methylthio)pyrimidine (Step C, 282 mg, 0.946 mmol) in THF (3 mL). The resulting yellow mixture was stirred in an ice bath and allowed to warm to ambient overnight. The reaction crude was then quenched by adding NH$_4$Cl (aq., sat.). The resulting mixture was worked up with brine, dried (Na$_2$SO$_4$), filtered and evaporated to give a yellow oil. The oil was purified by flash chromatography (SiO$_2$, Biotage 40M cartridge). The column was eluted with a EtOAc/hexanes gradient mixture (0% to 20%). Related fractions were pooled and evaporated into a colorless glass/gum as the titled compound. LCMS calc.=530.99; found=532.00.

Example 113

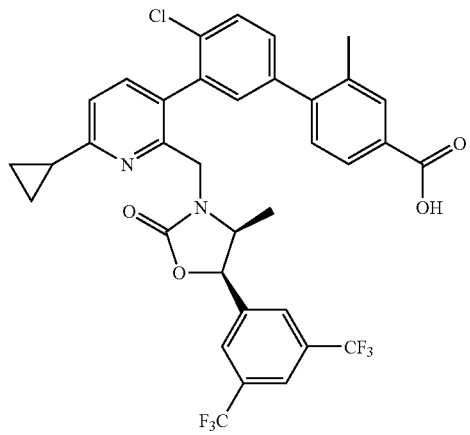

3'-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4'-chloro-2-methylbiphenyl-4-carboxylic acid Step A: (4S,5R)-5-[3,5-Bis(trifluoromethyl)phenyl]-3-{[6-chloro-3-(2-chloro-5-methoxyphenyl pyridin-2-yl]methyl}-4-methyl-1,3-oxazolidin-2-one 1,1'-bis(di-t-butylphosphino)ferrocene palladium dichloride (0.557 g, 0.819 mmol) was added to a stirred, degassed mixture of INTERMEDIATE 9 (2.12 g, 4.10 mmol), 2-chloro-5-methoxy phenyl boronic acid (0.763 g, 4.10 mmol) and K$_2$CO$_3$ (2.26 g, 16.38 mmol) in THF (30 mL). The mixture was stirred at room temperature for 30 min. LCMS showed that no starting material was left. Water was added and the mixture was extracted with EtOAc (3×60 mL). The combined organic layers were washed with brine and dried (Na$_2$SO$_4$). The title compound was obtained as a colorless solid after flash chromatography using CH$_2$Cl$_2$/hexane (8:2) as the eluant. $^1$H NMR (500 MHz, CDCl$_3$, 1:1 mixture of atopoisomers): δ 7.90 (s, 0.5H), 7.88 (s, 0.5H), 7.80 (s, 1H), 7.75 (s, 1H), 7.58 (d, J=8 Hz, 0.5H), 7.53 (d, J=8 Hz, 0.5H), 7.46-7.37 (m, 2H), 6.97 (d, J=3.0 Hz, 0.5H), 6.95 (d, J=3.0 Hz, 0.5H), 6.88 (d, J=3.0 Hz, 0.5H), 6.82 (d, J=3.0 Hz, 0.5H), 5.86 (d, J=8.0 Hz, 0.5H), 5.61 (d, J=8.0 Hz, 0.5H), 4.94 (d, J=16.0 Hz, 0.5H), 4.75 (d, J=17.0 Hz, 0.5H), 4.61 (m, 0.5H), 4.14 (m, 0.5H), 4.13 (d, J=16.0 Hz, 0.5H), 4.05 (d, J=17 Hz, 0.5H), 3.83 (s, 3H), 0.78 (d, J=7.0 Hz, 1.5H), 0.74 (d, J=6.5 Hz, 1.5H). LCMS M+H 579.29.

Step B: (4S,5R)-5-[3,5-Bis(trifluoromethyl)phenyl]-3-{[3-(2-chloro-5-methoxyphenyl)-6-cyclopropylpyridin-2-yl]methyl}-4-methyl-1,3-oxazolidin-2-one The mixture of the title compound from Step A (323 mg, 0.59 mmol), cyclopropyl boronic acid (239 mg, 2.79 mmol), 1,1'-bis(di-t-butylphosphino)ferrocene palladium dichloride (76 mg, 0.112 mmol) and K$_2$CO$_3$ (539 mg, 3.90 mmol) in THF (10 mL) was stirred under reflux for 24 h. The mixture was cooled and the solvent was removed. Water was added and the mixture was extracted with CH$_2$Cl$_2$ (3×10 mL). The combined organic layers were washed with brine, dried (Na$_2$SO$_4$), and filtered. The title compound was obtained after flash chromatography using EtOAc/hexane (2:8) as the eluant. $^1$H NMR (500 MHz, CDCl$_3$, 1:1 mixture of atopoisomers): δ 7.89 (s, 1H), 7.77 (s, 2H), 7.50-7.37 (m, 2H), 7.20 (m, 1H), 6.88-6.80 (m, 2H), 5.70 (m, 1H), 4.90 (m, 1H), 4.48 (m 0.5H), 4.30 (m, 0.5H), 4.05 (m, 1H), 3.87 (s, 1.5H), 3.84 (s, 1.5H), 2.18 (m, 1H), 1.11 (m, 4H), 0.76 (d, J=6.5 Hz, 1.5H), 0.69 (d, J=6.5 Hz, 1.5H).

Step C: (4S,5R)-5-[3,5-Bis(trifluoromethyl)phenyl]-3-{[3-(2-chloro-5-hydroxyphenyl)-6-cyclopropylpyridin-2-yl]methyl}-4-methyl-1,3-oxazolidin-2-one A solution of BBr$_3$ in CH$_2$Cl$_2$ (1.45 mL, 1.45 mmol, 1M solution) was added to a solution of the title compound in Step B (170 mg, 0.29 mmol) in CH$_2$Cl$_2$ (3 mL) at −78° C. The solution was stirred at −78° C. for 10 min and then warmed up to room temperature for 10 min. TLC showed no starting material left (EtOAc/hexane (2:8)). Water and CH$_2$Cl$_2$ were added. The solution was washed with saturated NaHCO$_3$, brine and dried (Na$_2$SO$_4$). The title compound was obtained after flash chromatography using EtOAc/hexane (3:7) as the eluant. $^1$H NMR (500 MHz, CDCl$_3$, 2:1 mixture of atopoisomers): δ 7.91 (s, 2/3H), 7.88 (s, 1/3H), 7.76 (s, 1.3H), 7.72 (s, 0.7H), 7.46-7.28 (m, 2H), 7.18 (m, 1H), 6.88-6.80 (m, 2H), 5.80 (d, J=8.5 Hz, 2/3H), 5.58 (d, J=8.5 Hz, 1/3H), 4.92 (d, J=15.5 Hz, 1/3H), 4.73 (d, J=17.0 Hz, 2/3H), 4.50 (m, 1H), 4.13-3.96 (m, 1H), 2.10 (m, 1H), 1.07 (m, 4H), 0.78 (d, J=6.5 Hz, 2H), 0.73 (d, J=7.0 Hz, 1H).

Step D: 3-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4-chlorophenyl trifluoromethanesulfonate Tf$_2$O (128 mg, 0.455 mmol) was added to a solution of the title compound from Step C (130 mg, 0.228 mmol) in CH$_2$Cl$_2$ (10 mL) at −78° C., followed by 2,6-lutidine (98 mg, 0.911 mmol). The solution was stirred at −78° C. for 10 min and then warmed to room temperature for 1 h. Water was added. The organic solution was then washed with brine, and dried (Na$_2$SO$_4$). The title compound was obtained after flash chromatography using EtOAc/hexane (15:85) as the eluant. $^1$H NMR (500 MHz, CDCl$_3$, 1:1 mixture of atopoisomers): δ 7.90 (s, 0.5H), 7.89 (s, 0.5H), 7.76 (s, 1H), 7.75 (s, 1H), 7.63 (t, J=9.0 Hz, 1H), 7.43 (d, J=7.5 Hz, 0.5H), 7.39 (d, J=8.0 Hz, 0.5H), 7.34-7.23 (m, 3H), 5.72 (d, J=9.0 Hz, 0.5H), 5.67 (d, J=8.5 Hz, 0.5H), 4.78 (d, J=15.5 Hz, 0.5H), 4.67 (d, J=16.5 Hz, 0.5H), 4.40 (m, 0.5H), 4.12 (m, 0.5H), 3.98 (d, J=16.5 Hz, 0.5H), 3.95 (d, J=15.5 Hz, 0.5H), 2.15 (m, 1H), 1.11 (m, 4H), 0.77 (d, J=6.5 Hz, 1.5H), 0.71 (d, J=7.0 Hz, 1.5H).

Step E: Methyl 3'-[2-({(4S,5R)-5-[3,5-bis(trifluoromethyl phenyl]-4-methyl-2-oxo-1,3-oxazolidin-3-yl}methyl)-6-cyclopropylpyridin-3-yl]-4'-chloro-2-methylbiphenyl-4-carboxylate A mixture of the title compound from Step D (60 mg, 0.085 mmol), methyl 3-methyl-4-(4,4,5,5-tetramethyl-1,3,2-dioxaborolan-2-yl)benzoate (47.1 mg, 0.171 mmol), tetrakis (triphenylphosphine) palladium (19.7 mg, 20% mol) and Na$_2$CO$_3$ (18.1 mg, 0.17 mmol) in 14 mL of water/EtOH/toluene (1:2:4) was heated to reflux for 2 h. TLC (CH$_2$Cl$_2$/hexane (7:3)) showed that the reaction was complete. The solvents were removed. Water (20 mL) was added. The organic was extracted with CH$_2$Cl$_2$ (3×10 mL). The combined CH$_2$Cl$_2$ layers were washed with brine, and dried (Na$_2$SO$_4$)— The title compound was obtained after flash chromatography using CH$_2$Cl$_2$/hexane (8:2) as the eluant. LCMS M+H 703.45.

Step F: 3'-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4'-chloro-2-methylbiphenyl-4-carboxylic acid The title compound from Step E (44 mg, mmol) was stirred with LiOH (10 eq) in a 2:1 mixture of 1,4-dioxane and water at room temperature overnight. The solvent was removed and the aqueous solution was acidified with 1N HCl to pH ~4. The organic was extracted with EtOAc (3×10 mL). The combined EtOAc layers were washed with brine and dried (Na$_2$SO$_4$). The title compound was obtained as a colorless solid after reverse phase HPLC. LCMS M+H 689.38.

Example 114

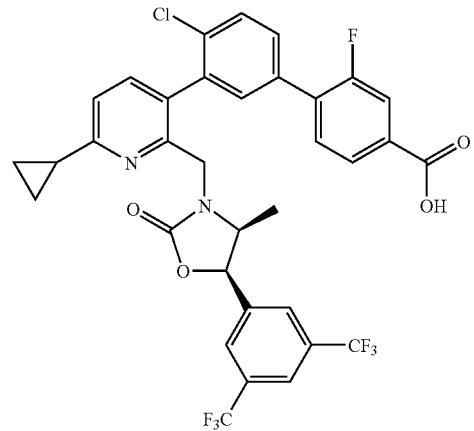

3'-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4'-chloro-2-fluorobiphenyl-4-carboxylic acid Step A: 3'-[2-({(4S,5R)-5-[3,5-Bis(trifluoromethyl) phenyl]-4-methyl-2-oxo-1,3-oxazolidin-3-yl}methyl)-6-cyclopropylpyridin-3-yl]-4'-chloro-2-fluorobiphenyl-4-carboxylic acid Followed the procedures described in EXAMPLE 113.

Example 115

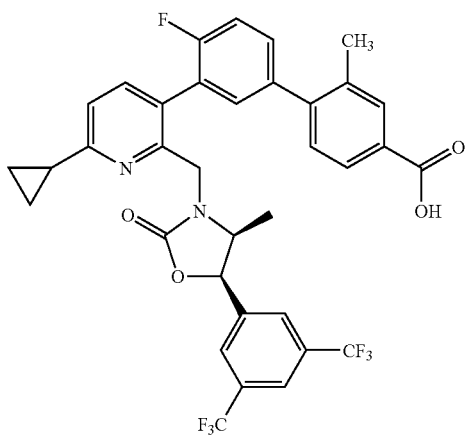

3'-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4-fluoro-2-methylbiphenyl-4-carboxylic acid

Step A: (4S,5R)-5-[3,5-Bis(trifluoromethyl)phenyl]-3-{[6-chloro-3-(2-fluoro-5-nitrophenyl)pyridin-2-yl]methyl}-4-methyl-1,3-oxazolidin-2-one A mixture of INTERMEDIATE 9 (1.0 g, 1.93 mmol), 2-fluoro-5-nitro phenyl boronic acid (0.51 g, 2.74 mmol), tetrakis(triphenylphosphine) palladium (223 mg, 10% mol) and $Na_2CO_3$ (410 mg, 3.86 mmol) in 14 mL of water/EtOH/toluene (1:2:4) was heated at reflux for 2 h. The solvents were removed. Water (20 mL) was added. The organic was extracted with $CH_2Cl_2$ (3×10 mL). The combined $CH_2Cl_2$ layers were washed with brine, and dried ($Na_2SO_4$). The title compound was obtained after flash chromatography using $CH_2Cl_2$/hexane (8:2) as the eluant. LCMS M+H 578.30.

Step B: (4S,5R)-5-[3,5-Bis(trifluoromethyl)phenyl]-3-{[6-cyclopropyl-3-(2-fluoro-5-nitrophenyl)pyridin-2-yl]methyl}-4-methyl-1,3-oxazolidin-2-one A mixture of the title compound from Step A (286 mg, 0.495 mmol), cyclopropyl boronic acid (213 mg, 2.46 mmol), 1,1'-bis(di-t-butylphosphino)ferrocene palladium dichloride (67 mg, 0.099 mmol) and $K_2CO_3$ (479 mg, 3.46 mmol) in THF (10 mL) was stirred at 70° C. for 6 h. The mixture was cooled and the solvent was removed. Water was added and the mixture was extracted with $CH_2Cl_2$ (3×10 mL). The combined organic layers were washed with brine, dried ($Na_2SO_4$), and filtered. The title compound was obtained after flash chromatography using EtOAc/hexane (2:8) as the eluant. $^1H$ NMR (500 MHz, $CDCl_3$, 1:1 mixture of atopoisomers): δ 8.35 (m, 1H), 8.25 (m, 1H), 7.90 (s, 1H), 7.76 (s, 2H), 7.49 (d, J=8.0 Hz, 1H), 7.38 (t, J=9.0 Hz, 1H), 7.28 (m, 1H), 5.69 (d, J=8.5 Hz, 1H), 4.78 (d, J=16 Hz, 1H), 4.30 (m, 1H), 4.06 (m, 1H), 2.16 (m, 1H), 1.11 (m, 4H), 0.78 (d, J=6.5 Hz, 3H).

Step C: (4S,5R)-3-{[3-(5-Amino-2-fluorophenyl)-6-cyclopropylpyridin-2-yl]methyl}-5-[3,5-bis(trifluoromethyl)phenyl]-4-methyl-1,3-oxazolidin-2-one A mixture of the title compound from Step B (171 mg, 0.293 mmol) and catalytic amount of 10% Pd/C in MeOH (5 mL) was charged with $H_2$ at 1 atm for 30 min. The mixture was filtered through Celite and the filtrate was evaporated. Reverse HPLC separated the title compound (isomer A) (4S,5R)-3-{[3-(5-amino-2-fluorophenyl)-6-cyclopropylpyridin-2-yl]methyl}-5-[3,5-bis(trifluoromethyl)phenyl]-4-methyl-1,3-oxazolidin-2-one and another isomer B (4S,5R)-5-[3,5-bis(trifluoromethyl)phenyl]-3-{[3-(2-fluoro-5-aminophenyl)-6-propylpyridin-2-yl]methyl}-4-methyl-1,3-oxazolidin-2-one.

Step D: (4S,5R)-5-[3,5-Bis(trifluoromethyl)phenyl]-3-{[6-cyclopropyl-3-(2-fluoro-5-iodophenyl)pyridin-2-yl]methyl}-4-methyl-1,3-oxazolidin-2-one A mixture of the title compound from Step C, isomer A (30 mg, 0.054 mmol), 12 (20.64 mg, 0.081 mmol), and n-amyl nitrite (12.7 mg, 0.108 mmol) in $CHCl_3$ (5 mL) was heat to reflux for 1 h. The mixture was cooled and diluted with $CH_2Cl_2$ (10 mL). It was then washed with saturated sodium thiosulfate and brine. The title compound was obtained as a yellow solid after flash chromatography using EtOAc/hexane (1:9) as the eluant.

Step E: Methyl 3'-[2-({(4S,5R)-5-[3,5-bis trifluoromethyl)phenyl]-4-methyl-2-oxo-1,3-oxazolidin-3-yl}methyl)-6-cyclopropylpyridin-3-yl]-4'-fluoro-2-methylbiphenyl-4-carboxylate A mixture of the title compound from Step D (17 mg, 0.026 mmol), methyl 3-methyl-4-(4,4,5,5-tetramethyl-1,3,2-dioxaborolan-2-yl)benzoate (14.13 mg, 0.051 mmol), tetrakis(triphenylphosphine) palladium (2.96 mg, 10% mol) and $Na_2CO_3$ (5.42 mg, 0.051 mmol) in 14 mL of water/EtOH/toluene (1:2:4) was heated to reflux for 2 h. TLC ($CH_2Cl_2$/hexane (7:3)) showed that the reaction was complete. The solvents were removed. Water (20 mL) was added. The organic was extracted with $CH_2Cl_2$ (3×10 mL). The combined $CH_2Cl_2$ layers were washed with brine, and dried ($Na_2SO_4$). The title compound was obtained as a colorless solid after flash chromatography using EtOAc/hexane (2:8) as the eluant.

Step F: 3'-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4'-fluoro-2-methylbiphenyl-4-carboxylic acid The title compound from Step E (14 mg, 0.02 mmol) was stirred with LiOH (10 eq) in a 2:1 mixture of 1,4-dioxane and water at room temperature overnight. The solvent was removed and the aqueous solution was acidified with 1N HCl to pH 4. The organic layer was extracted with EtOAc (3×10 mL). The combined EtOAc layers were washed with brine and dried ($Na_2SO_4$). The title compound was obtained as a colorless solid after reverse phase HPLC. LCMS M+H 673.33.

Example 116

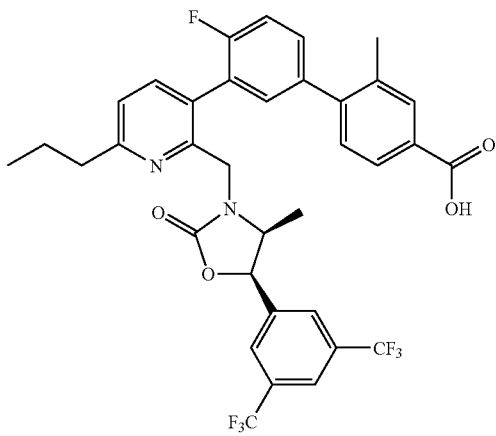

3'-[2-({(4S,5R)-5-[3,5-Bis(trifluoromethyl)phenyl]-4-methyl-2-oxo-1,3-oxazolidin-3-yl}methyl)-6-propylpyridin-3-yl]-4'-fluoro-2-methylbiphenyl-4-carboxylic acid Step A: (4S,5R)-5-[3,5-Bis(trifluoromethyl)phenyl]-3-{[3-(2-fluoro-5-iodophenyl)-6-propylpyridin-2-yl]methyl}-4-methyl-1,3-oxazolidin-2-one A mixture of the title compound from EXAMPLE 115, Step C, isomer B (30 mg, 0.112 mmol), 12 (42.5 mg, 0.167 mmol), and n-amyl nitrite (26.2 mg, 0.223 mmol) in CHCl₃ (5 mL) was heated at reflux for 1 h. The mixture was cooled and diluted with CH₂Cl₂ (10 mL). It was then washed with saturated sodium thiosulfate and brine. The title compound was obtained as a yellow solid after flash chromatography using EtOAc/hexane (1:9) as the eluant.

Step B: Methyl 3'-[2-({(4S,5R)-5-[3,5-bis(trifluoromethyl)phenyl]-4-methyl-2-oxo-1,3-oxazolidin-3-yl}methyl)-6-propylpyridin-3-yl]-4'-fluoro-2-methylbiphenyl-4-carboxylate A mixture of the title compound from Step A (30 mg, 0.045 mmol), methyl 3-methyl-4-(4,4,5,5-tetramethyl-1,3,2-dioxaborolan-2-yl)benzoate (24.86 mg, 0.09 mmol), tetrakis(triphenylphosphine) palladium (5.2 mg, 10% mol) and Na₂CO₃ (9.54 mg, 0.09 mmol) in 14 mL of water/EtOH/toluene (1:2:4) was heated at reflux for 2 h. TLC (CH₂Cl₂/hexane (7:3)) showed that the reaction was complete. The solvents were removed. Water (20 mL) was added. The organic was extracted with CH₂Cl₂ (3×10 mL). The combined CH₂Cl₂ layers were washed with brine, and dried (Na₂SO₄). The title compound was obtained as a colorless solid after flash chromatography using EtOAc/hexane (2:8) as the eluant.

Step C: 3'-[2-({(4S,5R)-5-[3,5-Bis(trifluoromethyl)phenyl]-4-methyl-2-oxo-1,3-oxazolidin-3-yl}methyl)-6-propylpyridin-3-yl]-4'-fluoro-2-methylbiphenyl-4-carboxylic acid The title compound from Step B (28 mg, 0.041 mmol) was stirred with LiOH (10 eq) in a 2:1 mixture of 1,4-dioxane and water at room temperature overnight. The solvent was removed and the aqueous solution was acidified with 1N HCl to pH ~4. The organic was extracted with EtOAc (3×10 mL). The combined EtOAc layers were washed with brine and dried (Na₂SO₄). The title compound was obtained as a colorless solid after reverse phase HPLC. LCMS M+H 675.40.

Example 117

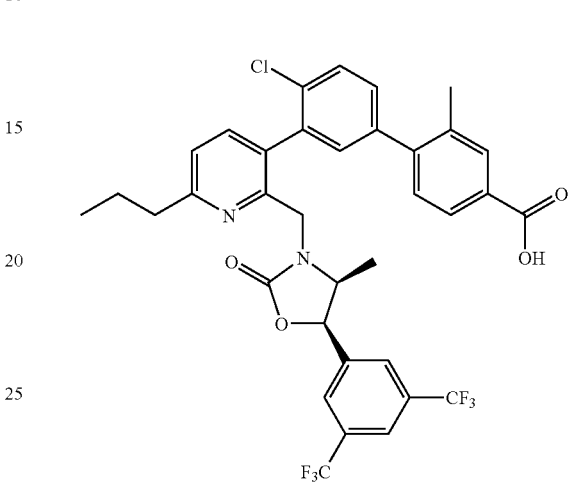

3'-[2-({(4S,5R)-5-[3,5-Bis(trifluoromethyl)phenyl]-4-methyl-2-oxo-1,3-oxazolidin-3-yl}methyl)-6-propylpyridin-3-yl]-4'-chloro-2-methylbiphenyl-4-carboxylic acid Step A: (4S,5R)-5-[3,5-Bis(trifluoromethyl)phenyl]-3-({3-(2-chloro-5-methoxyphenyl)-6-[(1E)-prop-1-en-1-yl]pyridin-2-yl}methyl)-4-methyl-1,3-oxazolidin-2-one A mixture of the title compound from EXAMPLE 113, Step A (1.10 g, 1.899 mmol), propenyl boronic acid (0.816 g, 9.49 mmol), tetrakis(triphenylphosphine) palladium (0.11 g, 5% mol) and Na₂CO₃ (1.0 g, 9.49 mmol) in 70 mL of water/EtOH/toluene (1:2:4) was heated at reflux overnight. TLC (CH₂Cl₂/hexane (7:3)) showed that the reaction was complete. The solvents were removed. Water (20 mL) was added. The organic was extracted with CH₂Cl₂ (3×50 mL). The combined CH₂Cl₂ layers were washed with brine, and dried (Na₂SO₄). The title compound was obtained as a colorless solid after flash chromatography using EtOAc/hexane (2:8) as the eluant.

Step B: (4S,5R)-5-[3,5-Bis(trifluoromethyl)phenyl]-3-{[3-(2-chloro-5-methoxyphenyl)-6-propylpyridin-2-yl]methyl}-4-methyl-1,3-oxazolidin-2-one A mixture of the title compound from Step A (1.0 g, 1.71 mmol) and catalytic amount of Pt/C with 1% V in MeOH (20 mL) was charged with H₂ at 1 atm for overnight. LCMS showed the reaction was over. The mixture was filtered through Celite and the filtrate was evaporated. The title compound was obtained as a colorless solid after flash chromatography using EtOAc/hexane (2:8) as the eluant.

Step C: (4S,5R)-5-[3,5-Bis(trifluoromethyl)phenyl]-3-{[3-(2-chloro-5-hydroxyphenyl)-6-propylpyridin-2-yl]methyl}-4-methyl-1,3-oxazolidin-2-one A solution of BBr$_3$ in CH$_2$Cl$_2$ (8.09 mL, 8.09 mmol, 1 M solution) was added to a solution of the title compound in Step B (0.95 g, 1.62 mmol) in CH$_2$Cl$_2$ (3 mL) at −78° C. The solution was stirred at −78° C. for 10 min and then warmed up to room temperature for 30 min. TLC showed no starting material left (EtOAc/hexane (2:8)). Water and CH$_2$Cl$_2$ were added. The solution was washed with saturated NaHCO$_3$, brine and dried (Na$_2$SO$_4$). The title compound was obtained after flash chromatography using EtOAc/hexane (3:7) as the eluant. LCMS M+H 573.22.

Step D: 3-[2-({(4S,5R)-5-[3,5-Bis(trifluoromethyl)phenyl]-4-methyl-2-oxo-1,3-oxazolidin-3-yl}methyl)-6-propylpyridin-3-yl]-4-chlorophenyl trifluoromethanesulfonate Tf$_2$O (143 mg, 0.506 mmol) was added to a solution of the title compound from Step C (145 mg, 0.253 mmol) in CH$_2$Cl$_2$ (10 mL) at −78° C., followed by 2,6-lutidine (108 mg, 1.01 mmol). The solution was stirred at −78° C. for 10 min and then warmed to room temperature for 1 h. Water was added. The organic solution was then washed with brine, and dried (Na$_2$SO$_4$). The title compound was obtained after flash chromatography using EtOAc/hexane (15:85) as the eluant.

Step E: methyl 3'-[2-({(4S,5R)-5-[3,5-Bis(trifluoromethyl)phenyl]-4-methyl-2-oxo-1,3-oxazolidin-3-yl}methyl)-6-propylpyridin-3-yl]-4'-chloro-2-methylbiphenyl-4-carboxylate A mixture of the title compound from Step D (176 mg, 0.25 mmol), methyl 3-methyl-4-(4,4,5,5-tetramethyl-1,3,2-dioxaborolan-2-yl)benzoate (138 mg, 0.171 mmol), tetrakis(triphenylphosphine) palladium (57.7 mg, 20% mol) and Na$_2$CO$_3$ (52.9 mg, 0.499 mmol) in 7 mL of water/EtOH/toluene (1:2:4) was heated to reflux for 4 h. TLC (CH$_2$Cl$_2$/hexane (7:3)) showed that the reaction was complete. The solvents were removed. Water (20 mL) was added. The organic was extracted with CH$_2$Cl$_2$ (3×10 mL). The combined CH$_2$Cl$_2$ layers were washed with brine, and dried (Na$_2$SO$_4$). The title compound was obtained as a colorless solid after flash chromatography using CH$_2$Cl$_2$/hexane (8:2) as the eluant. LCMS M+H 705.18

Step F: 3'-[2-({(4S,5R)-5-[3,5-Bis(trifluoromethyl)phenyl]-4-methyl-2-oxo-1,3-oxazolidin-3-yl}methyl)-6-propylpyridin-3-yl]-4'-chloro-2-methylbiphenyl-4-carboxylic acid The title compound from Step E (147 mg, 0.208 mmol) was stirred with LiOH (10 eq) in a 2:1 mixture of 1,4-dioxane and water at room temperature overnight. The solvent was removed and the aqueous solution was acidified with 1N HCl to pH 4. The organic was extracted with EtOAc (3×10 mL). The combined EtOAc layers were washed with brine and dried (Na$_2$SO$_4$). The title compound was obtained as a colorless solid after reverse phase HPLC. LCMS M+H 691.29.

Example 118

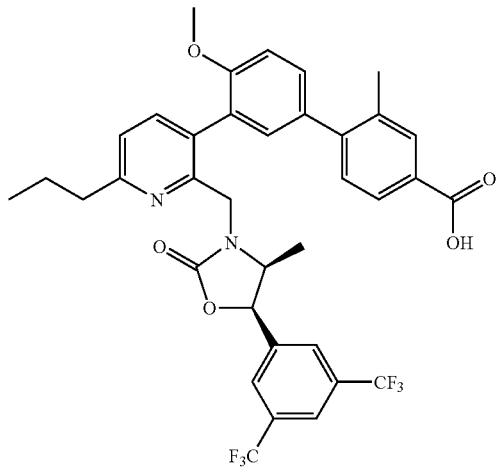

3'-[2-({(4S,5R)-5-[3,5-Bis(trifluoromethyl)phenyl]-4-methyl-2-oxo-1,3-oxazolidin-3-yl}methyl)-6-propylpyridin-3-yl]-4'-methoxy-2-methylbiphenyl-4-carboxylic acid

Step A: (4S,5R)-5-[3,5-Bis(trifluoromethyl)phenyl]-3-{[6-chloro-3-(5-chloro-2-methoxyphenyl)pyridin-2-yl]methyl}-4-methyl-1,3-oxazolidin-2-one 1,1'-bis(di-t-butylphosphino)ferrocene palladium dichloride (0.263 g, 0.386 mmol) was added to a stirred, degassed mixture of INTERMEDIATE 9 (4.00 g, 7.73 mmol), 5-chloro-2-methoxy phenyl boronic acid (1.44 g, 7.73 mmol) and K$_2$CO$_3$ (4.27 g, 30.9 mmol) in THF (30 mL). The mixture was stirred at room temperature for 1 h. LCMS showed that no starting material was left. Water was added and the mixture was extracted with EtOAc (3×60 mL). The combined organic layers were washed with brine and dried (Na$_2$SO$_4$). The title compound was obtained as a colorless solid after flash chromatography using CH$_2$Cl$_2$/hexane (8:2) as the eluant.

Step B: (4S,5R)-5-[3,5-Bis(trifluoromethyl)phenyl]-3-({3-(5-chloro-2-methoxyphenyl)-6-[(1E)-prop-1-en-1-yl]pyridin-2-yl}methyl)-4-methyl-1,3-oxazolidin-2-one A mixture of the title compound from Step A (1.0 g, 1.726 mmol), propenyl boronic acid (0.741 g, 8.63 mmol), tetrakis(triphenylphosphine) palladium (0.10 g, 5% mol) and Na$_2$CO$_3$ (0.915 g, 8.63 mmol) in 70 mL of water/EtOH/toluene (1:2:4) was heated to reflux overnight. TLC (CH$_2$Cl$_2$/hexane (7:3)) showed that the reaction was complete. The solvents were removed. Water (20 mL) was added. The organic was extracted with CH$_2$Cl$_2$ (3×50 mL). The combined CH$_2$Cl$_2$ layers were washed with brine, and dried (Na$_2$SO$_4$). The title compound was obtained as a colorless solid after flash chromatography using EtOAc/hexane (2:8) as the eluant.

Step C: (4S,5R)-5-[3,5-Bis(trifluoromethyl)phenyl]-3-{[3-(5-chloro-2-methoxyphenyl)-6-propylpyridin-2-yl]methyl}-4-methyl-1,3-oxazolidin-2-one A mixture of the title compound from Step B (1.0 g, 1.71 mmol) and catalytic amount of Pt/C with 1% V in MeOH (20 mL) was charged with H₂ at 1 atm for overnight. LCMS showed the reaction was over. The mixture was filtered through Celite and the filtrate was evaporated. The title compound was obtained as a colorless solid after flash chromatography using EtOAc/hexane (2:8) as the eluant.

Step D: Methyl 3'-[2-({(4S,5R)-5-[3,5-bis(trifluoromethyl)phenyl]-4-methyl-2-oxo-1,3-oxazolidin-3-yl}methyl)-6-propylpyridin-3-yl]-4'-methoxy-2-methylbiphenyl-4-carboxylate The mixture of the title compound from Step C (100 mg, 0.17 mmol), methyl 3-methyl-4-(4,4,5,5-tetramethyl-1,3,2-dioxaborolan-2-yl)benzoate (70.6 mg, 0.256 mmol), 1,1'-bis(di-t-butylphosphino)ferrocene palladium dichloride (11.6 mg, 0.017 mmol) and K₂CO₃ (165 mg, 1.19 mmol) in THF (10 mL) was stirred under reflex for 24 h. The mixture was cooled and the solvent was removed. Water was added and the mixture was extracted with CH₂Cl₂ (3×10 mL). The combined organic layers were washed with brine, dried (Na₂SO₄), and filtered. The title compound was obtained after flash chromatography using EtOAc/hexane (2:8) as the eluant. LCMS M+H 701.19.

Step E: 3'-[2-({(4S,5R)-5-[3,5-Bis(trifluoromethyl)phenyl]-4-methyl-2-oxo-1,3-oxazolidin-3-yl}methyl)-6-propylpyridin-3-yl]-4'-methoxy-2-methylbiphenyl-4-carboxylic acid The title compound from Step E (17 mg, 0.024 mmol) was stirred with LiOH (10 eq) in a 2:1 mixture of 1,4-dioxane and water at room temperature overnight. The solvent was removed and the aqueous solution was acidified with 1N HCl to pH 4. The organic was extracted with EtOAc (3×10 mL). The combined EtOAc layers were washed with brine and dried (Na₂SO₄). The title compound was obtained as a colorless solid after reverse phase HPLC. LCMS M+H 687.32.

Example 119

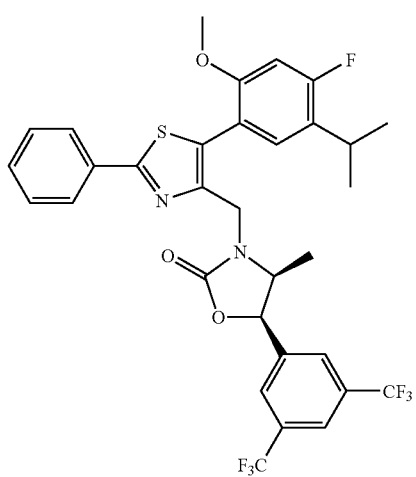

(4S,5R)-5-[3,5-Bis(trifluoromethyl)phenyl]-3-{[5-(4-fluoro-5-isopropyl-2-methoxyphenyl)-2-phenyl-1,3-thiazol-4-yl]methyl}-4-methyl-1,3-oxazolidin-2-one Step A:
5-Bromo-4-(bromomethyl)-2-phenyl-1,3-thiazole A mixture of 5-Bromo-4-methyl-2-phenyl-1,3-thiazole (1.00 g, 3.93 mmol), NBS (0.84 g, 4.72 mmol) and catalytic amount of AIBN in CCl₄ (20 mL) was heated at reflux for 24 h. No starting material was seen by ¹H NMR. The solvent was removed. The title compound was obtained as a colorless solid after flash chromatography using EtOAc/hexane (3:97) as the eluant. ¹H NMR (500 MHz, CDCl₃): δ 7.90 (m, 3H), 7.48 (m, 2H), 4.61 (s, 2H).

Step B: (4S,5R)-5-[3,5-Bis(trifluoromethyl)phenyl]-3-[(5-bromo-2-phenyl-1,3-thiazol-4-yl)methyl]-4-methyl-1,3-oxazolidin-2-one To a solution of (4S,5R)-5-[3,5-bis(trifluoromethyl)phenyl]-4-methyl-1,3-oxazolidin-2-one (0.6 g, 1.92 mmol) in THF (100 mL) was added sodium hydride (60% dispersion in mineral oil) (64 mg, 2.68 mmol) as a powder. The mixture was stirred at 0° C. for 30 min. A solution of the title compound (0.766 g, 2.3 mmol) in THF (20 mL) was added. The resulting mixture was stirred overnight at room temperature. The reaction was quenched with saturated NH₄Cl and extracted with EtOAc (3×). The combined organic layers were washed with brine (1×), dried (Na₂SO₄) and concentrated in vacuo. The residue was purified by flash chromatography to give the title compound as a colorless solid using EtOAc/hexane (2:8) as the eluant. ¹H NMR (500 MHz, CDCl₃): δ 7.91 (s, 1H), 7.88 (m, 2H), 7.81 (s, 2H), 7.49 (m, 3H), 5.74 (d, J=8.5 Hz, 1H), 5.01 (d, J=15.5 Hz, 1H), 4.34 (d, J=15.5 Hz, 1H), 4.29 (m, 1H), 0.89 (d, J=7.0 Hz, 3H).

Step C: (4S,5R)-5-[3,5-Bis(trifluoromethyl)phenyl]-3-{[5-(4-fluoro-5-isopropyl-2-methoxyphenyl)-2-phenyl-1,3-thiazol-4-yl]methyl}4-methyl-1,3-oxazolidin-2-one A mixture of the title compound from Step B (50 mg, 0.088 mmol), 4-fluoro-5-isopropyl-2-methoxy phenylboronic acid (37.5 mg, 0.177 mmol), tetrakis(triphenylphosphine) palladium (10.2 mg, 10% mol) and Na₂CO₃ (20.6 g, 0.195 mmol) in 7 mL of water/EtOH/toluene (1:2:4) was heated at reflux for 1 h. TLC (CH₂Cl₂/hexane (1:1)) showed that the reaction was complete. The solvents were removed. Water (20 mL) was added. The organic was extracted with CH₂Cl₂ (3×50 mL). The combined CH₂Cl₂ layers were washed with brine, and dried (Na₂SO₄). The title compound was obtained as a colorless solid after flash chromatography using EtOAc/hexane (2:8) as the eluant. ¹H NMR (500 MHz, CDCl₃): . 8.00 (m, 2H), 7.88 (s, 1H), 7.76 (s, 2H), 7.50 (m, 3H), 6.81 (d, J=7.5 Hz, 1H), 6.72 (d, J=12.0 Hz, 1H), 6.59 (d, J=11.0 Hz, 1H), 5.50 (m, 1H), 4.92 (d, J=15.0 Hz, 1H), 4.34 (m, 1H), 4.23

(m, 1H), 3.22 (m, 1H), 1.30 (t, J=6.5 Hz, 6H), 0.76 (d, J=6.5 Hz, 3H). LCMS M+H 653.12.

Example 120

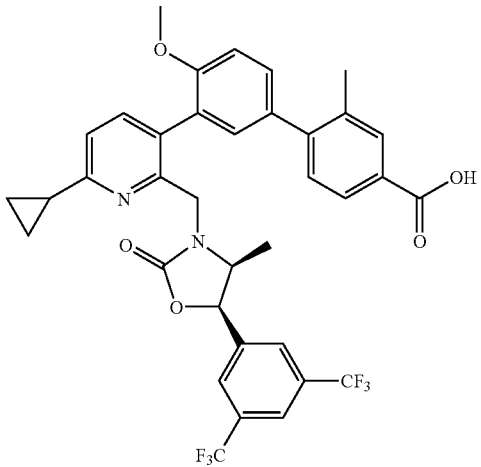

3'-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4'-methoxy-2-methylbiphenyl-4-carboxylic acid Step A: Methyl 3'-[2-({(4S,5R)-5-[3,5-bis(trifluoromethyl)phenyl]-4-methyl-2-oxo-1,3-oxazolidin-3-yl}methyl)-6-cyclopropylpyridin-3-yl]-4'-methoxy-2-methylbiphenyl-4-carboxylate Methyl 3'-[2-({(4S,5R)-5-[3,5-bis(trifluoromethyl)phenyl]-4-methyl-2-oxo-1,3-oxazolidin-3-yl}methyl)-6-chloropyridin-3-yl]-4'-methoxy-2-methylbiphenyl-4-carboxylate (EXAMPLE 59 100 mg, 0.144 mmol), cyclopropylboronic acid (62.0 mg, 0.721 mmol), 1,1'-bis(di-tert-butylphosphino)ferrocene palladium dichloride (19.62 mg, 0.029 mmol), aqueous $K_2CO_3$ (1M, 1.010 mL, 1.010 mmol) and THF (1.002 mL) were stirred at 80° C. for 3.5 h then slowly cooled to ambient overnight. Volatiles were removed under reduced pressure. The resulting pot residue was worked up with brine, extracted with EtOAc, dried ($Na_2SO_4$), filtered and evaporated to a dark mixture. The mixture was purified by reverse-phase preparative HPLC (Kromasil 100-5C18, 100×21.1 mm) eluting with MeCN/water+0.1% TFA (10% to 100% organic in 10 min, hold 100% in 2 min). Related fractions were pooled and evaporated in vacuo to afford an aqueous mixture. The aqueous mixture was extracted with EtOAc, washed with aqueous $NaHCO_3$, dried ($Na_2SO_4$), filtered and concentrated to afford the titled compound. LCMS calc.=698.22; found=699.30 $(M+H)^+$.

Step B: 3'-[2-({(4S,5R)-5-[3,5-Bis(trifluoromethyl)phenyl]-4-methyl-2-oxo-1,3-oxazolidin-3-yl}methyl)-6-cyclopropylpyridin-3-yl]-4'-methoxy-2-methylbiphenyl-4-carboxylic acid Methyl 3'-[2-({(4S,5R)-5-[3,5-bis(trifluoromethyl)phenyl]-4-methyl-2-oxo-1,3-oxazolidin-3-yl}methyl)-6-cyclopropylpyridin-3-yl]-4'-methoxy-2-methylbiphenyl-4-carboxylate (70 mg, 0.100 mmol), lithium hydroxide monohydrate (21.02 mg, 0.501 mmol), 1,4-dioxane (1.670 mL) and water (1.670 mL) were stirred at room temperature. LCMS indicated about 8% conversion when reaction time was 1 h. LCMS trace of reaction aliquot at reaction time 18 h indicated completion of reaction. Reaction mixture was acidified by HCl (aq., 1N). Volatiles were removed under reduced pressure. The resulting pot residue was purified by a reverse-phase prep-HPLC (Kromasil 100-5C18, 100×21.1 mm) eluting with MeCN/water+0.1% TFA (10% to 100% organic in 10 min, hold 100% in 2 min). Related fractions were pooled and evaporated in vacuo to afford an aqueous mixture. The resulting aqueous mixture was extracted with EtOAc, washed with water, dried ($Na_2SO_4$), filtered and concentrated to afford a light yellow solid as the titled compound. LCMS calc.=684.21; found=685.96 $(M+1)^+$. $^1H$ NMR (500 MHz, $CDCl_3$, 2:1 mixture of atropisomers): δ 8.02-7.90 (m, 3H), 7.85 (s, 1H), 7.70 (s, 2H), 7.50-7.44 (m, 1H), 7.37-7.28 (m, 1.5H), 7.16-7.09 (m, 2.5H), 5.70 (d, J=7 Hz, 0.67H), 5.63 (d, J=7.5 Hz, 0.33), 5.02 (d, J=15-5 Hz, 0.5H), 4.72 (d, J=15.5 Hz, 0.5H), 4.59 (d, J=16 Hz, 0.5H), 4.46 (d, J=16 Hz, 0.5H), 4.44-4.36 (m, 0.67H), 4.14-4.22 (m, 0.33H), 3.92-3.84 (m, 3H), 2.71 (br s, 0.67H), 2.61 (br s, 0.33H), 2.39 (s, 2H), 2.35 (s, 1H), 2.51-1.40 (m, 2H), 1.15-1.10 (m, 2H), 0.74 (d, J=6.5 Hz, 2H), 0.65 (d, J=5.5 Hz, 1H).

Example 121

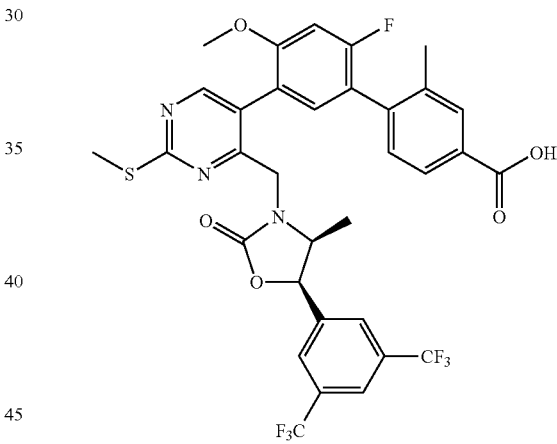

5'-[4-({(4S,5R)-5-[3,5-Bis(trifluoromethyl)phenyl]-4-methyl-2-oxo-1,3-oxazolidin-3-yl}methyl)-2-(methylthio)pyrimidin-5-yl]-2'-fluoro-4'-methoxy-2-methylbiphenyl-4-carboxylic acid Step A: Methyl 2'-fluoro-4'-methoxy-2-methylbiphenyl-4-carboxylate A mixture of 4-bromo-3-fluoro anisole (500 mg, 2.44 mmol), methyl 3-methyl-4-(4,4,5,5-tetramethyl-1,3,2-dioxaborolan-2-yl)benzoate (INTERMEDIATE 37, 875 mg, 3.17 mmol), tetrakis(triphenylphosphine) palladium (282 mg, 5% mol) and $Na_2CO_3$ (569 mg, 5.37 mmol) in 20 mL of water/EtOH/toluene (1:2:4) was heated at reflux for 4 h. TLC ($CH_2Cl_2$/hexane (1:1)) showed that the reaction was complete. The solvents were removed. Water (10 mL) was added. The organic was extracted with $CH_2Cl_2$ (3×10 mL). The combined $CH_2Cl_2$ layers were washed with brine and then dried ($Na_2SO_4$). The title compound was obtained after flash chromatography using CH$_2$Cl$_2$/hexanes (6:4) as the eluent. $^1$H NMR (500 MHz, CDCl$_3$): δ 7.98 (s, 1H), 7.92 (dd, J=8.0, 1.5 Hz, 1H), 7.29 (d, J=8.0 Hz, 1H), 7.16 (t, J=8.5 Hz, 1H), 6.80 (dd, J=8.5, 2.5 Hz, 1H), 6.77 (dd, J=11.5, 2.5 Hz, 1H), 3.95 (s, 3H), 3.88 (s, 3H), 2.28 (s, 3H).

Step B: Methyl 2'-fluoro-5'-iodo-4'-methoxy-2-methylbiphenyl-4-carboxylate

A solution of the title compound from Step A (1.30 g, 4.74 mmol) in MeOH/EtOAc (10:1) (10 mL) was added to a mixture of Ag$_2$SO$_4$ (1.47 g, 4.74 mmol) and I2 (1.20 g, 4.74 mmol) in MeOH (20 mL) at room temperature. The mixture was stirred at room temperature for 4 h. The color of solution turned to light yellow from brown. The mixture was filtered. The filtrate was concentrated. The residue was purified by flash chromatography eluting with EtOAc/hexane (5:95) to give the title compound as a colorless solid. $^1$H NMR (500 MHz, CDCl$_3$): δ 7.98 (s, 1H), 7.92 (dd, J=8.0, 2.0 Hz, 1H), 7.67 (d, J=8.5 Hz, 1H), 7.28 (d, J=9.0 Hz, 1H), 6.69 (d, J=11.5 Hz, 1H), 3.96 (s, 3H), 3.95 (s, 3H), 2.27 (s, 3H).

Step C: Methyl 2'-fluoro-4'-methoxy-2-methyl-5'-(4,4,5,5-tetramethyl-1,3,2-dioxaborolan-2-yl)biphenyl-4-carboxylate Methyl 2'-fluoro-5'-iodo-4'-methoxy-2-methylbiphenyl-4-carboxylate (Step B, 139.6 mg, 0.349 mmol), bis(pinacolato)diboron (106 mg, 0.419 mmol), KOAc (68.5 mg, 0.698 mmol), 1,1'-bis(diphenylphosphino) ferrocene-palladium dichloride dichloromethane adduct (57.0 mg, 0.070 mmol) and 1,4-dioxane (3.5 mL) were sealed in a microwave vessel and subjected to microwave irradiation at 130° C. for 20 min. Reaction progress was initially not clear due to identical LCMS retention time and TLC R$_f$s (20% EtOAc/hexanes). Resumed microwave heating at 140° C. for 10 min. LCMS confirmed that the reaction was complete after initial 20 min microwave heating (130° C.). Reaction crude (as Crude-C1) was combined with Crude-C2 for work-up.

Methyl 2'-fluoro-5'-iodo-4'-methoxy-2-methylbiphenyl-4-carboxylate (Step B, 181.8 mg, 0.454 mmol), bis(pinacolato)diboron (138 mg, 0.545 mmol), KOAc (89 mg, 0.909 mmol), 1,1'-bis(diphenylphosphino) ferrocene-palladium dichloride dichloromethane adduct (74.2 mg, 0.091 mmol) and 1,4-dioxane (4.5 mL) were sealed in a microwave vessel and subjected to microwave irradiation at 130° C. for 20 min. LCMS trace of aliquot indicated completion of reaction. Reaction crude (as Crude-C2) was combined with Crude-C1. Volatiles were removed from the combined crude mixture under reduced pressure. The resulting pot residue was worked up with brine, extracted with EtOAc, dried (Na$_2$SO$_4$), filtered and evaporated to a dark mixture as a crude mixture of the titled compound. LCMS calc.=400.19; found=401.17 (M+H).

Step D: Methyl 5'-[4-({(4S,5R)-5-[3,5-bis(trifluoromethyl)phenyl]-4-methyl-2-oxo-1,3-oxazolidin-3-yl}methyl)-2-(methylthio)pyrimidin-5-yl]-2'-fluoro-4'-methoxy-2-methylbiphenyl-4-carboxylate (4S,5R)-5-[3,5-bis(trifluoromethyl)phenyl]-3-{[5-bromo-2-(methylthio)pyrimidin-4-yl]methyl}-4-methyl-1,3-oxazolidin-2-one (INTERMEDIATE 38, 50 mg, 0.094 mmol), methyl 2'-fluoro-4'-methoxy-2-methyl-5'-(4,4,5,5-tetramethyl-1,3,2-dioxaborolan-2-yl)biphenyl-4-carboxylate (43.4 mg, 0.108 mmol), Cs$_2$CO$_3$ (64.5 mg, 0.198 mmol), 1,1'-bis(diphenylphosphino) ferrocene-palladium dichloride dichloromethane adduct (11.55 mg, 0.014 mmol) and 1,4-dioxane (2 mL) were sealed in a microwave vessel and subjected to microwave irradiation at 140° C. for a total of 20 min (2×10 min). LCMS trace of reaction aliquot indicated completion of reaction. Reaction crude was filtered and concentrated to a dark oil as Crude-D1.

(4S,5R)-5-[3,5-bis(trifluoromethyl)phenyl]-3-{[5-bromo-2-(methylthio)pyrimidin-4-yl]methyl}-4-methyl-1,3-oxazolidin-2-one (INTERMEDIATE 38, 50 mg, 0.094 mmol), methyl 2'-fluoro-4'-methoxy-2-methyl-5'-(4,4,5,5-tetramethyl-1,3,2-dioxaborolan-2-yl)biphenyl-4-carboxylate (43.4 mg, 0.108 mmol), K$_2$CO$_3$ (0.104 mL, 0.207 mmol), 1,1'-bis(diphenylphosphino) ferrocene-palladium dichloride dichloromethane adduct (11.55 mg, 0.014 mmol) and 1,4-dioxane (2 mL) were sealed in a microwave vessel and subjected to microwave irradiation at 140° C. for 20 min. LCMS trace of reaction aliquot indicated completion of reaction. Reaction crude was filtered and concentrated to a dark oil as Crude-D2

(4S,5R)-5-[3,5-bis(trifluoromethyl)phenyl]-3-{[5-bromo-2-(methylthio)pyrimidin-4-yl]methyl}-4-methyl-1,3-oxazolidin-2-one (INTERMEDIATE 38, 158.7 mg, 0.299 mmol), methyl 2'-fluoro-4'-methoxy-2-methyl-5'-(4,4,5,5-tetramethyl-1,3,2-dioxaborolan-2-yl)biphenyl-4-carboxylate (144 mg, 0.359 mmol), K$_2$CO$_3$ (0-329 mL, 0.658 mmol), 1,1'-bis(diphenylphosphino) ferrocene-palladium dichloride dichloromethane adduct (36.7 mg, 0.045 mmol) and 1,4-dioxane (7 mL) were sealed in a microwave vessel and subjected to microwave irradiation at 140° C. for 20 min. LCMS trace of aliquot indicated completion of reaction. The reaction crude was combined with Crude-D1 and Crude-D2. The combined crude mixture was worked up with brine, extracted with EtOAc, dried (Na$_2$SO$_4$), filtered and evaporated to afford a dark mixture. The resulting dark mixture was purified by flash chromatography (SiO$_2$, Biotage 40M cartridge). The column was eluted with a EtOAc/hexanes gradient mixture (0% to 30%). Related fractions were pooled and evaporated into 256 mg of yellow glass. TLC and LCMS trace indicated this yellow glass was not pure. The yellow glass was purified by preparative TLC (silica gel) developed with a EtOAc/hexanes mixture (30% EtOAc/hex, v/v) to give a yellow glass of 175 mg. This yellow glass was further purified by preparative TLC (silica gel, EtOAc/CH$_2$Cl$_2$, 2.5%, v/v) to give a yellow glass as the titled compound. LCMS calc.=723.16; found=724.03 (M+H)$^+$.

Step E: 5'-[4-({(4S,5R)-5-[3,5-Bis(trifluoromethyl)phenyl]-4-methyl-2-oxo-1,3-oxazolidin-3-yl}methyl)-2-(methylthio)pyrimidin-5-yl]-2'-fluoro-4'-methoxy-2-methylbiphenyl-4-carboxylic acid Methyl 5'-[4-({(4S,5R)-5-[3,5-bis(trifluoromethyl)phenyl]-4-methyl-2-oxo-1,3-oxazolidin-3-yl}methyl)-2-(methylthio)pyrimidin-5-yl]-2'-fluoro-4'-methoxy-2-methylbiphenyl-4-carboxylate (43.8 mg, 0.061 mmol) was dissolved in 1,4-dioxane (1.86 mL) and water (1.16 mL). To the above stirred solution was added lithium hydroxide monohydrate (12.70 mg, 0.303 mmol). The resulting mixture was stirred at room temperature overnight. The reaction crude was then acidified with HCl (1N, aq) to give a milky mixture. This white mixture was dissolved into a clear solution by adding MeCN. The clear solution was purified by preparative HPLC (Kromasil 100-5C18, 100×21.1 mm) eluting with MeCN/water+0.1% TFA (10% to 100% organic in 10 min, hold 100% for 2 min, 20 mL/min). Related fractions were pooled and evaporated in vacuo to afford an aqueous mixture. The resulting aqueous mixture was extracted with EtOAc, washed with aqueous $NaHCO_3$, dried ($Na_2SO_4$), filtered and concentrated to afford a light tan glass as the titled compound. LCMS calc.=709.15; found=710.06 $(M+H)_4$. $^1$H NMR (500 MHz, $CD_3OD$): δ 8.38 (s, 1H), 7.99 (s, 1H), 7.91 (s, 3H), 7.85 (d, J=8 Hz, 1H), 7.31 (d, J=8 Hz, 1H), 7.22 (d, J=8 Hz, 1H), 7.06 (d, J=11.5 Hz, 1H), 5.85 (br s, 1H), 4.75 (br d, J=17 Hz, 1H), 4.35 (t, J=7.25 Hz, 1H), 4.18 (br s, 1H), 3.90 (s, 3H), 2.60 (s, 3H), 2.26 (s, 3H), 0.69 (br d, J=5.5 Hz, 3H).

Following procedures analogous to those described in EXAMPLE 121, the compounds listed in Table 9 were prepared from the corresponding aryl boronic acid (INTERMEDIATE 2) or bi-phenyl borate (EXAMPLE 59, Step A) followed by hydrolysis where required.

TABLE 9

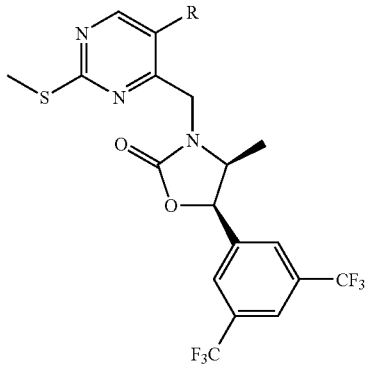

| Example | R | LCMS (M + H)+ |
|---|---|---|
| 122 | (methyl 4'-methoxy-2-methylbiphenyl group) | 706.08 |
| 123 | (4'-methoxy-2-methylbiphenyl-4-carboxylic acid group) | 692.14 |

TABLE 9-continued

| Example | R | LCMS (M + H)+ |
|---|---|---|
| 124 | (2-fluoro-4-methoxy-5-isopropylphenyl group) | 617.95 |

Example 125

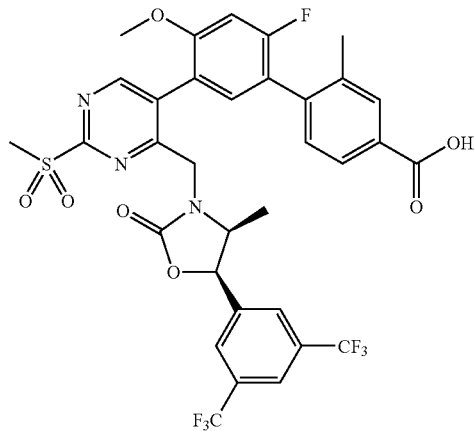

5'-[4-({(4S,5R)-5-[3,5-Bis(trifluoromethyl)phenyl]-4-methyl-2-oxo-1,3-oxazolidin-3-yl}methyl)-2-(methylsulfonyl)pyrimidin-5-yl]-2'-fluoro-4'-methoxy-2-methylbiphenyl-4-carboxylic acid 5'-[4-({(4S,5R)-5-[3,5-bis(trifluoromethyl)phenyl]-4-methyl-2-oxo-1,3-oxazolidin-3-yl}methyl)-2-(methylthio)pyrimidin-5-yl]-2'-fluoro-4'-methoxy-2-methylbiphenyl-4-carboxylic acid (EXAMPLE 121, 11.6 mg, 0.016 mmol), 3-chloroperoxybenzoic acid (11.28 mg, 0-065 mmol) and $CH_2Cl_2$ (1 mL) were stirred at room temperature. LCMS of an aliquot indicated formation of the desired product and complete consumption of starting material in 20 min. Volatiles were evaporated from the reaction crude. The pot residue was purified by preparative HPLC (Kromasil 100-5C18, 100× 21.1 mm) eluting with MeCN/water (25% to 100% organic in 10 min, hold 100% for 2 min, 20 mL/min) to give a colorless glass as the titled compound. LCMS calc.=741.14; found=741.99 (M+H)+. 1H NMR (500 MHz, CD3OD): δ 8.85 (s, 1H), 8.00 (s, 1H), 7.93 (br s, 3H), 7.88 (d, J=8 Hz, 1H), 7.36 (d, J=8 Hz, 1H), 7.34 (d, J=8.5 Hz, 1H), 7.14 (d, J=11.5 Hz, 1H), 5.93 (br s, 1H), 4.91 (br d, J=17 Hz, 1H), 4.48-4.34 (m, 2H), 3.92 (s, 3H), 3.42 (s, 3H), 2.29 (s, 3H), 0.74 (br d, J=6.5 Hz, 3H).

Following procedures analogous to that described in EXAMPLE 125, the compound listed in Table 10 was prepared from the corresponding methyl thioether (EXAMPLE 124).

TABLE 10

| Ex. | | LCMS (M + H)+ |
|---|---|---|
| 126 | (structure) | 650.00 |

Example 127

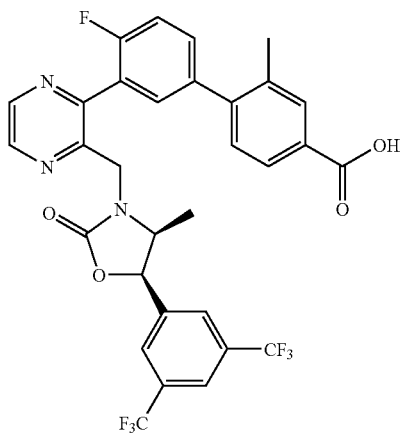

3'-[3-({(4S,5R)-5-[3,5-Bis(trifluoromethyl)phenyl]-4-methyl-2-oxo-1,3-oxazolidin-3-yl}methyl)pyrazin-2-yl]-4'-fluoro-2-methylbiphenyl-4-carboxylic acid Step A: 2-(Bromomethyl)-3-methoxypyrazine 2-methoxy-3-methylpyrazine (0.943 mL, 8.06 mmol), N-bromosuccinimide (1.505 g, 8.46 mmol) and 2,2'-azobis(2-methylpropionitrile) (0.132 g, 0.806 mmol) were heated at reflux in CCl4 (65.5 mL) (oil bath=100° C.) for 2.5 h. LCMS indicated formation of the product. The crude mixture was cooled, filtered and purified by flash chromatography (SiO2, Biotage 40M cartridge). The column was eluted with a CH2Cl2/hexanes mixture (0% to 100%). Related fractions were pooled and co-evaporated with toluene to afford a toluene solution (30 mL) of the product. To be used as it was for next step.

Step B: (4S,5R)-5-[3,5-Bis(trifluoromethyl)phenyl]-3-[(3-methoxypyrazin-2-yl)methyl]-4-methyl-1,3-oxazolidin-2-one (4S,5R)-5-[3,5-Bis(trifluoromethyl)phenyl]-4-methyl-1,3-oxazolidin-2-one (INTERMEDIATE 1, 2.018 g, 6.44 mmol) was dissolved in THF (64.4 mL) and cooled in an ice bath. To this cold solution was added NaH (0.271 g, 6.76 mmol) all at once. The resulting foaming mixture was stirred cold for an additional 1 h followed by addition of 2-(bromomethyl)-3-methoxypyrazine (1.308 g, 6.44 mmol) in a THF/toluene (30 mL/30 mL) mixture. The reaction mixture was slowly warmed to room temperature overnight. The reaction was then cooled and quenched by NH4OH (aq., sat.) and worked up with EtOAc/brine. The combined extracts were dried (Na2SO4), filtered and evaporated to afford a light yellow solid. The resulting yellow solid was purified by flash chromatography (SiO2, Biotage 40M cartridge). The column was eluted with a EtOAc/CH2Cl2 mixture (0% to 10%). Related fractions were pooled and evaporated into a white solid as the titled compound. LCMS calc.=435.10; found=436.21 (M+H)+.

Step C: (4S,5R)-5-[3,5-Bis(trifluoromethyl)phenyl]-3-[(3-hydroxypyrazin-2-yl)methyl]-4-methyl-1,3-oxazolidin-2-one To a cold (−78° C.) mixture of (4S,5R)-5-[3,5-bis(trifluoromethyl)phenyl]-3-[(3-methoxypyrazin-2-yl)methyl]-4-methyl-1,3-oxazolidin-2-one (1000 mg, 2.297 mmol) in CH2Cl2 (3 mL) was added BBr3 (11.49 mL, 11.49 mmol) dropwise through an addition funnel. The resulting mixture was stirred cold (−78° C.) for 1 h then allowed to warmed to room temperature overnight. The reaction was not completed after overnight stirring. The reaction mixture was stirred at room temperature for 4 more days and LCMS of aliquot indicated completion of reaction. The crude mixture was poured into crushed ice. The resulting organic layer was separated. The aqueous phase was back extracted with EtOAc. The combined extracts were dried (Na2SO4), filtered and evaporated to give a glass. This glass was purified by flash chromatography (SiO2, Biotage 40M cartridge). The column was eluted with a EtOAc/CH2Cl2 gradient mixture (0% to 100%). Related fractions were pooled and evaporated to afford a yellow solid as the titled compound. LCMS calc.=421.09; found=421.95 (M+H)+.

Step D: 3-({(4S,5R)-5-[3,5-Bis(trifluoromethyl)phenyl]-4-methyl-2-oxo-1,3-oxazolidin-3-yl}methyl)pyrazin-2-yl trifluoromethanesulfonate To a cold (−78° C.) mixture of trifluoromethanesulfonic anhydride (0.284 mL, 1.681 mmol), 2,6-lutidine (0.261 mL, 2.241 mmol) and CH2Cl2 (1 mL) was added (4S,5R)-5-[3,5-bis(trifluoromethyl)phenyl]-3-[(3-hydroxypyrazin-2-yl)methyl]-4-methyl-1,3-oxazolidin-2-one (472 mg, 1.120 mmol) in CH2Cl2 (1 mL). The resulting mixture was stirred at −78° C. for 30 min then the cold bath was switched to an ice bath.

Reaction mixture was stirred cold (0° C.) for additional 2 h. Crude mixture was worked up with water/CH$_2$Cl$_2$/Na$_2$SO$_4$/filtration/concentration to afford an orange oil. This was purified by preparative TLC (silica gel) developed with a EtOAc (30% v/v)/hexanes mixture to give a yellow oil as the titled compound. LCMS calc.=553.04; found=554.02 (M+H)$^+$.

Step E: (4S,5R)-5-[3,5-Bis(trifluoromethyl)phenyl]-3-{[3-(5-chloro-2-fluorophenyl)pyrazin-2-yl]methyl}-4-methyl-1,3-oxazolidin-2-one 3-({(4S,5R)-5-[3,5-bis(trifluoromethyl)phenyl]-4-methyl-2-oxo-1,3-oxazolidin-3-yl}methyl)pyrazin-2-yl trifluoromethanesulfonate (Step D, 80 mg, 0.145 mmol), (5-chloro-2-fluorophenyl)boronic acid (30.3 mg, 0.173 mmol), Cs$_2$CO$_3$ (118 mg, 0.361 mmol), 1,1'-bis(diphenylphosphino) ferrocene-palladium dichloride dichloromethane adduct (11.81 mg, 0.014 mmol) and 1,4-dioxane (1 mL) were sealed in a microwave vessel and subjected to microwave irradiation at 140° C. for 25 min. LCMS indicated formation of the desired product. The crude mixture was diluted with MeCN and filtered. The filtrate was purified by preparative HPLC (Kromasil 100-5C 18, 100×21.1 mm) eluting with MeCN/water+0.1% TFA (10% to 100% organic in 10 min, hold 100% in 2 min, 20 mL/min). Related fractions were pooled and evaporated in vacuo to afford an aqueous mixture. The resulting aqueous mixture was extracted with EtOAc, washed with aqueous NaHCO$_3$, dried (Na$_2$SO$_4$), filtered and concentrated to afford a brown glass as the titled compound. LCMS calc.=533.07; found=534.19 (M+H)$^+$.

Step F: Methyl 3'-[3-({(4S,5R)-5-[3,5-bis(trifluoromethyl)phenyl]-4-methyl-2-oxo-1,3-oxazolidin-3-yl}methyl)pyrazin-2-yl]4'-fluoro-2-methylbiphenyl-4-carboxylate (4S,5R)-5-[3,5-bis(trifluoromethyl)phenyl]-3-{[3-(5-chloro-2-fluorophenyl)pyrazin-2-yl]methyl}-4-methyl-1,3-oxazolidin-2-one (33 mg, 0.062 mmol), methyl 3-methyl-4-(4,4,5,5-tetramethyl-1,3,2-dioxaborolan-2-yl)benzoate (INTERMEDIATE 37, 14.39 mg, 0.052 mmol), 1,1'-bis(di-tert-butylphosphino) ferrocene palladium dichloride (6.30 mg, 9.27 mmol), K$_2$CO$_3$ (0.155 mL, 0.309 mmol) and THF (1 mL) were sealed in a microwave vessel and subjected to microwave irradiation at 140° C. for 20 min. LCMS of aliquot indicated about 40% conversion. Microwave heating was resumed at 140° C. for an additional 30 min. LCMS of the aliquot indicated about 10% of remaining unreacted starting material. Microwave heating was resumed for an additional 12 min at 140° C. The resulting crude material was diluted with MeCN and filtered. The filtrate was purified by preparative HPLC (Kromasil 100-5C18, 100×21.1 mm) eluting with MeCN/water+0.1% TFA (10% to 100% organic in 10 min, hold 100% in 2 min, 20 mL/min) to give a brown glass. The brown glass was further purified by preparative TLC (SiO$_2$, 30% EtOAc/hexanes) to afford a colorless glass as the titled compound. LCMS calc.=647.17; found=648.38 (M+H)$^+$.

Step G: 3'-[3-({(4S,5R)-5-[3,5-Bis(trifluoromethyl)phenyl]-4-methyl-2-oxo-1,3-oxazolidin-3-yl}methyl)pyrazin-2-yl]-4'-fluoro-2-methylbiphenyl-4-carboxylic acid Methyl 3'-[3-({(4S,5R)-5-[3,5-bis(trifluoromethyl)phenyl]-4-methyl-2-oxo-1,3-oxazolidin-3-yl}methyl)pyrazin-2-yl]-4'-fluoro-2-methylbiphenyl-4-carboxylate (Step F, 16 mg, 0.025 mmol) and lithium hydroxide monohydrate (5.18 mg, 0.124 mmol) were stirred in 1,4-dioxane (0.914 mL)/water (0.571 mL) at room temperature for 2 days. Crude mixture was acidified with HCl (1N) and purified by preparative HPLC (Kromasil 100-5C18, 100×21.1 mm) eluting with MeCN/water+0.1% TFA (10% to 100% organic in 10 min, hold 100% in 2 min, 20 mL/min). Related fractions were pooled and evaporated in vacuo to afford an aqueous mixture. The resulting aqueous mixture was extracted with EtOAc, washed with water and then with brine, dried (Na$_2$SO$_4$), filtered and concentrated to afford a colorless glass as the titled compound. LCMS calc. 633.15=; found=634.25 (M+H)$^+$. $^1$H NMR (500 MHz, CDCl$_3$, 1:1 mixture of atropisomers): δ 8.70 (d, J=2.5 Hz, 1H), 8.68 (d, J=2.5 Hz, 1H), 8.01 (s, 1H), 7.95 (dd, J=8, 1.5 Hz, 1H), 7.89 (s, 1H), 7.78 (s, 1H), 7.51-7.46 (m, 2H), 7.37 (d, J=8 Hz, 1H), 7.31 (t, J=8 Hz, 1H), 5.74 (d, J=8.5 Hz, 1H), 4.95 (d, J=17 Hz, 1H), 4.44-4.36 (m, 2H), 2.37 (s, 3H), 0.77 (d, J=6 Hz, 3H).

Following procedures analogous to the one described in EXAMPLE 127 Step E, the compound listed in Table 11 was prepared from the corresponding aryl triflate and aryl boronic acid (INTERMEDIATE 2).

TABLE 11

| Ex. | | LCMS (M + H)+ |
|---|---|---|
| 128 | 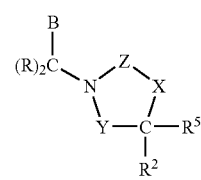 | 572.23 |

The invention claimed is:
1. A compound having Formula I, or a pharmaceutically acceptable salt thereof, wherein

$$\underset{\underset{R^2}{|}}{\overset{\overset{B}{|}}{(R)_2C}}\overset{}{\underset{N}{\diagdown}}\overset{Z}{\underset{Y-C-R^5}{\diagup}}\overset{X}{\diagdown}$$ I Y is selected from the group consisting of —C(=O)— and —(CRR$^1$)—;
X is selected from the group consisting of —O—, —NH—, —N(C$_1$-C$_5$alkyl)-, and —(CRR$^6$)—;
Z is selected from the group consisting of —C(=O)—, —S(O)$_2$—, and —C(=N—R$^9$)—, wherein R$^9$ is selected from the group consisting of H, —CN, and C$_1$-C$_5$alkyl optionally substituted with 1-11 halogens;

Each R is independently selected from the group consisting of H, —$C_1$-$C_5$ alkyl, and halogen, wherein —$C_1$-$C_5$ alkyl is optionally substituted with 1-11 halogens;

B is selected from the group consisting of $A^1$ and $A^2$, wherein $A^1$ has the structure:

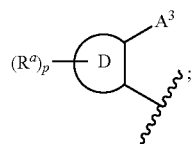

$R^1$ and $R^6$ are each selected from the group consisting of H, —$C_1$-$C_5$ alkyl, halogen, and —$(C(R)_2)_nA^2$, wherein —$C_1$-$C_5$ alkyl is optionally substituted with 1-11 halogens;

$R^2$ is selected from the group consisting of H, —$C_1$-$C_8$ alkyl, halogen, $A^1$, and —$(C(R)_2)_nA^2$, wherein —$C_1$-$C_5$ alkyl is optionally substituted with 1-11 halogens;

Wherein one of B and $R^2$ is $A^1$; and one of B, $R^1$, $R^2$, and $R^6$ is $A^2$ or —$(C(R)_2)_nA^2$; so that the compound of Formula I comprises one group $A^1$ and one group $A^2$;

D is selected from the group consisting of:
 (a) naphthyl;
 (b) a phenyl ring fused to a 5-7 membered non-aromatic cycloalkyl ring, which optionally comprises 1-2 double bonds;
 (c) a 5-6-membered heterocyclic ring having 1-4 heteroatoms independently selected from N, S, O, and —N(O)—, and optionally also comprising 1-3 double bonds and a carbonyl group; and
 (d) an 8-11-membered bicyclic heteroaromatic ring system comprising 2 fused rings and 1-5 heteroatoms independently selected from N, —S(O)$_x$—, O, and —N(O)—, wherein the ring system optionally comprises 1-5 double bonds, so that each ring is independently saturated, partly unsaturated, or aromatic;

wherein ring D comprises at least two carbon atoms that are bonded to each other, wherein one of the two carbon atoms is bonded to the group $A^3$ and the other of the two carbon atoms is connected to the remainder of the structure of Formula I, so that $A^3$ and the remainder of the structure of formula I are ortho to each other on ring D;

$A^3$ is selected from the group consisting of:
 (a) an aromatic ring selected from phenyl and naphthyl;
 (b) a phenyl ring fused to a 5-7 membered non-aromatic cycloalkyl ring, which optionally comprises 1-2 double bonds;
 (c) a 5-6-membered heterocyclic ring having 1-4 heteroatoms independently selected from N, S, O, and —N(O)—, and optionally also comprising 1-3 double bonds and a carbonyl group; and
 (d) an 8-11-membered bicyclic heteroaromatic ring system comprising 2 fused rings and 1-5 heteroatoms independently selected from N, —S(O)$_x$—, O, and —N(O)—, wherein the ring system optionally comprises 1-5 double bonds, so that each ring is independently saturated, partly unsaturated, or aromatic;

wherein the point of attachment of $A^3$ to the ring D to which $A^3$ is attached is a carbon atom of ring $A^3$;

wherein $A^3$ is optionally substituted with 1-5 substituent groups independently selected from $R^b$;

$A^2$ is selected from the group consisting of:
 (a) an aromatic ring selected from phenyl and naphthyl;
 (b) a phenyl ring fused to a 5-7 membered non-aromatic cycloalkyl ring, which optionally comprises 1-2 double bonds;
 (c) a 5-6-membered heterocyclic ring having 1-4 heteroatoms independently selected from N, S, O, and —N(O)—, and optionally also comprising 1-3 double bonds and a carbonyl group;
 (d) an 8-11-membered bicyclic heteroaromatic ring system comprising 2 fused rings and 1-5 heteroatoms independently selected from N, —S(O)$_x$—, O, and —N(O)—, wherein the ring system optionally comprises 1-5 double bonds, so that each ring is independently saturated, partly unsaturated, or aromatic; and
 (e) a —$C_3$-$C_8$ cycloalkyl ring optionally having 1-3 double bonds;

wherein $A^2$ is optionally substituted with 1-5 substituent groups independently selected from $R^a$;

wherein the point of attachment of $A^2$ to the structure of formula I to which $A^2$ is attached is a carbon atom of ring $A^2$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)$SC_1$-$C_6$alkyl, —OH, —$NR^3R^4$, —C(=O)$NR^3R^4$, —$NR^3$C(=O)$OC_1$-$C_6$ alkyl, —$NR^3$C(=O)$NR^3R^4$, —S(O)$_xC_1$-$C_6$ alkyl, —S(O)$_yNR^3R^4$, —$NR^3$S(O)$_yNR^3R^4$, halogen, —CN, —$NO_2$, phenyl, naphthyl, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom;

wherein for compounds in which $R^a$ is a cyclic group selected from phenyl, naphthyl, —$C_3$-$C_8$ cycloalkyl optionally having 1-3 double bonds, and a heterocyclic ring, $R^a$ is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —$CO_2C_1$-$C_6$alkyl, —C(=O)$SC_1$-$C_6$alkyl, —$NR^3$C(=O)$OC_1$-$C_6$ alkyl, and —S(O)$_xC_1$-$C_6$ alkyl, $R^a$ is optionally substituted with 1-15 halogens and is optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally substituted with 1-2 substituent groups independently selected from —$OC_1$-$C_2$ alkyl and phenyl, (f) —$OC_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j)

phenyl which is optionally substituted with 1-3 groups independently selected from halogen, —CH$_3$, —CF$_3$, —OCH$_3$, and —OCF$_3$;

Each R$^b$ is independently selected from the group consisting of —C$_1$-C$_6$ alkyl, —C$_2$-C$_6$ alkenyl, —C$_2$-C$_6$ alkynyl, —C$_3$-C$_8$ cycloalkyl optionally having 1-3 double bonds, —OC$_1$-C$_6$alkyl, —OC$_2$-C$_6$ alkenyl, —OC$_2$-C$_6$ alkynyl, —OC$_3$-C$_8$ cycloalkyl optionally having 1-3 double bonds, —C(=O)C$_1$-C$_6$alkyl, —C(=O)C$_3$-C$_8$ cycloalkyl, —C(=O)H, —CO$_2$H, —CO$_2$C$_1$-C$_6$alkyl, —C(=O)SC$_1$-C$_6$alkyl, —NR$^3$R$^4$, —C(=O)NR$^3$R$^4$, —NR$^3$C(=O)OC$_1$-C$_6$alkyl, —NR$^3$C(=O)NR$^3$R$^4$, —S(O)$_x$C$_1$-C$_6$ alkyl, —S(O)$_y$NR$^3$R$^4$, —NR$^3$S(O)$_y$NR$^3$R$^4$, halogen, —CN, —NO$_2$, phenyl, naphthyl, and a 5-6-membered heterocyclic ring having 1-4 heteroatoms independently selected from N, S, and O, said heterocyclic ring optionally also comprising a carbonyl group and optionally also comprising 1-3 double bonds, wherein when R$^b$ is selected from the group consisting of a heterocyclic ring, —C$_3$-C$_8$ cycloalkyl, naphthyl, —OC$_3$-C$_8$ cycloalkyl, and —C(=O)C$_3$-C$_8$ cycloalkyl, then the heterocyclic ring, naphthyl, and —C$_3$-C$_8$ cycloalkyl groups of R$^b$ are optionally substituted with 1-5 substituent groups independently selected from halogen, —C$_1$-C$_3$ alkyl, —C$_2$-C$_3$ alkenyl, —NR$^3$R$^4$, —OC$_1$-C$_3$ alkyl, —CO$_2$H, —CN, and —CO$_2$C$_1$-C$_3$alkyl, wherein —C$_1$-C$_3$ alkyl and —C$_2$-C$_3$ alkenyl in all uses are optionally substituted with 1-7 halogens and optionally one group —OH;

when R$^b$ is selected from the group consisting of —C$_1$-C$_6$ alkyl, —C$_2$-C$_6$ alkenyl, —C$_2$-C$_6$ alkynyl, —OC$_1$-C$_6$alkyl, —OC$_2$-C$_6$ alkenyl, —OC$_2$-C$_6$ alkynyl, —C(=O)C$_1$-C$_6$alkyl, —CO$_2$C$_1$-C$_6$alkyl, —C(=O)SC$_1$-C$_6$alkyl, —NR$^3$C(=O)OC$_1$-C$_6$alkyl, and —S(O)$_x$C$_1$-C$_6$ alkyl, then the alkyl, alkenyl, and alkynyl groups of R$^b$ are optionally substituted with 1-13 halogens and are optionally substituted with 1-3 substituent groups independently selected from (a) —OH, (b) —CN, (c) —NR$^3$R$^4$, (d) —C$_3$-C$_8$ cycloalkyl optionally having 1-3 double bonds and optionally substituted with 1-15 halogens, (e) —OC$_1$-C$_4$alkyl optionally substituted with 1-9 halogens and optionally substituted with 1-2 substituent groups independently selected from —OC$_1$-C$_2$ alkyl, (f) —OC$_3$-C$_8$ cycloalkyl optionally having 1-3 double bonds and optionally substituted with 1-15 halogens, (g) —CO$_2$H, (h) —C(=O)CH$_3$, (i)—CO$_2$C$_1$-C$_4$alkyl which is optionally substituted with 1-9 halogens, and (j) phenyl which is optionally substituted with 1-3 groups independently selected from halogen, —CH$_3$, —CF$_3$, —OCH$_3$, and —OCF$_3$;

and when R$^b$ is phenyl, said phenyl is optionally substituted with 1-5 halogens and is optionally substituted with 1-3 substituents independently selected from —C$_1$-C$_4$ alkyl, —C$_2$-C$_4$ alkenyl, —C$_2$-C$_4$ alkynyl, —C$_3$-C$_6$ cycloalkyl, —OC$_1$-C$_4$alkyl, —OC$_2$-C$_4$ alkenyl, —OC$_2$-C$_4$ alkynyl, —OC$_3$-C$_6$ cycloalkyl, —C(=O)C$_1$-C$_4$alkyl, —C(=O)H, —CO$_2$H, —CO$_2$C$_1$-C$_4$alkyl, —NR$^3$R$^4$, —C(=O)NR$^3$R$^4$, —NR$^3$C(=O)OC$_1$-C$_4$ alkyl, —NR$^3$C(=O)NR$^3$R$^4$, —S(O)$_x$C$_1$-C$_4$ alkyl, —S(O)$_y$NR$^3$R$^4$, —NR$^3$S(O)$_y$NR$^3$R$^4$, —CN, —NO$_2$, and a 5-6-membered heterocyclic ring having 1-4 heteroatoms independently selected from N, S, and O, said heterocyclic ring optionally also comprising a carbonyl group and optionally also comprising 1-3 double bonds and optionally comprising 1-3 substituents independently selected from halogen, —CH$_3$, —OCH$_3$, —CF$_3$, and —OCF$_3$; wherein when the substituents on phenyl when Rb is phenyl are selected from —C$_1$-C$_4$ alkyl, —C$_2$-C$_4$ alkenyl, —C$_2$-C$_4$ alkynyl, —C$_3$-C$_6$ cycloalkyl, —OC$_1$-C$_4$alkyl, —OC$_2$-C$_4$ alkenyl, —OC$_2$-C$_4$ alkynyl, —OC$_3$-C$_6$ cycloalkyl, —C(=O)C$_1$-C$_4$alkyl, —CO$_2$C$_1$-C$_4$alkyl, —NR$^3$C(=O)OC$_1$-C$_4$ alkyl, and —S(O)$_x$C$_1$-C$_4$ alkyl, then the alkyl, alkenyl, alkynyl, and cycloalkyl groups of said substituent groups optionally comprise 1-5 halogen substituents and also optionally comprise one substituent selected from —OH, —NR$^3$R$^4$, —OCH$_3$ optionally substituted with 1-3 F, and phenyl which is optionally substituted with 1-3 substituents independently selected from halogen, —CH$_3$, —OCH$_3$, —CF$_3$, and —OCF$_3$;

n is 0 or 1;

p is an integer from 0-4;

x is 0, 1, or 2;

y is 1 or 2;

R$^3$ and R$^4$ are each independently selected from H, —C$_1$-C$_5$ alkyl, —C(=O)C$_1$-C$_5$ alkyl and —S(O)$_y$C$_1$-C$_5$ alkyl, wherein —C$_1$-C$_5$ alkyl in all instances is optionally substituted with 1-11 halogens; and R$^5$ is selected from the group consisting of H, —OH, —C$_1$-C$_5$ alkyl, and halogen, wherein —C$_1$-C$_5$ alkyl is optionally substituted with 1-11 halogens.

2. The compound of claim 1, which is selected from the group consisting of compounds having Formula Ia, Ib, and Id, or a pharmaceutically acceptable salt thereof:

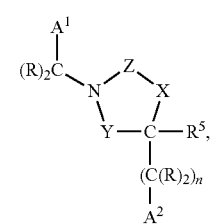

Ia

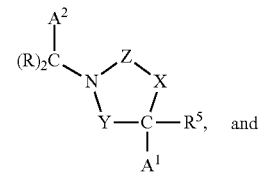

Ib

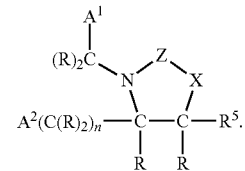

Id

3. The compound of claim 1, or a pharmaceutically acceptable salt thereof, wherein:

Y is —(CHR$^1$)—;

X is —O—;

Z is —C(=O)—;

R is H;

n is 0;

p is an integer from 0-2; and

R$^1$ and R$^5$ are each independently selected from the group consisting of H and —C$_1$-C$_3$ alkyl.

4. The compound of claim 1, or a pharmaceutically acceptable salt thereof, wherein:

D is selected from the group consisting of naphthyl, pyridyl, quinolyl, indanyl, benzothienyl, tetrahydronaphthyl, isoxazolyl, thienyl, imidazolyl, pyrrolyl, pyrazolyl, pyridyl, N-oxido-pyridyl, 1,3-thiazolyl, 1,3-oxazolyl, pyridazinyl, pyrimidinyl, pyrazinyl, pyridazinyl, benzofuranyl, dihydrobenzofuranyl, benzothienyl-5-oxide, benzothienyl-5-dioxide, dihydroindolyl; dihydroisoindolyl, dihydroisobenzofuranyl, and benzodioxolanyl;

$A^3$ is selected from the group consisting of phenyl, naphthyl, tetrahydronaphthyl, pyridyl, thienyl, imidazolyl, pyrrolyl, pyrazolyl, N-oxido-pyridyl, 1,3-thiazolyl, 1,3-oxazolyl, pyridazinyl, pyrimidinyl, pyrazinyl, indanyl, benzothienyl, benzothienyl-5-oxide, benzothienyl-S-dioxide, dihydroindolyl; dihydroisoindolyl, dihydroisobenzofuranyl, and benzodioxolanyl; and $A^2$ is selected from the group consisting of phenyl, thienyl, imidazolyl, thiazolyl, pyrrolyl, pyrazolyl, 1,2,4-triazolyl, tetrazolyl, benzodioxolyl, pyridyl, N-oxido-pyridyl, pyridazinyl, pyrimidinyl, pyrazinyl, cyclopentyl, cyclohexyl, and tetrahydropyranyl.

5. The compound of claim 1, or a pharmaceutically acceptable salt thereof, wherein:

D is selected from the group consisting of naphthyl, pyridyl, quinolyl, indanyl, benzothienyl, tetrahydronaphthyl, isoxazolyl, 1,3-thiazolyl, pyrimidinyl, pyrazinyl, dihydroisoindolyl, dihydroisobenzofuranyl, and benzodioxolanyl;

$A^3$ is selected from the group consisting of phenyl, naphthyl, indanyl, and tetrahydronaphthyl; and $A^2$ is phenyl.

6. The compound of claim 1, or a pharmaceutically acceptable salt thereof, wherein:

$R^a$ and $R^b$ are each independently selected from the group consisting of —$C_1$-$C_5$ alkyl, —$C_2$-$C_5$ alkenyl, —$C_3$-$C_6$ cycloalkyl optionally having 1-2 double bonds, —$OC_1$-$C_3$alkyl, —C(=O)H, —$CO_2$H, —$CO_2C_1$-$C_4$alkyl, —OH, —$NR^3R^4$, halogen, —CN, —$NO_2$, phenyl, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-3 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ and $R^b$ are selected from the group consisting of —$C_1$-$C_5$ alkyl, —$C_2$-$C_5$ alkenyl, —$OC_1$-$C_3$alkyl, and —$CO_2C_1$-$C_4$alkyl, $R^a$ is optionally substituted with 1-7 halogens and is optionally substituted with one substituent group —OH;

wherein for compounds in which $R^a$ and $R^b$ are selected from the group consisting of phenyl and —$C_3$-$C_6$ cycloalkyl optionally having 1-2 double bonds, $R^a$ is optionally substituted with 1-5 halogens and is optionally substituted with 1-3 groups independently selected from —$C_1$-$C_5$ alkyl, —$C_2$-$C_5$ alkenyl, —$C_3$-$C_6$ cycloalkyl optionally having 1-2 double bonds, —$OC_1$-$C_3$alkyl, —C(=O)H, —$CO_2$H, —$CO_2C_1$-$C_4$alkyl, —OH, —$NR^3R^4$, halogen, —CN, and —$NO_2$, wherein —$C_1$-$C_5$ alkyl, —$C_2$-$C_5$ alkenyl, —$C_3$-$C_6$ cycloalkyl optionally having 1-2 double bonds, —$OC_1$-$C_3$alkyl, and —$CO_2C_1$-$C_4$alkyl are optionally substituted with 1-5 halogens, and —$C_1$-$C_5$ alkyl also is optionally substituted with one —OH; and $R^3$ and $R^4$ are each independently selected from H and $C_1$-$C_3$alkyl.

7. The compound of claim 1, or a pharmaceutically acceptable salt thereof, wherein:

Y is —(CHR$^1$)—, wherein R$^1$ is selected from H and $C_1$-$C_2$ alkyl;

$R^5$ is H;

X is —O—;

Z is —C(=O)—;

R is H;

n is 0;

$R^2$ is $A^2$, where $A^2$ is phenyl which is optionally substituted with 1-3 substituents independently selected from halogen, —$C_1$-$C_3$ alkyl which is optionally substituted with 1-3 halogens, and —$OC_1$-$C_3$alkyl which is optionally substituted with 1-3 halogens;

B is $A^1$ and has the structure:

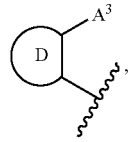

wherein D is selected from the group consisting of naphthyl, pyridyl, quinolyl, indanyl, benzothienyl, tetrahydronaphthyl, isoxazolyl, 1,3-thiazolyl, pyrimidinyl, pyrazinyl, dihydroisoindolyl, dihydroisobenzofuranyl, and benzodioxolanyl, wherein D is optionally substituted with 1-2 substituent groups independently selected from (a) halogen, (b) —$C_1$-$C_5$ alkyl which is optionally substituted with 1-3 halogens, (c) —$C_2$-$C_3$ alkenyl, (d) —$C_3$-$C_6$ cycloalkyl, (e) —$C_5$-$C_6$ cycloalkenyl, (f) —$OC_1$-$C_3$alkyl optionally substituted with 1-3 halogens; (g) —$SC_1$-$C_3$alkyl, (h) —$SO_2C_1$-$C_3$alkyl, (i) —C(=O)OCH$_2$-Phenyl, (j) Phenyl optionally substituted with 1-3 substituents independently selected from halogen, CH$_3$, CF$_3$, —OCH$_3$, and —OCF$_3$, (k) —$NR^3R^4$, where $R^3$ and $R^4$ are each independently selected from H and CH$_3$, (l) —CN, and (m) —$NO_2$; and $A^3$ is selected from the group consisting of phenyl, naphthyl, indanyl, and tetrahydronaphthyl, wherein $A^3$ is optionally substituted with 1-3 substituents independently selected from (a) halogen, (b) —$C_1$-$C_5$ alkyl which is optionally substituted with 1-3 halogens and optionally one group selected from —OH, —$CO_2$H, and —$CO_2C_1$-$C_3$ alkyl, (c) —$C_2$-$C_3$ alkenyl, (d) —$C_3$-$C_6$ cycloalkyl which is optionally substituted with one group selected from [i] —$CO_2$H, [ii] —OH, and [iii] —$C_1$-$C_5$ alkyl which is optionally substituted with 1-3 halogens and optionally with 1 group selected from —OH, —$CO_2$H, and —$CO_2CH_3$, (e) —$C_5$-$C_6$ cycloalkenyl, (f) phenyl which is optionally substituted with 1-2 substituent groups independently selected from halogen, CH$_3$, CF$_3$, —OCH$_3$, —OCF$_3$, and optionally one group —$CO_2$H or —$CO_2C_1$-$C_3$ alkyl, and (g) —$OC_1$-$C_3$alkyl optionally substituted with 1-3 halogens.

8. A pharmaceutical composition comprising the compound of claim 1, or a pharmaceutically acceptable salt thereof, and a pharmaceutically acceptable carrier.

9. The compound of claim 1, which is selected from the group consisting of the following compounds, or a pharmaceutically acceptable salt thereof:

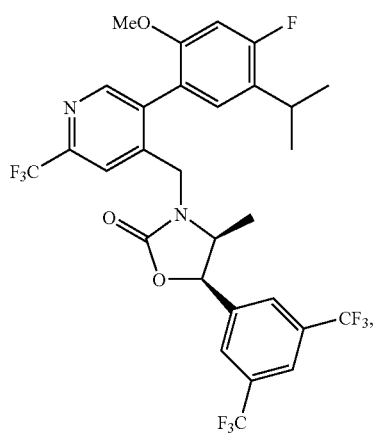
Ex 1
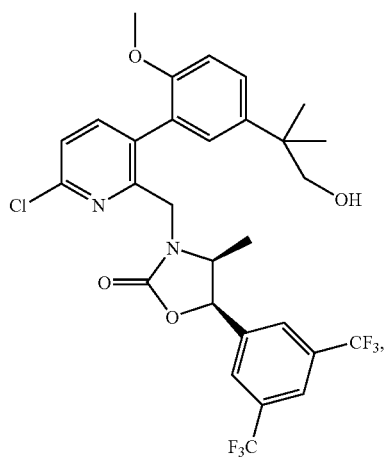
Ex 26
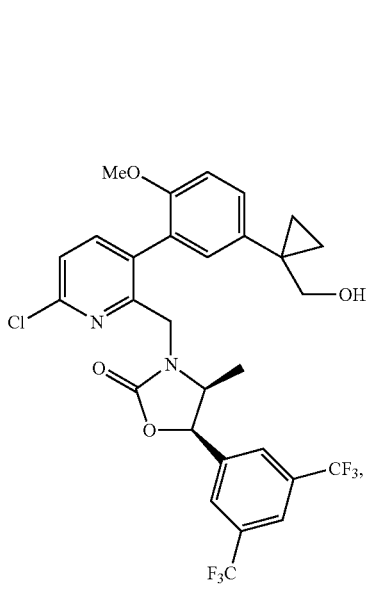
Ex 27
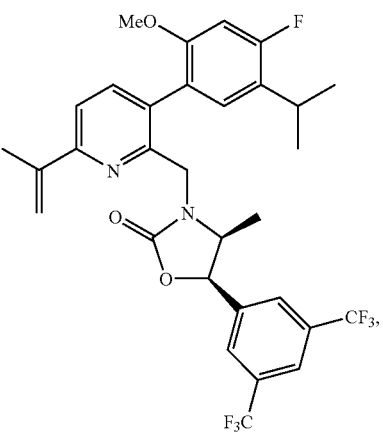
Ex 28
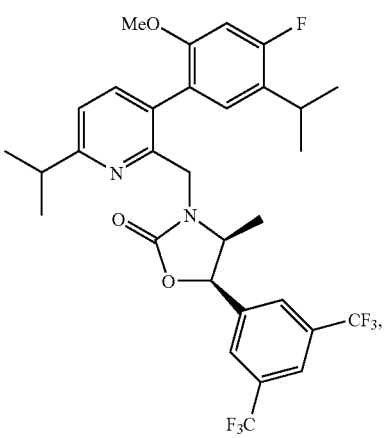
Ex. 29
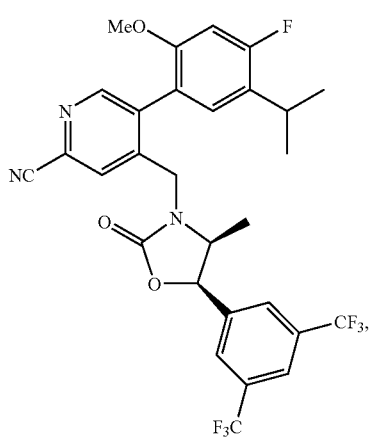
Ex. 51

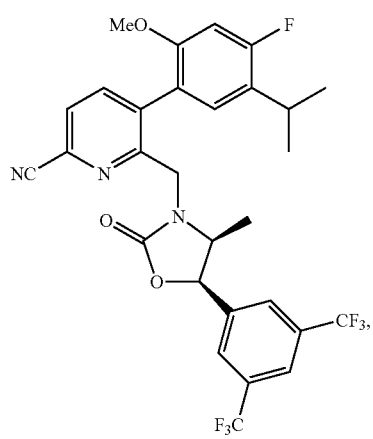
Ex. 52
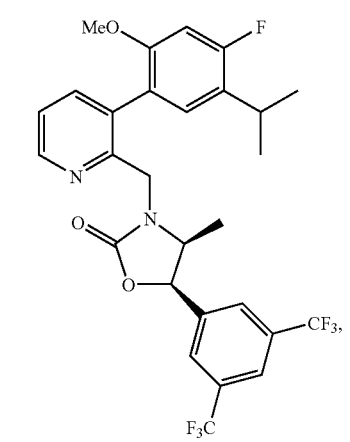
Ex. 53
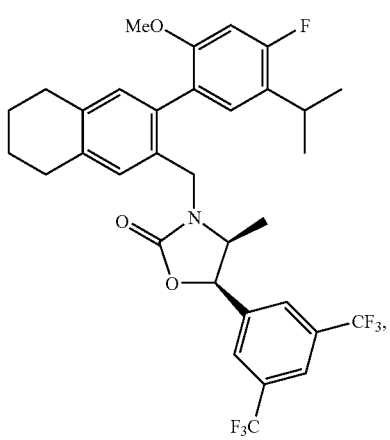
Ex. 54
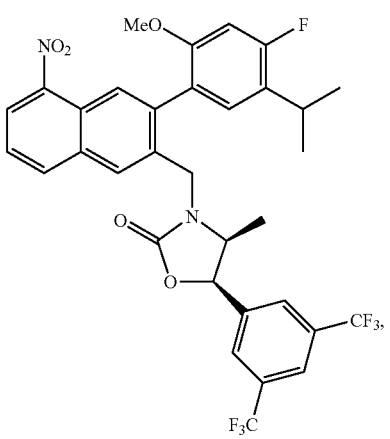
Ex. 55
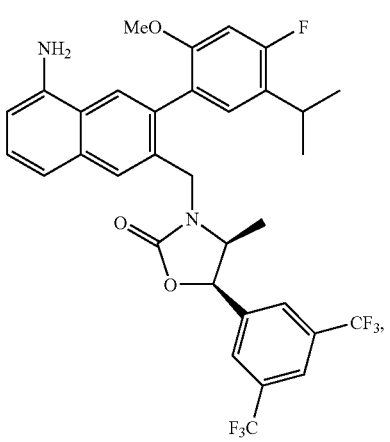
Ex. 56
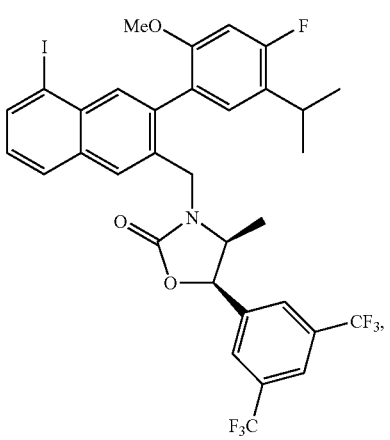
Ex. 57

-continued
Ex. 58
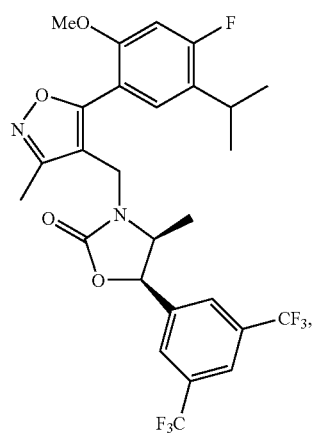
Ex. 59
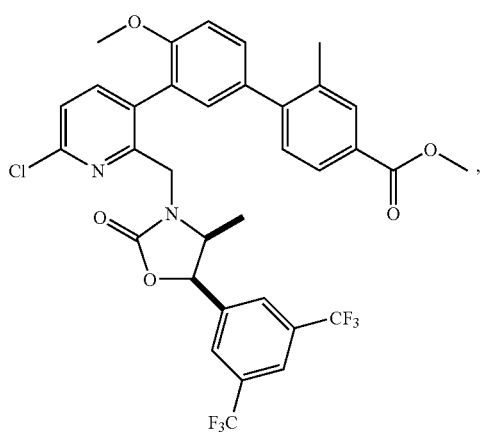
Ex. 60
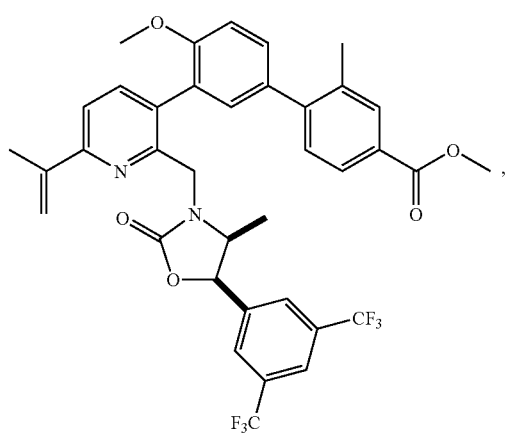
-continued
Ex. 61
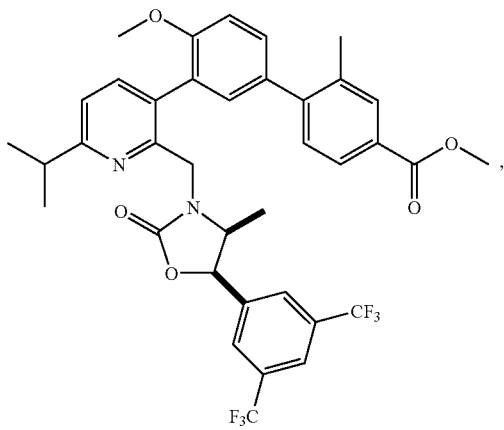
Ex. 62
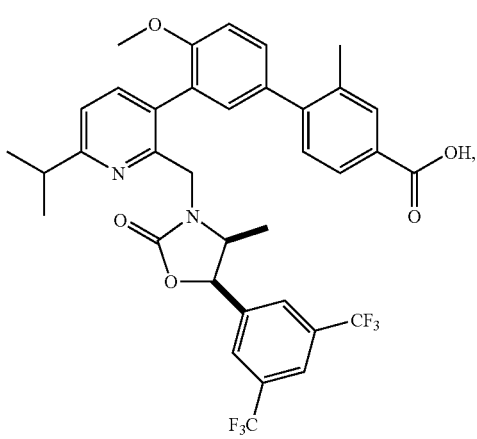
Ex. 63
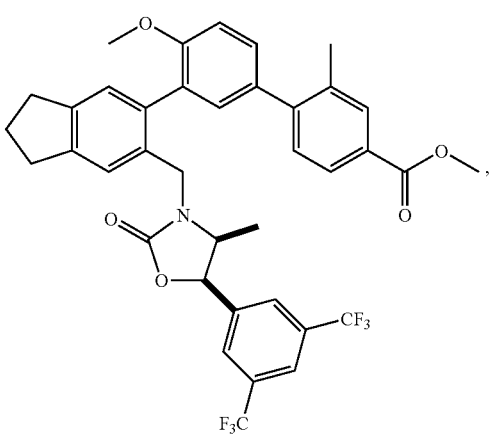

-continued
Ex. 64
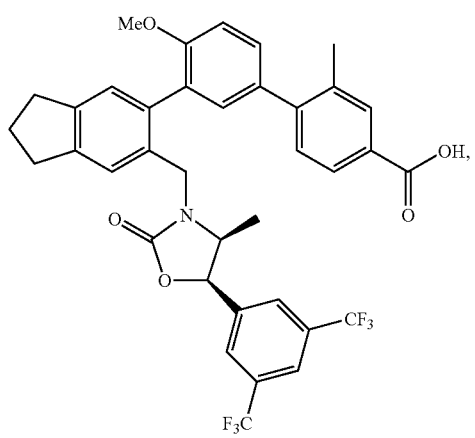
Ex. 91
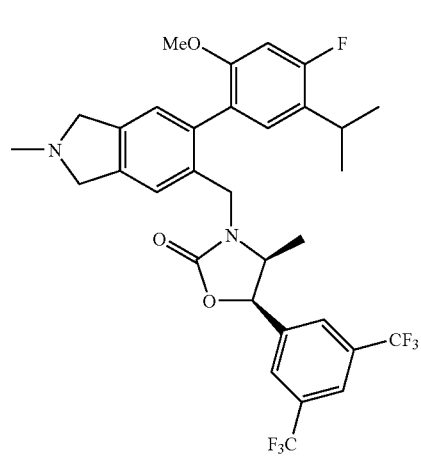
Ex. 92
-continued
Ex. 93
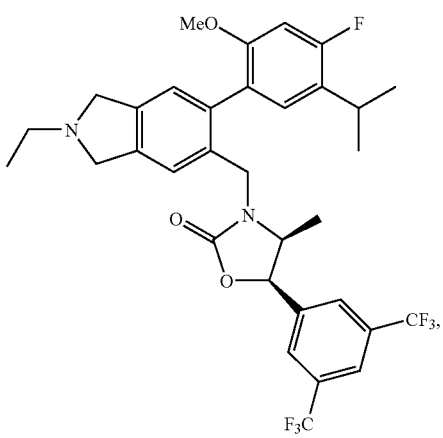
Ex. 98
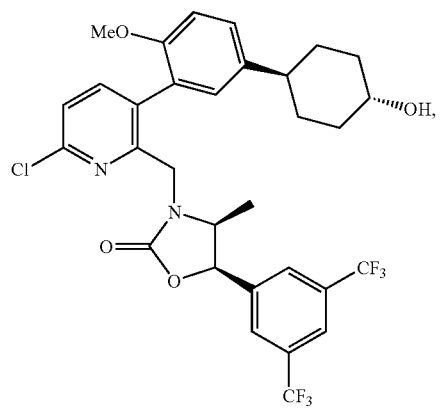
Ex. 99
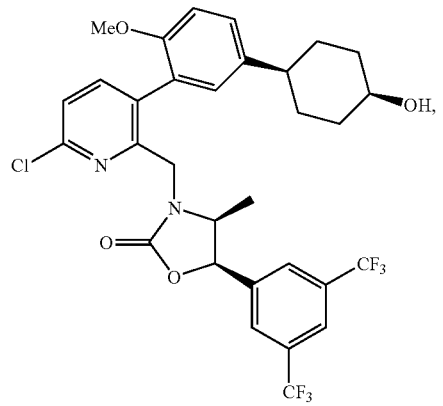

-continued
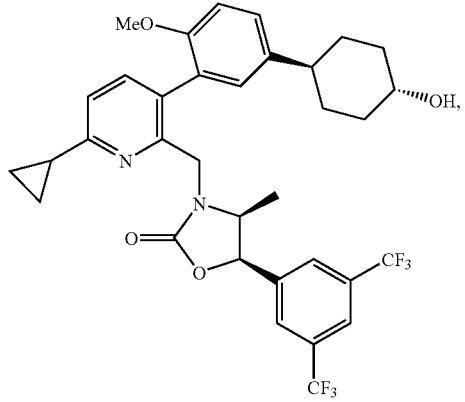
Ex. 105
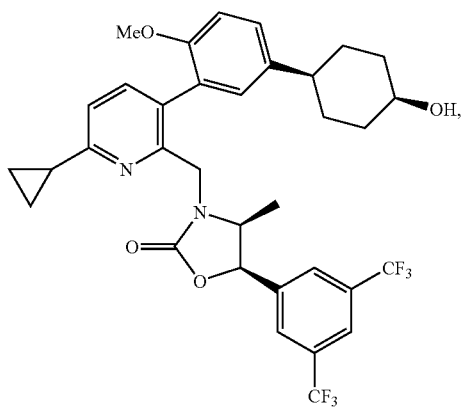
Ex. 106
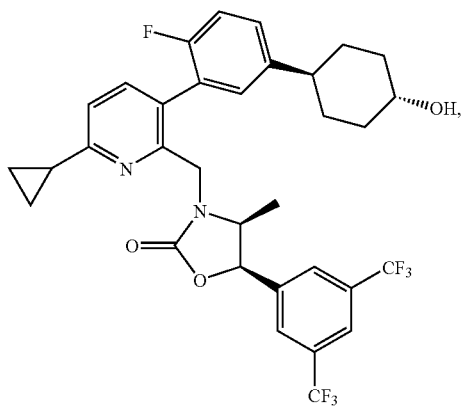
Ex. 107
-continued
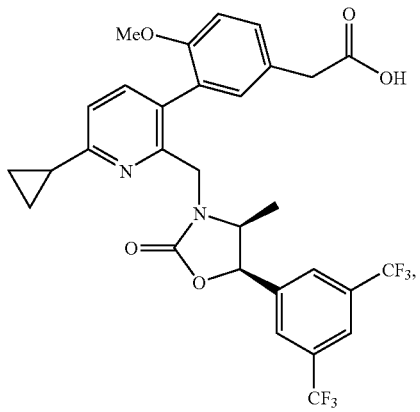
Ex. 108
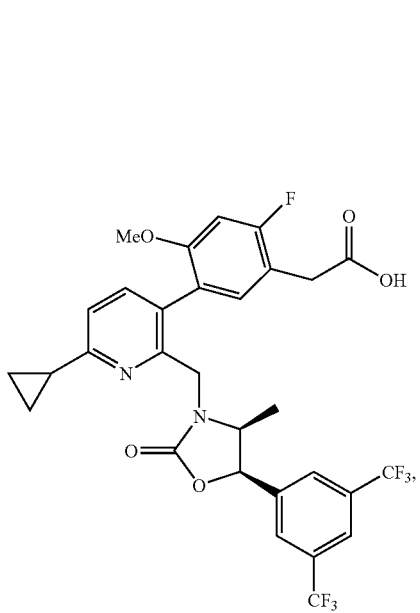
Ex. 109
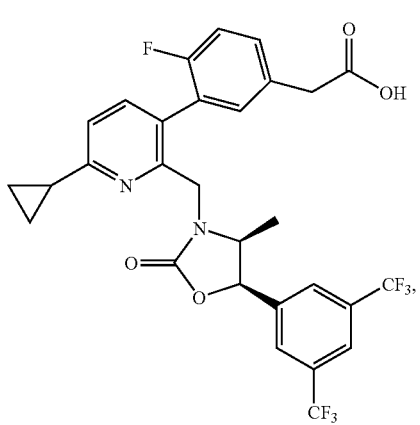
Ex. 110

Ex. 111
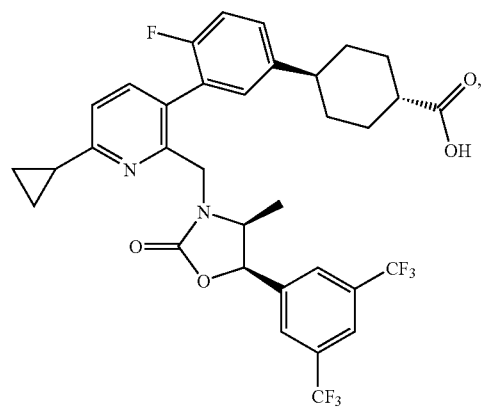
Ex. 114
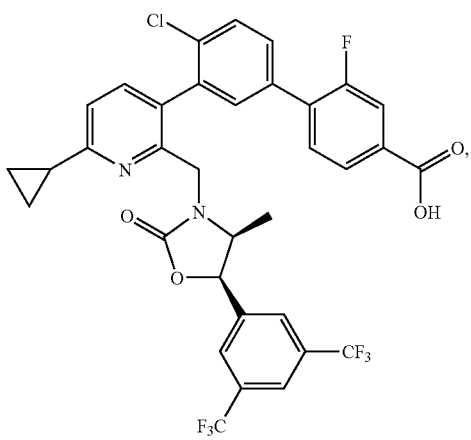
Ex. 112
Ex. 115
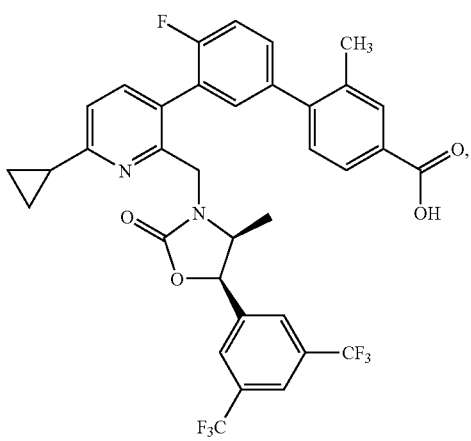
Ex. 113
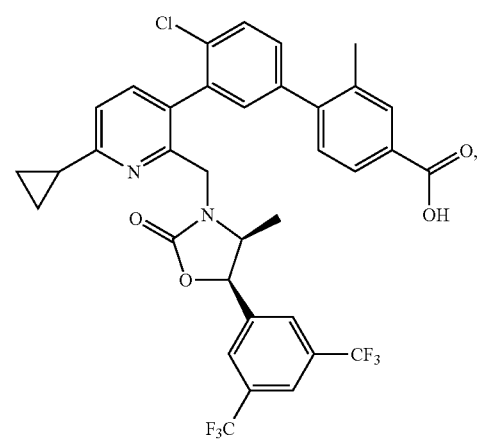
Ex. 116
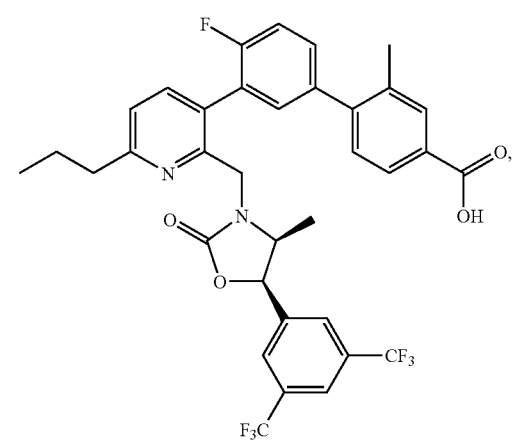

-continued
Ex. 117
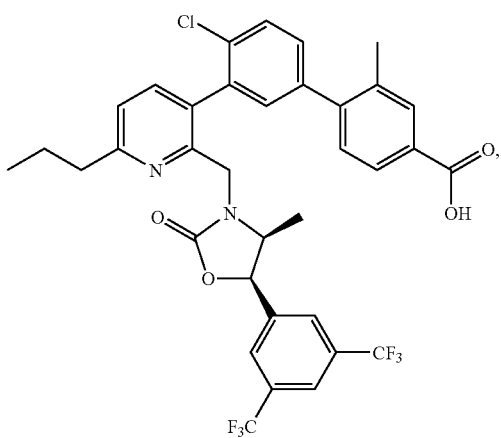
Ex. 118
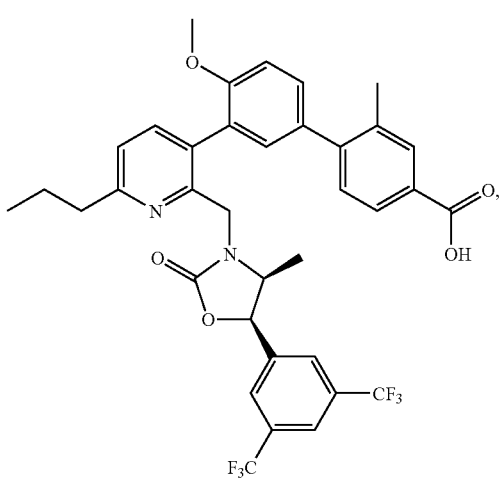
Ex. 119
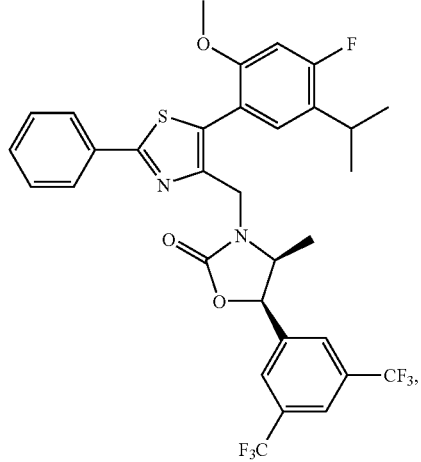
-continued
Ex. 120
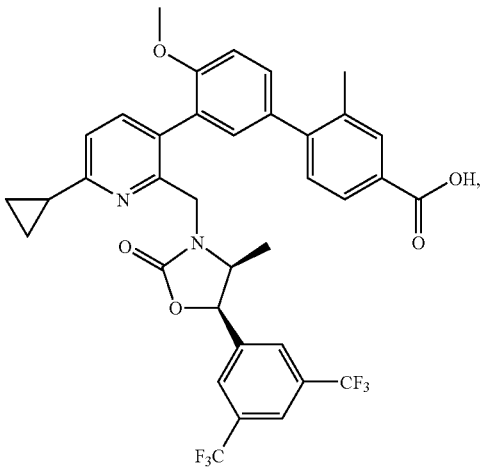
Ex. 121
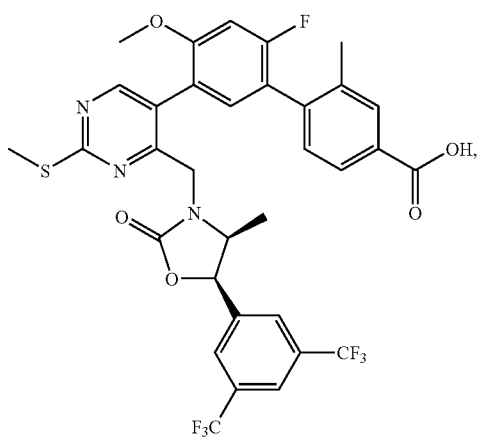
Ex. 125
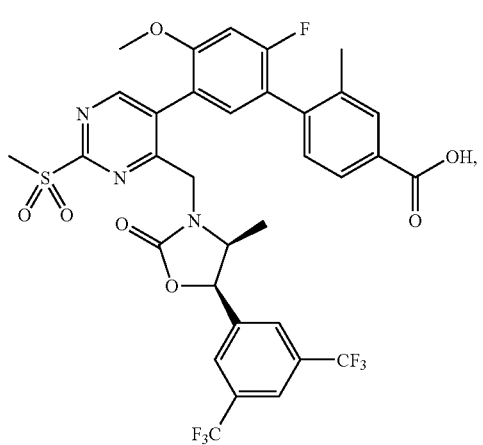

Ex. 126
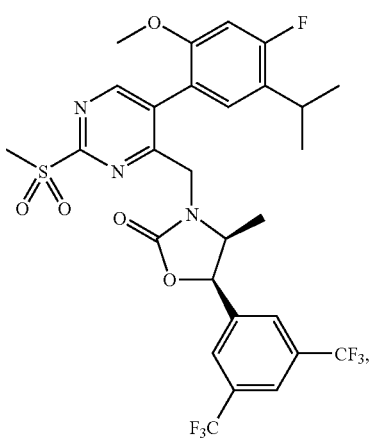
Ex. 127
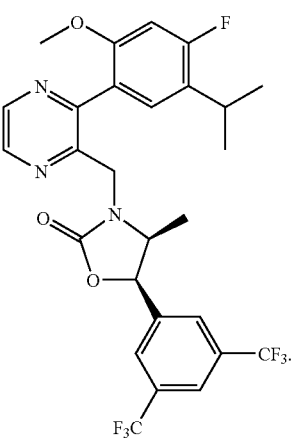
Ex. 128
and
10. The compound of claim 1, which is selected from the following compounds, or a pharmaceutically acceptable salt thereof:
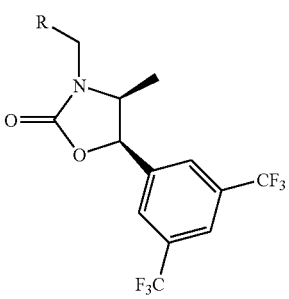
(a)
wherein R is selected from the group consisting of:
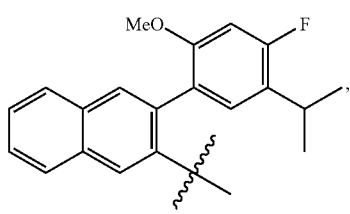
Ex. 2
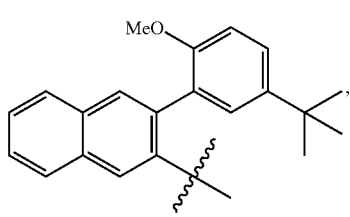
Ex. 3
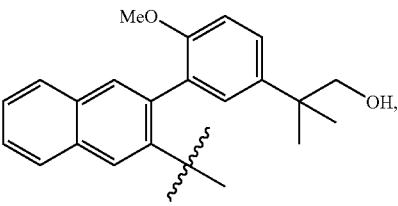
Ex. 4
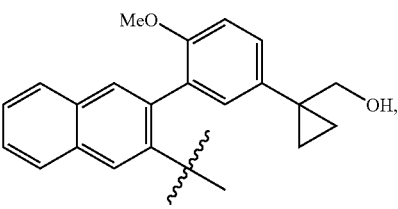
Ex. 5

| | |
|---|---|
| 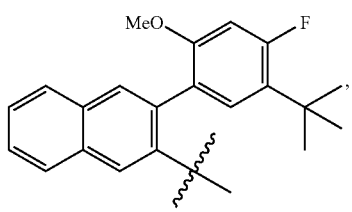 Ex. 6 | 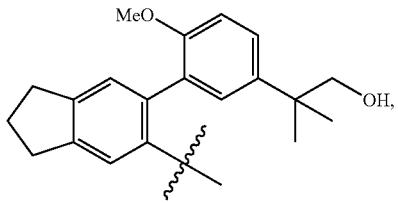 Ex. 13 |
| 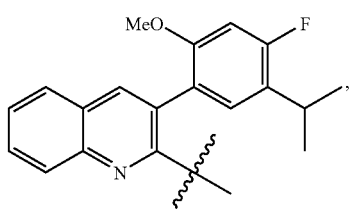 Ex. 7 | 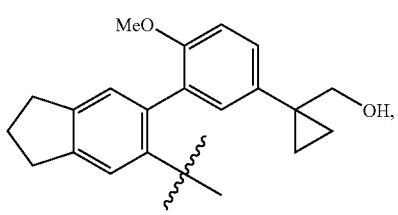 Ex. 14 |
| 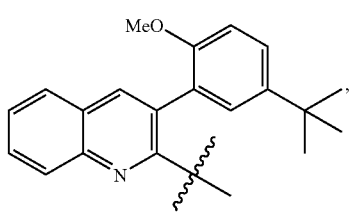 Ex. 8 | 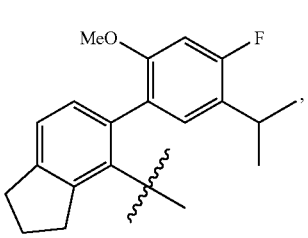 Ex. 15 |
| 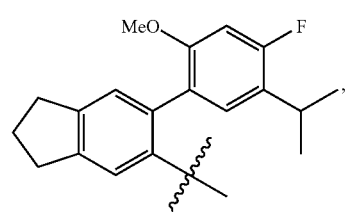 Ex. 9 | 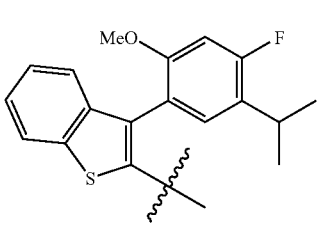 Ex. 16 |
| 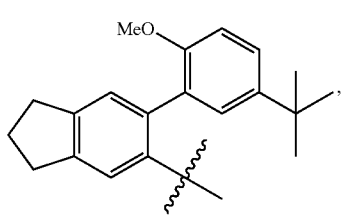 Ex. 10 | 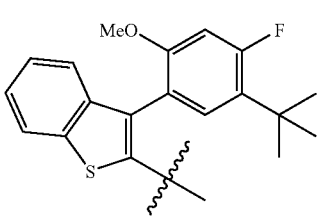 Ex. 17 |
| 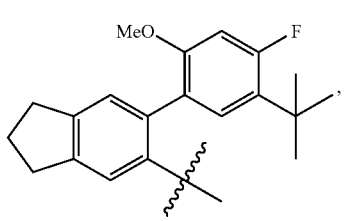 Ex. 11 | 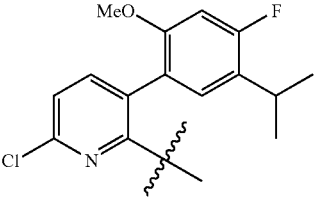 Ex. 18 |
| 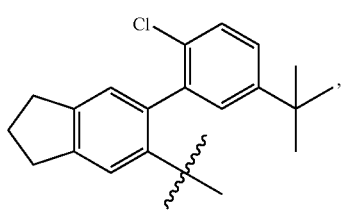 Ex. 12 | 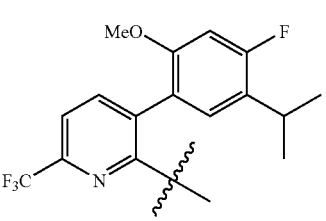 Ex. 19 |

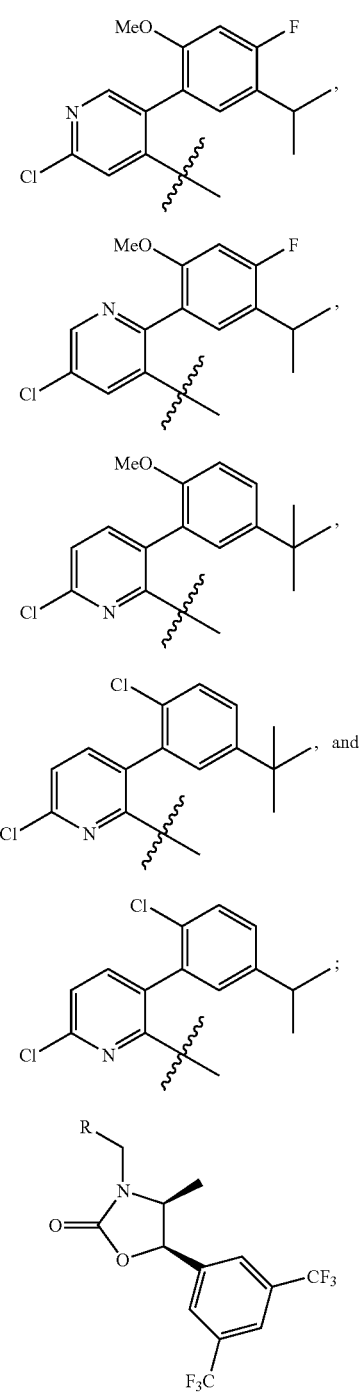
Ex. 20
Ex. 21
Ex. 22
Ex. 23, and
Ex. 24;
(b)
wherein R is selected from the group consisting of:
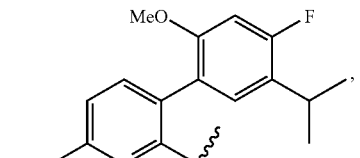
Ex. 31
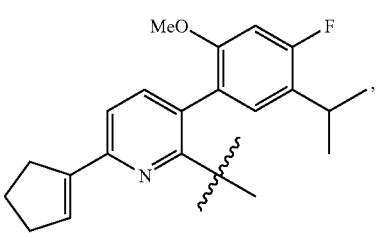
Ex. 32
Ex. 33
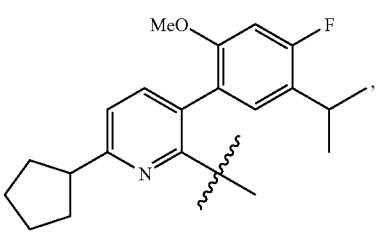
Ex. 34
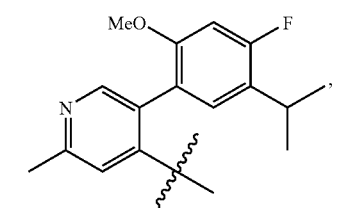
Ex. 35
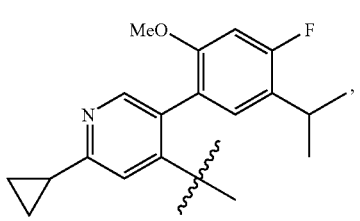
Ex. 36
Ex. 30
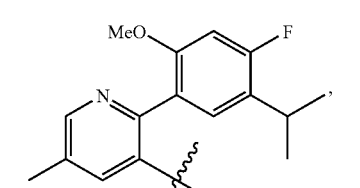
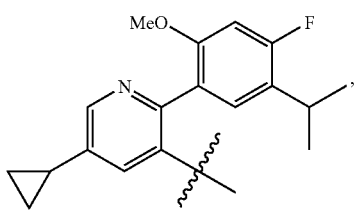
Ex. 37

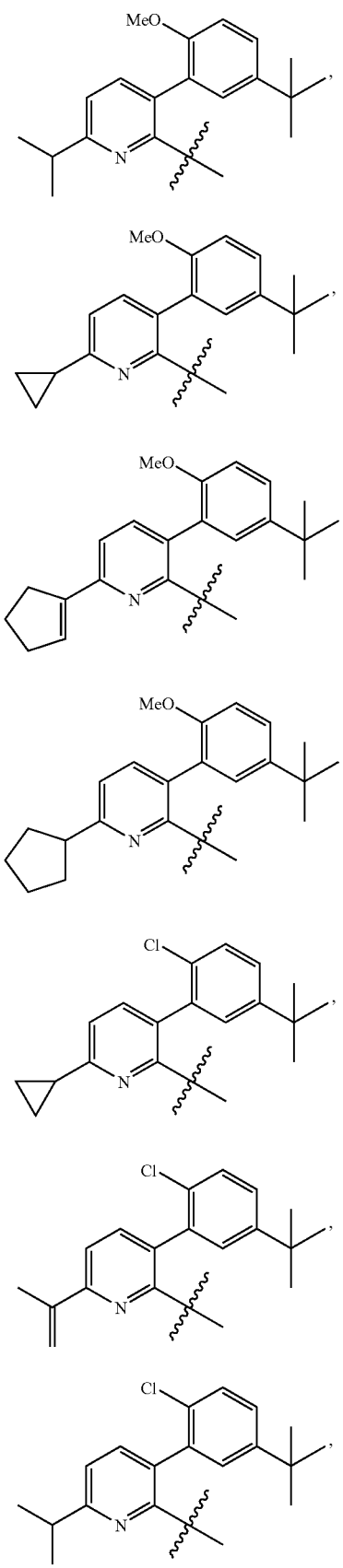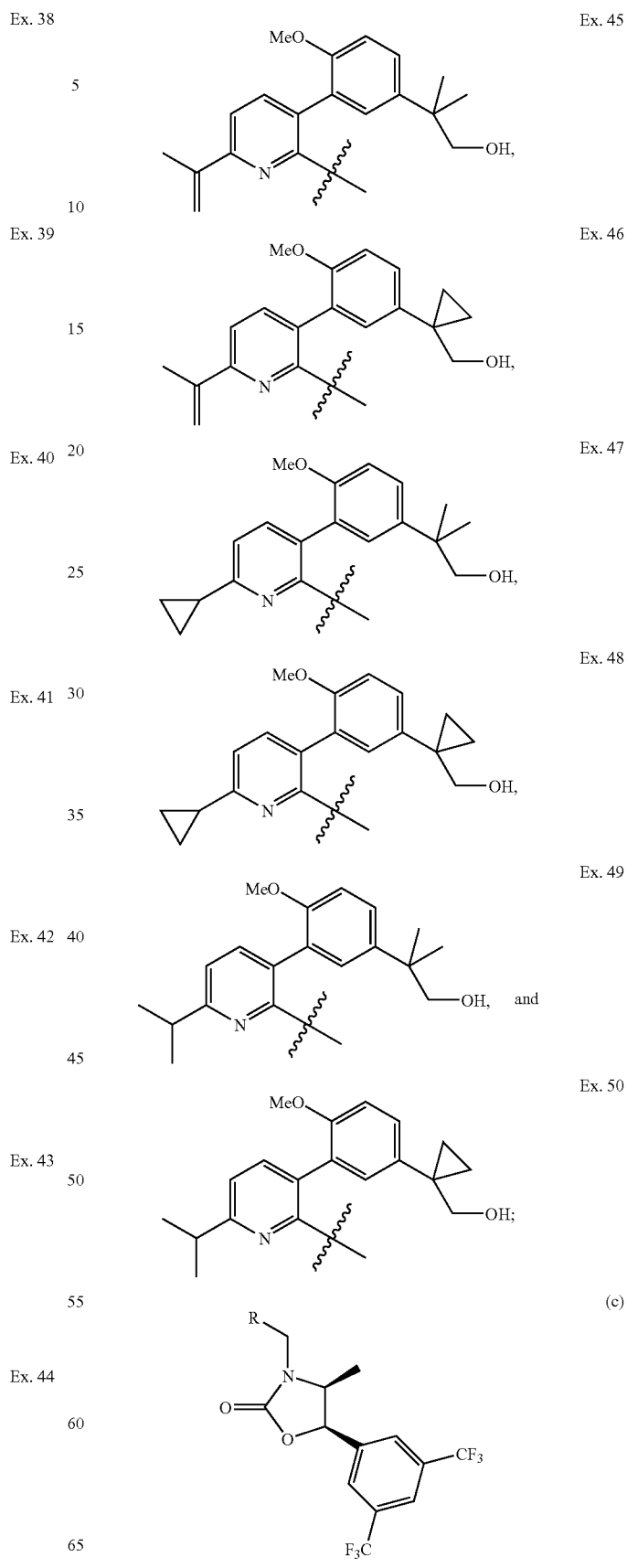

wherein R is selected from the group consisting of:
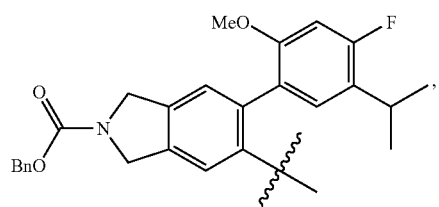
Ex. 65
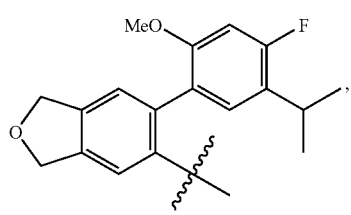
Ex. 66
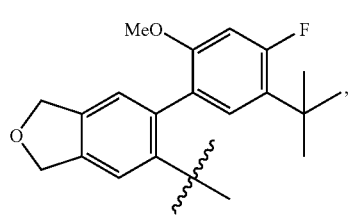
Ex. 67
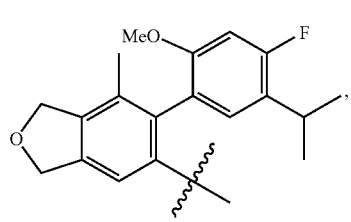
Ex. 68
atropisomer 1
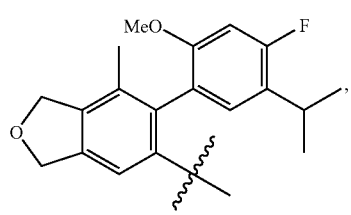
Ex. 69
atropisomer 2
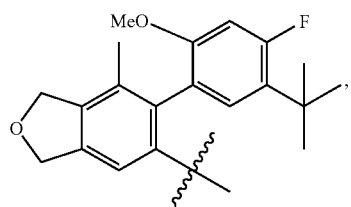
Ex. 70
atropisomer 1
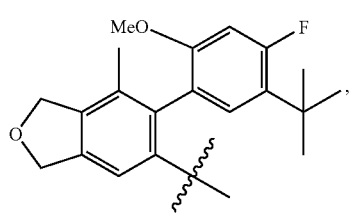
Ex. 71
atropisomer 2
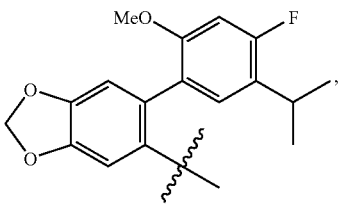
Ex. 72
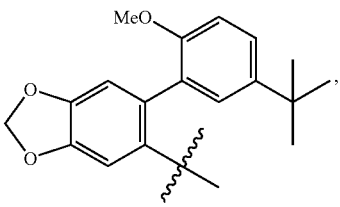
Ex. 73
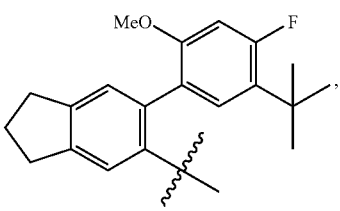
Ex. 74
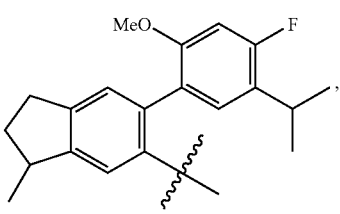
Ex. 75
diastereoisomer 1
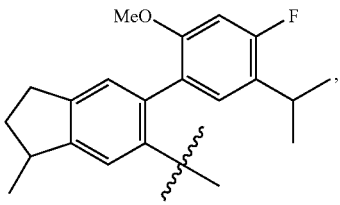
Ex. 76
diastereoisomer 2
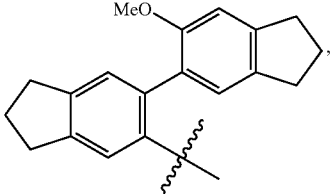
Ex. 77
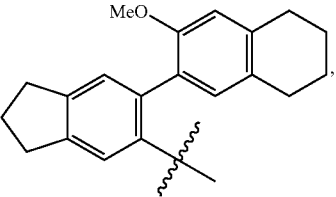
Ex. 78

Ex. 79
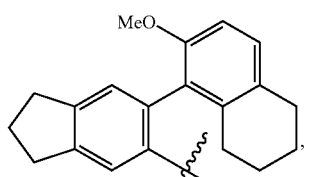
atropisomer 1
Ex. 80
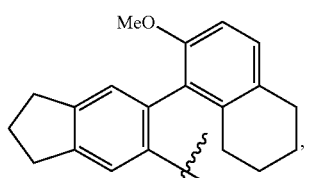
atropisomer 2
Ex. 81
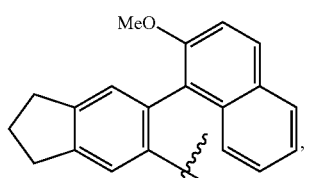
atropisomer 1
Ex. 82
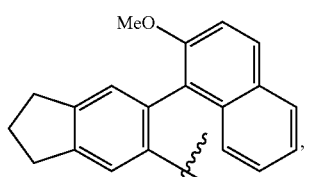
atropisomer 2
Ex. 83
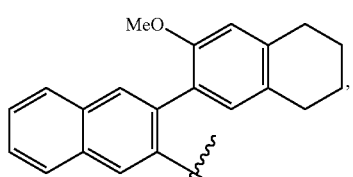
Ex. 84
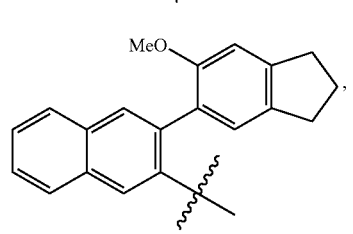
Ex. 85
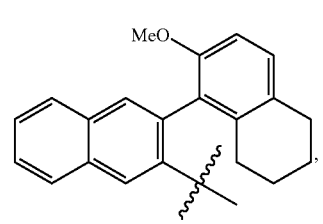
Ex. 86
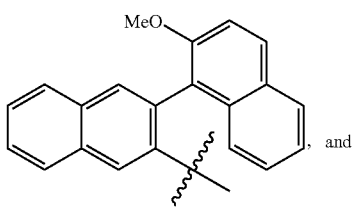
, and
Ex. 87
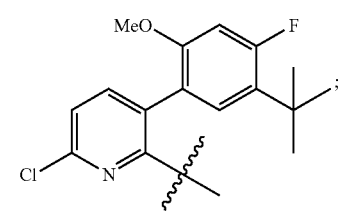
;
(d)
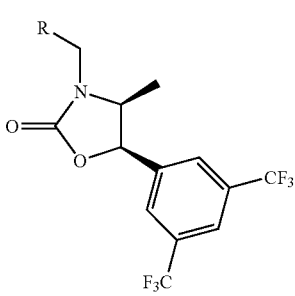
wherein R is selected from the group consisting of:
Ex. 88
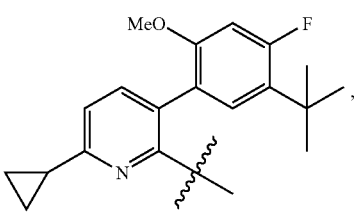
,
Ex. 89
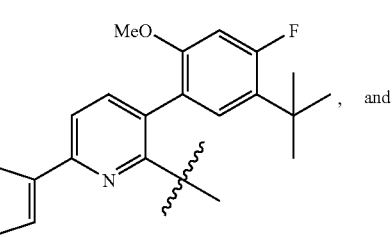
, and
Ex. 90
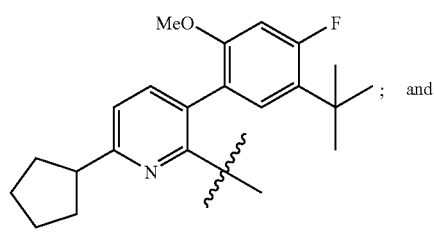
; and -continued (e)
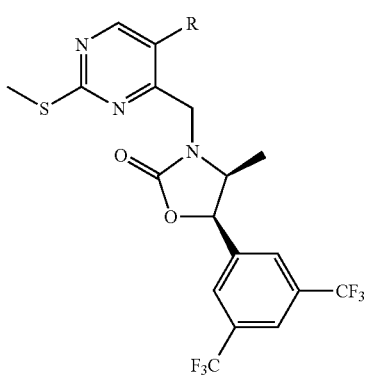

wherein R is selected from the group consisting of:

Ex. 122
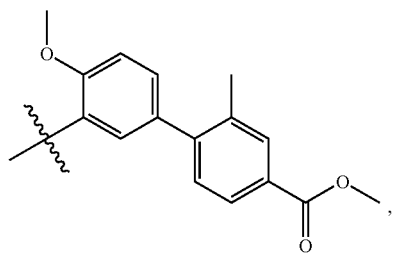

Ex. 123
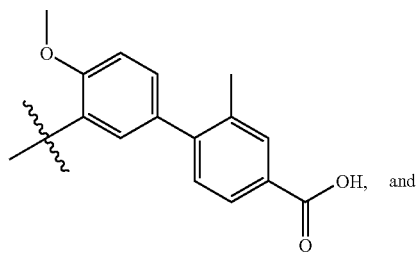
,

Ex. 124
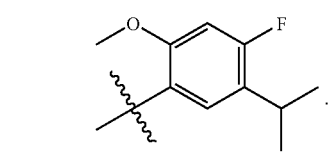

11. A method of treating atherosclerosis in a patient in need of treatment comprising the administration of a therapeutically effective amount of the compound of claim 1 to said patient, or a pharmaceutically acceptable salt thereof.

12. A method of raising HDL-C in a patient in need of treatment comprising the administration of a therapeutically effective amount of the compound of claim 1 to said patient, or a pharmaceutically acceptable salt thereof.

13. A method of lowering LDL-C in a patient in need of treatment comprising the administration of a therapeutically effective amount of the compound of claim 1 to said patient, or a pharmaceutically acceptable salt thereof.

14. A pharmaceutical composition comprising the compound of claim 1 or a pharmaceutically acceptable salt thereof, a pharmaceutically acceptable carrier, and one or more active ingredients selected from the group consisting of
(i) HMG-CoA reductase inhibitors;
(ii) bile acid sequestrants;
(iii) niacin and related compounds;
(iv) PPARα agonists;
(v) cholesterol absorption inhibitors;
(vi) acyl CoA:cholesterol acyltransferase (ACAT) inhibitors;
(vii) phenolic anti-oxidants;
(viii) microsomal triglyceride transfer protein (MTP)/ApoB secretion inhibitors;
(ix) anti-oxidant vitamins;
(x) thyromimetics;
(xi) LDL (low density lipoprotein) receptor inducers;
(xii) platelet aggregation inhibitors;
(xiii) vitamin B12 (also known as cyanocobalamin);
(xiv) folic acid or a pharmaceutically acceptable salt or ester thereof;
(xv) FXR and LXR ligands;
(xvi) agents that enhance ABCA1 gene expression; and
(xvii) ileal bile acid transporters.

15. The compound of claim 2 having formula Ia, or a pharmaceutically acceptable salt thereof, wherein:
Y is —(CHR$^1$)—, wherein R$^1$ is selected from H and C$_1$-C$_2$ alkyl;
R$^5$ is H;
X is —O—;
Z is —C(=O)—;
R is H;
n is 0;
A$^2$ is phenyl which is optionally substituted with 1-3 substituents independently selected from halogen, —C$_1$-C$_3$ alkyl which is optionally substituted with 1-3 halogens, and —OC$_1$-C$_3$alkyl which is optionally substituted with 1-3 halogens;
A$^1$ has the structure:

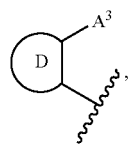
, wherein D is selected from the group consisting of naphthyl, pyridyl, quinolyl, indanyl, benzothienyl, tetrahydronaphthyl, isoxazolyl, 1,3-thiazolyl, pyrimidinyl, pyrazinyl, dihydroisoindolyl, dihydroisobenzofuranyl, and benzodioxolanyl, wherein D is optionally substituted with 1-2 substituent groups independently selected from (a) halogen, (b) —C$_1$-C$_5$ alkyl which is optionally substituted with 1-3 halogens, (c) —C$_2$-C$_3$ alkenyl, (d) —C$_3$-C$_6$ cycloalkyl, (e) —C$_5$-C$_6$ cycloalkenyl, (f) —OC$_1$-C$_3$alkyl optionally substituted with 1-3 halogens; (g) —SC$_1$-D$_3$alkyl, (h) —SO$_2$C$_1$-C$_3$alkyl, (i) —C(=O)OCH$_2$Phenyl, (j) Phenyl optionally substituted with 1-3 substituents independently selected from halogen, CH$_3$, CF$_3$, —OCH$_3$, and —OCF$_3$, (k) —NR$^3$R$^4$, where R$^3$ and R$^4$ are each independently selected from H and CH$_3$, (l) —CN, and (m) —NO$_2$; and
A$^3$ is selected from the group consisting of phenyl, naphthyl, indanyl, and tetrahydronaphthyl, wherein A$^3$ is optionally substituted with 1-3 substituents independently selected from (a) halogen, (b) —C$_1$-C$_5$ alkyl which is optionally substituted with 1-3 halogens and optionally one group selected from —OH, —CO$_2$H, and —CO$_2$C$_1$-C$_3$ alkyl, (c) —C$_2$-C$_3$ alkenyl, (d) —C$_3$-C$_6$ cycloalkyl which is optionally substituted with one group selected from [i] —CO$_2$H, [ii] —OH, and [iii]

$C_1$-$C_5$ alkyl which is optionally substituted with 1-3 halogens and optionally with 1 group selected from —OH, —$CO_2H$, and —$CO_2CH_3$, (e) —$C_5$-$C_6$ cycloalkenyl, (f) phenyl which is optionally substituted with 1-2 substituent groups independently selected from halogen, $CH_3$, $CF_3$, —$OCH_3$, —$OCF_3$, and optionally one group —$CO_2H$ or —$CO_2C_1$-$C_3$ alkyl, and (g) —$OC_1$-$C_3$alkyl optionally substituted with 1-3 halogens.

* * * * *